(12) United States Patent
Goetz et al.

(10) Patent No.: US 11,884,862 B2
(45) Date of Patent: Jan. 30, 2024

(54) LIQUID-CRYSTALLINE MEDIUM

(71) Applicant: MERCK PATENT GMBH, Darmstadt (DE)

(72) Inventors: Achim Goetz, Alsbach-Haehnlein (DE); Christian Hock, Mainaschaff (DE); Lars Lietzau, Rossdorf (DE); Mark Goebel, Winchester (GB)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/228,666

(22) Filed: Aug. 4, 2016

(65) Prior Publication Data

US 2017/0037316 A1 Feb. 9, 2017

(30) Foreign Application Priority Data

Aug. 5, 2015 (DE) ...................... 10 2015 009 955.8

(51) Int. Cl.

| | | |
|---|---|---|
| C09K 19/30 | (2006.01) |
| G02B 30/24 | (2020.01) |
| G02B 30/27 | (2020.01) |
| C07C 13/28 | (2006.01) |
| C07C 22/08 | (2006.01) |
| C07C 43/225 | (2006.01) |
| C09K 19/34 | (2006.01) |
| C09K 19/54 | (2006.01) |
| G02F 1/137 | (2006.01) |

(52) U.S. Cl.
CPC .......... C09K 19/3098 (2013.01); C07C 13/28 (2013.01); C07C 22/08 (2013.01); C07C 43/225 (2013.01); C09K 19/3402 (2013.01); C09K 19/3405 (2013.01); C09K 19/3491 (2013.01); C09K 19/54 (2013.01); C09K 19/542 (2013.01); G02B 30/24 (2020.01); G02B 30/27 (2020.01); G02F 1/137 (2013.01); C07C 2601/14 (2017.05); C07C 2601/16 (2017.05); C09K 2019/3408 (2013.01); C09K 2019/3422 (2013.01); G02F 1/13706 (2021.01)

(58) Field of Classification Search
CPC ................................................. C09K 19/3098
See application file for complete search history.

(56) References Cited

U.S. PATENT DOCUMENTS

| | | | |
|---|---|---|---|
| 4,405,488 A | 9/1983 | Sugimori et al. |
| 4,422,951 A | 12/1983 | Sugimori et al. |
| 5,064,565 A | 11/1991 | Uchida et al. |
| 5,536,442 A | 7/1996 | Reiffenrath et al. |
| 5,714,088 A | 2/1998 | Miyazawa et al. |
| 10,040,998 B2 | 8/2018 | Yun et al. |
| 10,364,392 B2 * | 7/2019 | Manabe ............ C09K 19/3001 |
| 10,550,327 B2 | 2/2020 | Engel et al. |
| 10,738,243 B2 * | 8/2020 | Junge ..................... C09K 19/20 |
| 10,774,061 B2 * | 9/2020 | Manabe ................. G02F 1/137 |
| 10,774,263 B2 * | 9/2020 | Manabe ............. C09K 19/3098 |
| 2013/0182202 A1 * | 7/2013 | Graziano ............... C09K 19/42 349/86 |
| 2013/0207038 A1 * | 8/2013 | Haensel ............. C09K 19/3098 252/299.61 |
| 2017/0015906 A1 * | 1/2017 | Yun .................... C09K 19/3402 |

FOREIGN PATENT DOCUMENTS

| | | | |
|---|---|---|---|
| CN | 1626492 A | 6/2005 |
| CN | 104797688 A | 7/2015 |
| DE | 3139130 A1 | 5/1982 |
| DE | 4035509 A1 * | 5/1992 | ............ C07C 22/08 |
| DE | 4445224 A1 | 6/1996 |
| DE | 102004036068 A1 | 3/2005 |
| EP | 0062470 A1 | 10/1982 |
| EP | 0062470 B1 | 8/1984 |
| EP | 0410756 B1 | 9/1994 |
| EP | 0733692 A1 | 9/1996 |
| EP | 0733692 B1 | 6/2000 |

(Continued)

OTHER PUBLICATIONS

English Translation of DE4035509.*
English Translation of JP2001226675.*
Pavluchenko, A. I., "Synthesis and Properties of Liquid Crystals with Fluorinated Terminal Substituents", Dec. 1991, Molecular Crystals and Liquid Crystals, vol. 209 Issue 1, 225-235.*
English abstracts of JP58198427. (Year: 1983).*
European Search Report for EP16001729 dated Dec. 16, 2016.
English Abstract for JP2001226675, Publication Date: Aug. 21, 2001.
Searh Report in corresponding EP appln. No. 16001729.9 dated Nov. 16, 2018 (pp. 1-4).

(Continued)

Primary Examiner — Chanceity N Robinson
Assistant Examiner — Anna Malloy
(74) Attorney, Agent, or Firm — MILLEN, WHITE, ZELANO & BRANIGAN, P.C.; Csaba Henter

(57) ABSTRACT

Compounds of the formula I

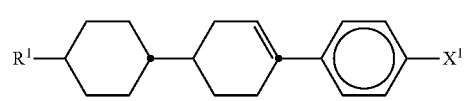

in which
$R^1$ is alkyl or alkoxy in which $CH_2$ groups are optionally replaced, and $X^1$ is alkyl $OCF_3$, $CF_3$, $CHF_2$, $OCF_2CF_3$, $CCF_2CHFCF_3$, $OCF=CF_2$, $OCH=CF_2$ or F,
a liquid-crystalline medium containing a compound of formula I,
and use thereof in electro-optical liquid-crystal displays, in particular in TN, STN, TN-TFT, OCB, IPS, PS-IPS, FFS, HB-FFS or PS-FFS-, positive VA displays and in shutter spectacles for 3D effects and LC lenses.

23 Claims, No Drawings

(56) References Cited

FOREIGN PATENT DOCUMENTS

| JP | 58198427 A | * | 11/1983 |
|----|------------|---|---------|
| JP | H0495045 A |   | 3/1992  |
| JP | 6313170 A  |   | 11/1994 |
| JP | 8176033 A  |   | 7/1996  |
| JP | 2001226675 A | | 8/2001  |
| TW | 201518481 A | | 5/2015  |

OTHER PUBLICATIONS

English translation of Office Action in corresponding ROC (Taiwan) Patent Application No. 109132387 dated Feb. 5, 2021 (pp. 1-3).
Notice of Reasons for Rejection in corresponding JP Patent Application No. 2016-154001 dated Oct. 6, 2020 (pp. 1-3).
Office Action in corresponding Chinese Patent Application No. 201610841375.X dated Feb. 2, 2021 (pp. 1-7).
English translation of Office Action in corresponding Chinese Patent Application No. 201610841375.X dated Dec. 9, 2021 (pp. 1-9).
English translation of Office Action in corresponding ROC (Taiwan) Patent Application No. 110108572 .: dated Nov. 11, 2021 (pp. 1-14).
English translation of Office Action in corresponding Korean Patent Appln. No. 2016-0099808.: dated Sep. 26, 2023 (pp. 1-9).

* cited by examiner

LIQUID-CRYSTALLINE MEDIUM

The present invention relates to a liquid-crystalline medium (LC medium), to the use thereof for electro-optical purposes, and to LC displays containing this medium.

Liquid crystals are used principally as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN cells having a "twisted nematic" structure, STN ("super-twisted nematic") cells, SBE ("super-birefringence effect") cells and OMI ("optical mode interference") cells. The commonest display devices are based on the Schadt-Helfrich effect and have a twisted nematic structure. In addition, there are also cells which work with an electric field parallel to the substrate and liquid-crystal plane, such as, for example, IPS ("in-plane switching") cells. TN, STN, FFS (fringe field switching) and IPS cells, in particular, are currently commercially interesting areas of application for the media according to the invention.

The liquid-crystal materials must have good chemical and thermal stability and good stability to electric fields and electromagnetic radiation. Furthermore, the liquid-crystal materials should have low viscosity and produce short addressing times, low threshold voltages and high contrast in the cells.

They should furthermore have a suitable mesophase, for example a nematic or cholesteric mesophase for the above-mentioned cells, at the usual operating temperatures, i.e. in the broadest possible range above and below room temperature. Since liquid crystals are generally used as mixtures of a plurality of components, it is important that the components are readily miscible with one another. Further properties, such as the electrical conductivity, the dielectric anisotropy and the optical anisotropy, have to satisfy various requirements depending on the cell type and area of application. For example, materials for cells having a twisted nematic structure should have positive dielectric anisotropy and low electrical conductivity.

For example, for matrix liquid-crystal displays with integrated non-linear elements for switching individual pixels (MLC displays), media having large positive dielectric anisotropy, broad nematic phases, relatively low birefringence, very high specific resistance, good UV and temperature stability and low vapour pressure are desired.

Matrix liquid-crystal displays of this type are known. Examples of non-linear elements which can be used to individually switch the individual pixels are active elements (i.e. transistors). The term "active matrix" is then used, where a distinction can be made between two types:

1. MOS (metal oxide semiconductor) or other diodes on silicon wafers as substrate.
2. Thin-film transistors (TFTs) on a glass plate as substrate.

The use of single-crystal silicon as substrate material restricts the display size, since even modular assembly of various part-displays results in problems at the joints.

In the case of the more promising type 2, which is preferred, the electro-optical effect used is usually the TN effect. A distinction is made between two technologies: TFTs comprising compound semiconductors, such as, for example, CdSe, or TFTs based on polycrystalline or amorphous silicon. Intensive work is being carried out worldwide on the latter technology.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully color-capable displays, in which a mosaic of red, green and blue filters is arranged in such a way that a filter element is opposite each switchable pixel.

The TFT displays usually operate as TN cells with crossed polarizers in transmission and are backlit.

The term MLC displays here encompasses any matrix display with integrated non-linear elements, i.e., besides the active matrix, also displays with passive elements, such as varistors or diodes (MIM=metal-insulator-metal).

MLC displays of this type are particularly suitable for TV applications (for example pocket televisions) or for high-information displays for computer applications (laptops) and in automobile or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210-288 Matrix LCD Controlled by Double Stage Diode Rings, pp. 141 ff., Paris; STROMER, M., Proc. Eurodisplay 84, September 1984: Design of Thin Film Transistors for Matrix Addressing of Television Liquid Crystal Displays, pp. 145 ff., Paris]. With decreasing resistance, the contrast of an MLC display deteriorates, and the problem of after-image elimination may occur. Since the specific resistance of the liquid-crystal mixture generally drops over the life of an MLC display owing to interaction with the interior surfaces of the display, a high (initial) resistance is very important in order to obtain acceptable lifetimes. In particular in the case of low-volt mixtures, it was hitherto impossible to achieve very high specific resistance values. It is furthermore important that the specific resistance exhibits the smallest possible increase with increasing temperature and after heating and/or UV exposure. The low-temperature properties of the mixtures from the prior art are also particularly disadvantageous. It is demanded that no crystallization and/or smectic phases occur, even at low temperatures, and the temperature dependence of the viscosity is as low as possible. The MLC displays from the prior art thus do not satisfy today's requirements.

Besides liquid-crystal displays which use backlighting, i.e. are operated transmissively and if desired transflectively, reflective liquid-crystal displays are also particularly interesting. These reflective liquid-crystal displays use the ambient light for information display. They thus consume significantly less energy than backlit liquid-crystal displays having a corresponding size and resolution. Since the TN effect is characterized by very good contrast, reflective displays of this type can even be read well in bright ambient conditions. This is already known of simple reflective TN displays, as used, for example, in watches and pocket calculators. However, the principle can also be applied to high-quality, higher-resolution active matrix-addressed displays, such as, for example, TFT displays. Here, as already in the transmissive TFT-TN displays which are generally conventional, the use of liquid crystals of low birefringence ($\Delta n$) is necessary in order to achieve low optical retardation (d·Δn). This low optical retardation results in usually acceptably low viewing-angle dependence of the contrast (cf. DE 30 22 818). In reflective displays, the use of liquid crystals of low birefringence is even more important than in transmissive displays since the effective layer thickness through which the light passes is approximately twice as large in reflective displays as in transmissive displays having the same layer thickness.

For TV and video applications, displays having fast response times are required in order to be able to reproduce multimedia content, such as, for example, films and video games, in near-realistic quality. Such short response times can be achieved, in particular, if liquid-crystal media having low values for the viscosity, in particular the rotational viscosity $\gamma_1$, and having high optical anisotropy (Δn) are used.

In order to achieve 3D effects by means of shutter spectacles, use is made of, in particular, fast-switching mixtures having low rotational viscosities and correspondingly high optical anisotropy (Δn). Electro-optical lens systems by means of which a 2-dimensional representation of a display can be converted into a 3-dimensional autostereoscopic representation can be achieved using mixtures having high optical anisotropy (Δn).

In the case of TN (Schadt-Helfrich) cells, media are desired which facilitate the following advantages in the cells:
   extended nematic phase range (in particular down to low temperatures)
   the ability to switch at extremely low temperatures (outdoor use, automobiles, avionics)
   increased resistance to UV radiation (longer lifetime)
   low threshold voltage.

The media available from the prior art do not enable these advantages to be achieved while simultaneously retaining the other parameters.

In the case of supertwisted (STN) cells, media are desired which facilitate greater multiplexability and/or lower threshold voltages and/or broader nematic phase ranges (in particular at low temperatures). To this end, a further widening of the available parameter latitude (clearing point, smectic-nematic transition or melting point, viscosity, dielectric parameters, elastic parameters) is urgently desired.

One of the most important properties of modern LCDs is correct reproduction of moving images. If the response speed of the liquid-crystalline medium used is too slow, this causes undesired artefacts in the display of such content. The physical parameters which essentially determine the response time of a liquid-crystal mixture are the rotational viscosity $\gamma_1$ and the elastic constants. The latter are also particularly important for ensuring a good black state of the LCD. In general, however, it is observed that the clearing point of the mixture and thus the rotational viscosity of the mixture is also increased with an increase in the elastic constants, meaning that an improvement in the response time is not possible. In particular in the case of LC displays for TV and video applications (for example LCD TVs, monitors, PDAs, notebooks, games consoles), a significant reduction in the response times is desired. A reduction in the layer thickness d ("cell gap") of the LC medium in the LC cell theoretically results in faster response times, but requires LC media having higher birefringence Δn in order to ensure an adequate optical retardation (dΔn). However, the LC materials of high birefringence known from the prior art generally also have high rotational viscosity at the same time, which in turn has an adverse effect on the response times.

There is thus still a great need for liquid-crystalline media having good reliability properties, such as, for example, high VHR (voltage holding ratio), which do not exhibit these properties or only do so to a lesser extent.

The invention is based on the object of providing media, in particular for MLC, TN, STN, OCB, positive VA, FFS, HB (=high brightness)-FFS, PS (=polymer stabilized)-FFS, IPS, PS-IPS displays of this type, which have the desired properties indicated above and do not exhibit the disadvantages indicated above or only do so to a reduced extent. In particular, the LC media should have fast response times and low rotational viscosities at the same time as relatively high birefringence. In addition, the LC media should have a high clearing point and very good low-temperature stability (LTS).

It has now been found that this object can be achieved if LC media comprising one or more compounds of the formula I are used.

The invention relates to a liquid-crystalline medium, characterized in that it comprises one or more compounds of the formula I,

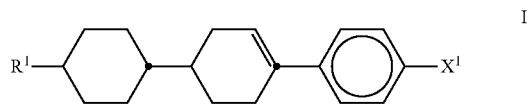

in which
   $R^1$ denotes an alkyl or alkoxy radical having 1 to 15 C atoms, where, in addition, one or more $CH_2$ groups in these radicals may each be replaced, independently of one another, by

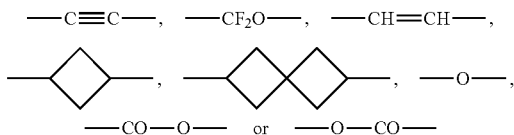

in such a way that O atoms are not linked directly to one another, and in which, in addition, one or more H atoms may be replaced by halogen, and
   $X^1$ denotes an alkyl radical having 1 to 5 C atoms, $OCF_3$, $CF_3$, $CHF_2$, $OCHF_2$, $OCF_2CF_3$, $OCF_2CHFCF_3$, $OCF=CF_2$, $OCH=CF_2$ or F.

The compounds of the formula I lead to LC mixtures having the desired properties indicated above, in particular in LC mixtures having very low rotational viscosity. The mixtures according to the invention have very large elastic constants and thus facilitate very good response times. Furthermore, the mixtures according to the invention are stable at at least −20° C. and exhibit no tendency towards crystallization. The rotational viscosities $\gamma_1$ are generally <120 mPa·s. Furthermore, the mixtures according to the invention are distinguished by a very good ratio of rotational viscosity $\gamma_1$ and clearing point, low $\gamma_1/K_{11}$ values, which lead to faster response times, as well as a high clearing point and a broad nematic phase range. Furthermore, the compounds of the formula I are readily soluble in liquid-crystalline media.

The compounds of the formula I have a broad range of applications and are distinguished, in particular, by their very large elastic constants. Depending on the choice of substituents, they can serve as base materials of which liquid-crystalline media are predominantly composed; however, liquid-crystalline base materials from other classes of compound can also be added to the compounds of the formula I in order, for example, to influence the dielectric and/or optical anisotropy of a dielectric of this type and/or to optimise its threshold voltage and/or its rotational viscosity. The result are LC mixtures according to the invention which support a good black state of the display, which is crucial for the contrast of the display, owing to high elastic constants and at the same time facilitate very good response times.

$R^1$ in the compounds of the formula I and the sub-formulae preferably denotes a straight-chain alkyl radical, in particular having 3-5 C atoms. In a further preferred embodiment, one or more $CH_2$ groups in the alkyl radical may also be replaced by —CH=CH—.

Particularly preferred compounds of the formula I are shown below:

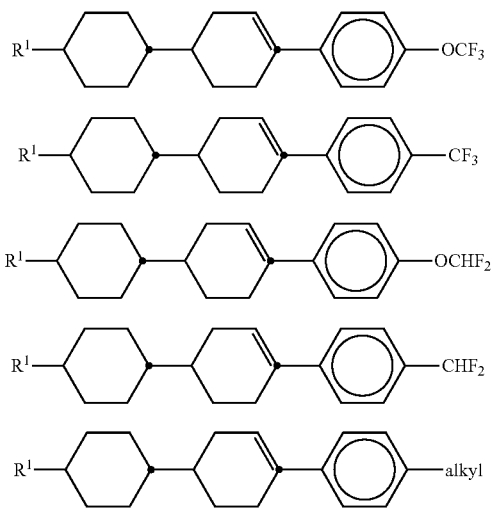

in which $R^1$ has the meanings indicated in claim 1, preferably straight-chain alkyl or alkenyl having up to 5 C atoms, and "alkyl" denotes a straight-chain alkyl radical having 1-5 C atoms.

Very particular preference is given to the compounds of the formulae I-1, I-2 and I-5.

Very particularly preferred compounds are shown below:

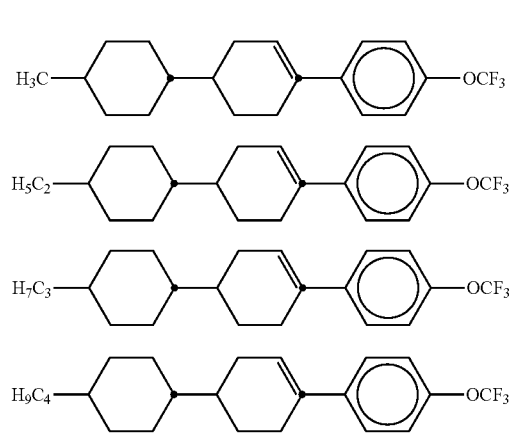

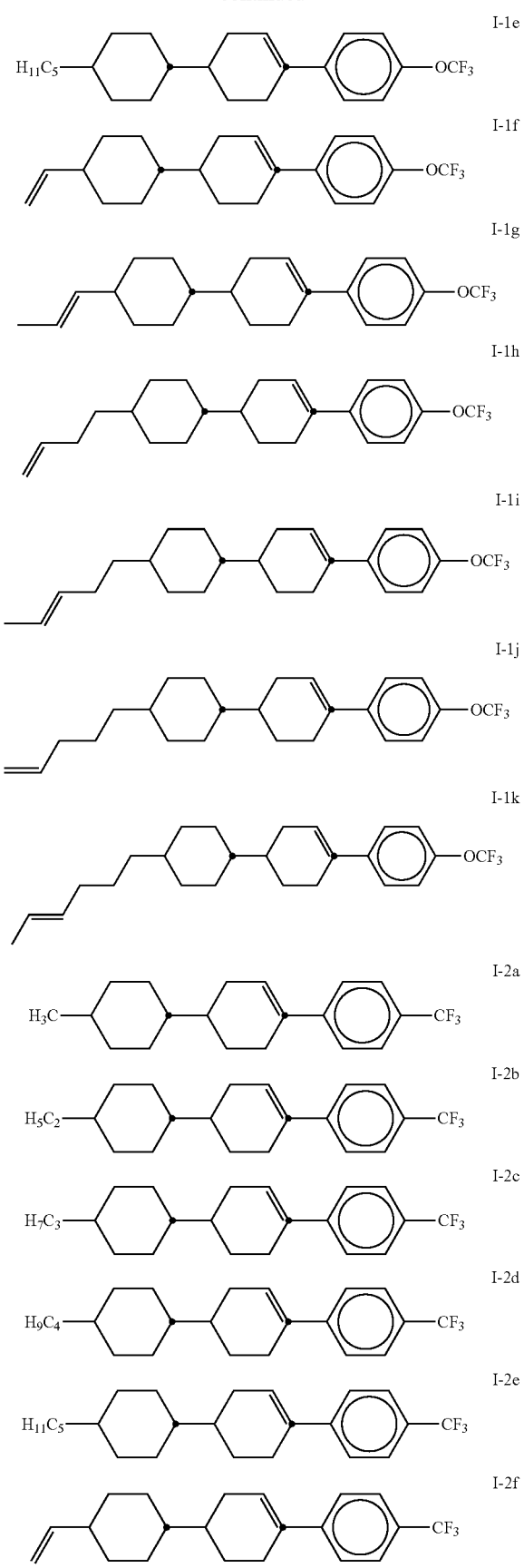

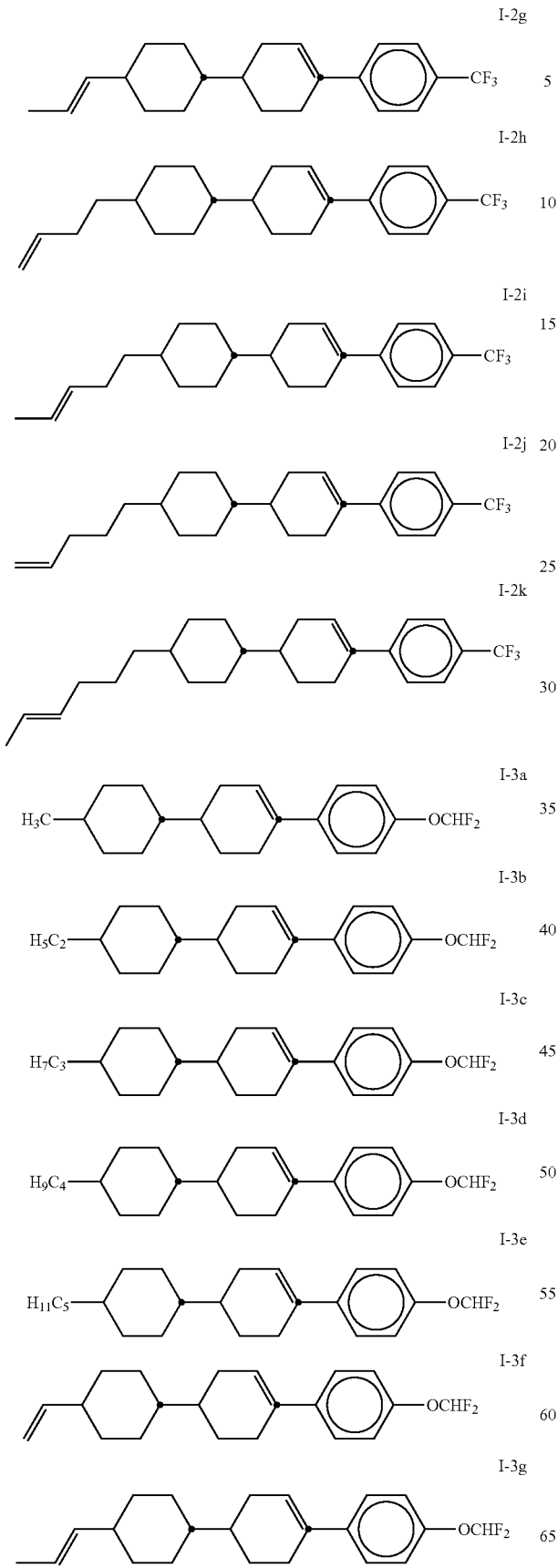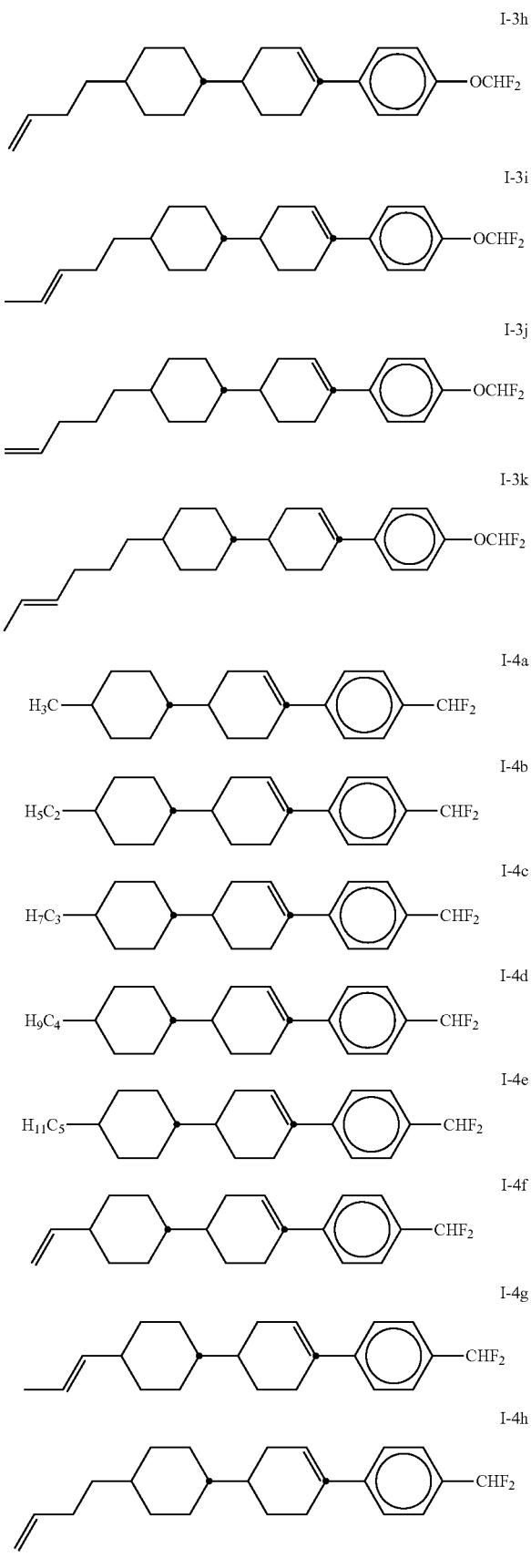

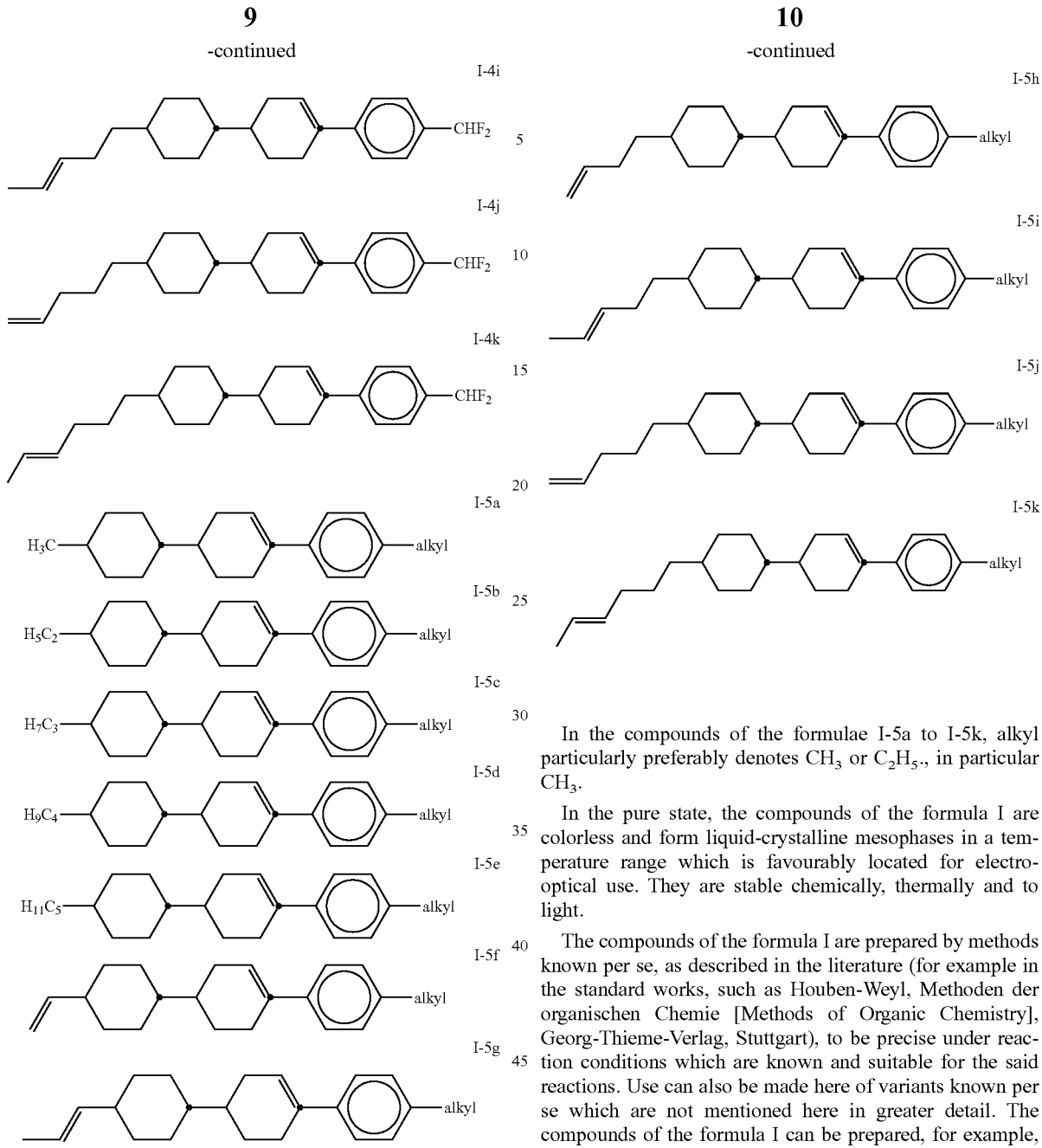

In the compounds of the formulae I-5a to I-5k, alkyl particularly preferably denotes $CH_3$ or $C_2H_5$., in particular $CH_3$.

In the pure state, the compounds of the formula I are colorless and form liquid-crystalline mesophases in a temperature range which is favourably located for electro-optical use. They are stable chemically, thermally and to light.

The compounds of the formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail. The compounds of the formula I can be prepared, for example, as follows:

Scheme 1

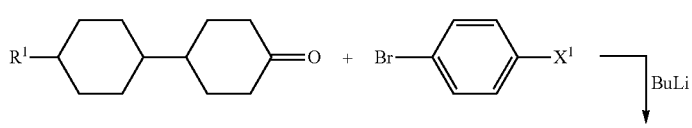

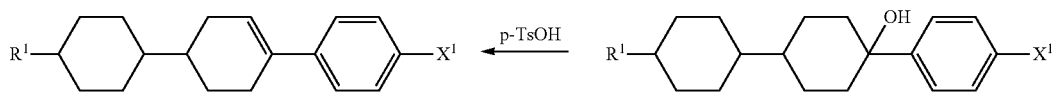

Scheme 2

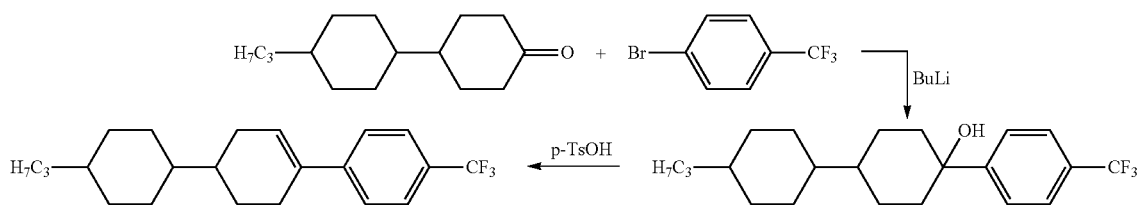

If R[1] in the compounds of the formula I above and below denotes an alkyl radical and/or an alkoxy radical, this may be straight-chain or branched. It is preferably straight-chain, has 2, 3, 4, 5, 6, or 7 C atoms and accordingly preferably denotes ethyl, propyl, butyl, pentyl, hexyl, heptyl, ethoxy, propoxy, butoxy, pentoxy, hexoxy or heptoxy, furthermore, nonyl, decyl, undecyl, dodecyl, tridecyl, tetradecyl, pentadecyl, methoxy, octoxy, nonoxy, decoxy, undecoxy, dodecoxy, tridecoxy or tetradedoxy.

Oxaalkyl preferably denotes straight-chain 2-oxapropyl (=methoxymethyl), 2-(=ethoxymethyl) or 3-oxabutyl (=2-methoxyethyl), 2-, 3- or 4-oxaheptyl, 2-, 3-, 4- or 5-oxahexyl, 2-, 3-, 4-, 5- or 6-oxaheptyl, 2-, 3-, 4-, 5-, 6-, or 7-oxaoctyl, 2-, 3-, 4-, 5-, 6-, 7- or 8-oxanonyl, 2-, 3-, 4-, 5-, 6-, 7-, 8- or 9-oxadexyl.

If R[1] denotes an alkyl radical in which one CH$_2$ group has been replaced by —CH=CH—, this may be straight-chain or branched. It is preferably straight-chain and has 2 to 10 C atoms. Accordingly, it denotes, in particular, vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl. These radicals may also be mono- or polyhalogenated.

If R[1] denotes an alkyl or alkenyl radical which is at least monosubstituted by halogen, this radical is preferably straight-chain and halogen is preferably F or Cl. In the case of polysubstitution, halogen is preferably F. The resultant radicals also include perfluorinated radicals. In the case of monosubstitution, the fluorine or chlorine substituent can be in any desired position, but is preferably in the ω position.

X[1] preferably denotes an alkyl radical, in particular CH$_3$, and CF$_3$, furthermore OCF$_3$.

The present invention likewise relates to the compounds of the formula I and sub-formulae thereof.

Preferred embodiments of the liquid-crystal mixtures according to the invention are indicated below:
  The medium additionally comprises one or more neutral compounds of the formulae II and/or III,

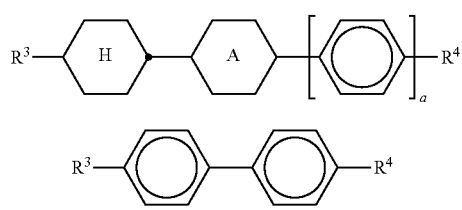

in which
A denotes 1,4-phenylene or trans-1,4-cyclohexylene,
a is 0 or 1,
R[3] denotes alkenyl having 2 to 9 C atoms,
and R[4] has the meaning indicated for R[1] in formula I and preferably denotes alkyl having 1 to 12 C atoms or alkenyl having 2 to 9 C atoms.
The compounds of the formula II are preferably selected from the compounds of the following formulae:

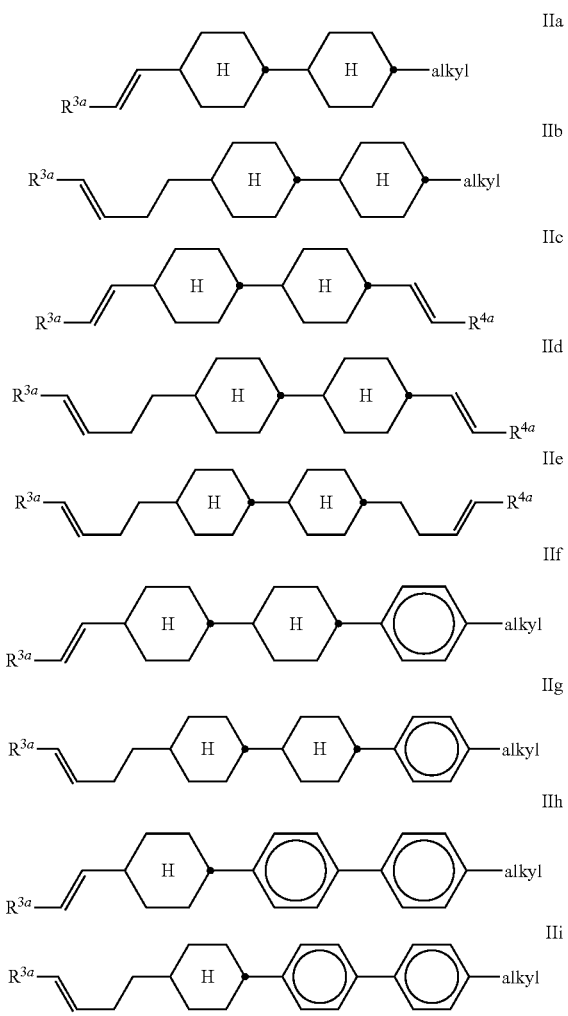

in which R[3a] and R[4a] each, independently of one another, denote H, CH$_3$, C$_2$H$_5$ or C$_3$H$_7$, and "alkyl" denotes a straight-chain alkyl group having 1 to 8 C atoms. Particular preference is given to compounds of the formulae IIa and IIf, in particular in which $R^{3a}$ denotes H or $CH_3$, and compounds of the formula IIc, in particular in which $R^{3a}$ and $R^{4a}$ denote H, $CH_3$ or $C_2H_5$.

Preference is furthermore given to compounds of the formula II which have a non-terminal double bond in the alkenyl side chain:

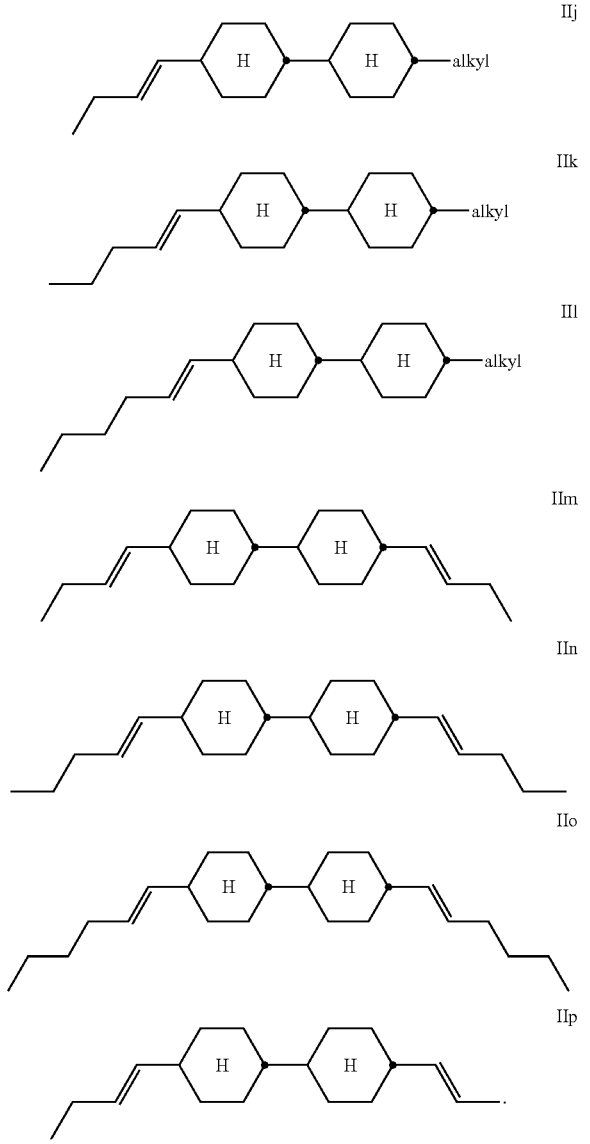

Very particularly preferred compounds of the formula IIa are the compounds of the formulae

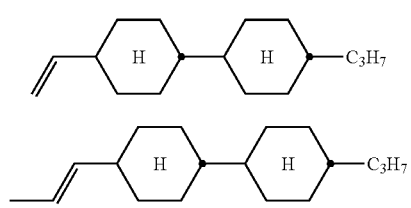

-continued

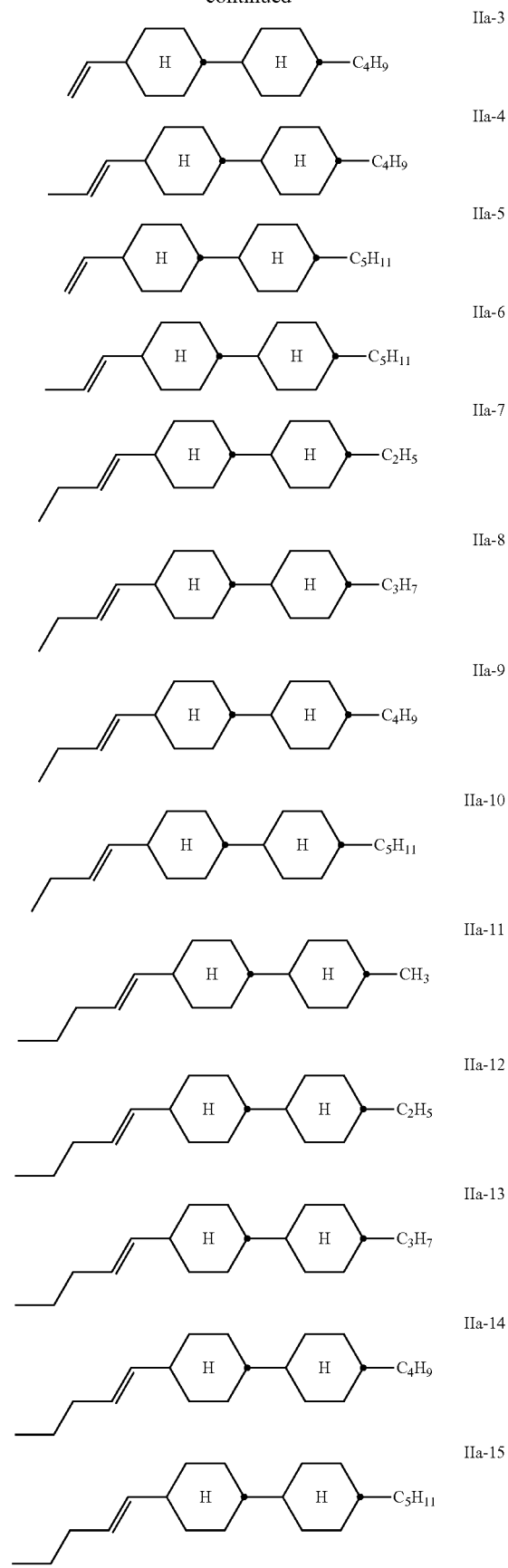

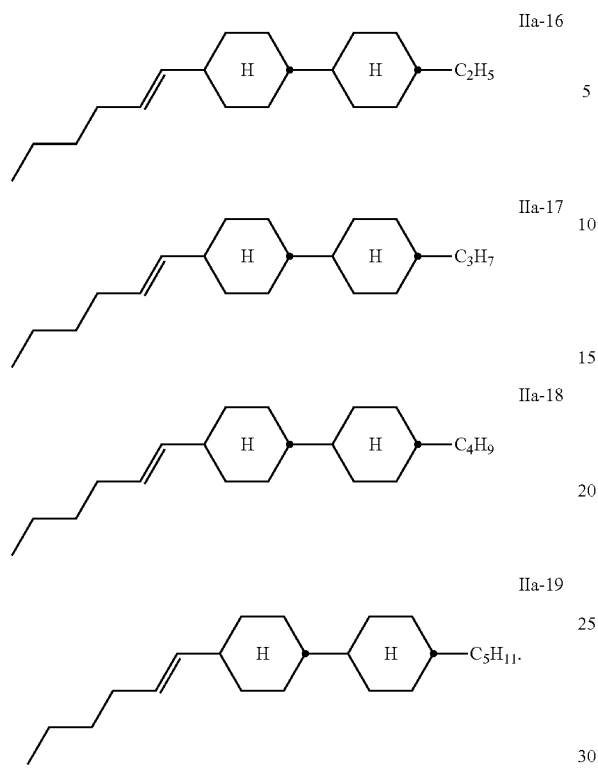

Of the compounds of the formulae IIa-1 to IIa-19, particular preference is given, in particular, to the compounds of the formulae IIa-1, IIa-2, IIa-3, IIa-5 and 11c-1.

Besides one or more compounds of the formula I, the liquid-crystalline media according to the invention particularly preferably additionally comprise the compound of the formula (CC-3-V),

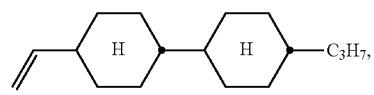

preferably in concentrations of 5-70% by weight, in particular 10-65% by weight and very particularly preferably 20-55% by weight, based on the mixture.

Preferred compounds of the formula IIb are the compounds of the formulae

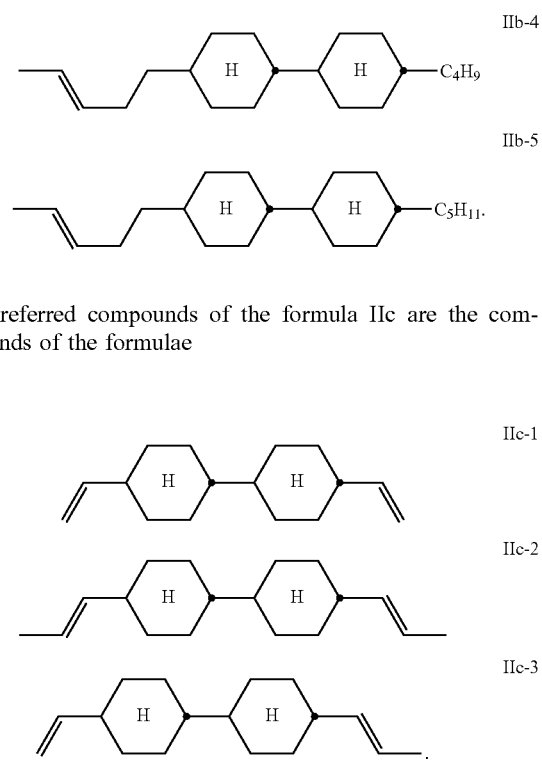

Preferred compounds of the formula IIc are the compounds of the formulae

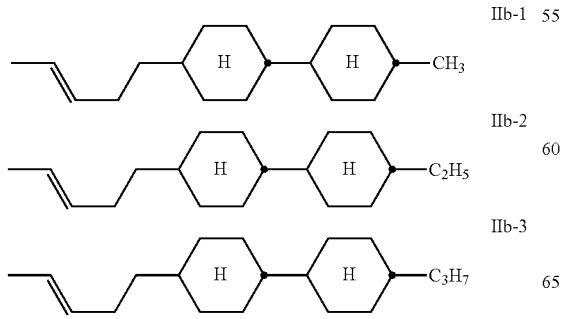

The compounds of the formula III are preferably selected from the following formulae:

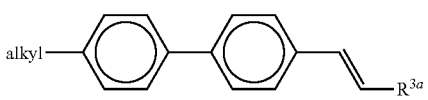

in which "alkyl" and $R^{3a}$ have the meanings indicated above, and $R^{3a}$ preferably denotes H or $CH_3$. Particular preference is given to compounds of the formula IIIb;

Very particular preference is given to the compound of the formula IIIb-1,

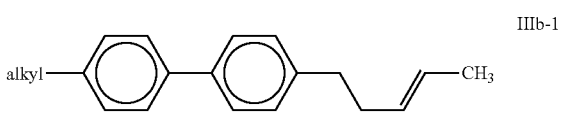

in which "alkyl" has the meaning indicated above and preferably denotes $CH_3$, furthermore $C_2H_5$ or n-$C_3H_7$.

The medium preferably additionally comprises one or more compounds selected from the following formulae IV to VIII:

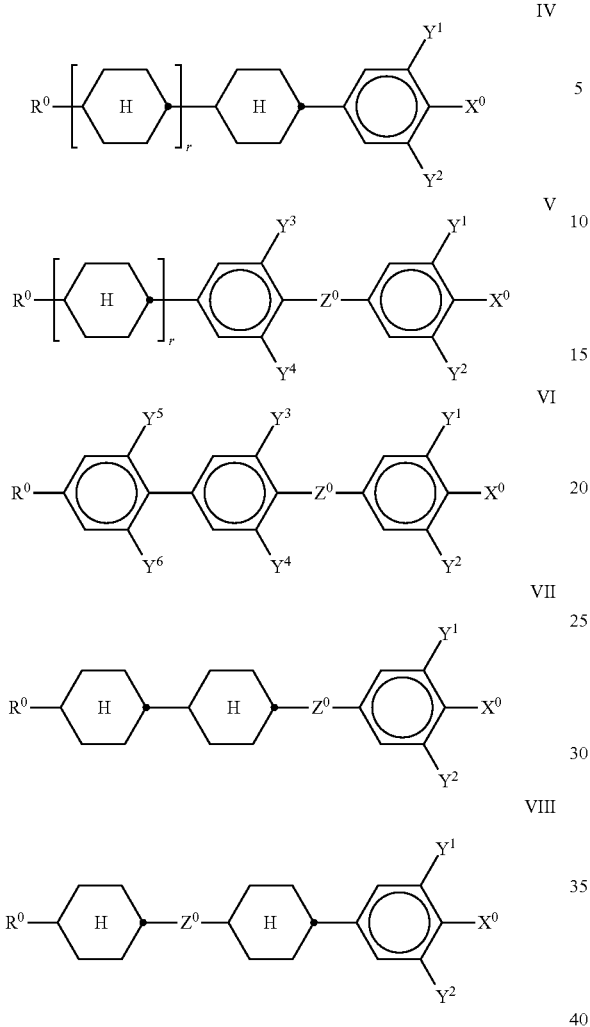

in which

R⁰ has the meanings indicated in claim 6,

X⁰ denotes F, Cl, a mono- or polyfluorinated alkyl or alkoxy radical, in each case having 1 to 6 C atoms, a mono- or polyfluorinated alkenyl or alkenyloxy radical, in each case having 2 to 6 C atoms, Y$^{1-6}$ each, independently of one another, denote H or F, Z⁰ denotes —C$_2$H$_4$—, —(CH$_2$)$_4$—, —CH=CH—, —CF=CF, —C$_2$F$_4$—, —CH$_2$CF$_2$—, —CF$_2$CH$_2$—, —CH$_2$O—, —OCH$_2$—, —COO—, —CF$_2$O— or —OCF$_2$—, in the formulae V and VI also a single bond, and r denotes 0 or 1.

In the above formulae, X⁰ is preferably F, Cl or a mono- or polyfluorinated alkyl or alkoxy radical having 1, 2 or 3 C atoms or a mono- or polyfluorinated alkenyl radical or alkenyloxy radical having 2 or 3 C atoms. X⁰ is particularly preferably F, Cl, CF$_3$, CHF$_2$, OCF$_3$, OCHF$_2$, OCHFCF$_3$, OCHFCHF$_2$, OCHFCH$_2$F, OCF$_2$CH$_3$, OCF$_2$CHF$_2$, OCF$_2$CH$_2$F, OCF$_2$CF$_2$CHF$_2$, OCF$_2$CF$_2$CH$_2$F, OCFHCF$_2$CF$_3$, OCFHCF$_2$CHF$_2$, OCH=CF$_2$, OCF=CF$_2$, OCF$_2$CHFCF$_3$, OCF$_2$CF$_2$CF$_3$, OCF$_2$CF$_2$CClF$_2$, OCClFCF$_2$CF$_3$, CF=CF$_2$, CF=CHF, OCH=CF$_2$, OCF=CF$_2$, or CH=CF$_2$.

In the compounds of the formulae IV to VIII, X⁰ preferably denotes F or OCF$_3$, furthermore OCHF$_2$, CF$_3$, CF$_2$H, Cl, OCH=CF$_2$. R⁰ is preferably straight-chain alkyl or alkenyl having up to 6 C atoms.

The compounds of the formula IV are preferably selected from the following formulae:

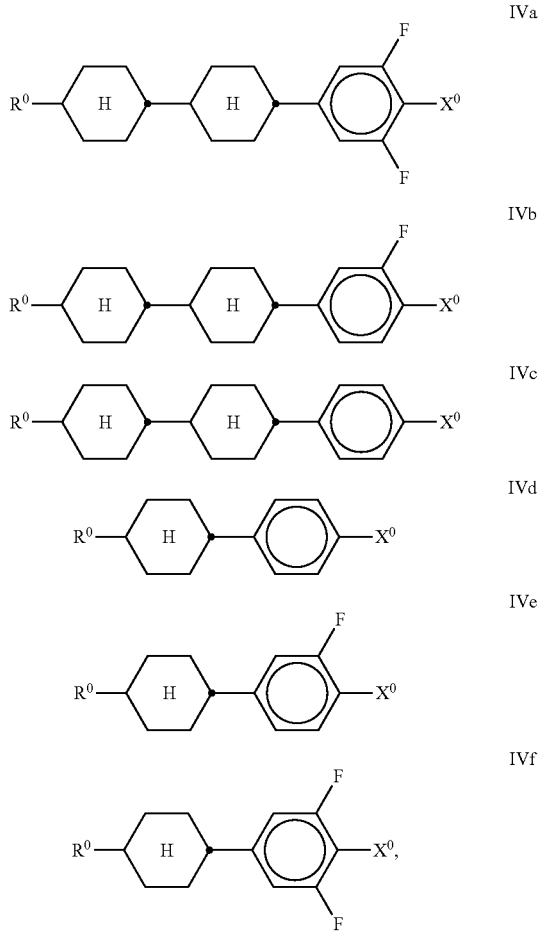

in which R⁰ and X⁰ have the meanings indicated in claim 6.

In formula IV, R⁰ preferably denotes alkyl having 1 to 8 C atoms and X⁰ preferably denotes F, Cl, OCHF$_2$ or OCF$_3$, furthermore OCH=CF$_2$. In the compound of the formula IVb, R⁰ preferably denotes alkyl or alkenyl. In the compound of the formula IVd, X⁰ preferably denotes Cl, furthermore F.

The compounds of the formula V are preferably selected from the formulae Va to Vj,

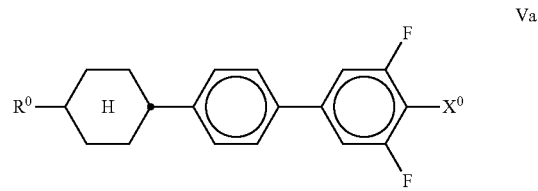

-continued

Vb: R⁰—[H]—[Ph(F,F)]—[Ph(F,F)]—X⁰

Vc: R⁰—[H]—[Ph]—[Ph(F,F)]—X⁰

Vd: R⁰—[H]—[Ph(F)]—[Ph(F)]—X⁰

Ve: R⁰—[H]—[Ph(F,F)]—[Ph(F,F)]—X⁰

Vf: R⁰—[H]—[Ph]—[Ph]—F

Vg: R⁰—[H]—[Ph(F,F)]—[Ph(F)]—X⁰

Vh: R⁰—[H]—[Ph(F)]—COO—[Ph]—X⁰

Vi: R⁰—[H]—[Ph(F)]—COO—[Ph(F)]—X⁰

Vj: R⁰—[H]—[Ph(F)]—COO—[Ph(F,F)]—X⁰ in which R⁰ and X⁰ have the meanings indicated in claim 6. Preferably, R⁰ in formula V denotes alkyl having 1 to 8 C atoms and X° denotes F, OCF₃ or OCH=CF₂.

The medium comprises one or more compounds of the formula VI-1,

VI-1: R⁰—[Ph]—[Ph(Y³,Y⁴)]—[Ph(Y¹,Y²)]—X⁰ particularly preferably those selected from the following formulae:

VI-1a: R⁰—[Ph]—[Ph(F)]—[Ph(F,F)]—X⁰

VI-1b: R⁰—[Ph]—[Ph(F)]—[Ph(F)]—X⁰

VI-1c: R⁰—[Ph]—[Ph(F,F)]—[Ph(F,F)]—X⁰

VI-1d: R⁰—[Ph]—[Ph(F,F)]—[Ph(F,F)]—X⁰ in which R⁰ and X⁰ have the meanings indicated in claim 6. Preferably, R⁰ in formula VI denotes alkyl having 1 to 8 C atoms and X° denotes F, furthermore CF₃ and OCF₃.

The medium comprises one or more compounds of the formula VI-2,

VI-2: R⁰—[Ph(Y⁵,Y⁶)]—[Ph(Y³,Y⁴)]—CF₂O—[Ph(Y¹,Y²)]—X⁰ particularly preferably those selected from the following formulae:

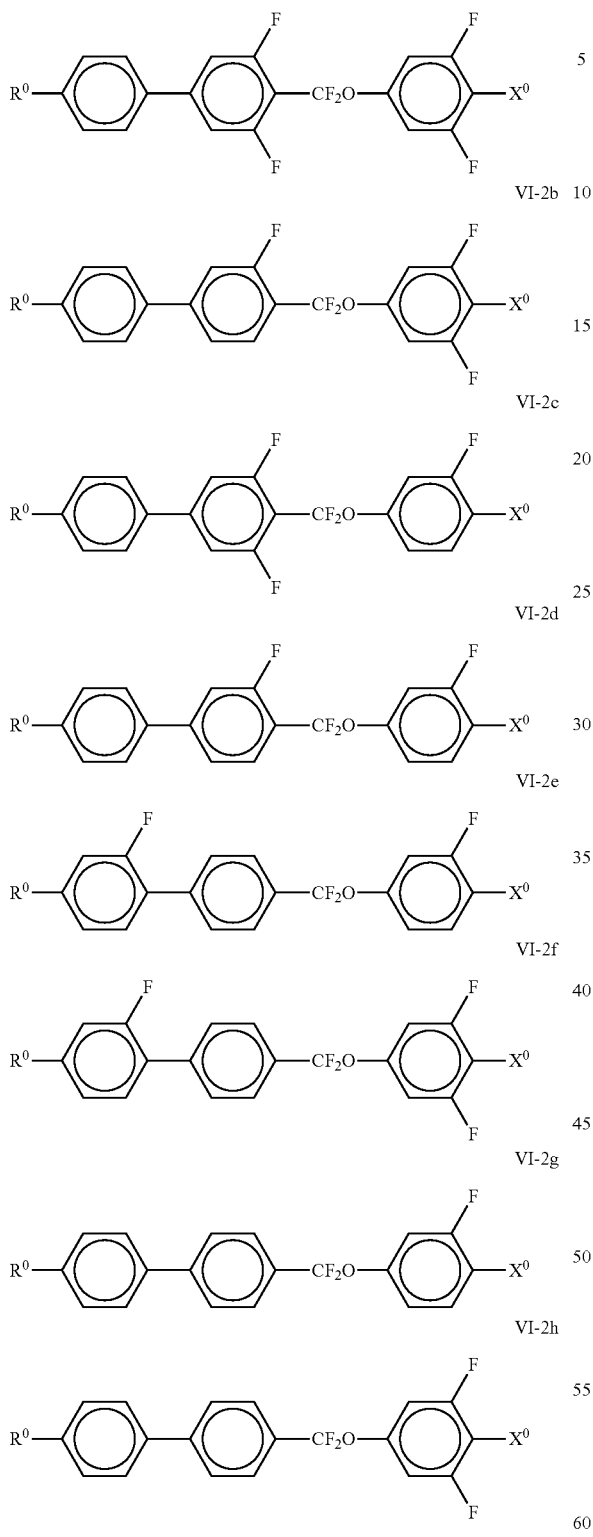

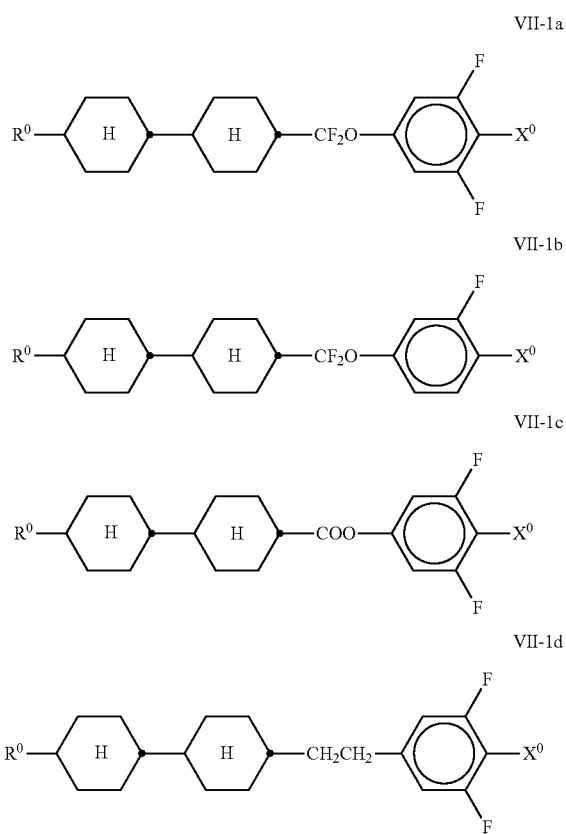

in which $R^0$ and $X^0$ have the meanings indicated in claim 6. Preferably, $R^0$ in formula VI denotes alkyl having 1 to 8 C atoms and $X^0$ denotes F;

The medium preferably comprises one or more compounds of the formula VII in which $Z^0$ denotes —$CF_2O$—, —$CH_2CH_2$— or —OCO—, particularly preferably those selected from the following formulae:

in which $R^0$ and $X^0$ have the meanings indicated in claim 6. Preferably, $R^0$ in formula VII denotes alkyl having 1 to 8 C atoms and $X^0$ denotes F, furthermore $OCF_3$ and $CF_3$.

The compounds of the formula VIII are preferably selected from the following formulae:

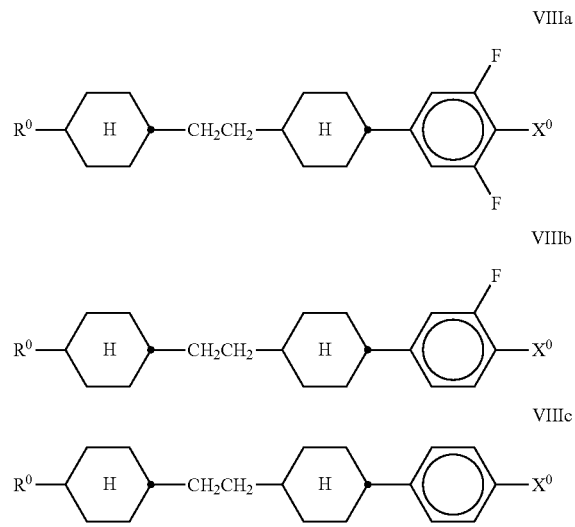

-continued

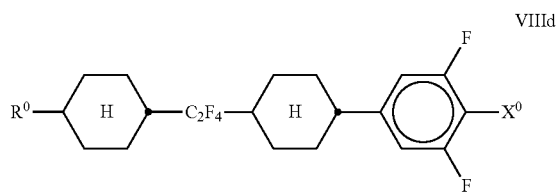
VIIId

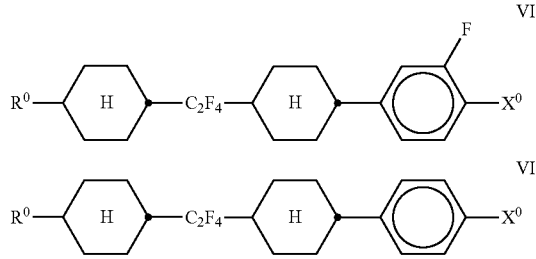
VIIIe

VIIIf in which R⁰ and X⁰ have the meanings indicated above. R⁰ in formula VIII preferably denotes a straight-chain alkyl radical having 1 to 8 C atoms. X⁰ preferably denotes F.

The medium additionally comprises one or more compounds of the following formula:

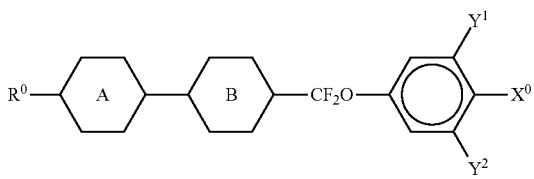
IX in which R⁰, X⁰, Y¹ and Y² have the meaning indicated above, and

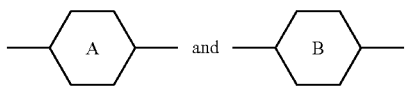

each, independently of one another, denote

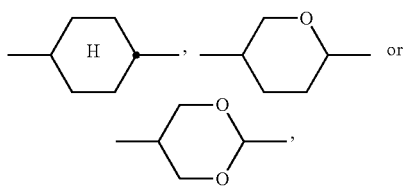

where the rings A and B do not both simultaneously denote 1,4-cyclohexylene;

The compounds of the formula IX are preferably selected from the following formulae:

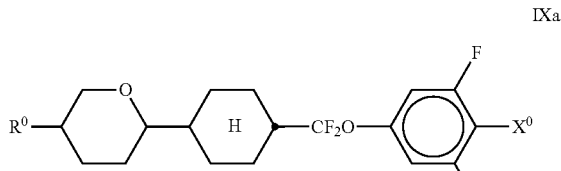
IXa

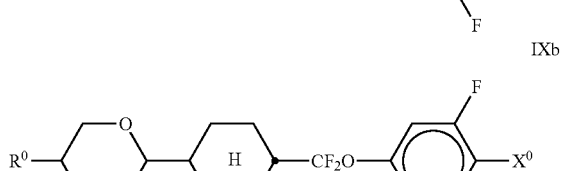
IXb

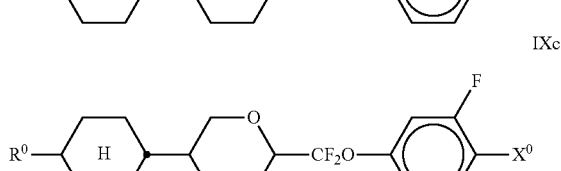
IXc

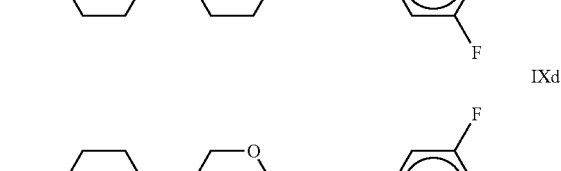
IXd

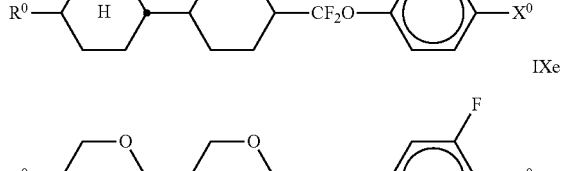
IXe

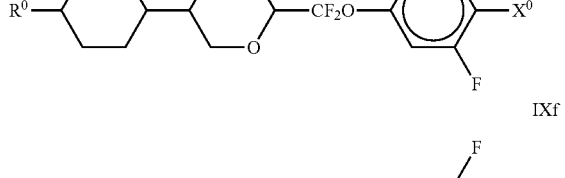
IXf

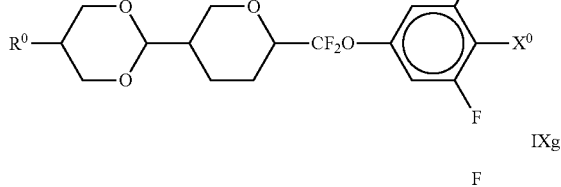
IXg

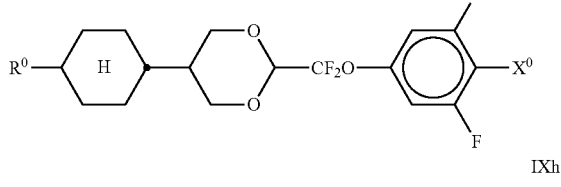
IXh

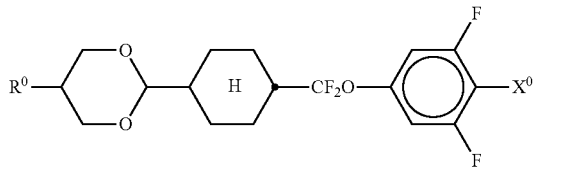

in which R⁰ and X⁰ have the meanings indicated in claim 6. Preferably, R⁰ in formula IX denotes alkyl having 1 to 8 C atoms and X° denotes F. Particular preference is given to compounds of the formula IXa;

The medium additionally comprises one or more compounds selected from the following formulae:

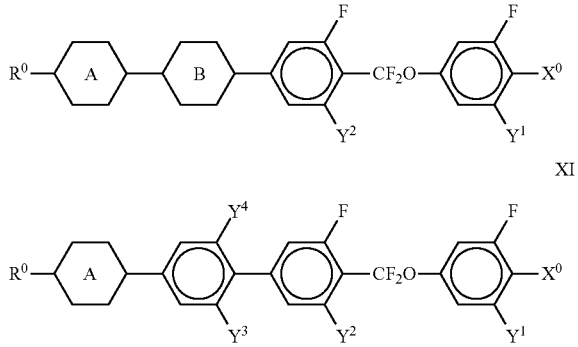

in which R⁰, X⁰ and Y¹⁻⁴ have the meanings indicated in claim 6, and

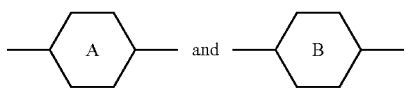

each, independently of one another, denote

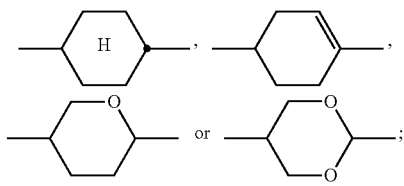

The compounds of the formulae X and XI are preferably selected from the following formulae:

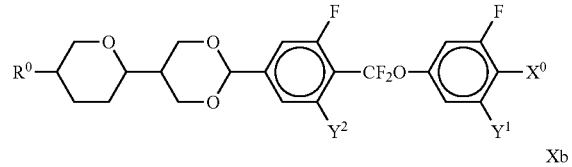

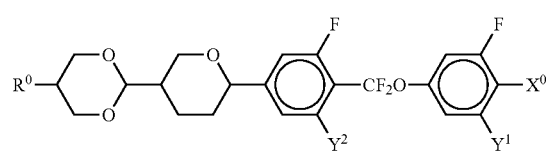

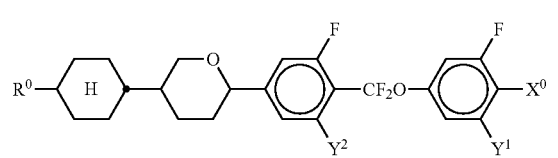

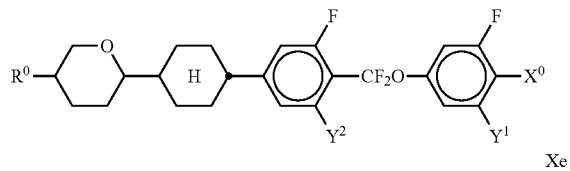

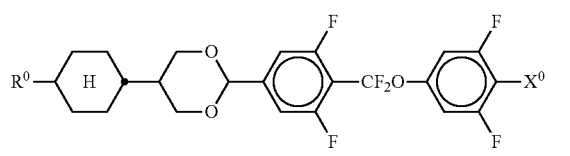

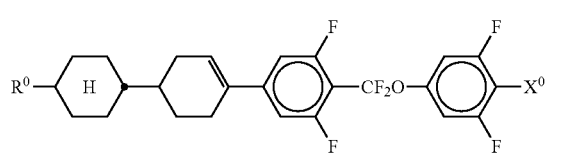

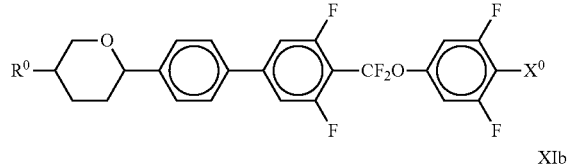

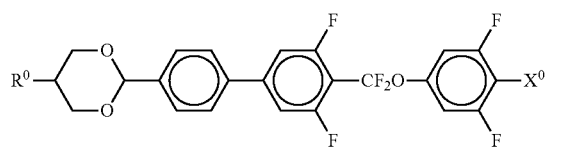

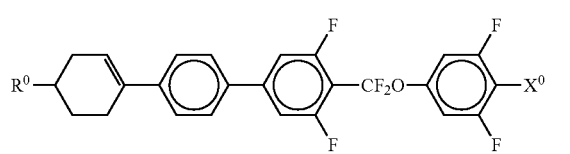

in which R⁰ and X⁰ have the meanings indicated in claim 6. Preferably, R⁰ denotes alkyl having 1 to 8 C atoms and X⁰ denotes F. Particularly preferred compounds are those in which Y¹ denotes F and Y² denotes H or F, preferably F.

The medium additionally comprises one or more compounds of the following formula XII:

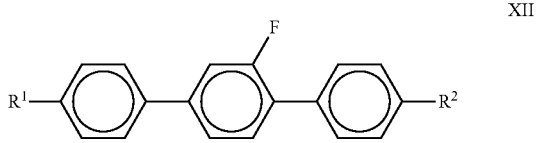

in which R¹ and R² each, independently of one another, denote alkyl, alkenyl, alkoxy, oxaalkyl, fluoroalkyl or alkenyloxy, each having up to 9 C atoms, and preferably each, independently of one another, denote alkyl or alkenyl having 1 to 8 C atoms or 2 to 8 C atoms respectively.

Preferred compounds of the formula XII are the compounds of the formulae

XII-1
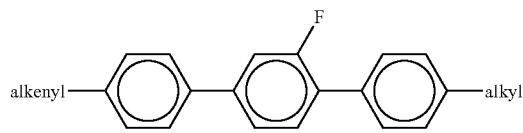

XII-2
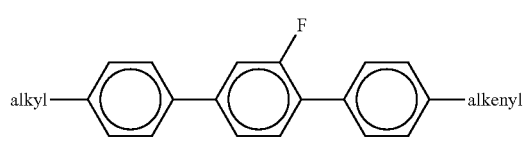

XII-3
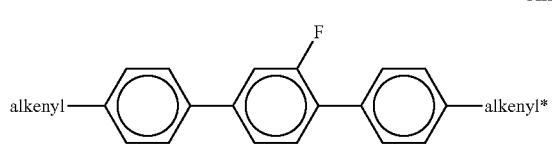

XII-4
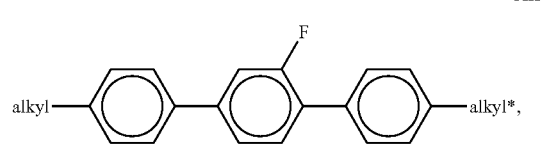

in which alkyl and alkyl* each, independently of one another, denote a straight-chain alkyl radical having 1 to 8 C atoms, and alkenyl and alkenyl* each, independently of one another, denote a straight-chain alkenyl radical having 2 to 8 C atoms.

Particular preference is given to the compounds of the formulae XII-2 and XII-4.

Particularly preferred compounds of the formula XII-2 are the compounds of the formulae XII-2a, XII-2b and XII-2c:

XII-2a
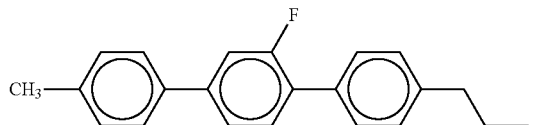

XII-2b
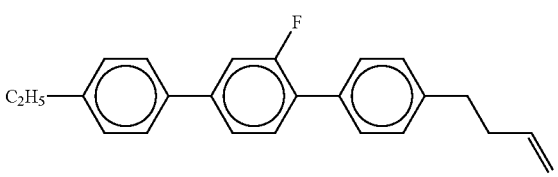

XII-2c
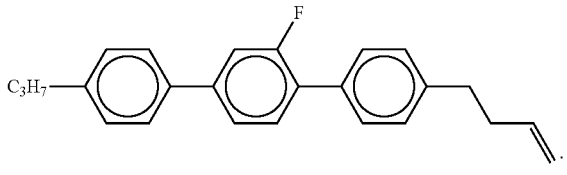

Particularly preferred compounds of the formula XII-4 are the compounds of the formulae XII-4a, XII-4b and XII-4c:

XII-4a
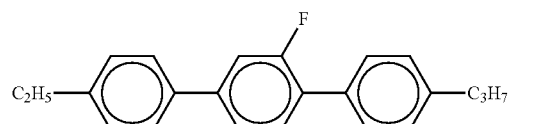

XII-4b
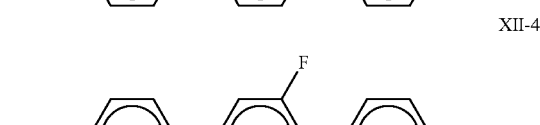

XII-4c
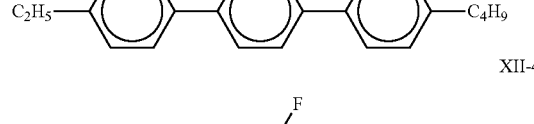

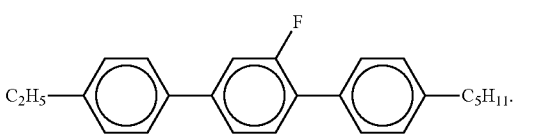

The compound(s) of the formula XII are preferably employed in amounts of 3-40% by weight.

The medium additionally comprises one or more compounds selected from the following formulae:

XIII
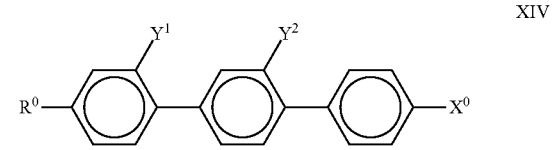

XIV
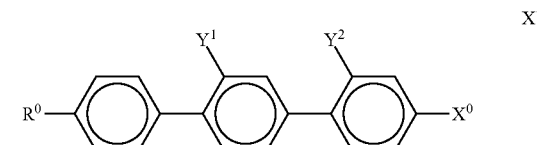

XV

XVI
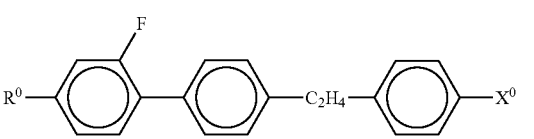

in which $R^0$, $X^0$, $Y^1$ and $Y^2$ have the meanings indicated in claim 6. Preferably, $R^0$ denotes alkyl having 1 to 8 C atoms and $X^0$ denotes F or Cl;

The compounds of the formulae XIII and XIV are preferably selected from the compounds of the formulae

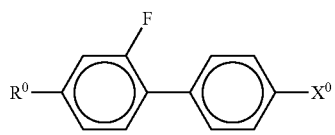
XIIIa

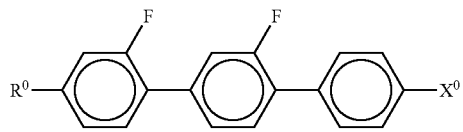
XIVa

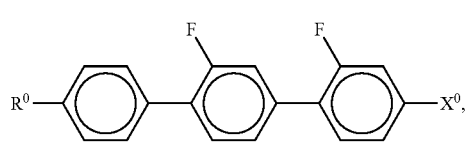
XVa in which $R^0$ and $X^0$ have the meanings indicated in claim 6. $R^0$ preferably denotes alkyl having 1 to 8 C atoms. In the compounds of the formula XIII, $X^0$ preferably denotes F or Cl.

The medium additionally comprises one or more compounds of the formulae D1, D2, D3, D4 and/or D5, D1
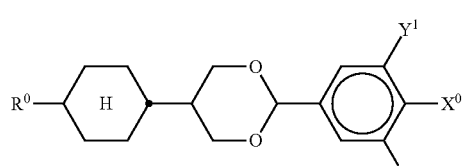

D2
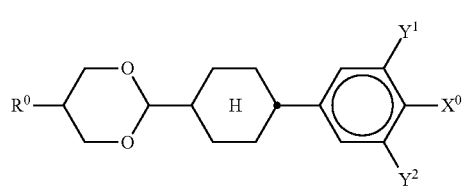

D3
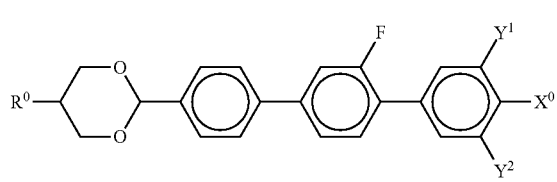

D4
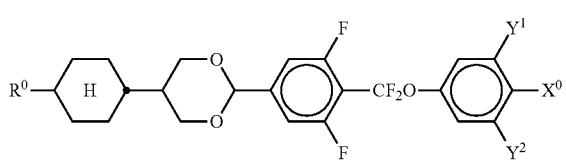

D5
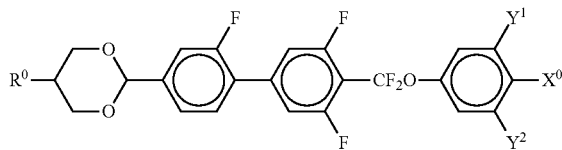

in which $Y^1$, $Y^2$, $R^0$ and $X^0$ have the meanings indicated in claim 6. Preferably, $R^0$ denotes alkyl having 1 to 8 C atoms and $X^0$ denotes F.

Particular preference is given to compounds of the formulae

D1-1
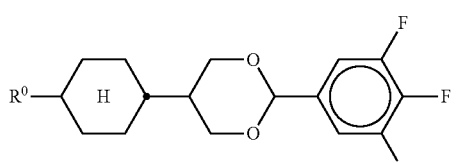

D2-1
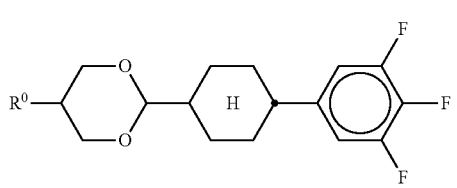

D3-1
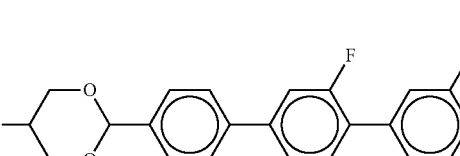

D3-2
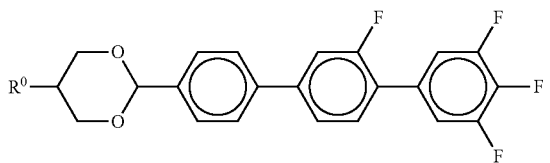

D4-1
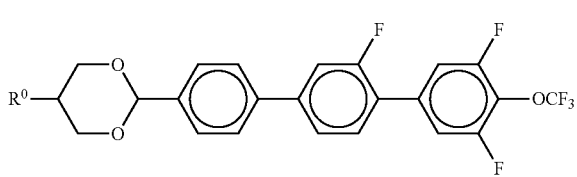

D5-1
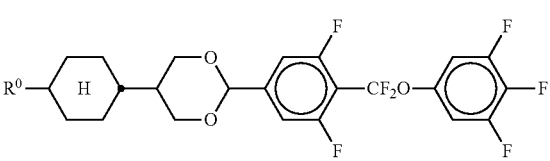

in which $R^0$ has the meanings indicated above and preferably denotes straight-chain alkyl having 1 to 6 C atoms, in particular $C_2H_5$, n-$C_3H_7$ or n-$C_5H_{11}$.

The medium additionally comprises one or more compounds of the following formula XVII:

XVII

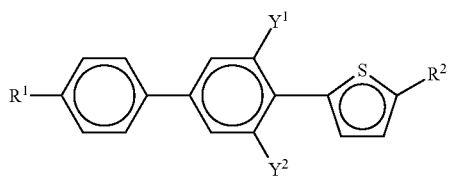

in which $Y^1$, $R^1$ and $R^2$ have the meanings indicated above. $R^1$ and $R^2$ preferably each, independently of one another, denote alkyl or alkenyl having 1 or 2 to 8 C atoms; $Y^1$ and $Y^2$ preferably both denote F. The compound(s) of the formula XVII are preferably employed in amounts of 3-30% by weight, based on the medium.

The medium additionally comprises one or more compounds of the following formula:

XVIII

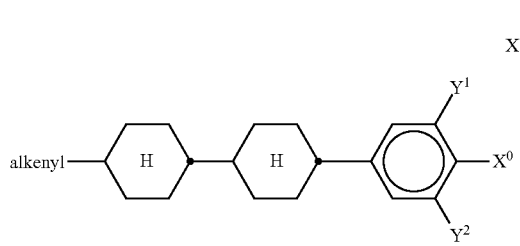

in which $X^0$, $Y^1$ and $Y^2$ have the meanings indicated in claim 6, and "alkenyl" denotes $C_{2-7}$-alkenyl. Particular preference is given to compounds of the following formula:

XVIIIa

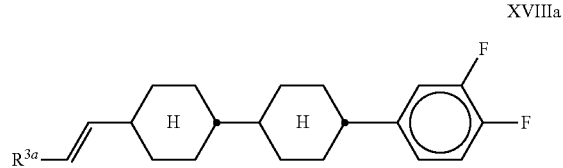

in which $R^{3a}$ has the meaning indicated above and preferably denotes H;

The medium additionally comprises one or more tetracyclic compounds selected from the formulae XIX to XXVIII,

XIX

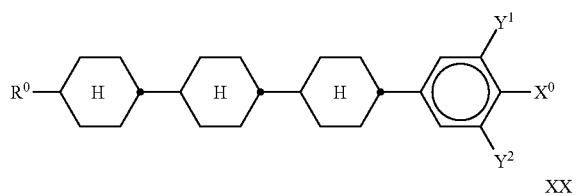

XX

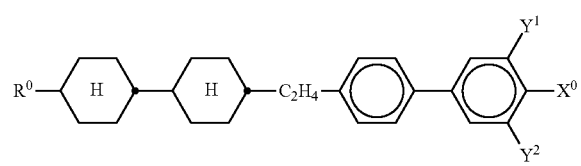

XXI

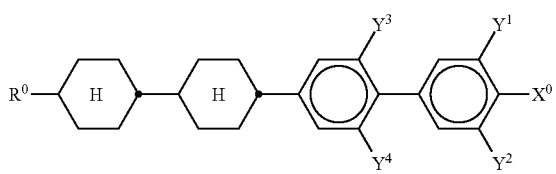

XXII

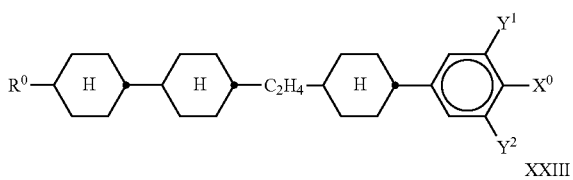

XXIII

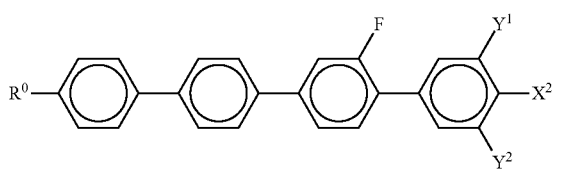

XXIV

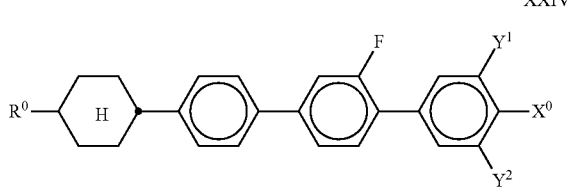

XXV

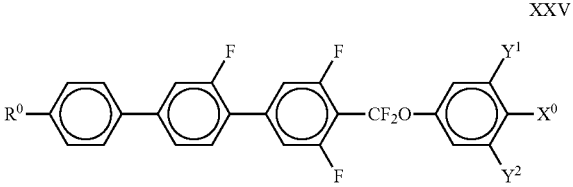

XXVI

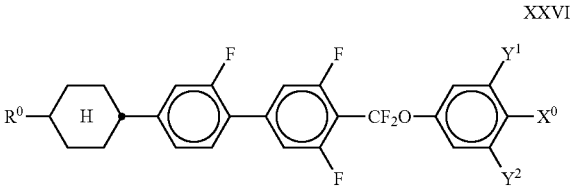

XXVII

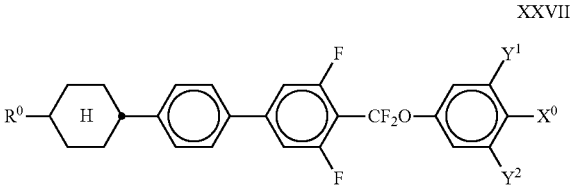

XXVIII

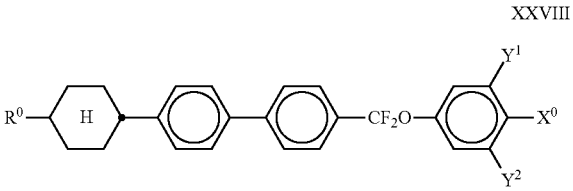

in which $Y^{1-4}$, $R^0$ and $X^0$ each, independently of one another, have one of the meanings indicated above. $X^0$ is preferably F, Cl, $CF_3$, $OCF_3$ or $OCHF_2$. $R^0$ preferably denotes alkyl, alkoxy, oxaalkyl, fluoroalkyl, cycloalkyl or alkenyl, each having up to 8 C atoms.

In the compounds of the formulae XIX to XXVIII, R⁰ preferably denotes straight-chain alkyl. X⁰ is preferably F or OCF₃, furthermore CF₃. Y¹ and Y² preferably denote Y¹=F and Y²=H or Y¹=Y²=F.

Particularly preferred compounds of the formula XIX to XXVIII are the compounds of the formula XXV in which X⁰ preferably denotes F, furthermore OCF₃.

Preferred mixtures comprise at least one compound from the group S-1, S-2, S-3 and S-4,

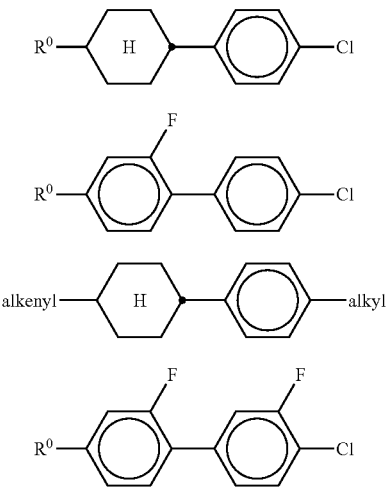

since these compounds help, inter alia, to suppress the smectic phases of the mixtures.

The medium preferably comprises one or more neutral compounds of the general formula N,

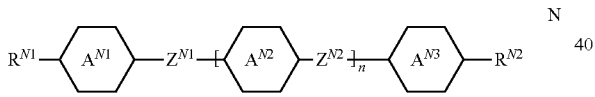

in which $R^{N1}$ and $R^{N2}$ each, independently of one another, denote an alkyl or alkoxy radical having 1 to 15 C atoms, where, in addition, one or more CH₂ groups in these radicals may each be replaced, independently of one another, by

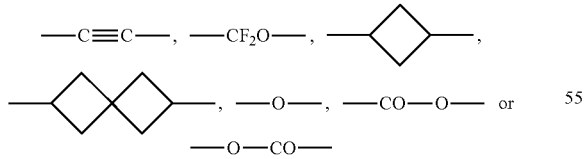

in such a way that O atoms are not linked directly to one another, and in which, in addition, one or more H atoms may be replaced by halogen, rings $A^{N1}$, $A^{N2}$ and $A^{N3}$ each, independently of one another, denote 1,4-phenylene, 2-fluoro-1,4-phenylene, 3-fluoro-1,4-phenylene, trans-1,4-cyclohexylene, in which, in addition, one or two CH₂ groups may be replaced by —O—, or 1,4-cyclohexenylene, $Z^{N1}$ and $Z^{N2}$ each, independently of one another, denote a single bond, —CH₂CH₂—, —COO—, —OCO—, —C≡C—, —CH₂O—, —OCH₂—, —CF₂O—, —OCF₂—, or —CH=CH—, n denotes 0, 1 or 2, where the compound of the formula N is not identical with the compound of the formula I.

Preferred compounds of the formula N are shown below:

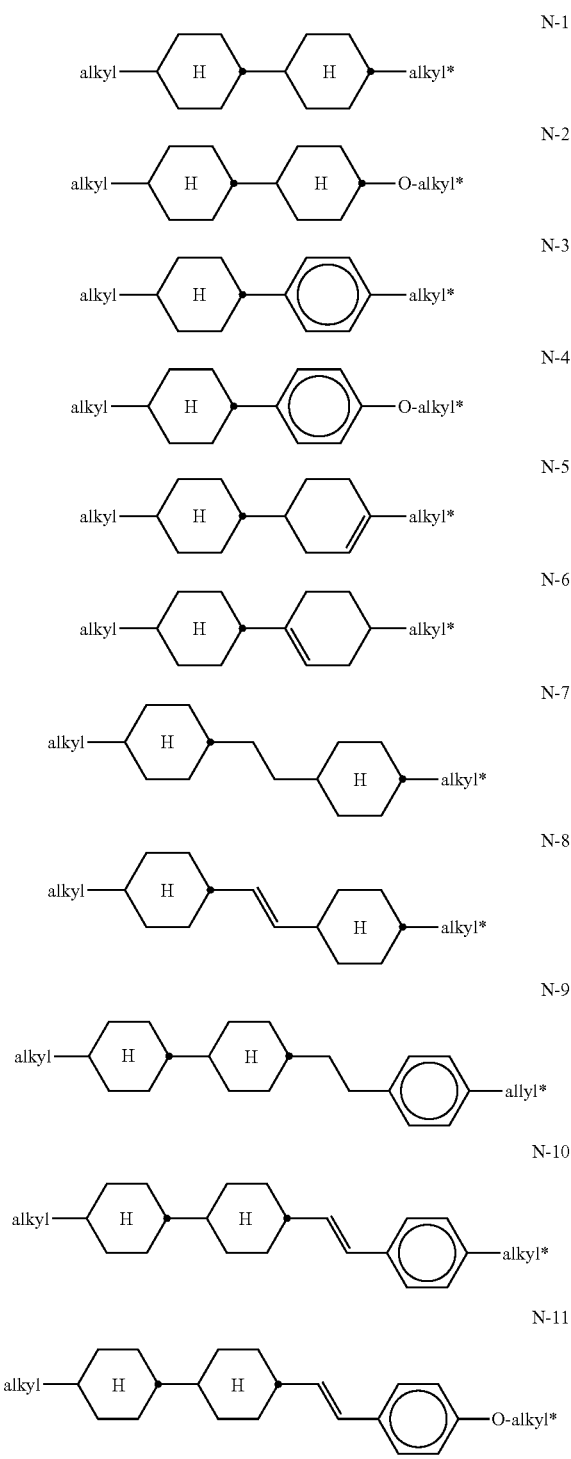

N-12
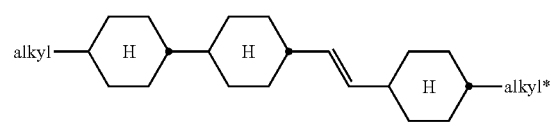
N-13
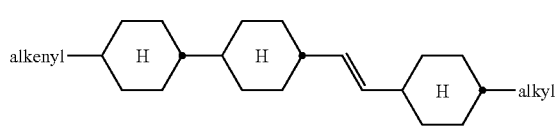
N-14
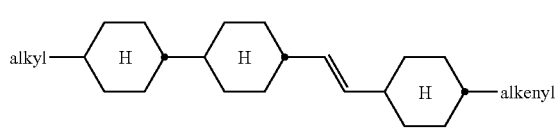
N-15
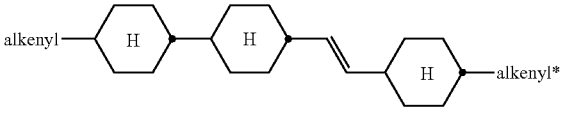
N-16
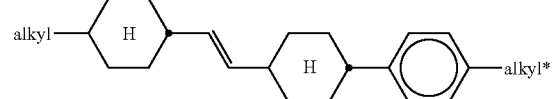
N-17
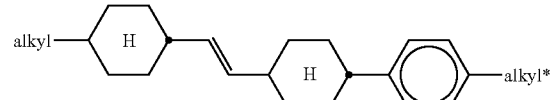
N-18
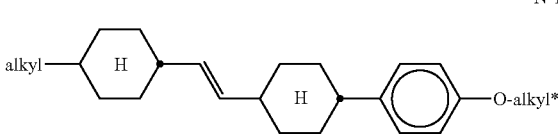
N-19
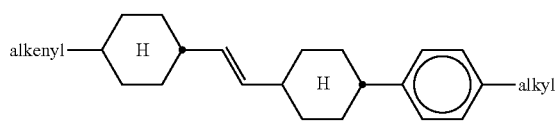
N-20
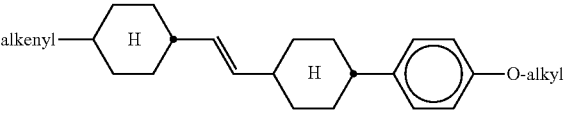
N-21
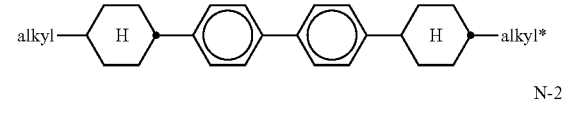
N-22
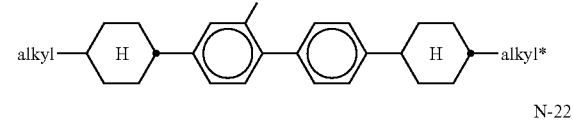
N-23
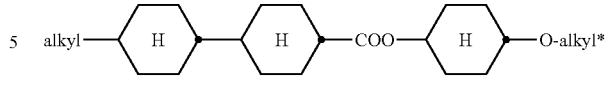
N-24
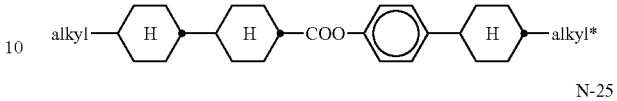
N-25
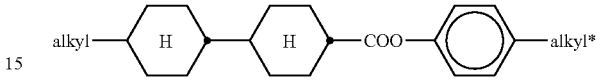
N-26
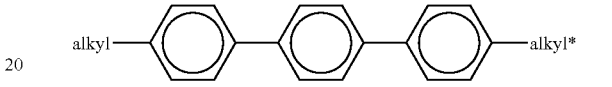
N-27
N-28
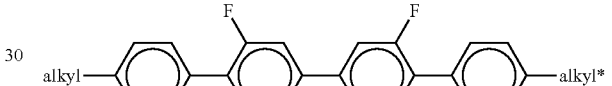
N-29
N-30
N-31
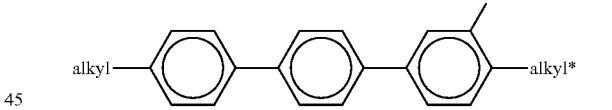
N-32
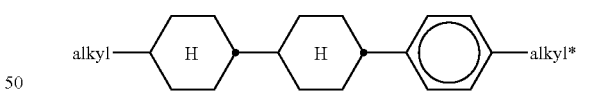
N-33
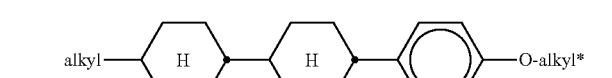
N-34
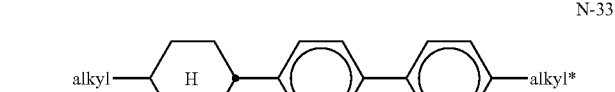

-continued

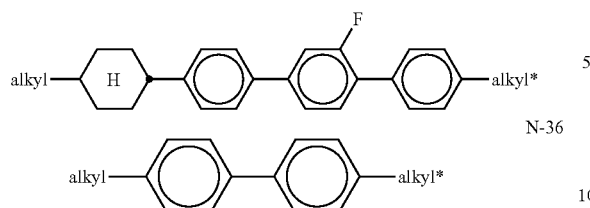

in which alkyl and alkyl* each, independently of one another, denote a straight-chain alkyl radical having 1 to 9 C atoms, preferably 2 to 6 C atoms, and alkenyl and alkenyl* each, independently of one another, denote a straight-chain alkenyl radical having 2-6 C atoms Of the compounds of the formula N, particular preference is given to the compounds of the formulae N-1, N-2, N-3, N-4, N-8, N-9, N-14, N-15, N-17, N-18, N-19, N-20, N-21, N-22, N-23, N-24, N-25, N-31, N-33 and N-36.

The medium additionally comprises one or more compounds of the formulae St-1 to St-3,

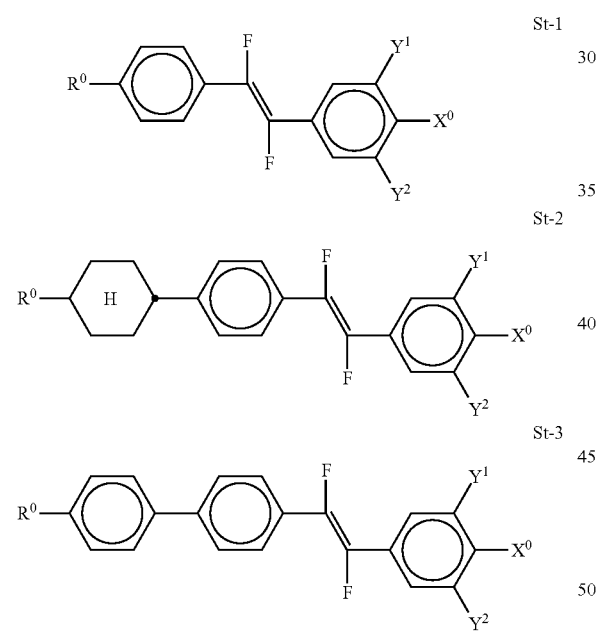

in which $R^0$, $Y^1$, $Y^2$ and $X^0$ have the meanings indicated in claim 6. $R^0$ preferably denotes straight-chain alkyl, preferably having 1-6 C atoms. $X^0$ is preferably F, $CF_3$ or $OCF_3$. $Y^1$ preferably denotes F. $Y^2$ preferably denotes F. Furthermore, preference is given to compounds in which $Y^1$=F and $Y^2$=H. The compounds of the formulae St-1 to St-3 are preferably employed in the mixtures according to the invention in a concentration of 3-30% by weight, in particular 5-25% by weight.

The medium additionally comprises one or more pyrimidine or pyridine compounds of the formulae Py-1 to Py-5,

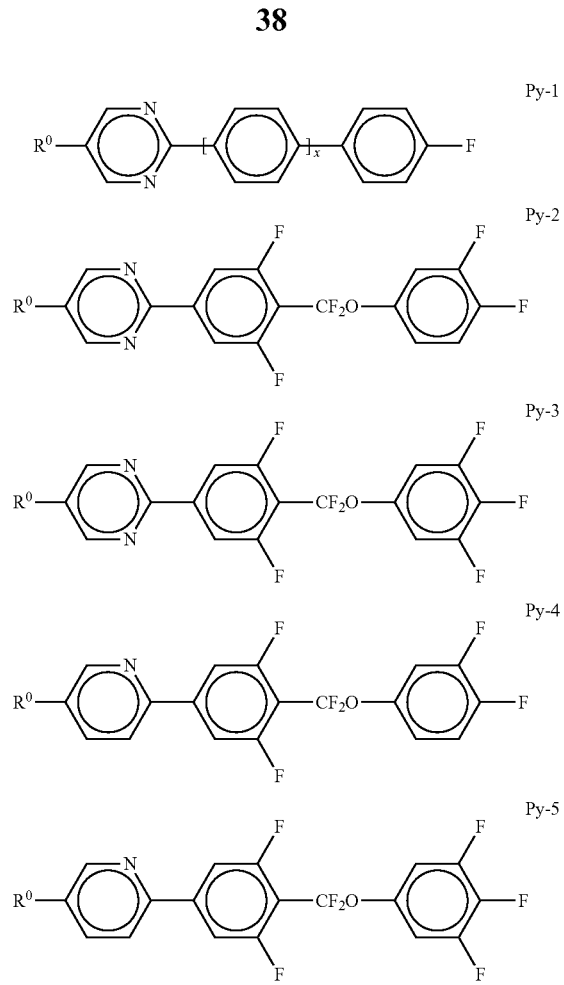

in which $R^0$ is preferably straight-chain alkyl having 2-5 C atoms. x denotes 0 or 1, preferably x=1. Preferred mixtures comprise 3-30% by weight, in particular 5-20% by weight, of this (these) pyri(mi)dine compound(s).

The medium additionally comprises one or more compounds selected from the group of the compounds of the formulae Y-1, Y-2, Y-3 and Y-4,

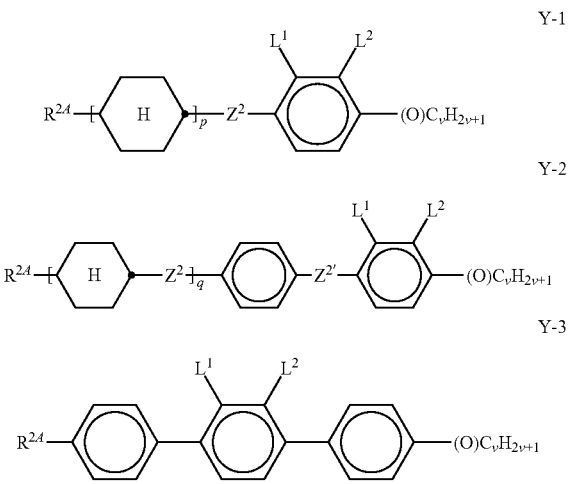

Y-4

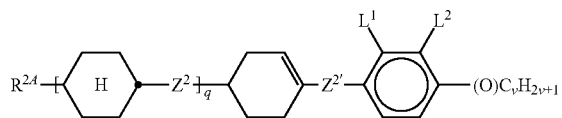

in which

R²⁴ denotes H, an alkyl or alkoxy radical having 1 to 15 C atoms, where, in addition, one or more $CH_2$ groups in these radicals may each be replaced, independently of one another, by

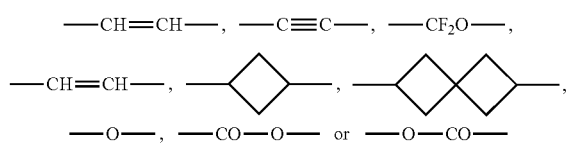

in such a way that O atoms are not linked directly to one another, and in which, in addition, one or more H atoms may be replaced by halogen, $L^{1-4}$ and $L^2$ each, independently of one another, denote F, Cl, $CF_3$ or $CHF_2$, preferably each denote F, $Z^2$ and $Z^{2'}$ each, independently of one another, denote a single bond, $-CH_2CH_2-$, $-CH=CH-$, $-CF_2O-$, $-OCF_2-$, $-CH_2O-$, $-OCH_2-$, $-COO-$, $-OCO-$, $-C_2F_4-$, $-CF=CF-$ or $-CH=CHCH_2O-$, p denotes 0, 1 or 2, q denotes 0 or 1, $(O)C_vH_{2v+1}$ denotes $OC_vH_{2v+1}$ or $C_vH_{2v+1}$, and v denotes 1 to 6.

Particularly preferred compounds of the formulae Y-1 to Y-4 are shown below:

Y-1a
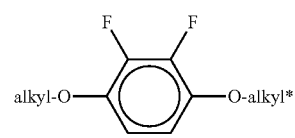

Y-1b
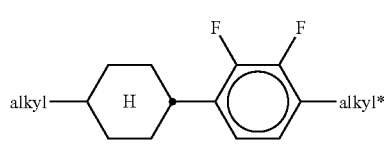

Y-1c
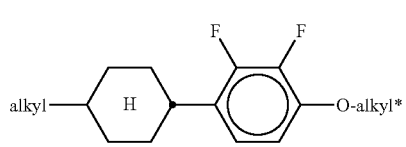

Y-1d
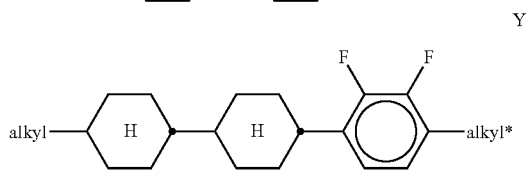

Y-1e
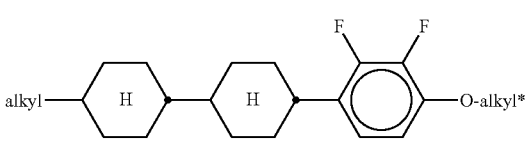

Y-1f
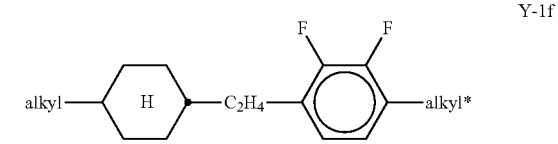

Y-1g
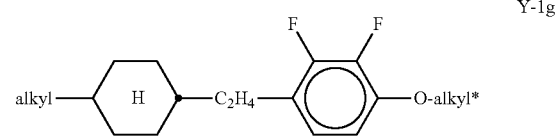

Y-1h
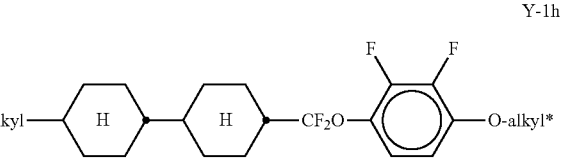

Y-1i
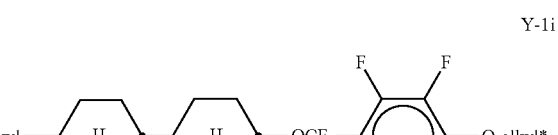

Y-1j
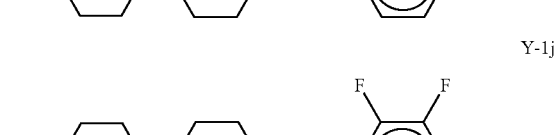

Y-1k
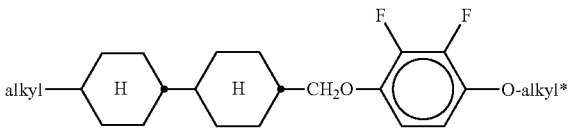

Y-1l
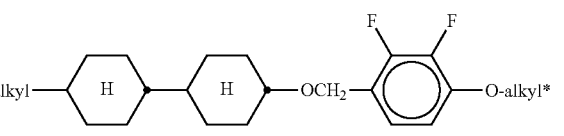

Y-1m
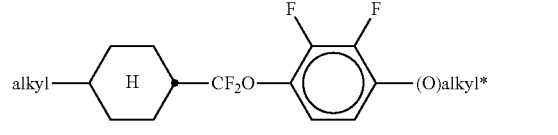

Y-1n
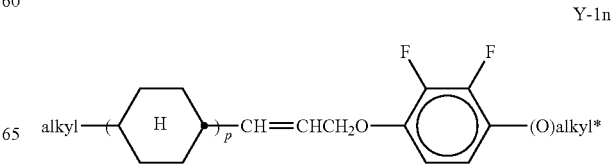

-continued

Y-1o: alkenyl—H—CH₂O—[2,3-F₂-phenyl]—(O)alkyl*

Y-1p: alkyl—H—OCH₂—[2,3-F₂-phenyl]—(O)alkyl*

Y-1q: alkenyl—H—[2,3-F₂-phenyl]—alkyl*

Y-1r: alkenyl—H—[2,3-F₂-phenyl]—O-alkyl*

Y-1s: alkenyl—H—H—[2,3-F₂-phenyl]—alkyl*

Y-1t: alkenyl—H—H—[2,3-F₂-phenyl]—O-alkyl*

Y-1u: alkenyl—H—C₂H₄—[2,3-F₂-phenyl]—alkyl*

Y-1v: alkenyl—H—C₂H₄—[2,3-F₂-phenyl]—O-alkyl*

Y-2a: alkyl—H—[phenyl]—[2,3-F₂-phenyl]—alkyl*

Y-2b: alkyl—H—[phenyl]—[2,3-F₂-phenyl]—O-alkyl*

Y-2c: alkyl—H—CH=CH—[phenyl]—[2,3-F₂-phenyl]—(O)alkyl*

Y-2d: alkyl—H—C₂H₄—[phenyl]—[2,3-F₂-phenyl]—(O)alkyl*

Y-2e: alkyl—H—[phenyl]—OCF₂—[2,3-F₂-phenyl]—(O)alkyl*

Y-2f: alkyl—H—[phenyl]—CF₂O—[2,3-F₂-phenyl]—(O)alkyl*

Y-2g: alkyl—[phenyl]—[2,3-F₂-phenyl]—alkyl*

Y-2h: alkyl—[phenyl]—[2,3-F₂-phenyl]—O-alkyl*

Y-2i: alkenyl—H—[phenyl]—[2,3-F₂-phenyl]—alkyl*

Y-2j: alkenyl—H—[phenyl]—[2,3-F₂-phenyl]—O-alkyl*

Y-3a: alkyl—[phenyl]—[2,3-F₂-phenyl]—[phenyl]—alkyl* in which
alkyl and alkyl* each, independently of one another, denote a straight-chain alkyl radical having 1-6 C atoms and
alkenyl and alkenyl* each, independently of one another, denote a straight-chain alkenyl radical having 1-6 C atoms.
Of the compounds shown, particular preference is given to the compounds of the formulae Y-1a, Y-1c, Y-1e, Y-1g, Y-1j, Y-1r, Y-1t, Y-2b, Y-2h, Y-2j and Y-3a.
The proportion of the compounds of the formulae Y-1 to Y-3 in the mixtures according to the invention is preferably 0-30% by weight.
The medium additionally comprises one or more compounds selected from the group of the compounds of the formulae BC, CR, PH-1, PH-2, BF and BS,

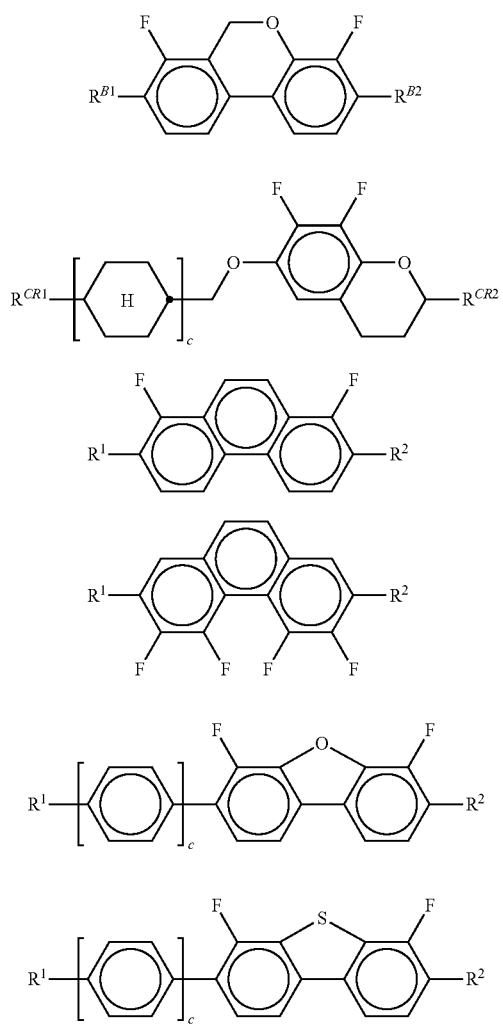

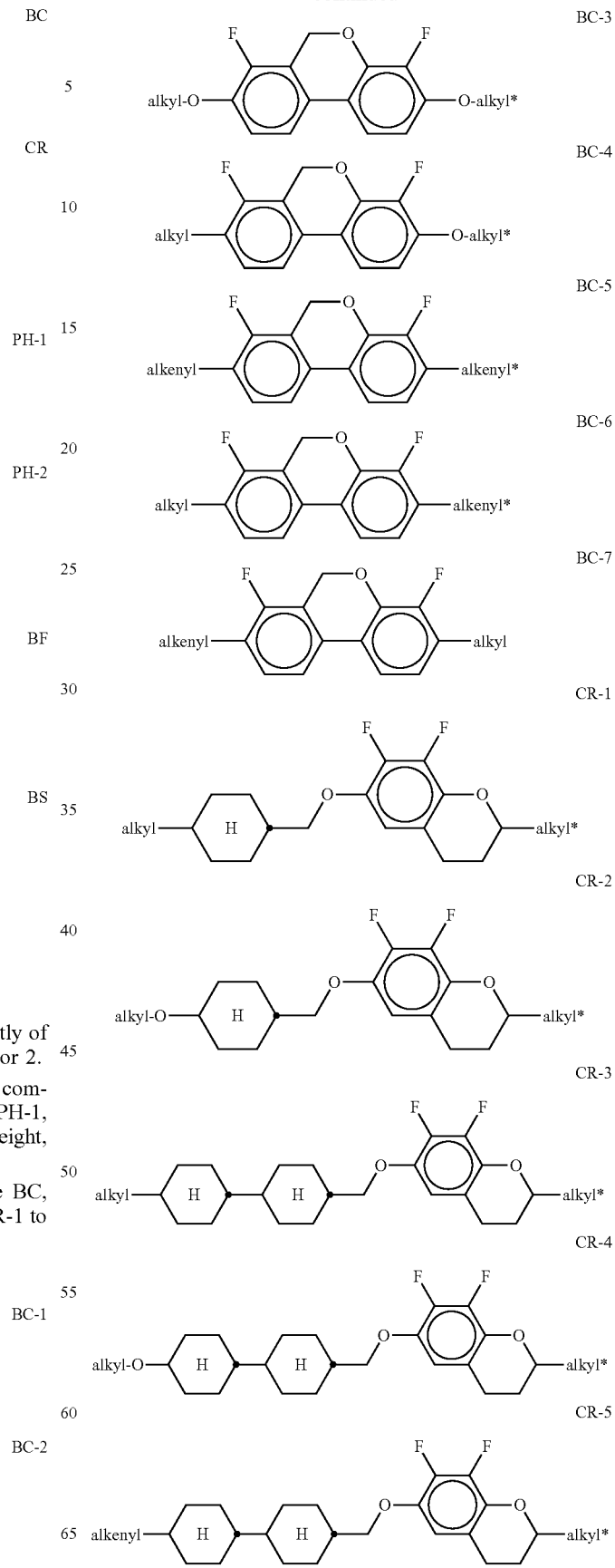

in which

R$^{B1}$, R$^{B2}$, R$^{CR1}$, R$^{CR2}$, R$^1$ and R$^2$ each, independently of one another, have the meaning of R$^{2A}$. c is 0, 1 or 2.

The mixtures according to the invention preferably comprise the compounds of the formulae BC, CR, PH-1, PH-2 and/or BF in amounts of 0.5 to 20% by weight, in particular in amounts of 1 to 15% by weight.

Particularly preferred compounds of the formulae BC, CR, BF and BS are the compounds BC-1 to BC-7, CR-1 to CR-5, BF-1 to BF-3 and BS-1 to BS-3, -continued

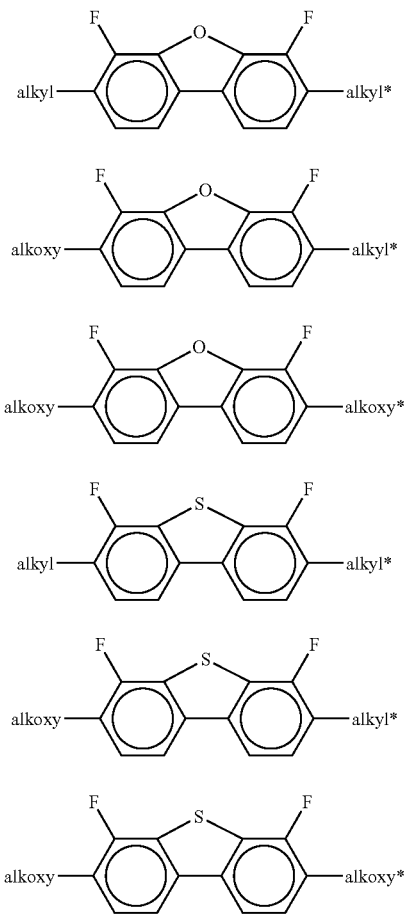

BF-1

BF-2

BF-3

BS-1

BS-2

BS-3 in which alkyl and alkyl* each, independently of one another, denote a straight-chain alkyl radical having 1-6 C atoms, alkenyl and alkenyl* each, independently of one another, denote a straight-chain alkenyl radical having 2-6 C atoms, and alkoxy and alkoxy* each, independently of one another, denote a straight-chain alkoxy radical having 2-6 C atoms.

Very particular preference is given to mixtures comprising one, two or three compounds of the formulae BF-3 and/or BS-3.

In the formulae given above and below,

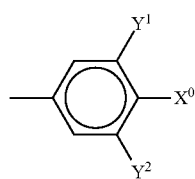

preferably denotes

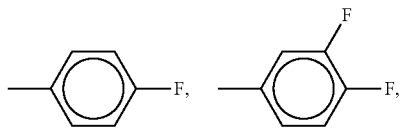

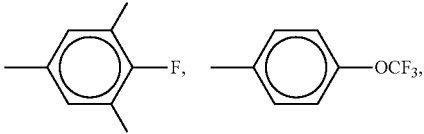

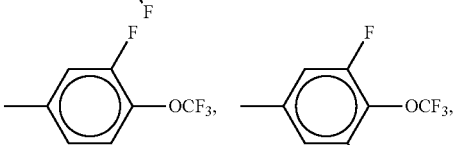

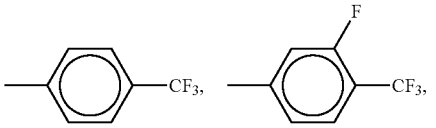

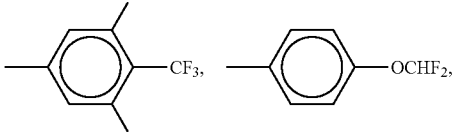

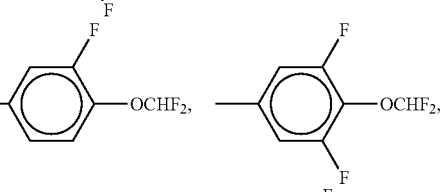

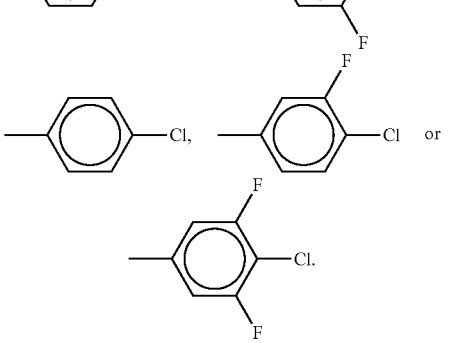

$R^0$ is preferably straight-chain alkyl or alkenyl having 2 to 7 C atoms;

$X^1$ in formula I is preferably $CF_3$, furthermore $OCF_3$;

The medium preferably comprises one, two or three compounds of the formula I;

The medium comprises CLP-n-T and/or CLP-n-OT, where n denotes 2, 3, 4 or 5,

The medium comprises CLP-n-T, where n denotes 2, 3, 4 or 5, and/or CLP-V-n, where n denotes 1, 2 or 3, preferably 1;

The medium comprises CLP-V-T, CLP-nV-T or CLP-Vn-T, where n denotes 1 or 2;

The medium comprises CLP-V-OT, CLP-nV-OT or CLP-Vn-OT, where n denotes 1 or 2;

The medium comprises CLP-nV-m or CLP-Vn-m, where m denotes 1 or 2 and n denotes 1 or 2;

The medium comprises CLP-nV2-m, CLP-nV2-T or CLP-nV2-OT, where m denotes 1 or 2 and n denotes 1 or 2;

The medium preferably comprises one or more compounds selected from the group of the compounds of the formulae I, II, III, V, VI-1, VI-2, XII, XIII, XIV, XVII, XXIII, XXV;

The medium preferably comprises one or more compounds of the formula VI-1;

The medium preferably comprises one or more compounds of the formula VI-2;

The medium preferably comprises 1-30% by weight, preferably 2-20% by weight, particularly preferably 2-15% by weight, of compounds of the formula I;

The proportion of compounds of the formulae II-XXVII in the mixture as a whole is preferably 20 to 99% by weight;

The medium preferably comprises 25-80% by weight, particularly preferably 30-70% by weight, of compounds of the formulae II and/or III;

The medium preferably comprises 0-70% by weight, particularly preferably 20-60% by weight, of compounds of the formula IIa-1;

The medium preferably comprises 0-25% by weight, particularly preferably 5-25% by weight, of compounds of the formula IIa-2;

The medium preferably comprises 0-30% by weight, particularly preferably 5-25% by weight, of compounds of the formula IIa-3;

The medium preferably comprises 0-25% by weight, particularly preferably 5-25% by weight, of compounds of the formula IIa-5;

The medium preferably comprises 5-40% by weight, particularly preferably 10-30% by weight, of compounds of the formula V;

The medium preferably comprises 3-30% by weight, particularly preferably 6-25% by weight, of compounds of the formula VI-1;

The medium preferably comprises 2-30% by weight, particularly preferably 4-25% by weight, of compounds of the formula VI-2;

The medium preferably comprises 5-40% by weight, particularly preferably 10-30% by weight, of compounds of the formula XII;

The medium preferably comprises 1-25% by weight, particularly preferably 2-15% by weight, of compounds of the formula XIII;

The medium preferably comprises 5-45% by weight, particularly preferably 10-35% by weight, of compounds of the formula XIV;

The medium preferably comprises 1-20% by weight, particularly preferably 2-15% by weight, of compounds of the formula XVI;

The medium preferably comprises 5-30% by weight, particularly preferably 8-22% by weight, of compounds of the formula Va in which $X^0$=OCH=CF$_2$;

The medium preferably comprises the compound of the formula CC-3-2V and the compound of the formula CC-3-V and/or CC-3-V1;

The medium preferably comprises the compound of the formula CC-3-2V and the compound of the formula APUQU-2-F and/or APUQU-3-F;

The medium preferably comprises the compound CC-3-2V and the compound of the formula CC-3-2V1;

The medium preferably comprises the compound CC-3-2V and the compound of the formula PP-1-2V1;

The medium preferably comprises the compound CC-3-2V and at least one compound of the formula PGUQU-n-F, where n=3, 4 or 5;

The medium preferably comprises the compound CC-3-2V and at least one compound of the formula DPGU-n-F, where n=2, 3, 4, or 5.

It has been found that even a relatively small proportion of compounds of the formula I mixed with conventional liquid-crystal materials, but in particular with one or more compounds of the formulae II to XXVIII, results in a clear reduction in the switching-time parameter $\gamma_1/K_1$. The liquid-crystalline medium according to the invention is furthermore distinguished by its relatively high values for the birefringence and by its light stability. At the same time, the mixtures exhibit very good values for the VHR after exposure to UV.

The expression "alkyl" or "alkyl*" in this application encompasses straight-chain and branched alkyl groups having 1-7 carbon atoms, in particular the straight-chain groups methyl, ethyl, propyl, butyl, pentyl, hexyl and heptyl. Groups having 1-6 carbon atoms are generally preferred.

The expression "O-alkyl" in this application encompasses straight-chain and branched alkoxy groups.

The expression "alkenyl" or "alkenyl*" in this application encompasses straight-chain and branched alkenyl groups having 2-7 carbon atoms, in particular the straight-chain groups. Preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples of particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The expression "fluoroalkyl" in this application encompasses straight-chain groups having at least one fluorine atom, preferably a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The expression "oxaalkyl" or "alkoxy" in this application encompasses straight-chain radicals of the formula $C_nH_{2n+1}$—O—$(CH_2)_m$, in which n and m each, independently of one another, denote 1 to 6. m may also denote 0. Preferably, n=1 and m=1-6 or m=0 and n=1-3.

Through a suitable choice of the meanings of $R^1$ and $R^2$ in formula I, the addressing times, the threshold voltage, the steepness of the transmission characteristic lines, etc., can be modified in the desired manner. For example, 1E-alkenyl radicals, 3E-alkenyl radicals, 2E-alkenyloxy radicals and the like generally result in shorter addressing times, improved nematic tendencies and a higher ratio between the elastic constants $k_{33}$ (bend) and $k_{11}$ (splay) compared with alkyl and alkoxy radicals. 4-Alkenyl radicals, 3-alkenyl radicals and the like generally give lower threshold voltages and lower values of $k_{33}/k_{11}$ compared with alkyl and alkoxy radicals. The mixtures according to the invention are distinguished, in particular, by high $K_1$ values and thus have significantly faster response times than the mixtures from the prior art.

The optimum mixing ratio of the compounds of the above-mentioned formulae depends substantially on the desired properties, on the choice of the components of the above-mentioned formulae and on the choice of any further components that may be present.

Suitable mixing ratios within the range indicated above can easily be determined from case to case.

The total amount of compounds of the above-mentioned formulae in the mixtures according to the invention is not crucial. The mixtures can therefore comprise one or more further components for the purposes of optimization of various properties. However, the observed effect on the desired improvement in the properties of the mixture is generally greater, the higher the total concentration of compounds of the above-mentioned formulae.

In a particularly preferred embodiment, the media according to the invention comprise compounds of the formulae IV to VIII in which $X^0$ denotes F, $OCF_3$, $OCHF_2$, $OCH=CF_2$, $OCF=CF_2$ or $OCF_2-CF_2H$. A favourable synergistic action with the compounds of the formula I results in particularly advantageous properties. In particular, mixtures comprising compounds of the formulae I and VI, or I and XI, or I and VI and XI are distinguished by their low threshold voltages.

The individual compounds of the above-mentioned formulae and the sub-formulae thereof which can be used in the media according to the invention are either known or can be prepared analogously to the known compounds.

The invention also relates to electro-optical displays, such as, for example, TN, STN, TFT, OCB, IPS, PS-IPS, FFS, PS-FFS, positive VA or MLC displays, having two plane-parallel outer plates, which, together with a frame, form a cell, integrated non-linear elements for switching individual pixels on the outer plates, and a nematic liquid-crystal mixture having positive dielectric anisotropy and high specific resistance located in the cell, which contain media of this type, and to the use of these media for electro-optical purposes.

Furthermore, the mixtures according to the invention are also suitable for positive VA applications, also referred to as HT-VA applications. These are taken to mean electro-optical displays having an in-plane drive electrode configuration and homeotropic arrangement of the liquid-crystal medium having positive dielectric anisotropy. The mixtures according to the invention are particularly preferably suitable for TN-TFT display applications having a low operating voltage, i.e. particularly preferably for notebook applications.

The liquid-crystal mixtures according to the invention enable a significant broadening of the available parameter latitude. The achievable combinations of clearing point, rotational viscosity and elastic constants, thermal and UV stability and high optical anisotropy are far superior to previous materials from the prior art.

The mixtures according to the invention are particularly suitable for mobile applications and high-$\Delta n$ TFT applications, such as, for example, PDAs, notebooks, LCD TVs and monitors.

The liquid-crystal mixtures according to the invention, while retaining the nematic phase down to $-20°$ C. and preferably down to $-30°$ C., particularly preferably down to $-40°$ C., and the clearing point $\geq 70°$ C., preferably $74°$ C., at the same time allow rotational viscosities $\gamma_1$ of $\leq 120$ mPa·s, particularly preferably 60 mPa·s, to be achieved, enabling excellent MLC displays having fast response times to be achieved.

The dielectric anisotropy $\Delta \varepsilon$ of the liquid-crystal mixtures according to the invention is preferably $\geq +2$, particularly preferably $\geq +4$.

The birefringence $\Delta n$ of the liquid-crystal mixtures according to the invention is preferably $\geq 0.08$, in particular $\geq 0.10$.

The nematic phase range of the liquid-crystal mixtures according to the invention preferably has a width of at least $90°$, in particular at least $100°$. This range preferably extends at least from $-20°$ C. to $+70°$ C.

If the mixtures according to the invention are used in IPS or FFS applications, the mixtures preferably have a dielectric anisotropy value of 2-30 and an optical anisotropy value of 0.07-0.13.

It goes without saying that, through a suitable choice of the components of the mixtures according to the invention, it is also possible for higher clearing points (for example above $100°$ C.) to be achieved at higher threshold voltages or lower clearing points to be achieved at lower threshold voltages with retention of the other advantageous properties. At viscosities correspondingly increased only slightly, it is likewise possible to obtain mixtures having higher $\Delta \varepsilon$ and thus low thresholds. The MLC displays according to the invention preferably operate at the first Gooch and Tarry transmission minimum [C. H. Gooch and H. A. Tarry, Electron. Lett. 10, 2-4, 1974; C. H. Gooch and H. A. Tarry, Appl. Phys., Vol. 8, 1575-1584, 1975], where, besides particularly favourable electro-optical properties, such as, for example, high steepness of the characteristic line and low angle dependence of the contrast (German patent 30 22 818), lower dielectric anisotropy is sufficient at the same threshold voltage as in an analogous display at the second minimum. This enables significantly higher specific resistance values to be achieved using the mixtures according to the invention at the first minimum than in the case of mixtures comprising cyano compounds. Through a suitable choice of the individual components and their proportions by weight, the person skilled in the art is able to set the birefringence necessary for a pre-specified layer thickness of the MLC display using simple routine methods.

The construction of the MLC display according to the invention from polarizers, electrode base plates and surface-treated electrodes corresponds to the usual design for displays of this type. The term usual design is broadly drawn here and also encompasses all derivatives and modifications of the MLC display, in particular including matrix display elements based on poly-Si TFTs or MIM.

A significant difference between the displays according to the invention and the hitherto conventional displays based on the twisted nematic cell consists, however, in the choice of the liquid-crystal parameters of the liquid-crystal layer.

The liquid-crystal mixtures which can be used in accordance with the invention are prepared in a manner conventional per se, for example by mixing one or more compounds of the formula I with one or more compounds of the formulae II-XXVII or with further liquid-crystalline compounds and/or additives. In general, the desired amount of the components used in the smaller amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing.

The dielectrics may also comprise further additives known to the person skilled in the art and described in the literature, such as, for example, UV stabilizers, such as Tinuvin® from Ciba Chemicals, in particular Tinuvin® 770, antioxidants, free-radical scavengers, nanoparticles, etc. For example, 0-15% of pleochroic dyes or chiral dopants can be added. Suitable stabilizers and dopants are mentioned below in Tables C and D.

In order to increase the anchoring force, polymerizable compounds, so-called "reactive mesogens", may also additionally be added to the mixtures according to the invention. Preferred polymerizable compounds are listed in Table E.

The following examples are intended to explain the invention without limiting it. Above and below, percentage data denote percent by weight; all temperatures are indicated in degrees Celsius.

Throughout the patent application, 1,4-cyclohexylene rings and 1,4-phenylene rings are represented as follows:

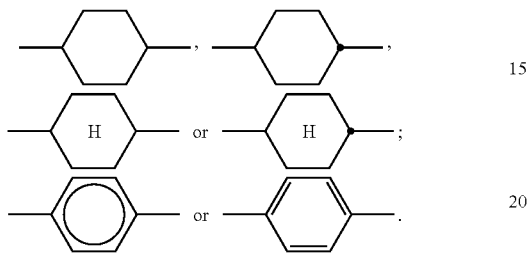

The cyclohexylene rings are trans-1,4-cyclohexylene rings.

Throughout the patent application and in the working examples, the structures of the liquid-crystal compounds are indicated by means of acronyms. Unless indicated otherwise, the transformation into chemical formulae takes place in accordance with Tables I-3. All radicals $C_nH_{2n+1}$, $C_mH_{2m+1}$ and $C_{m'}H_{2m'+1}$ or $C_nH_{2n}$ and $C_mH_{2m}$ are straight-chain alkyl radicals or alkenyl radicals respectively, in each case having n, m, m' or z C atoms; n, m, m' and z each, independently of one another, denote 1, 2, 3, 4, 5, 6, 7, 8, 9, 10, 11 or 12, preferably 1, 2, 3, 4, 5 or 6. In Table 1 the ring elements of the respective compound are coded, in Table 2 the bridging members are listed and in Table 3 the meanings of the symbols for the left-hand and right-hand side chains of the compounds are indicated.

TABLE 1

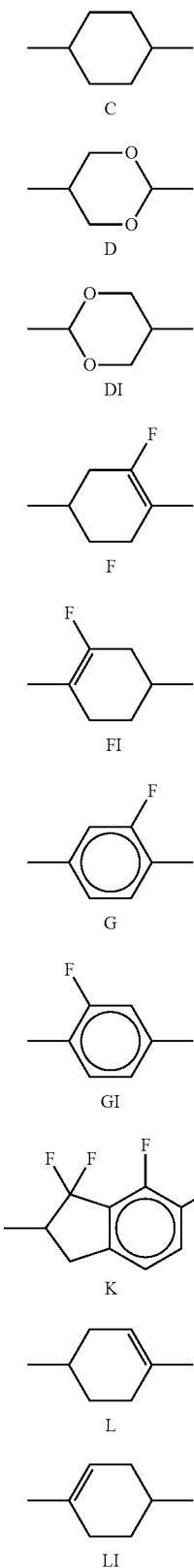

TABLE 1-continued

| Ring elements |
|---|
| 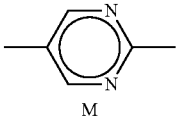 M |
| 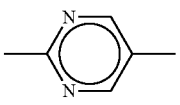 MI |
| 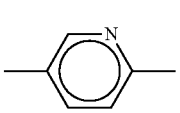 N |
| 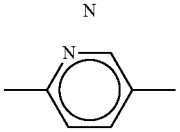 NI |
| 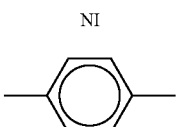 P |
| 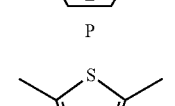 S |
| 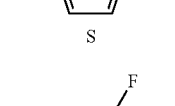 U |

TABLE 1-continued

| Ring elements |
|---|
| 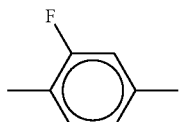 UI |
| 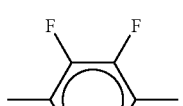 Y |
| 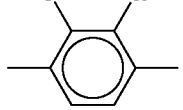 Y(F, Cl) |
| 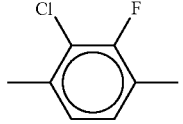 Y(Cl, F) |

TABLE 2

| Bridging members | | | |
|---|---|---|---|
| E | —CH$_2$CH$_2$— | | |
| V | —CH=CH— | | |
| T | —CC— | | |
| W | —CF$_2$CF$_2$— | | |
| Z | —COO— | ZI | —OCO— |
| O | —CH$_2$O— | OI | —OCH$_2$— |
| Q | —CF$_2$O— | QI | —OCF$_2$— |

TABLE 3

| Side chains | | | |
|---|---|---|---|
| Left-hand side chain | | Right-hand side chain | |
| n- | C$_n$H$_{2n+1}$— | -n | —C$_n$H$_{2n+1}$ |
| nO— | C$_n$H$_{2n+1}$—O— | —On | —O—C$_n$H$_{2n+1}$ |
| V— | CH$_2$=CH— | —V | —CH=CH$_2$ |
| nV— | C$_n$H$_{2n+1}$—CH=CH— | -nV | —C$_n$H$_{2n}$—CH=CH$_2$ |
| Vn- | CH$_2$=CH—C$_n$H$_{2n}$— | —Vn | —CH=CH—C$_n$H$_{2n+1}$ |
| nVm- | C$_n$H$_{2n+1}$—CH=CH—C$_m$H$_{2m}$— | -nVm | —C$_n$H$_{2n}$—CH=CH—C$_m$H$_{2m+1}$ |
| N— | N≡C— | —N | —C≡N |
| F— | F— | —F | —F |
| Cl— | Cl— | —Cl | —Cl |
| M— | CFH$_2$— | —M | —CFH$_2$ |
| D— | CF$_2$H— | —D | —CF$_2$H |
| T— | CF$_3$— | —T | —CF$_3$ |
| MO— | CFH$_2$O— | —OM | —OCFH$_2$ |
| DO— | CF$_2$HO— | —OD | —OCF$_2$H |
| TO— | CF$_3$O— | —OT | —OCF$_3$ |
| T— | CF$_3$— | —T | —CF$_3$ |
| A— | H—C≡C— | —A | —C≡C—H |
| FXO— | CF$_2$=CHO— | —OXF | —OCH=CF$_2$ |

TABLE 3-continued

| Side chains | | | |
|---|---|---|---|
| Left-hand side chain | | Right-hand side chain | |
| C3— | △ | —C3 | △ |
| C4— | ◇ | —C4 | ◇ |
| C5— | ⬠ | —C5 | ⬠ |

Preferred mixture components are shown in Tables A and B.

TABLE A

PYP

PYRP

BCH

CBC

CCH

CCP

TABLE A-continued

CPTP

CEPTP

ECCP

CECP

EPCH

TABLE A-continued
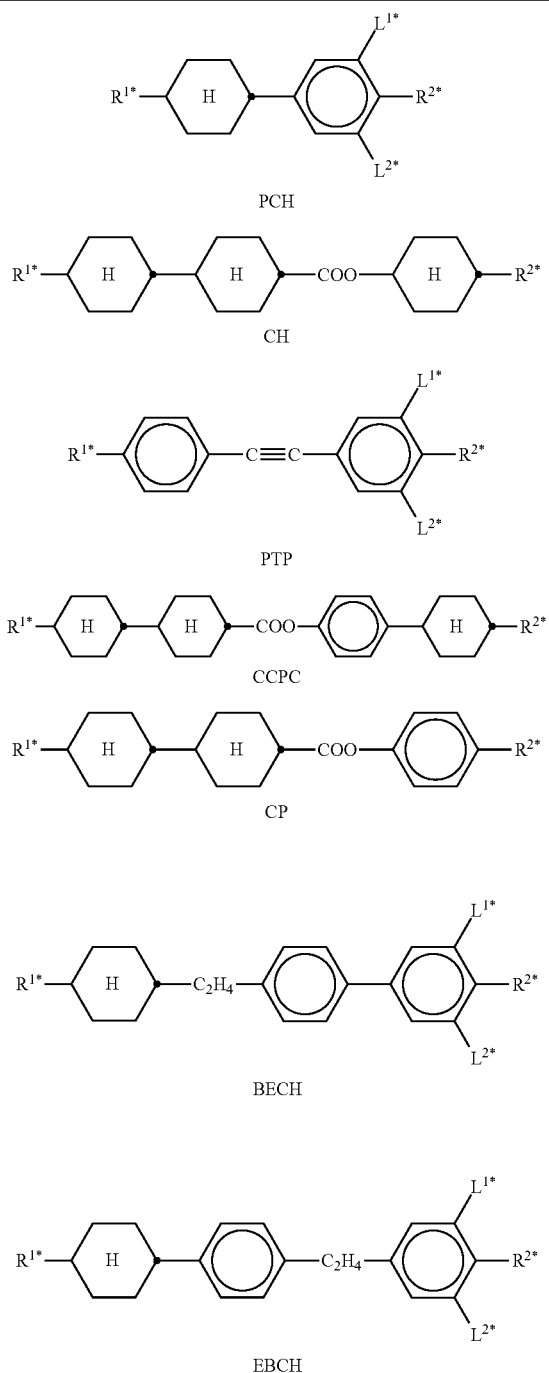
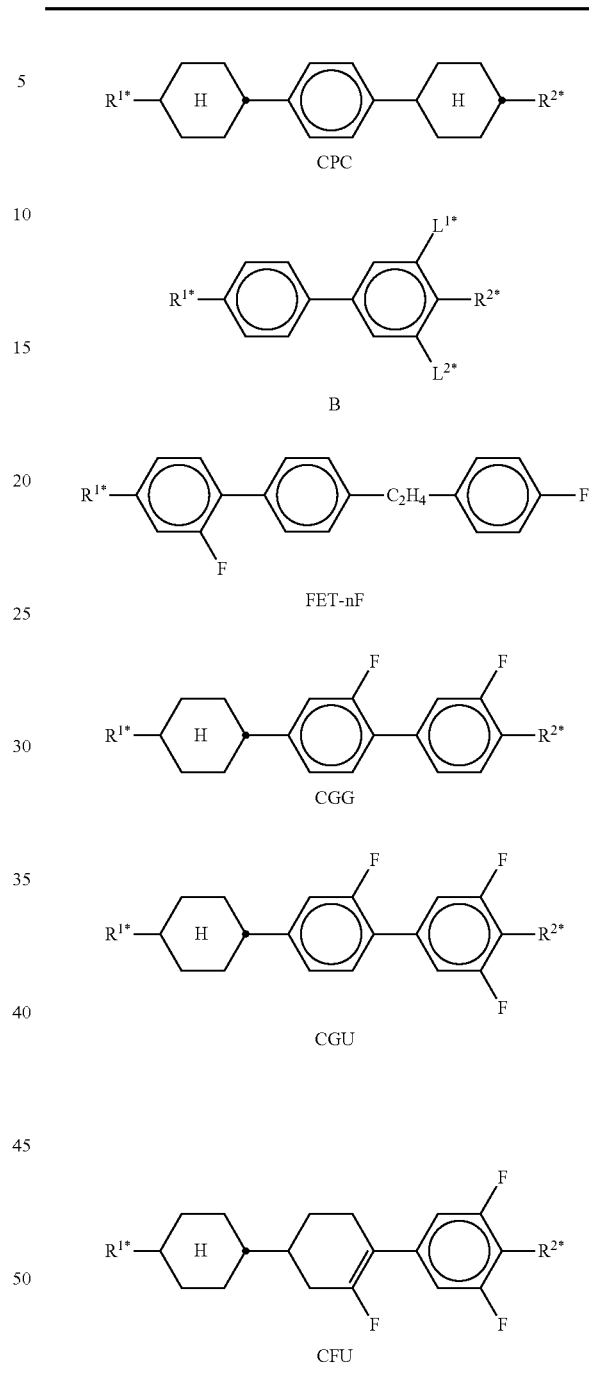
TABLE B
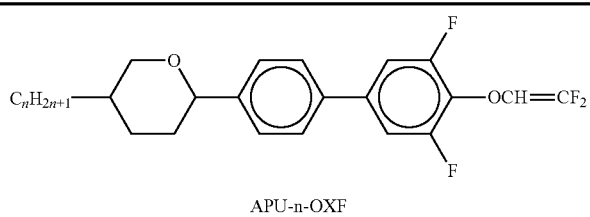

TABLE B-continued
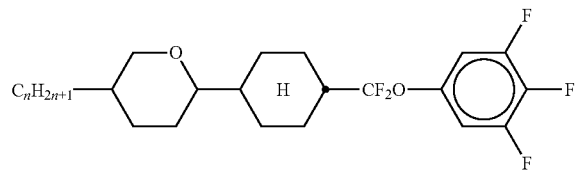
ACQU-n-F
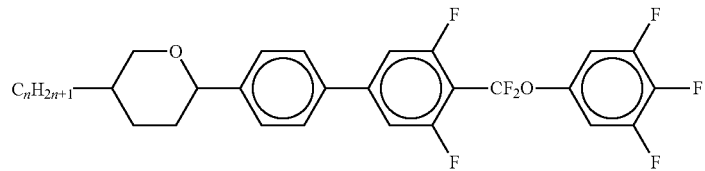
APUQU-n-F
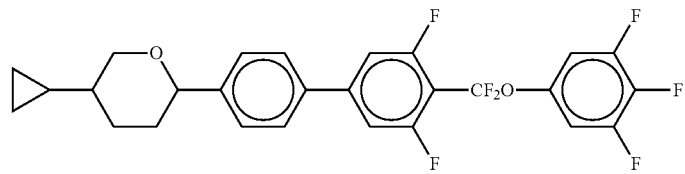
APUQU-C3-F
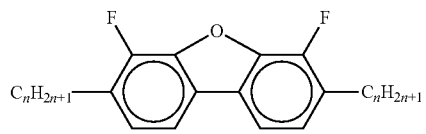
B-n-m
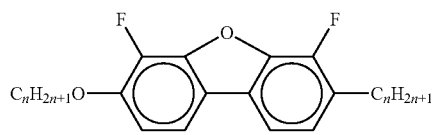
B-nO-m
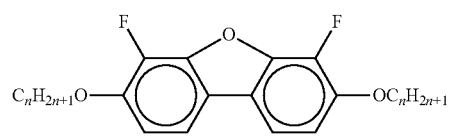
B-nO-Om
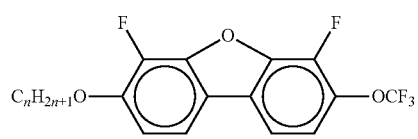
B-nO-OT
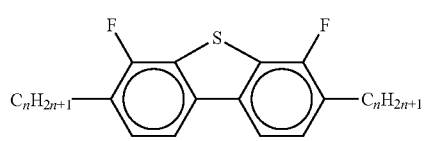
B(S)-n-m TABLE B-continued
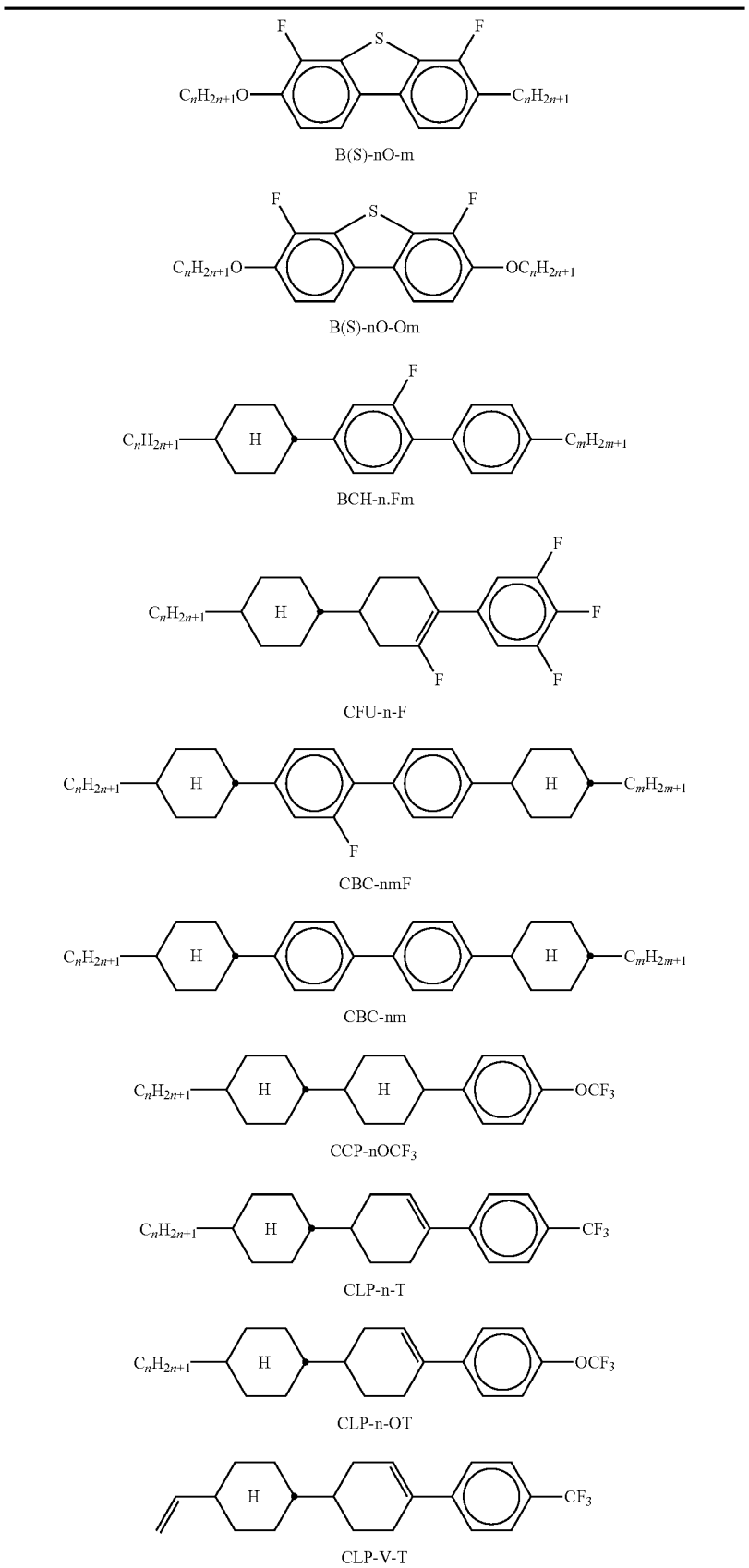

TABLE B-continued
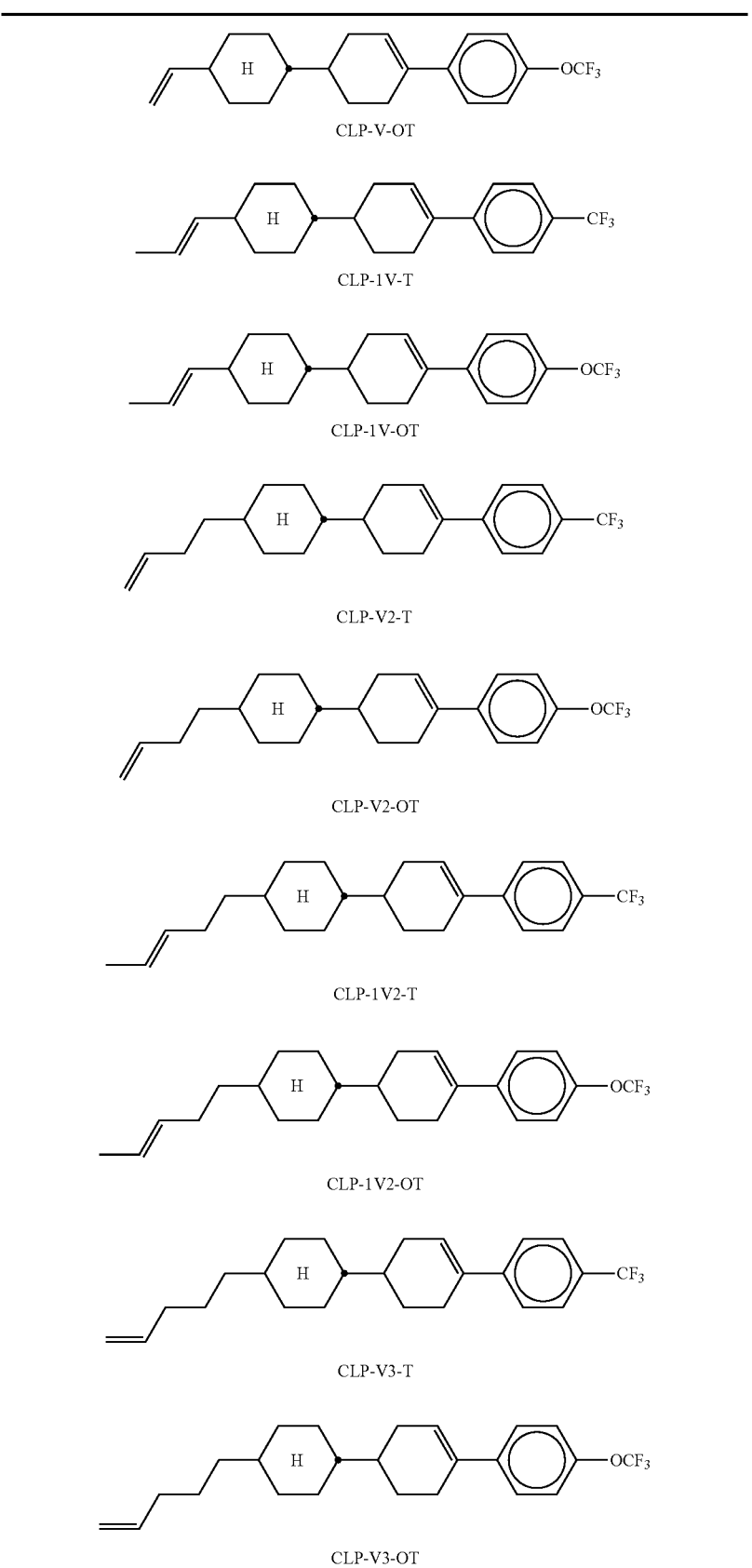

TABLE B-continued
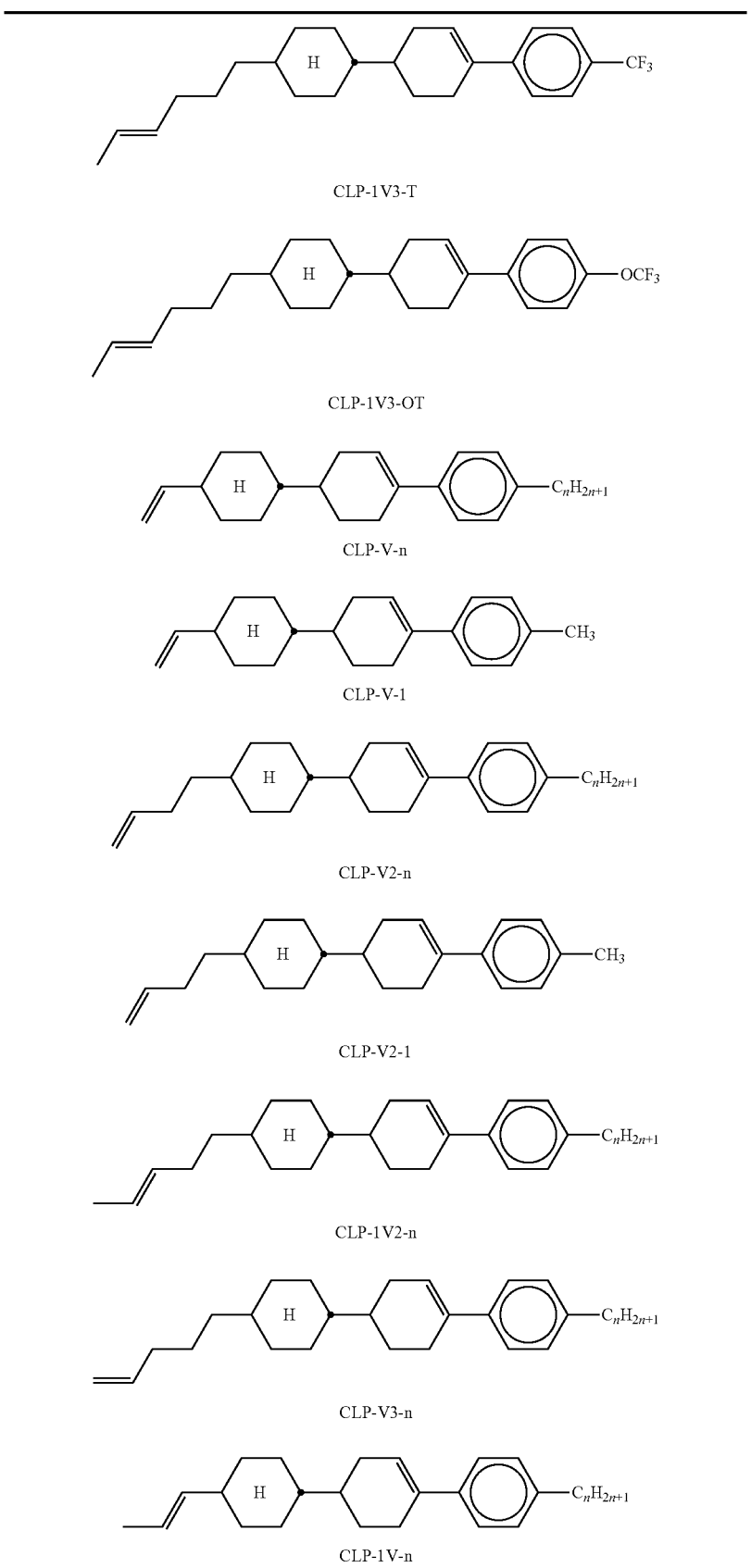

TABLE B-continued
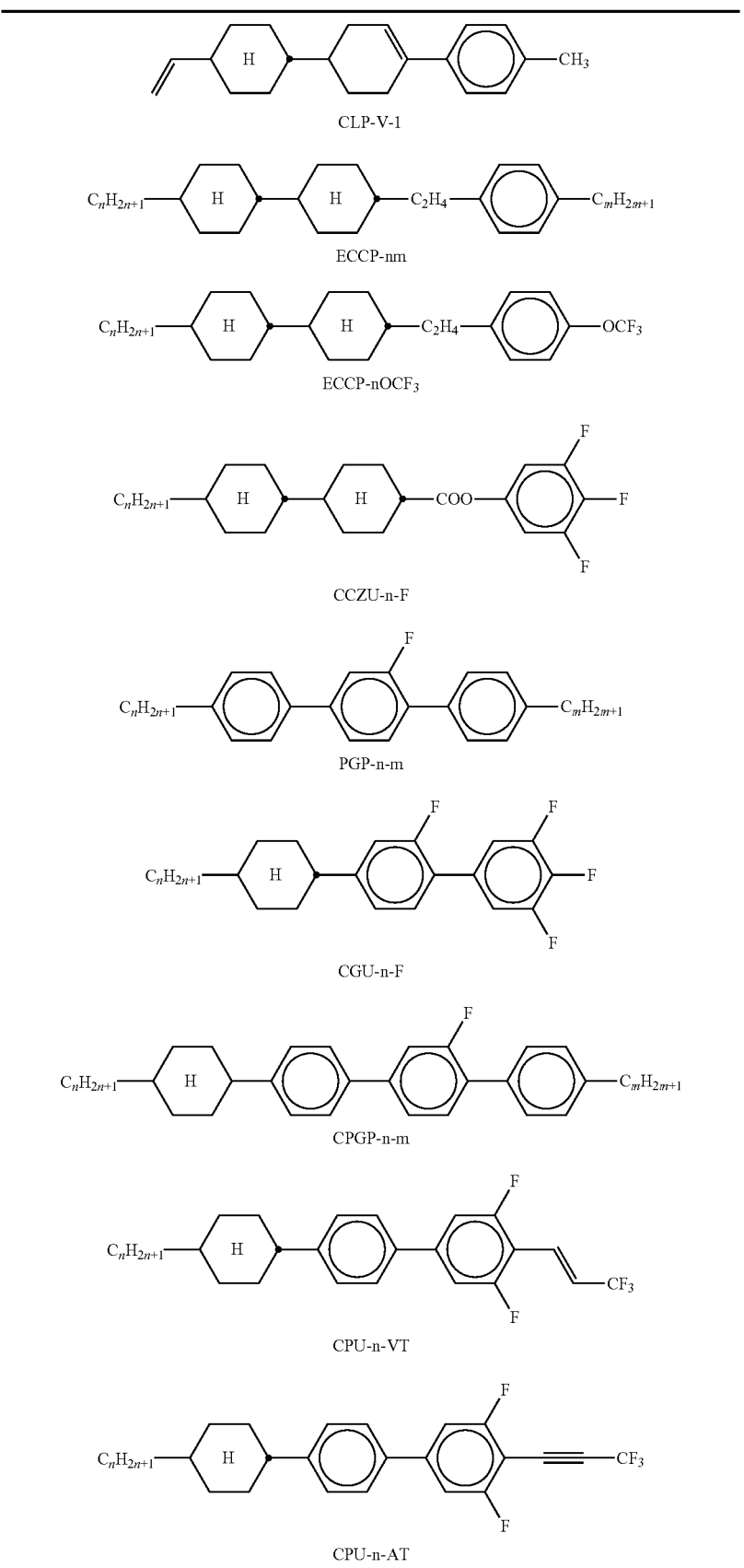

TABLE B-continued
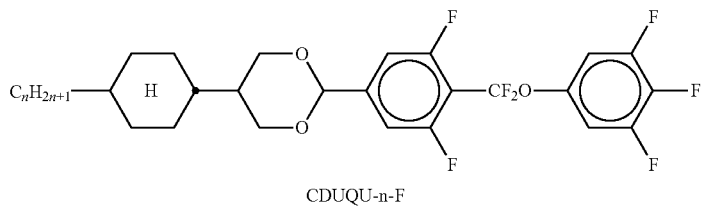
CDUQU-n-F
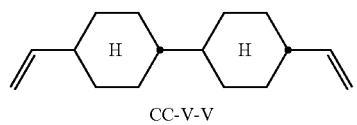
CC-V-V
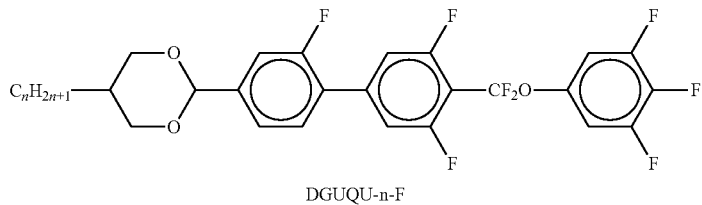
DGUQU-n-F
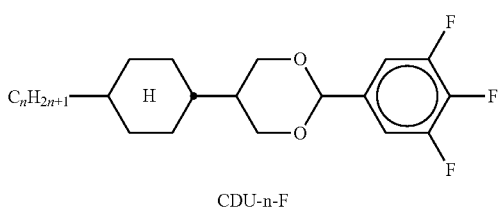
CDU-n-F
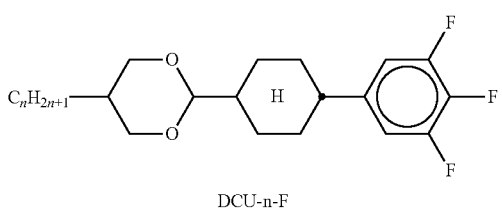
DCU-n-F
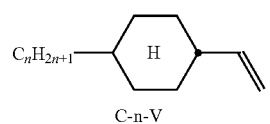
C-n-V
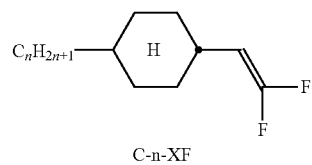
C-n-XF
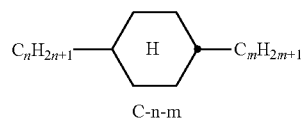
C-n-m
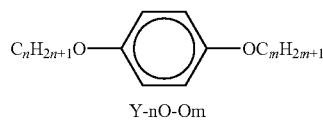
Y-nO-Om TABLE B-continued
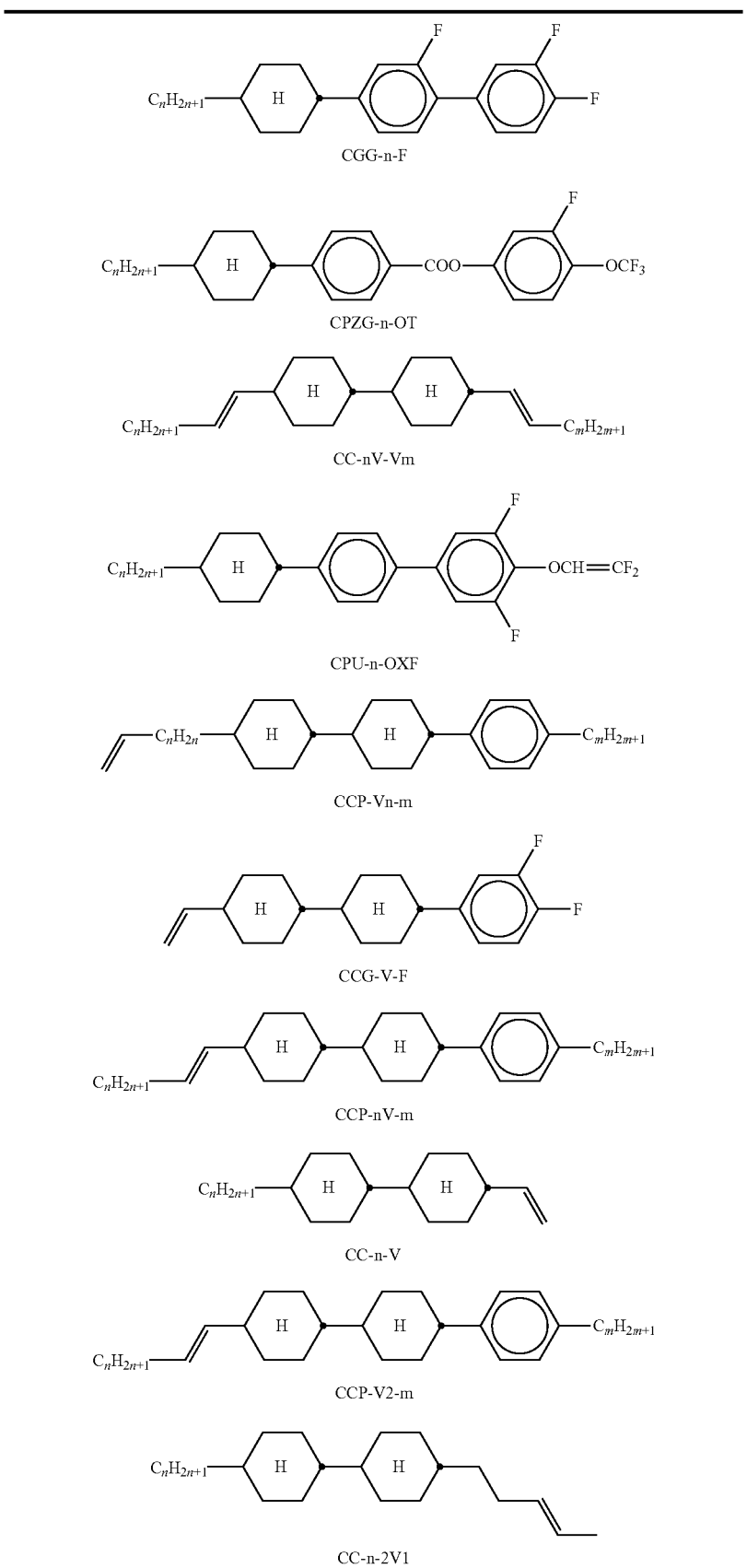

TABLE B-continued
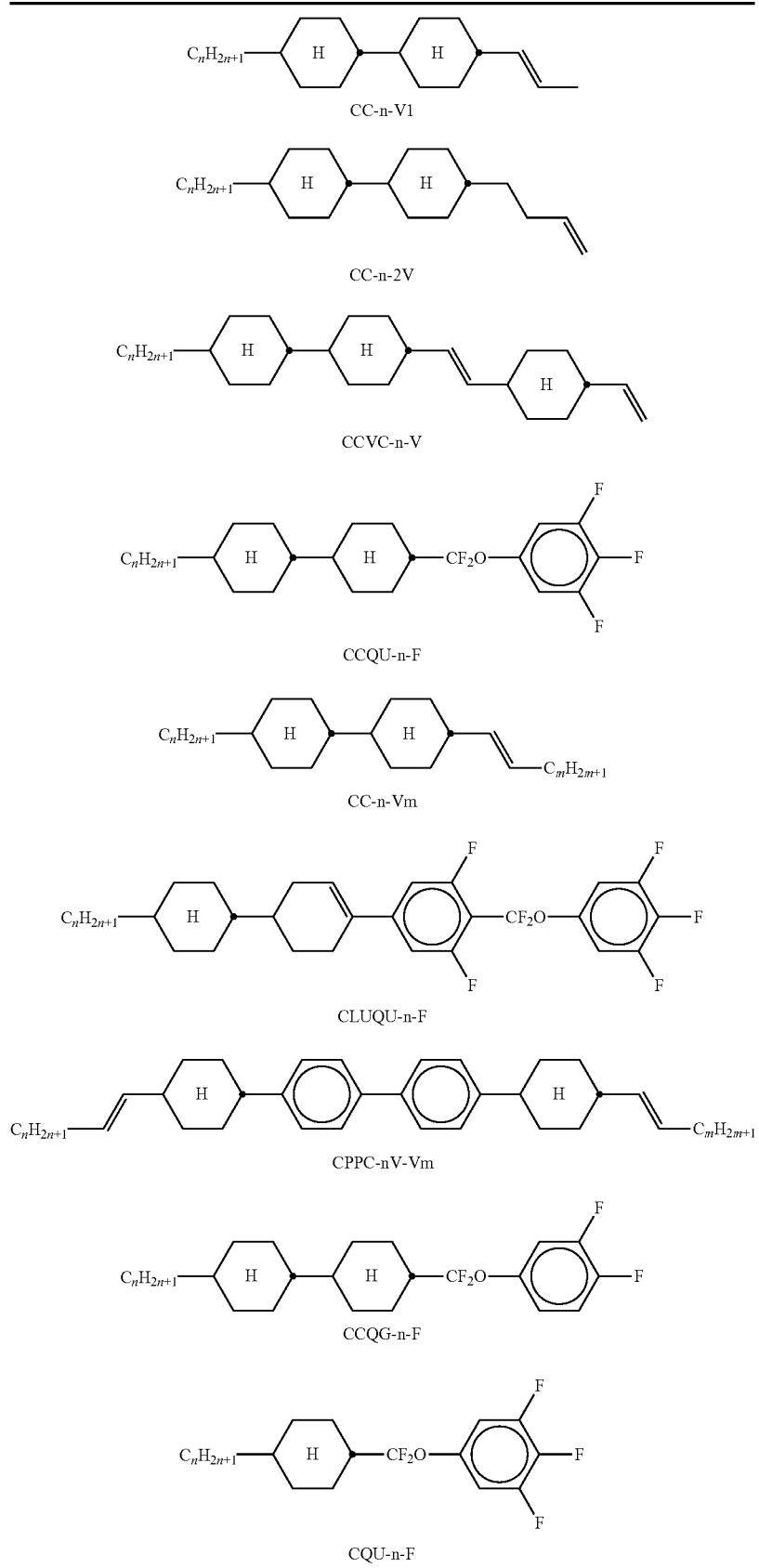

TABLE B-continued
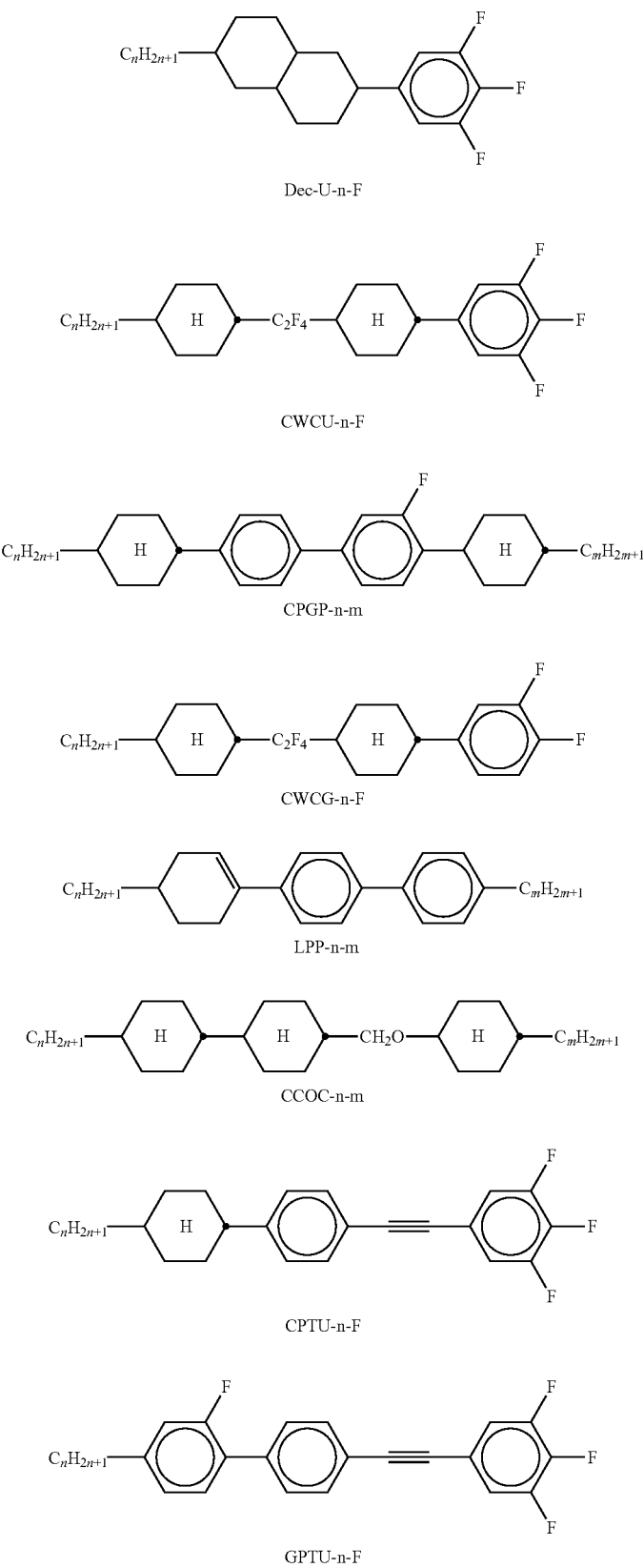

TABLE B-continued
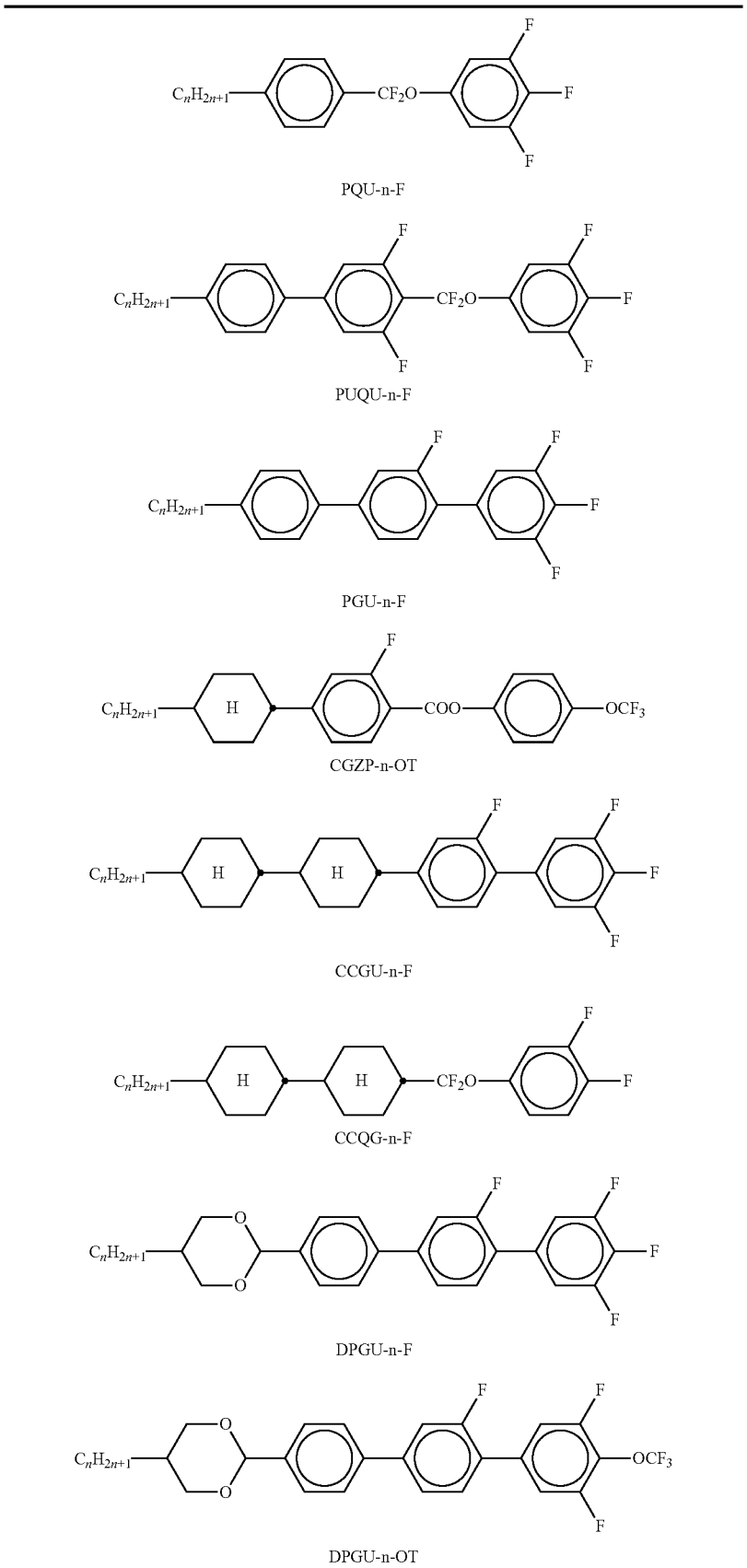

TABLE B-continued
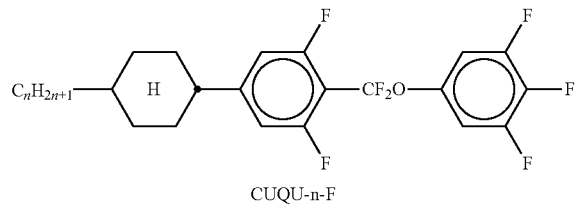
CUQU-n-F
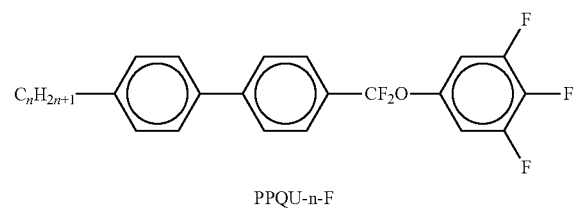
PPQU-n-F
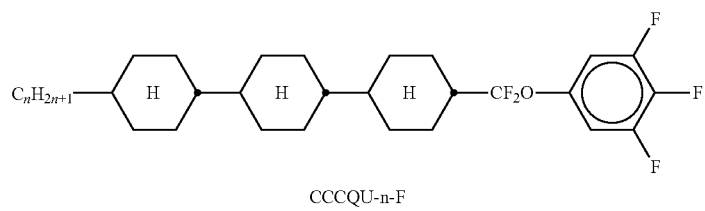
CCCQU-n-F
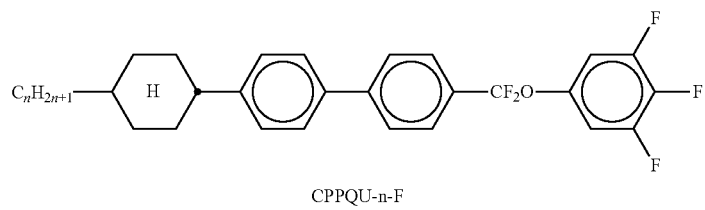
CPPQU-n-F
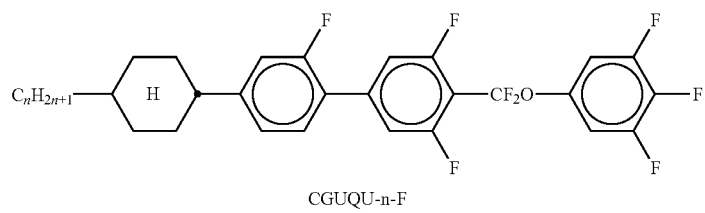
CGUQU-n-F
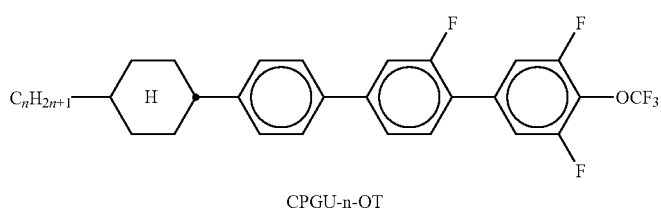
CPGU-n-OT
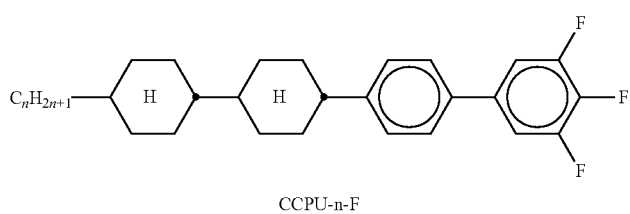
CCPU-n-F TABLE B-continued
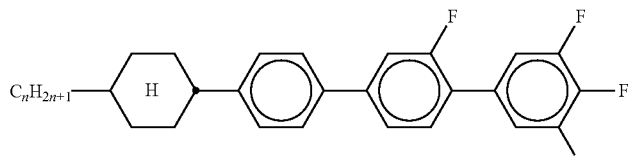
CPGU-n-F
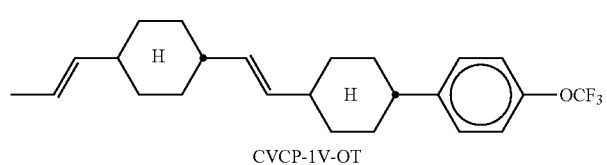
CVCP-1V-OT
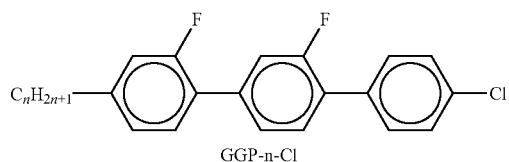
GGP-n-Cl
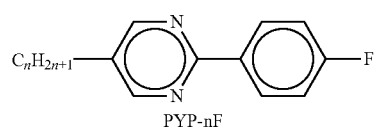
PYP-nF
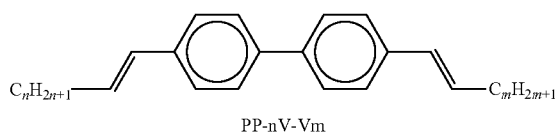
PP-nV-Vm
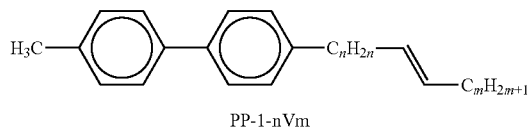
PP-1-nVm
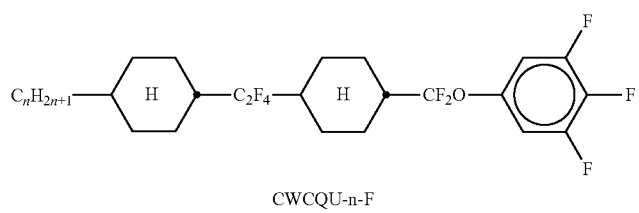
CWCQU-n-F
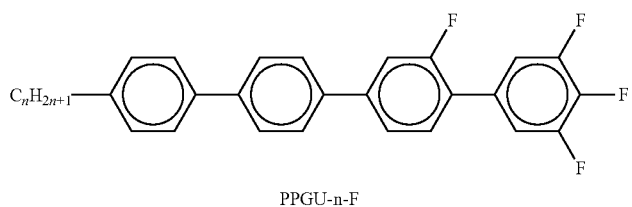
PPGU-n-F
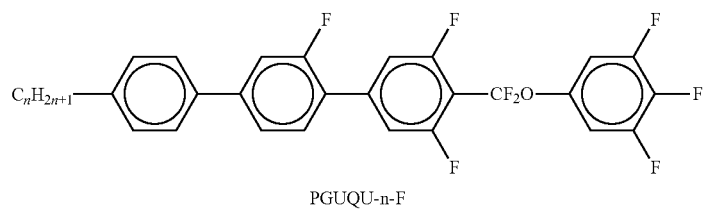
PGUQU-n-F TABLE B-continued
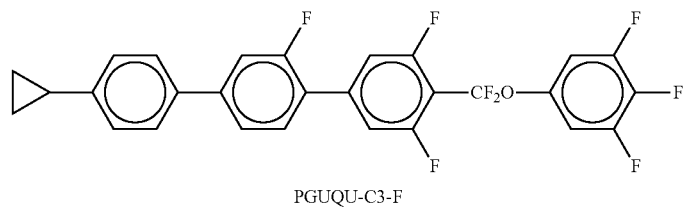
PGUQU-C3-F
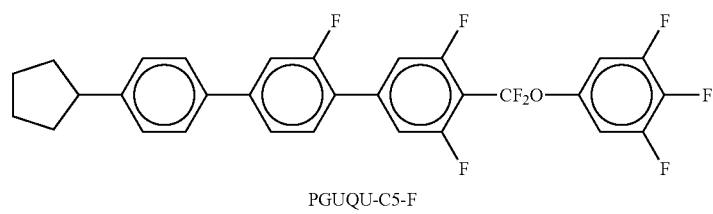
PGUQU-C5-F
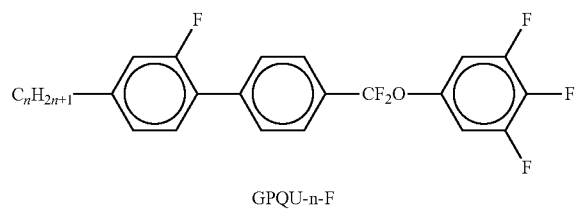
GPQU-n-F
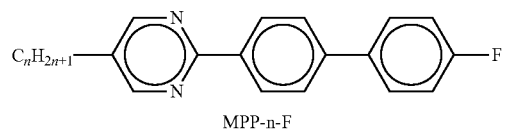
MPP-n-F
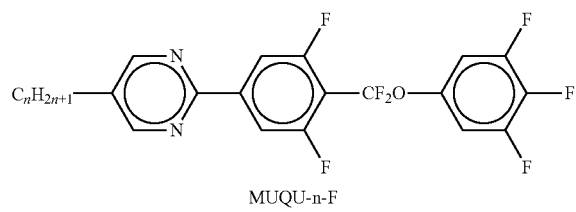
MUQU-n-F
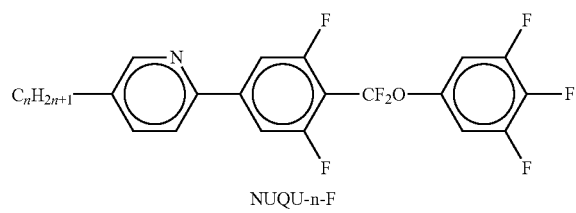
NUQU-n-F
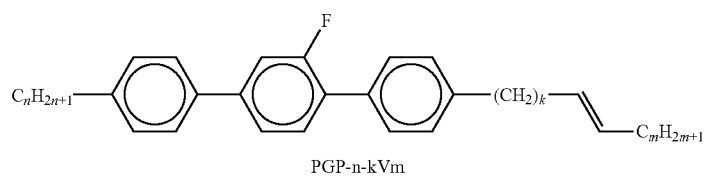
PGP-n-kVm
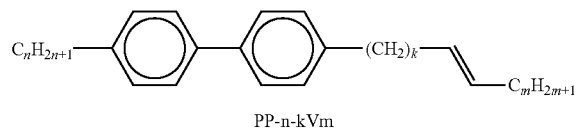
PP-n-kVm TABLE B-continued

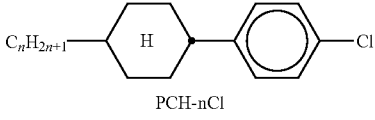
PCH-nCl

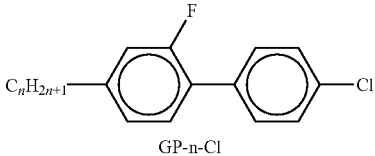
GP-n-Cl

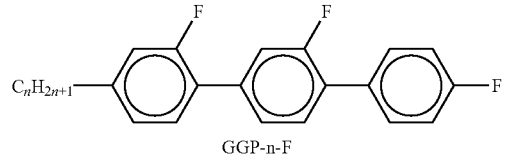
GGP-n-F

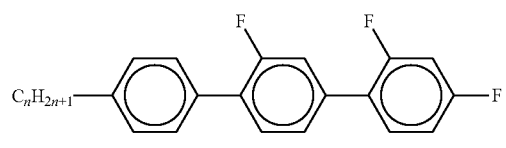
PGIGI-n-F

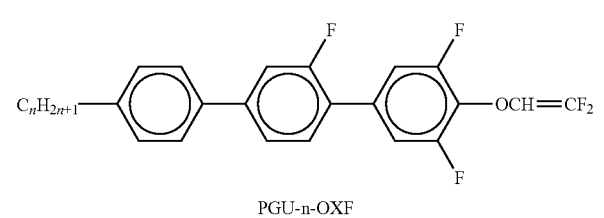
PGU-n-OXF

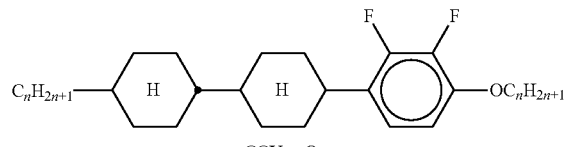
CCY-n-Om

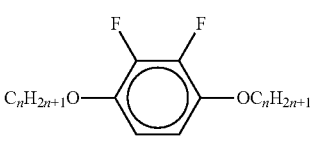
Y-nO-Om

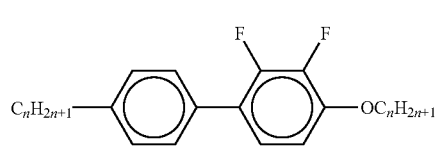
PY-n-Om (n = 1-15; (O)$C_nH_{2n+1}$ means $C_nH_{2n+1}$ or $OC_nH_{2n+1}$)

Particular preference is given to liquid-crystalline mixtures which, besides the compounds of the formula I, comprise at least one, two, three, four or more compounds from Table B.

Table C indicates possible dopants which are generally added to the mixtures according to the invention. The mixtures preferably comprise 0-10% by weight, in particular 0.001-5% by weight and particularly preferably 0.001-3% by weight, of dopants.

TABLE C
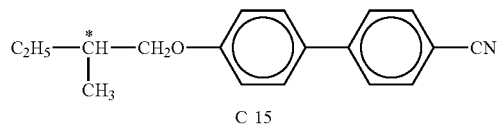
C 15
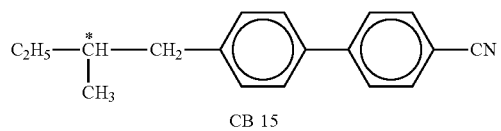
CB 15
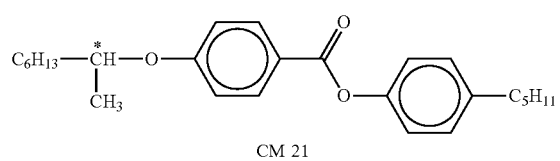
CM 21
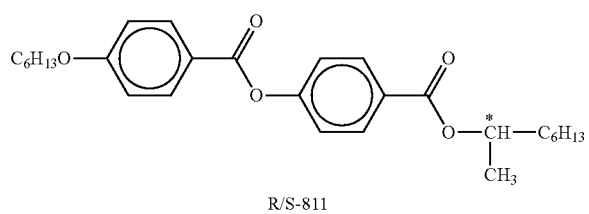
R/S-811
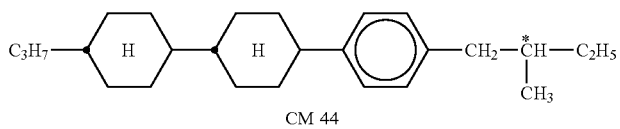
CM 44
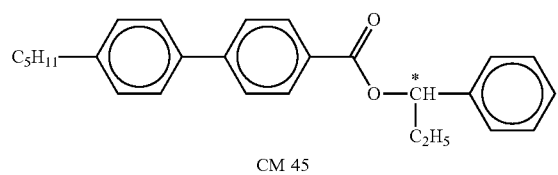
CM 45
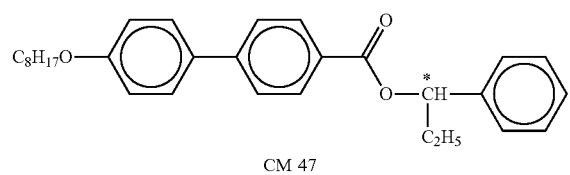
CM 47
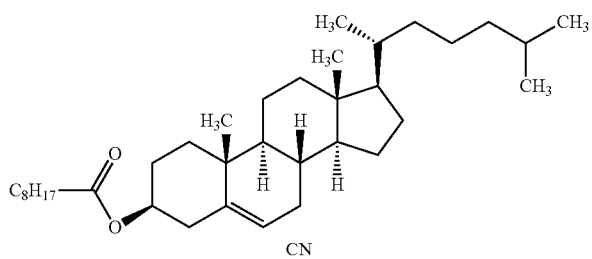
CN
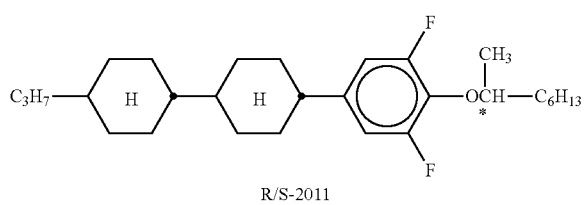
R/S-2011

TABLE C-continued
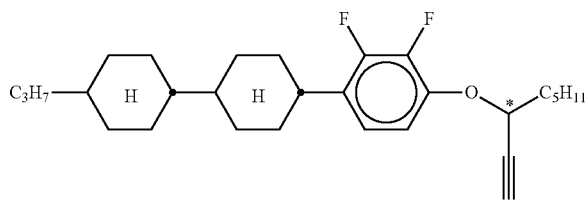
R/S-3011
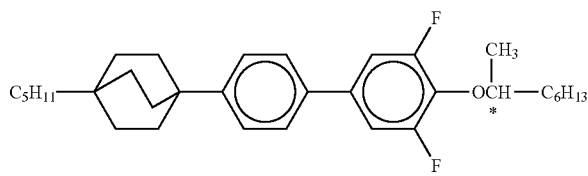
R/S-4011
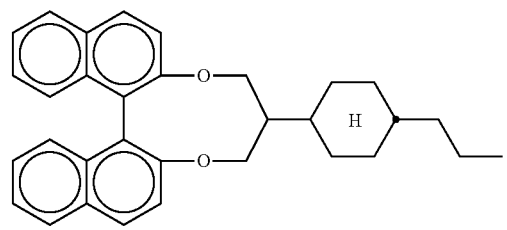
R/S-5011
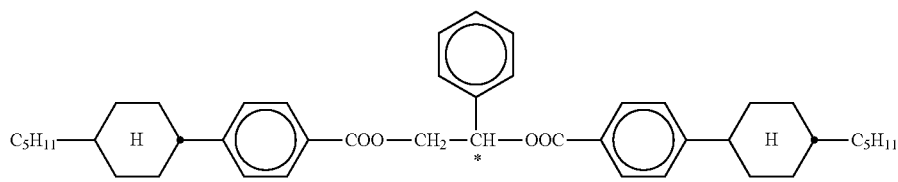
R/S-1011
TABLE D
Stabilizers which can be added, for example, to the mixtures according to the invention in amounts of 0-10% by weight are mentioned below.
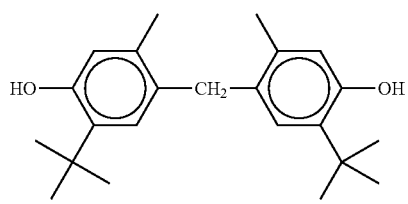
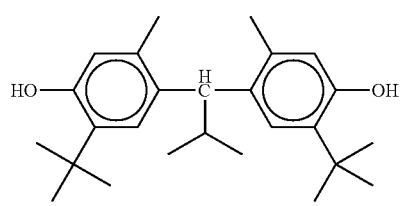

TABLE D-continued
Stabilizers which can be added, for example, to the mixtures according to the invention in amounts of 0-10% by weight are mentioned below.
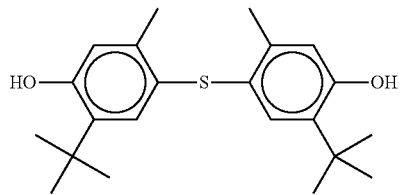
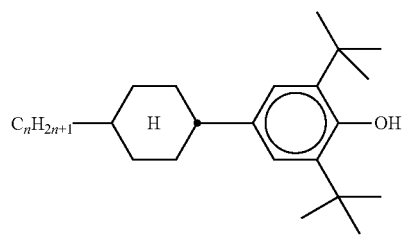
n = 1, 2, 3,4, 5, 6 or 7
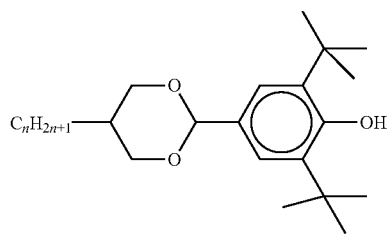
n = 1, 2, 3,4, 5, 6 or 7
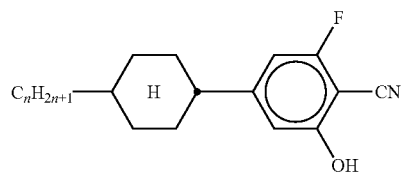
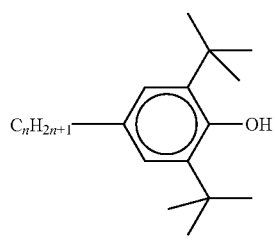
n = 1, 2, 3,4, 5, 6 or 7
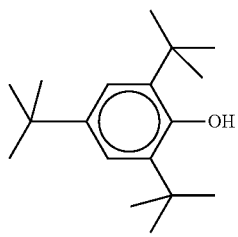

TABLE D-continued
Stabilizers which can be added, for example, to the mixtures according to the invention in amounts of 0-10% by weight are mentioned below.
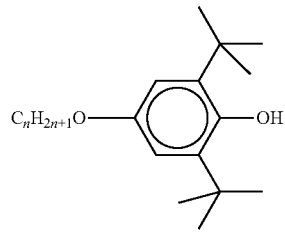
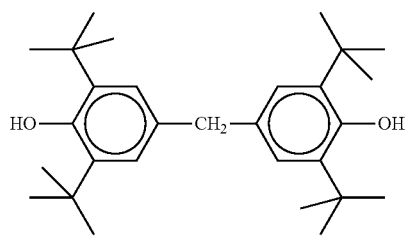
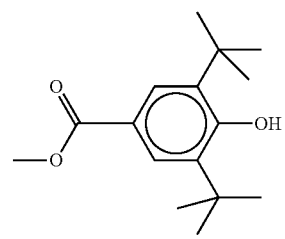
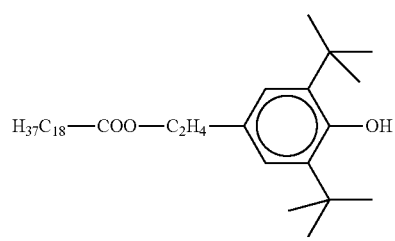
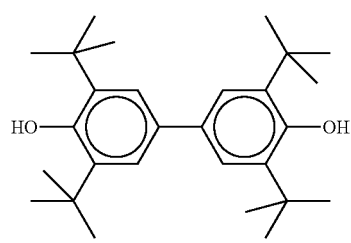

TABLE D-continued
Stabilizers which can be added, for example, to the mixtures according to the invention in amounts of 0-10% by weight are mentioned below.
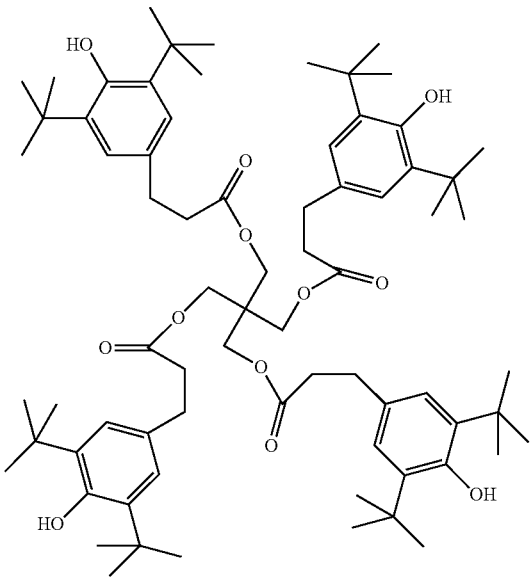 [SMILES: CC(C)(C)c1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]
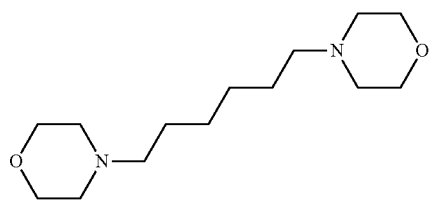 [SMILES: C(CCCN1CCOCC1)CCN1CCOCC1]
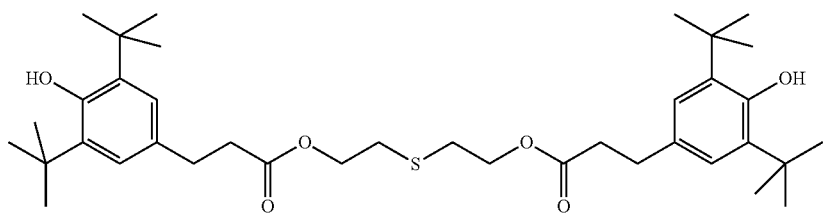 [SMILES: CC(C)(C)c1cc(CCC(=O)OCCSCCOC(=O)CCc2cc(C(C)(C)C)c(O)c(C(C)(C)C)c2)cc(C(C)(C)C)c1O]
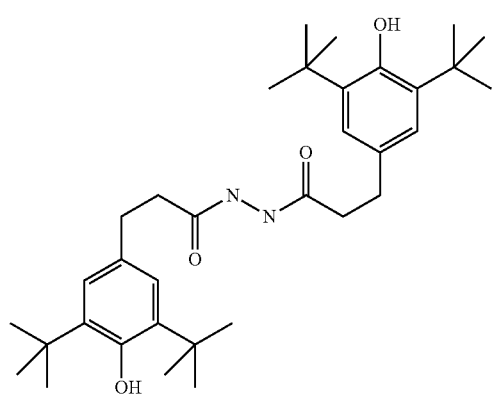 [SMILES: CC(C)(C)c1cc(CCC(=O)NNC(=O)CCc2cc(C(C)(C)C)c(O)c(C(C)(C)C)c2)cc(C(C)(C)C)c1O]

TABLE D-continued
Stabilizers which can be added, for example, to the mixtures according to the invention in amounts of 0-10% by weight are mentioned below.
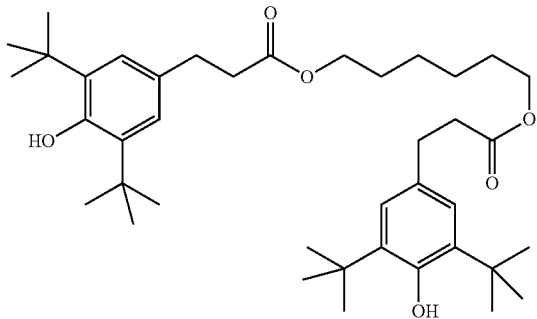 [SMILES: CC(C)(C)c1cc(CCC(=O)OCCCCCCOC(=O)CCc2cc(C(C)(C)C)c(O)c(C(C)(C)C)c2)cc(C(C)(C)C)c1O]
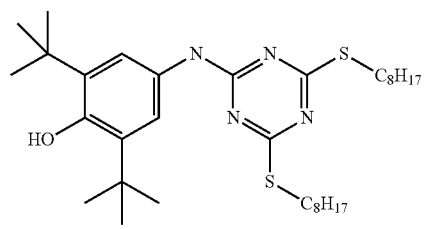
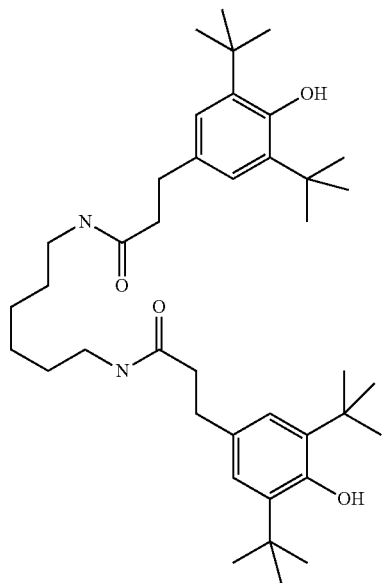 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]

TABLE D-continued
Stabilizers which can be added, for example, to the mixtures according to the invention in amounts of 0-10% by weight are mentioned below.
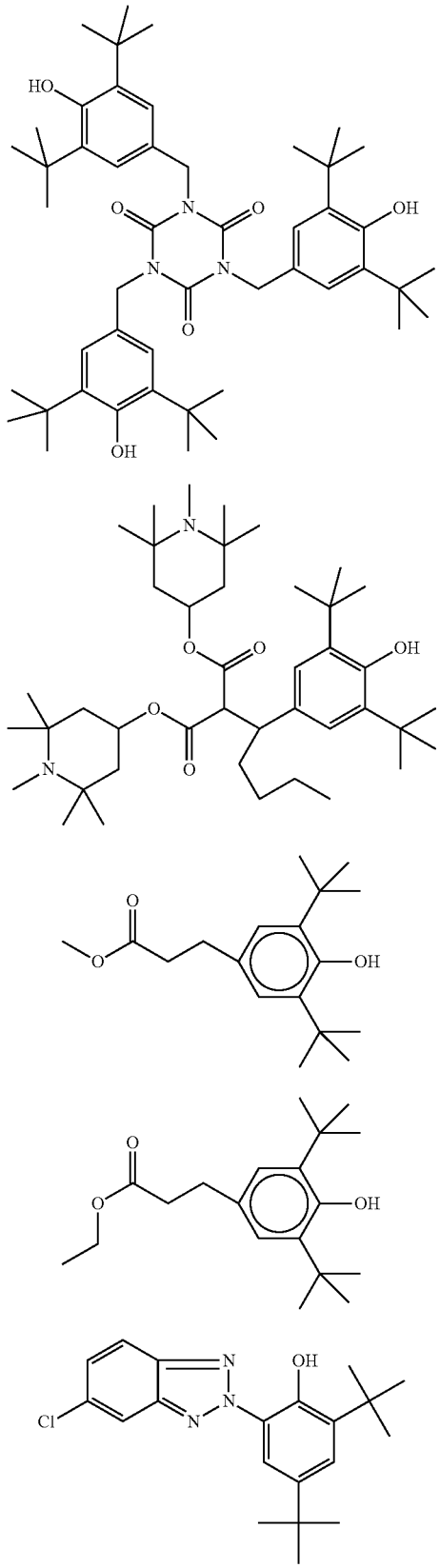

TABLE D-continued
Stabilizers which can be added, for example, to the mixtures according to the invention in amounts of 0-10% by weight are mentioned below.
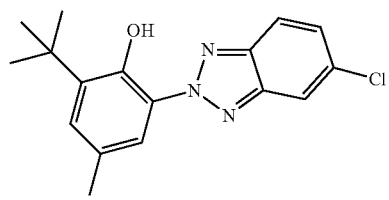 [SMILES: Cc1cc(-n2nc3ccc(Cl)cc3n2)c(O)c(C(C)(C)C)c1]
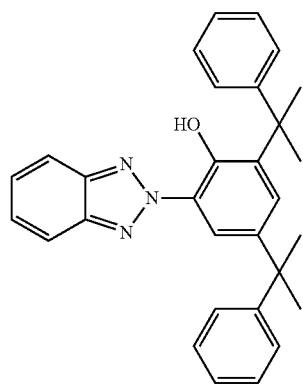 [SMILES: CC(C)(c1ccccc1)c1cc(-n2nc3ccccc3n2)c(O)c(C(C)(C)c2ccccc2)c1]
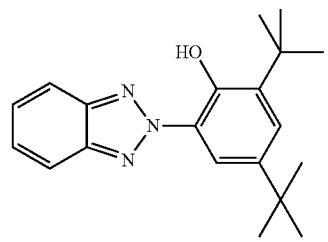 [SMILES: CC(C)(C)c1cc(-n2nc3ccccc3n2)c(O)c(C(C)(C)C)c1]
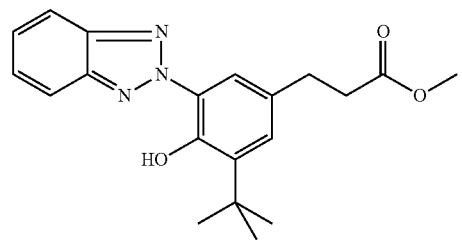 [SMILES: COC(=O)CCc1cc(-n2nc3ccccc3n2)c(O)c(C(C)(C)C)c1]
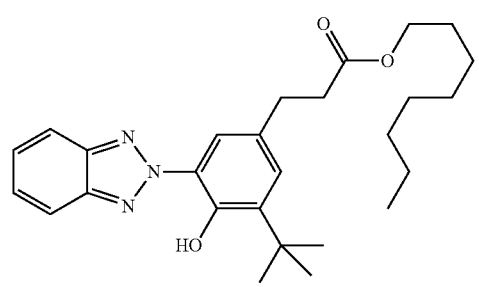 [SMILES: CCCCCCCCOC(=O)CCc1cc(-n2nc3ccccc3n2)c(O)c(C(C)(C)C)c1]

TABLE D-continued
Stabilizers which can be added, for example, to the mixtures according to the invention in amounts of 0-10% by weight are mentioned below.
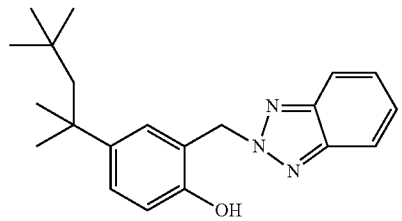 [SMILES: CC(C)(C)CC(C)(C)c1ccc(O)c(Cn2nc3ccccc3n2)c1]
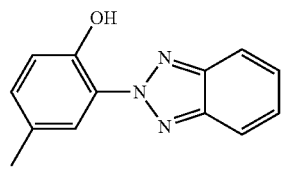 [SMILES: Cc1ccc(O)c(-n2nc3ccccc3n2)c1]
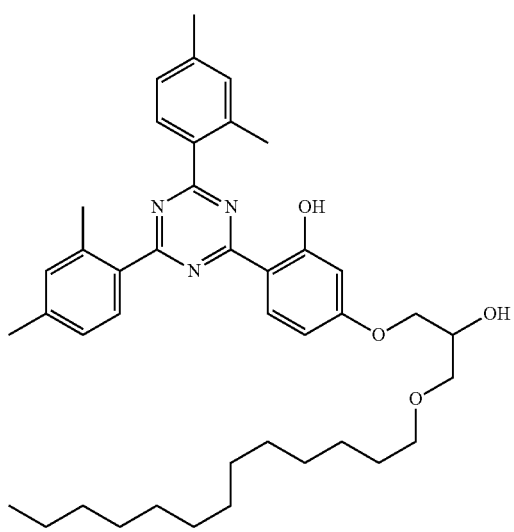 [SMILES: CCCCCCCCCCCCCOCC(O)COc1ccc(-c2nc(-c3ccc(C)cc3C)nc(-c3ccc(C)cc3C)n2)c(O)c1]
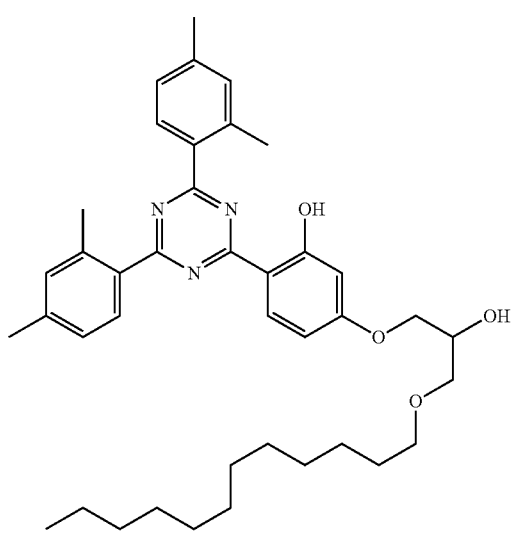 [SMILES: CCCCCCCCCCCCOCC(O)COc1ccc(-c2nc(-c3ccc(C)cc3C)nc(-c3ccc(C)cc3C)n2)c(O)c1]

TABLE D-continued
Stabilizers which can be added, for example, to the mixtures according to the invention in amounts of 0-10% by weight are mentioned below.
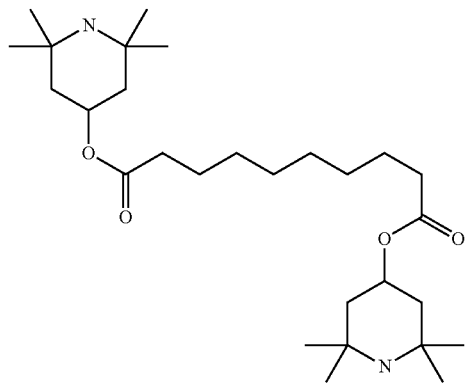
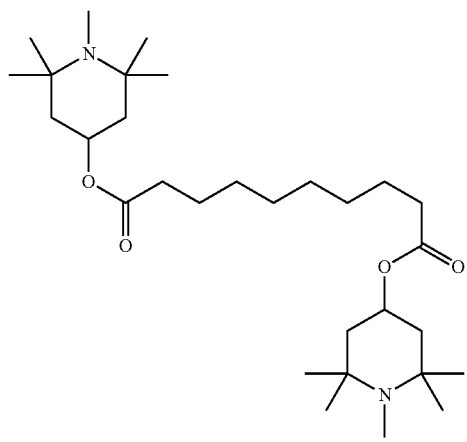
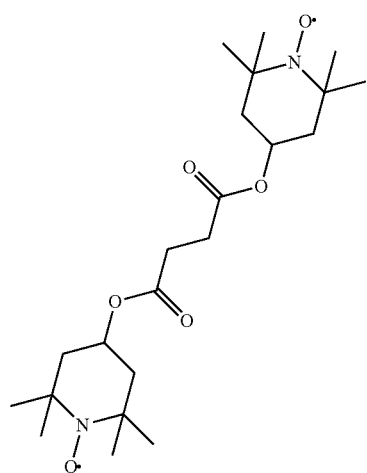

TABLE D-continued
Stabilizers which can be added, for example, to the mixtures according to the invention in amounts of 0-10% by weight are mentioned below.
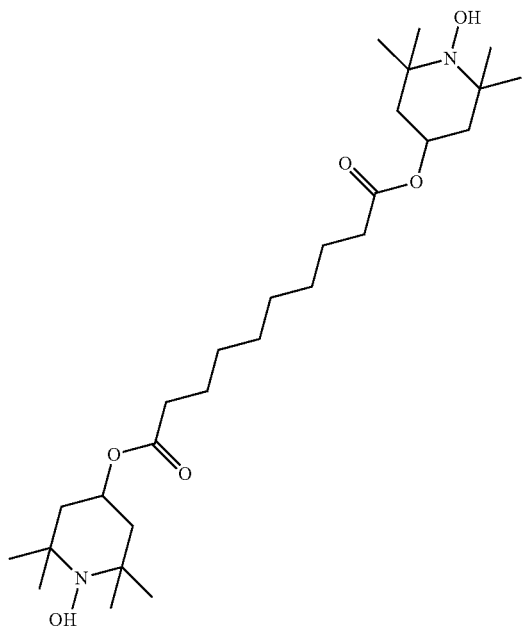
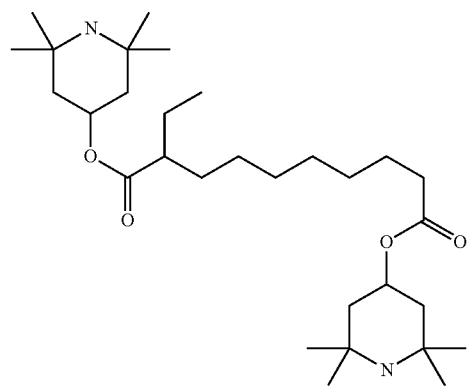
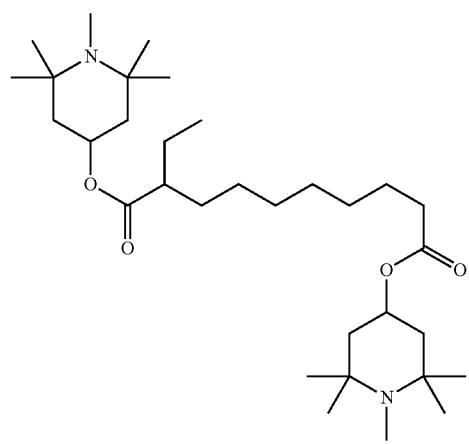

TABLE D-continued
Stabilizers which can be added, for example, to the mixtures according to the invention in amounts of 0-10% by weight are mentioned below.
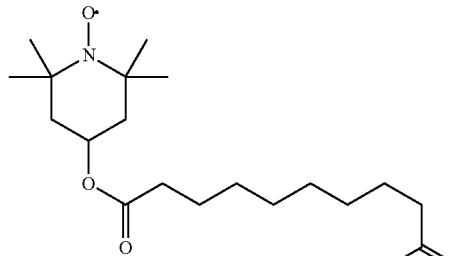
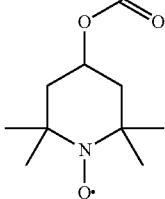
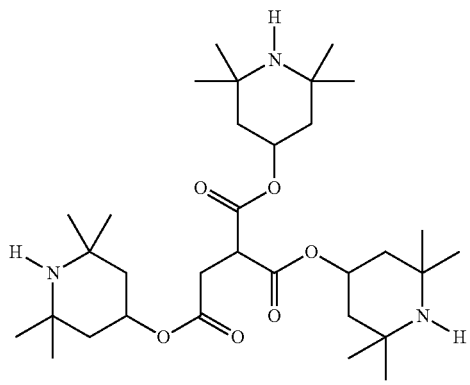 [SMILES: CC1(C)CC(OC(=O)CC(C(=O)OC2CC(C)(C)NC(C)(C)C2)C(=O)OC2CC(C)(C)NC(C)(C)C2)CC(C)(C)N1]
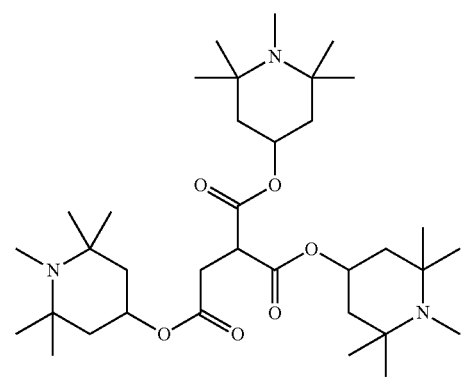
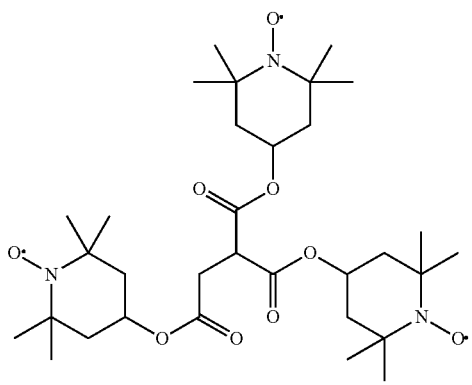

TABLE D-continued
Stabilizers which can be added, for example, to the mixtures according to the invention in amounts of 0-10% by weight are mentioned below.
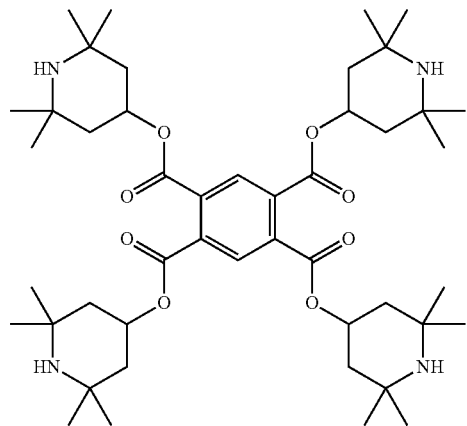
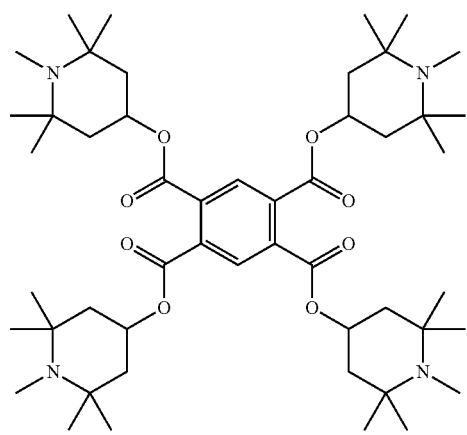
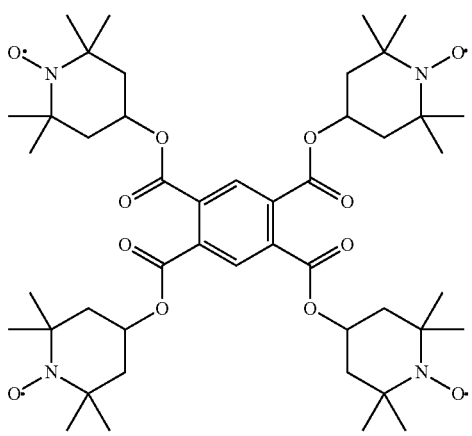

TABLE D-continued

Stabilizers which can be added, for example, to the mixtures according to the invention in amounts of 0-10% by weight are mentioned below.

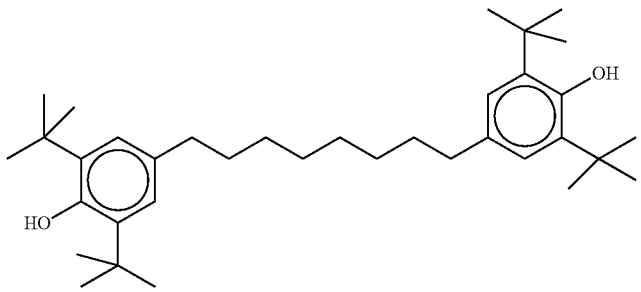

TABLE E

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

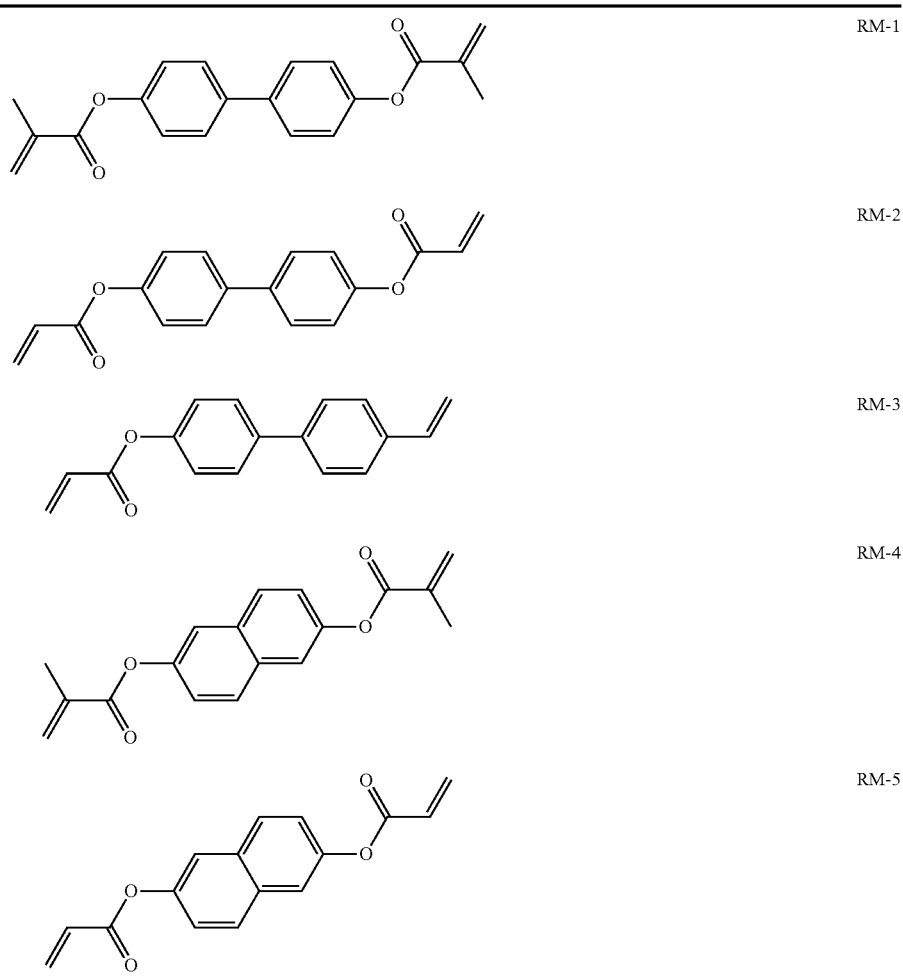

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

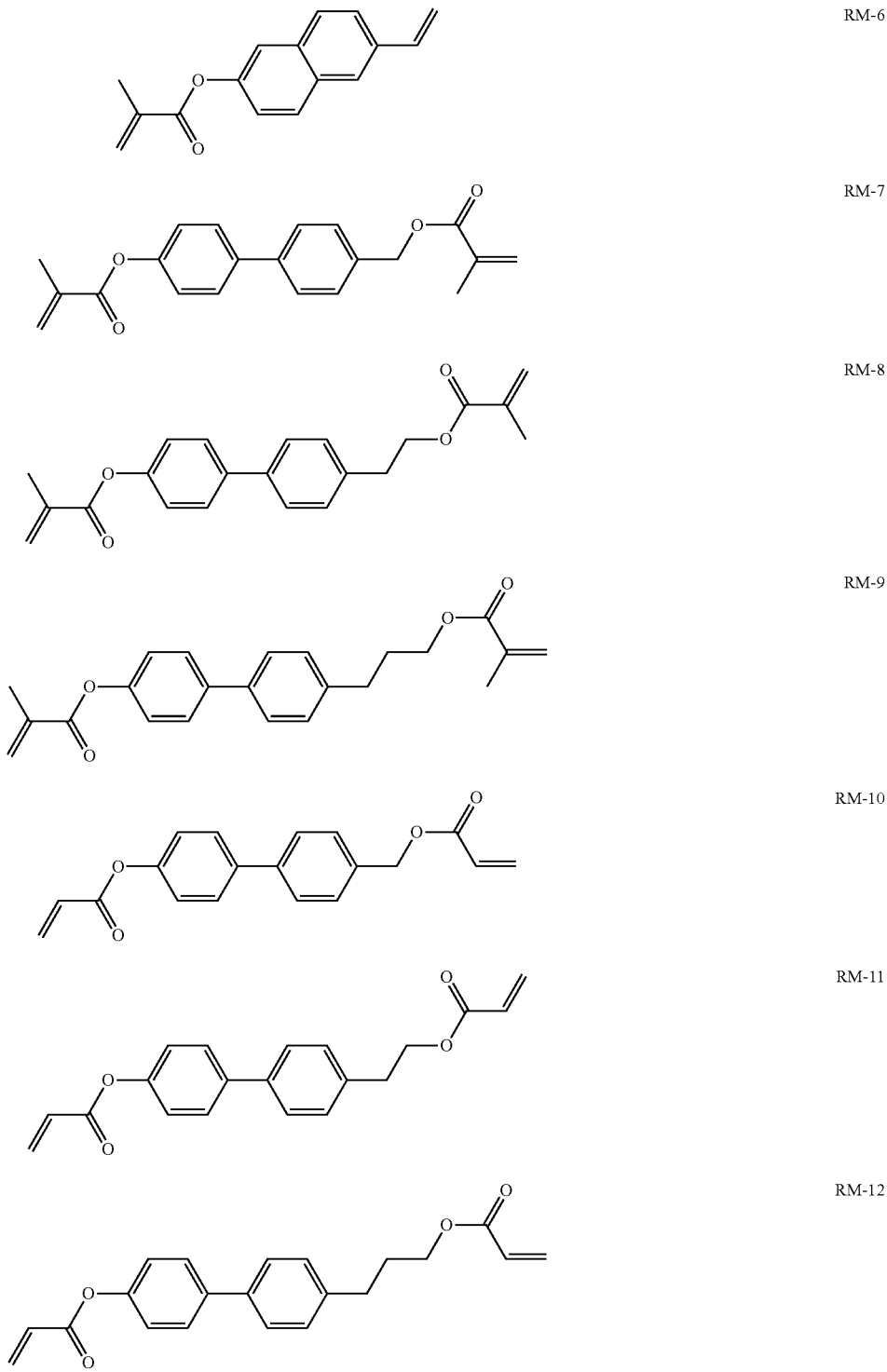

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

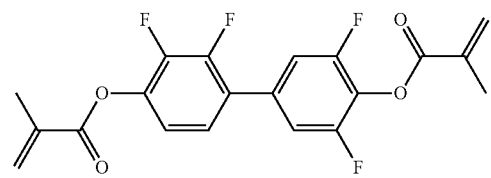

RM-13

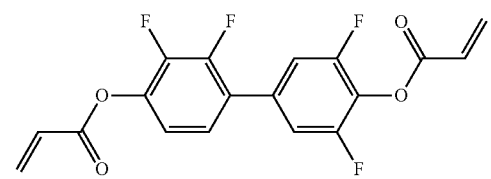

RM-14

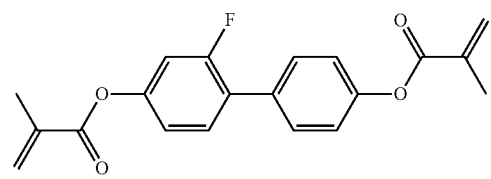

RM-15

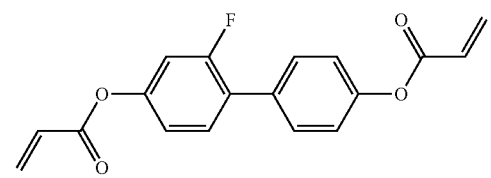

RM-16

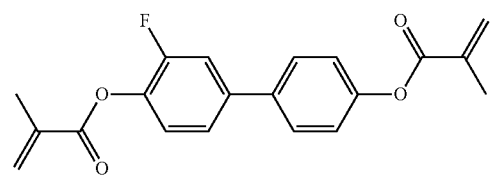

RM-17

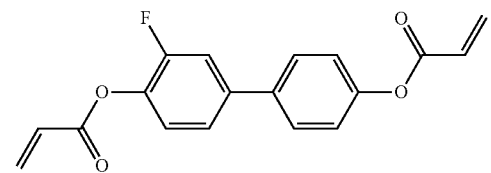

RM-18

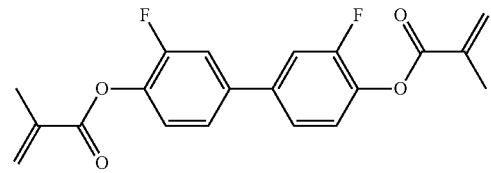 [SMILES: C=C(C)C(=O)Oc1ccc(-c2ccc(OC(=O)C(=C)C)c(F)c2)cc1]

RM-19

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

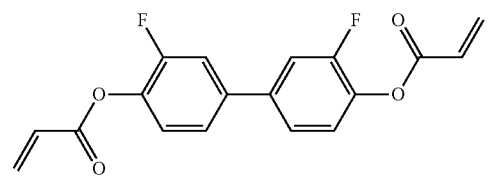 [SMILES: C=CC(=O)Oc1ccc(-c2ccc(OC(=O)C=C)c(F)c2)cc1F]
RM-20

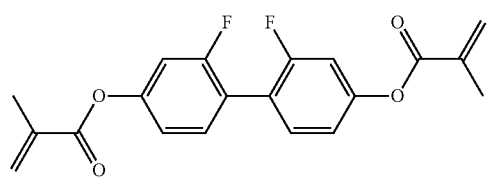 [SMILES: C=C(C)C(=O)Oc1ccc(-c2ccc(OC(=O)C(=C)C)cc2F)c(F)c1]
RM-21

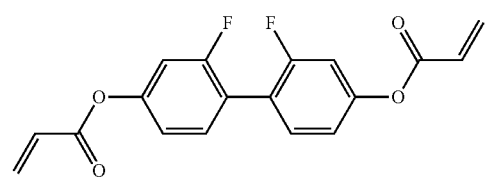 [SMILES: C=CC(=O)Oc1ccc(-c2ccc(OC(=O)C=C)cc2F)c(F)c1]
RM-22

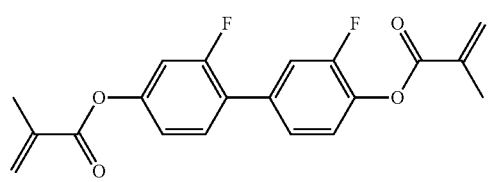
RM-23

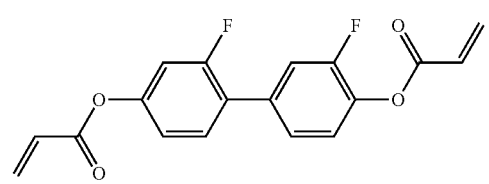 [SMILES: C=CC(=O)Oc1ccc(-c2ccc(OC(=O)C=C)c(F)c2)c(F)c1]
RM-24

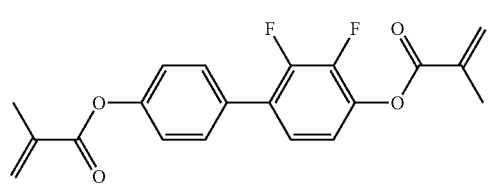
RM-25

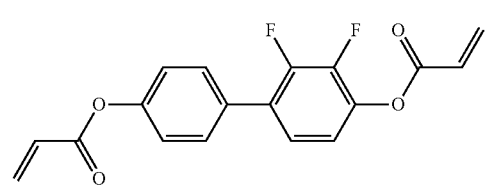
RM-26

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

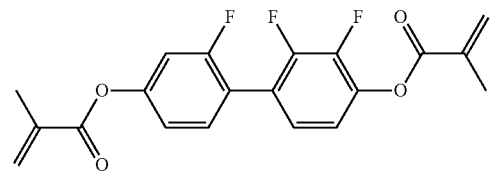
RM-27

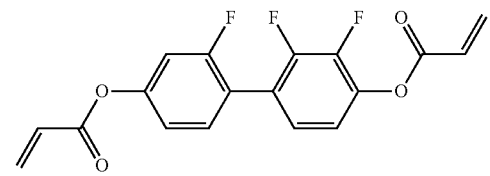
RM-28

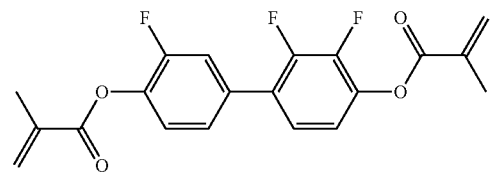 [SMILES: C=C(C)C(=O)Oc1ccc(-c2ccc(OC(=O)C(=C)C)c(F)c2F)cc1]
RM-29

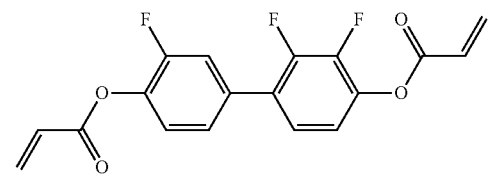
RM-30

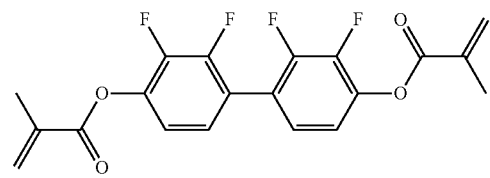 [SMILES: C=C(C)C(=O)Oc1ccc(-c2ccc(OC(=O)C(=C)C)c(F)c2F)c(F)c1F]
RM-31

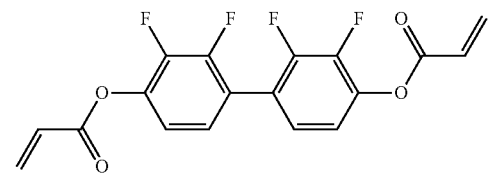 [SMILES: C=CC(=O)Oc1ccc(-c2ccc(OC(=O)C=C)c(F)c2F)c(F)c1F]
RM-32

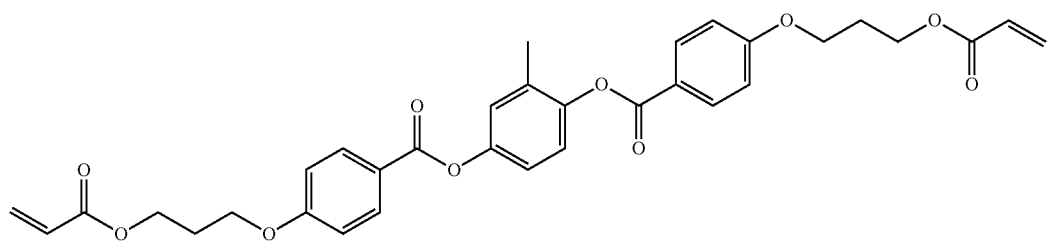 [SMILES: C=CC(=O)OCCCOc1ccc(C(=O)Oc2ccc(OC(=O)c3ccc(OCCCOC(=O)C=C)cc3)c(C)c2)cc1]
RM-33

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

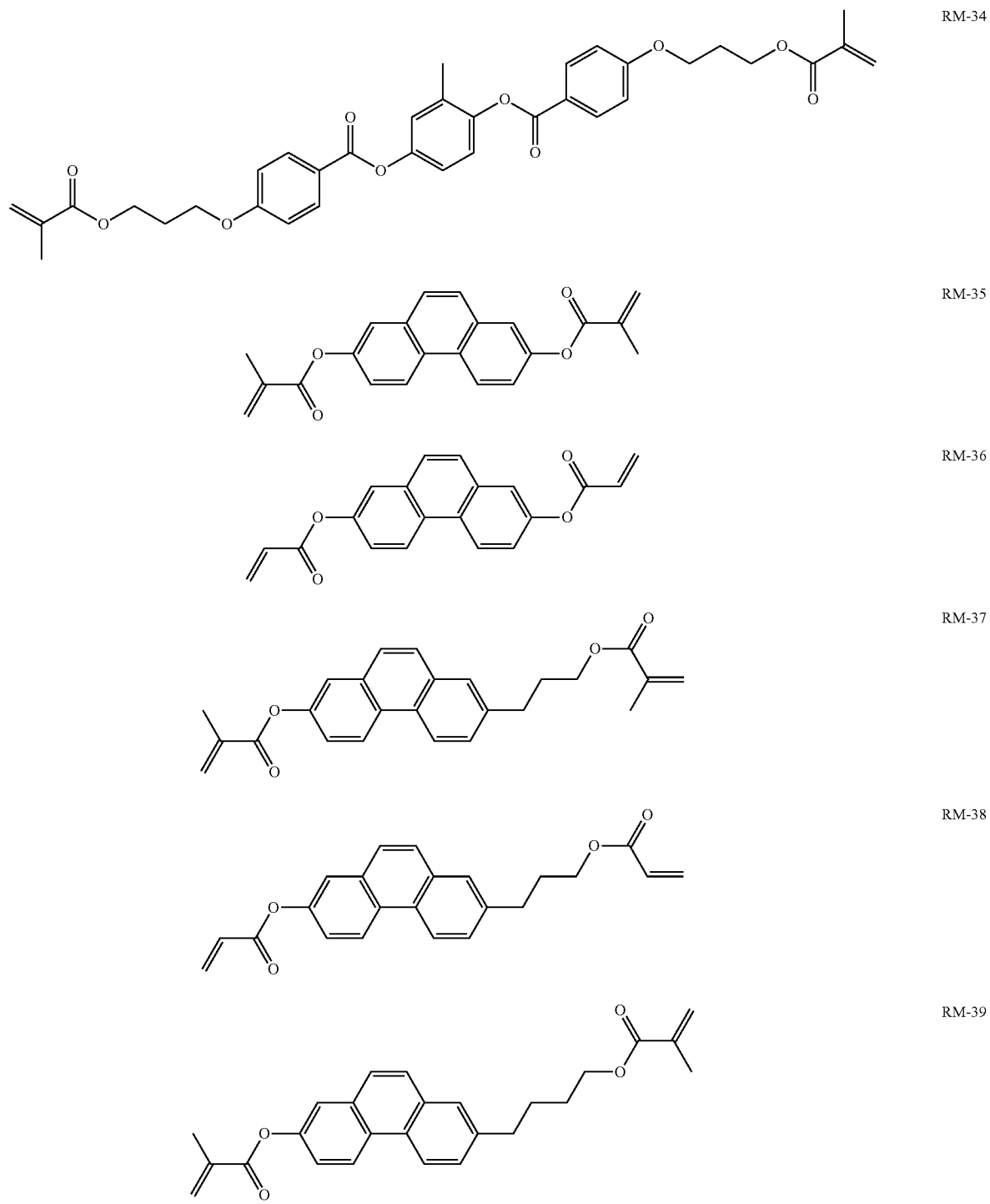

RM-34

RM-35

RM-36

RM-37

RM-38

RM-39

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

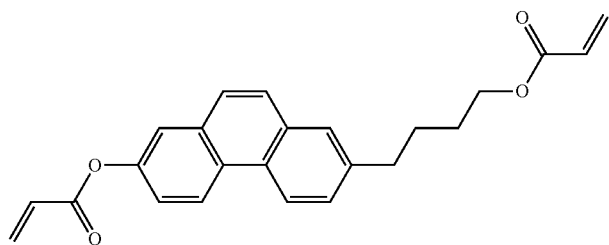 [SMILES: C=CC(=O)OCCCCc1ccc2c(ccc3cc(OC(=O)C=C)ccc32)c1]

RM-40

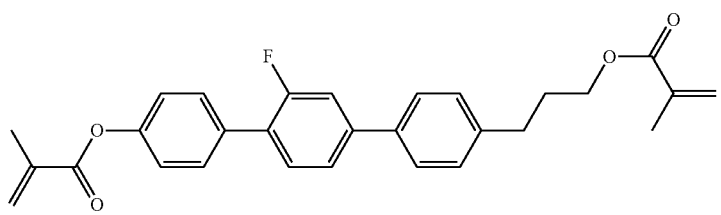 [SMILES: C=C(C)C(=O)OCCCc1ccc(-c2ccc(-c3ccc(OC(=O)C(=C)C)cc3)c(F)c2)cc1]

RM-41

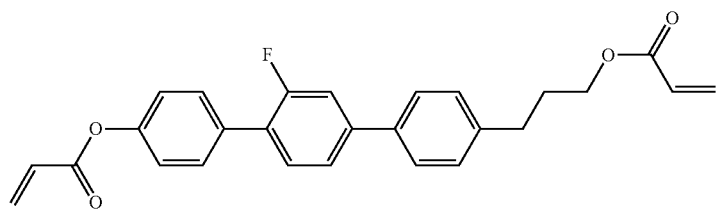 [SMILES: C=CC(=O)OCCCc1ccc(-c2ccc(-c3ccc(OC(=O)C=C)cc3)c(F)c2)cc1]

RM-42

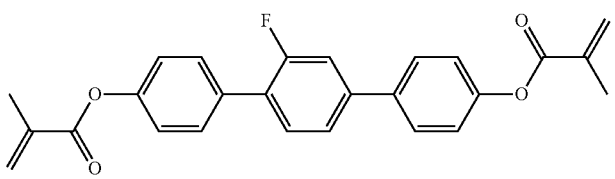

RM-43

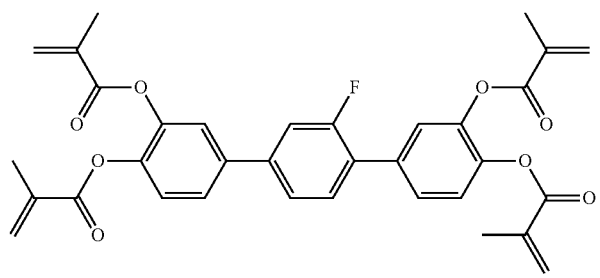 [SMILES: C=C(C)C(=O)Oc1ccc(-c2ccc(-c3ccc(OC(=O)C(=C)C)c(OC(=O)C(=C)C)c3)c(F)c2)cc1OC(=O)C(=C)C]

RM-44

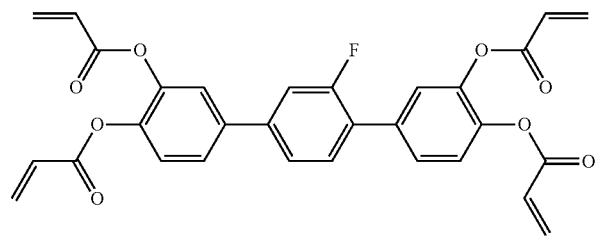 [SMILES: C=CC(=O)Oc1ccc(-c2ccc(-c3ccc(OC(=O)C=C)c(OC(=O)C=C)c3)c(F)c2)cc1OC(=O)C=C]

RM-45

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

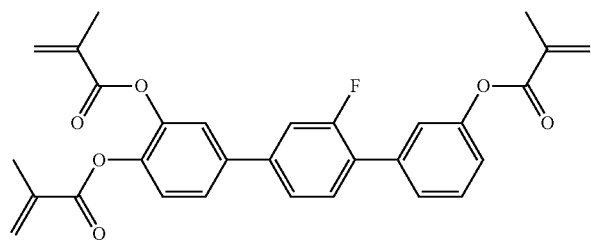 [SMILES: C=C(C)C(=O)Oc1cccc(-c2ccc(-c3ccc(OC(=O)C(=C)C)c(OC(=O)C(=C)C)c3)cc2F)c1]

RM-46

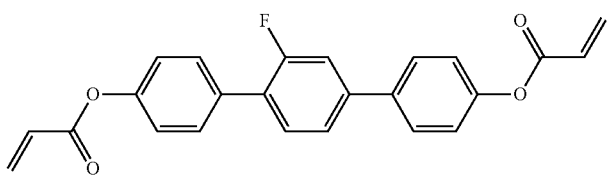

RM-47

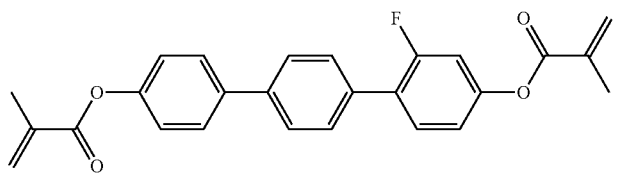

RM-48

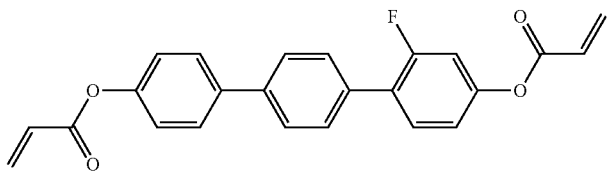

RM-49

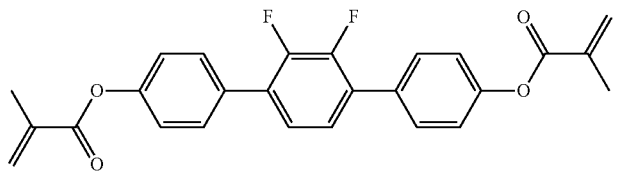

RM-50

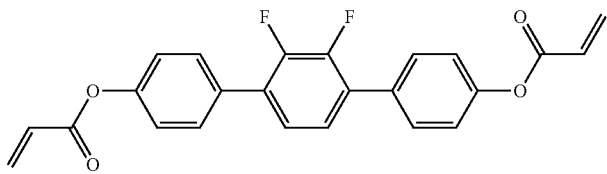 [SMILES: C=CC(=O)Oc1ccc(-c2ccc(-c3ccc(OC(=O)C=C)cc3)c(F)c2)cc1]

RM-51

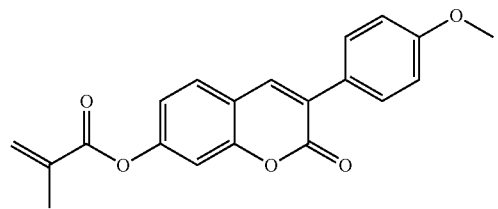 [SMILES: C=C(C)C(=O)Oc1ccc2cc(-c3ccc(OC)cc3)c(=O)oc2c1]

RM-52

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

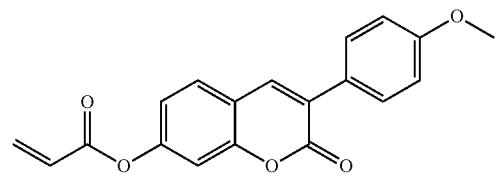 [SMILES: C=CC(=O)Oc1ccc2cc(-c3ccc(OC)cc3)c(=O)oc2c1]

RM-53

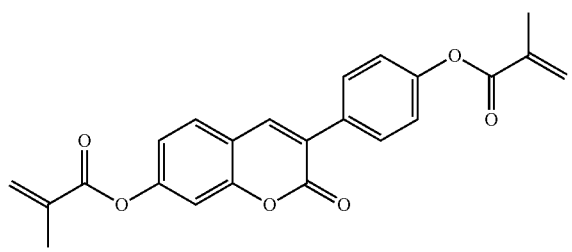 [SMILES: C=C(C)C(=O)Oc1ccc(-c2cc3ccc(OC(=O)C(=C)C)cc3oc2=O)cc1]

RM-54

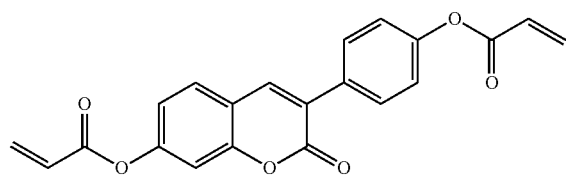 [SMILES: C=CC(=O)Oc1ccc(-c2cc3ccc(OC(=O)C=C)cc3oc2=O)cc1]

RM-55

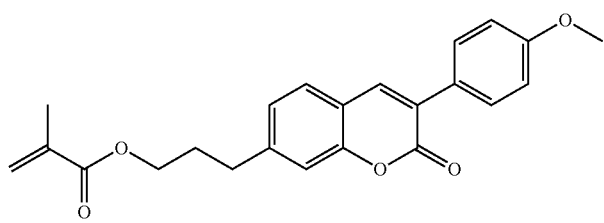 [SMILES: C=C(C)C(=O)OCCCc1ccc2cc(-c3ccc(OC)cc3)c(=O)oc2c1]

RM-56

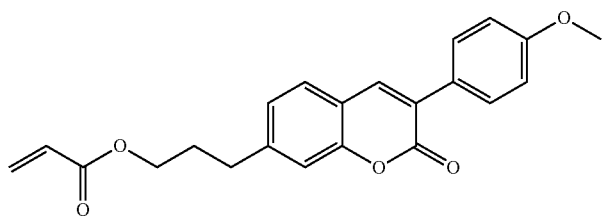 [SMILES: C=CC(=O)OCCCc1ccc2cc(-c3ccc(OC)cc3)c(=O)oc2c1]

RM-57

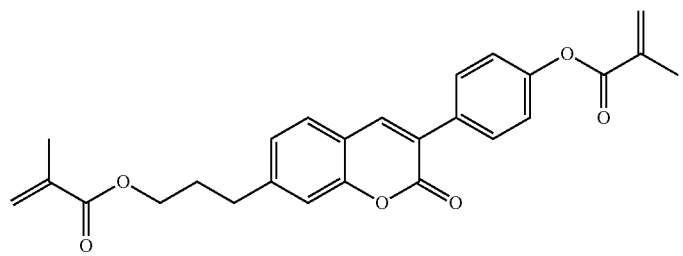 [SMILES: C=C(C)C(=O)OCCCc1ccc2cc(-c3ccc(OC(=O)C(=C)C)cc3)c(=O)oc2c1]

RM-58

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

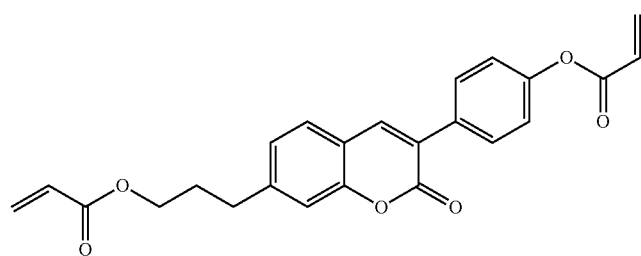 [SMILES: C=CC(=O)OCCCc1ccc2cc(-c3ccc(OC(=O)C=C)cc3)c(=O)oc2c1]
RM-59

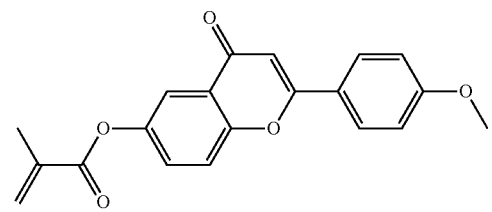 [SMILES: C=C(C)C(=O)Oc1ccc2oc(-c3ccc(OC)cc3)cc(=O)c2c1]
RM-60

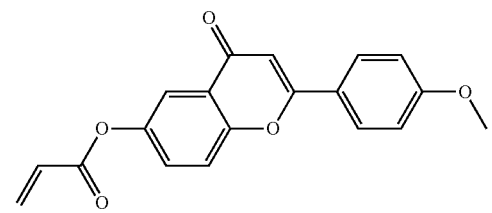 [SMILES: C=CC(=O)Oc1ccc2oc(-c3ccc(OC)cc3)cc(=O)c2c1]
RM-61

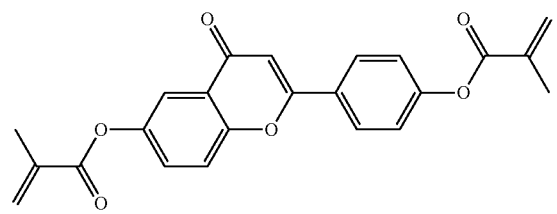 [SMILES: C=C(C)C(=O)Oc1ccc(-c2cc(=O)c3cc(OC(=O)C(=C)C)ccc3o2)cc1]
RM-62

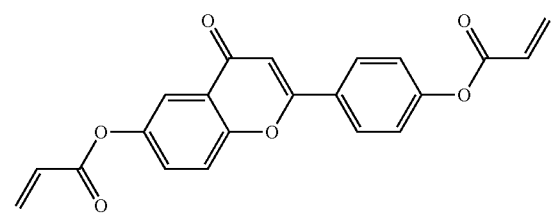 [SMILES: C=CC(=O)Oc1ccc(-c2cc(=O)c3cc(OC(=O)C=C)ccc3o2)cc1]
RM-63

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

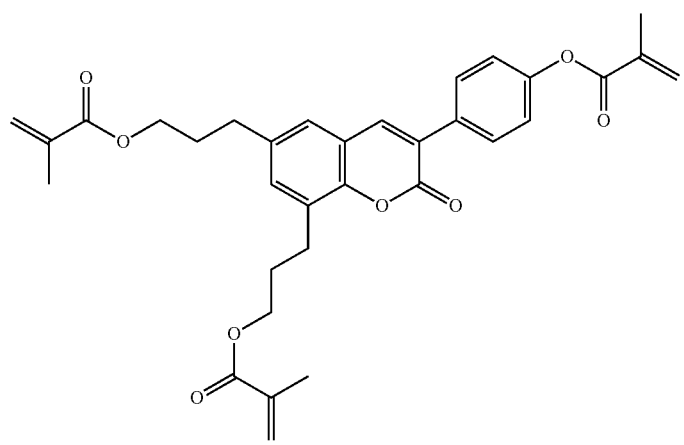 [SMILES: C=C(C)C(=O)OCCCc1cc(CCCOC(=O)C(=C)C)c2oc(=O)c(-c3ccc(OC(=O)C(=C)C)cc3)cc2c1]

RM-64

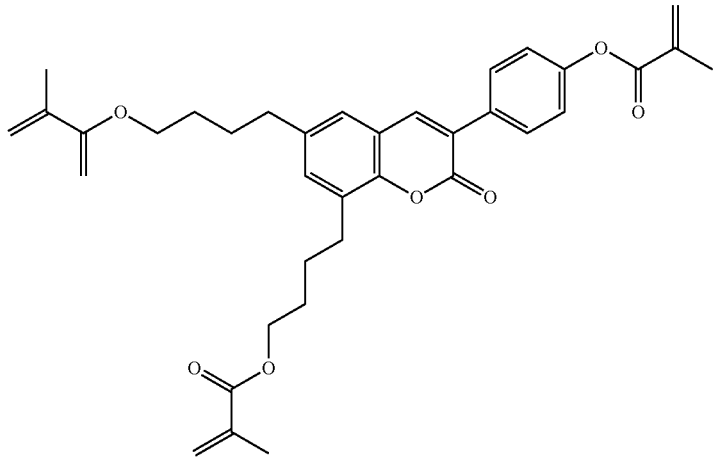 [SMILES: C=C(C)C(=C)OCCCCc1cc(CCCCOC(=O)C(=C)C)c2oc(=O)c(-c3ccc(OC(=O)C(=C)C)cc3)cc2c1]

RM-65

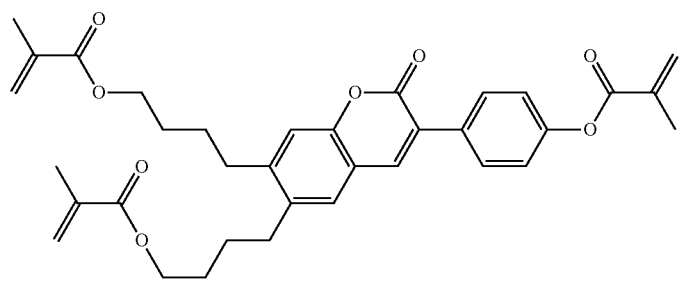 [SMILES: C=C(C)C(=O)OCCCCc1cc2cc(-c3ccc(OC(=O)C(=C)C)cc3)c(=O)oc2cc1CCCCOC(=O)C(=C)C]

RM-66

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

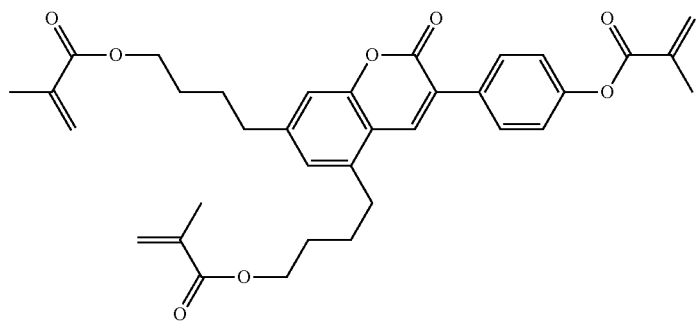 [SMILES: C=C(C)C(=O)OCCCCc1cc(CCCCOC(=O)C(=C)C)c2cc(-c3ccc(OC(=O)C(=C)C)cc3)c(=O)oc2c1]

RM-67

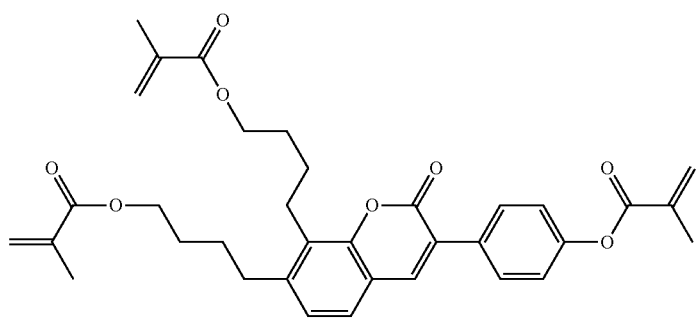 [SMILES: C=C(C)C(=O)OCCCCc1ccc2cc(-c3ccc(OC(=O)C(=C)C)cc3)c(=O)oc2c1CCCCOC(=O)C(=C)C]

RM-68

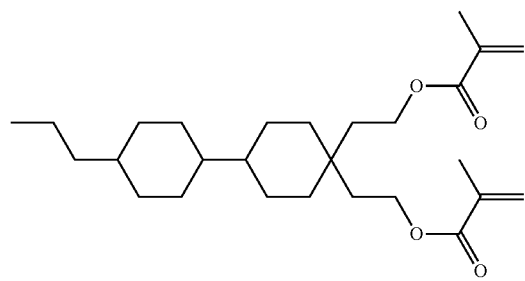 [SMILES: C=C(C)C(=O)OCCC1(CCOC(=O)C(=C)C)CCC(C2CCC(CCC)CC2)CC1]

RM-69

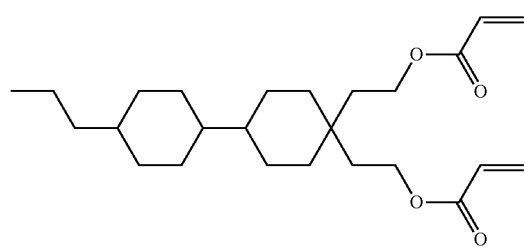 [SMILES: C=CC(=O)OCCC1(CCOC(=O)C=C)CCC(C2CCC(CCC)CC2)CC1]

RM-70

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

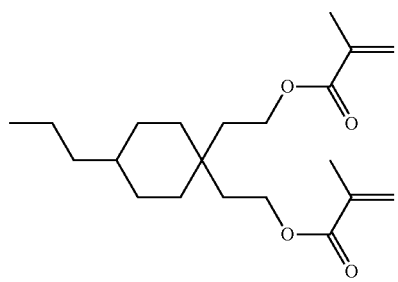 [SMILES: C=C(C)C(=O)OCCC1(CCOC(=O)C(=C)C)CCC(CCC)CC1]

RM-71

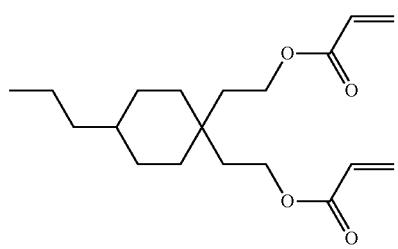 [SMILES: C=CC(=O)OCCC1(CCOC(=O)C=C)CCC(CCC)CC1]

RM-72

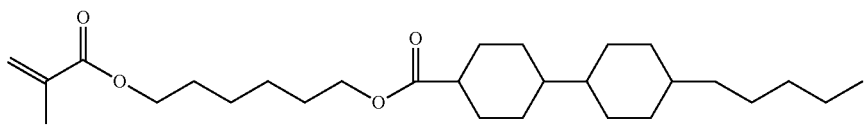 [SMILES: C=C(C)C(=O)OCCCCCCOC(=O)C1CCC(C2CCC(CCCCC)CC2)CC1]

RM-73

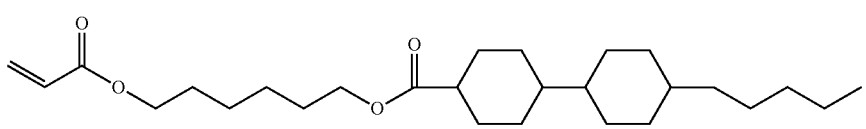 [SMILES: C=CC(=O)OCCCCCCOC(=O)C1CCC(C2CCC(CCCCC)CC2)CC1]

RM-74

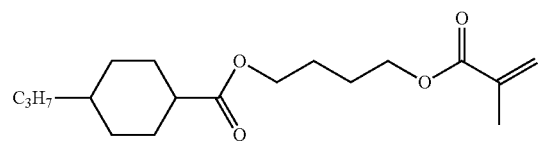

RM-75

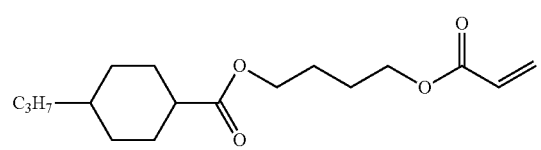

RM-76

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

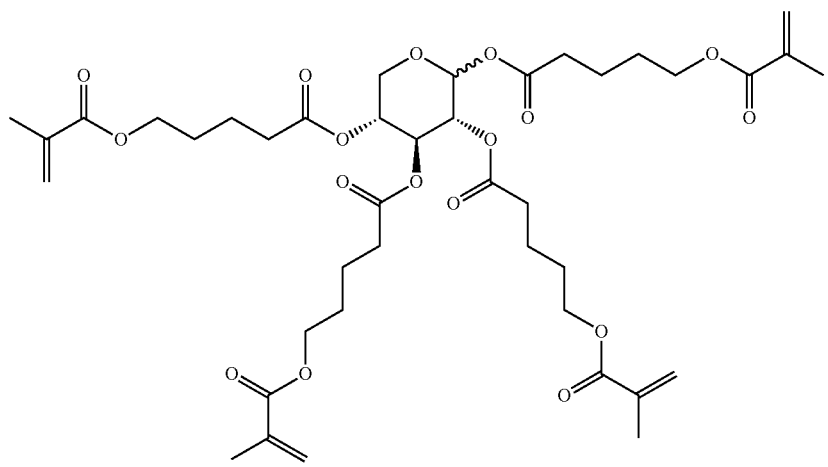 [SMILES: C=C(C)C(=O)OCCCCC(=O)OC1OC[C@@H](OC(=O)CCCCOC(=O)C(=C)C)[C@H](OC(=O)CCCCOC(=O)C(=C)C)[C@H]1OC(=O)CCCCOC(=O)C(=C)C]

RM-77

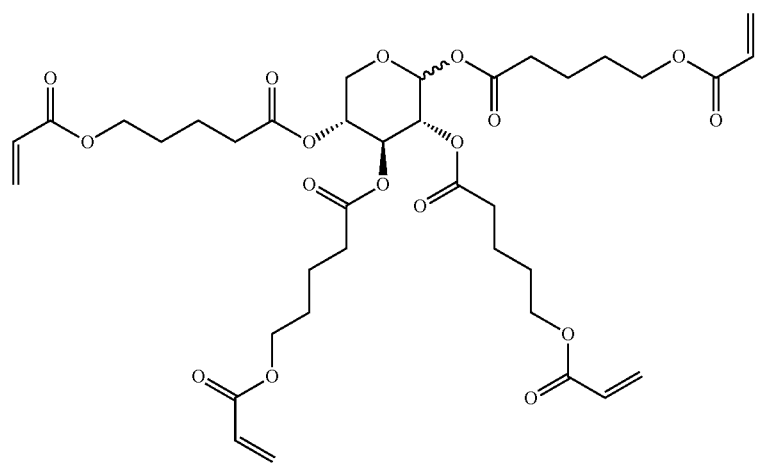 [SMILES: C=CC(=O)OCCCCC(=O)OC1OC[C@@H](OC(=O)CCCCOC(=O)C=C)[C@H](OC(=O)CCCCOC(=O)C=C)[C@H]1OC(=O)CCCCOC(=O)C=C]

RM-78

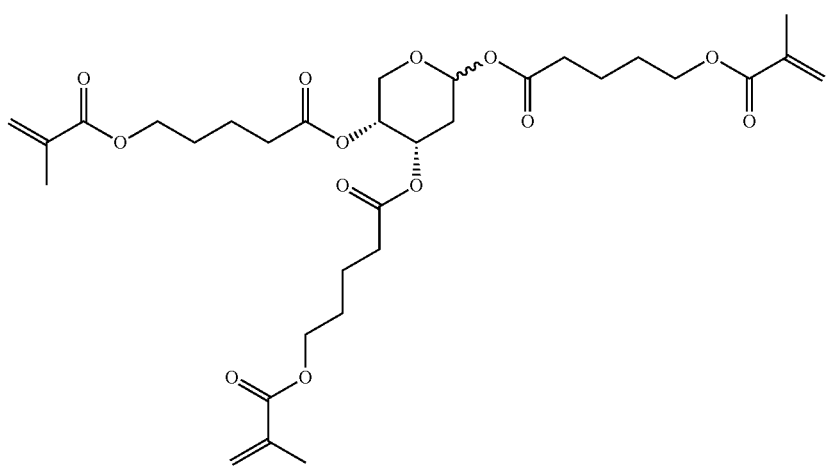 [SMILES: C=C(C)C(=O)OCCCCC(=O)OC1C[C@H](OC(=O)CCCCOC(=O)C(=C)C)[C@H](OC(=O)CCCCOC(=O)C(=C)C)CO1]

RM-79

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

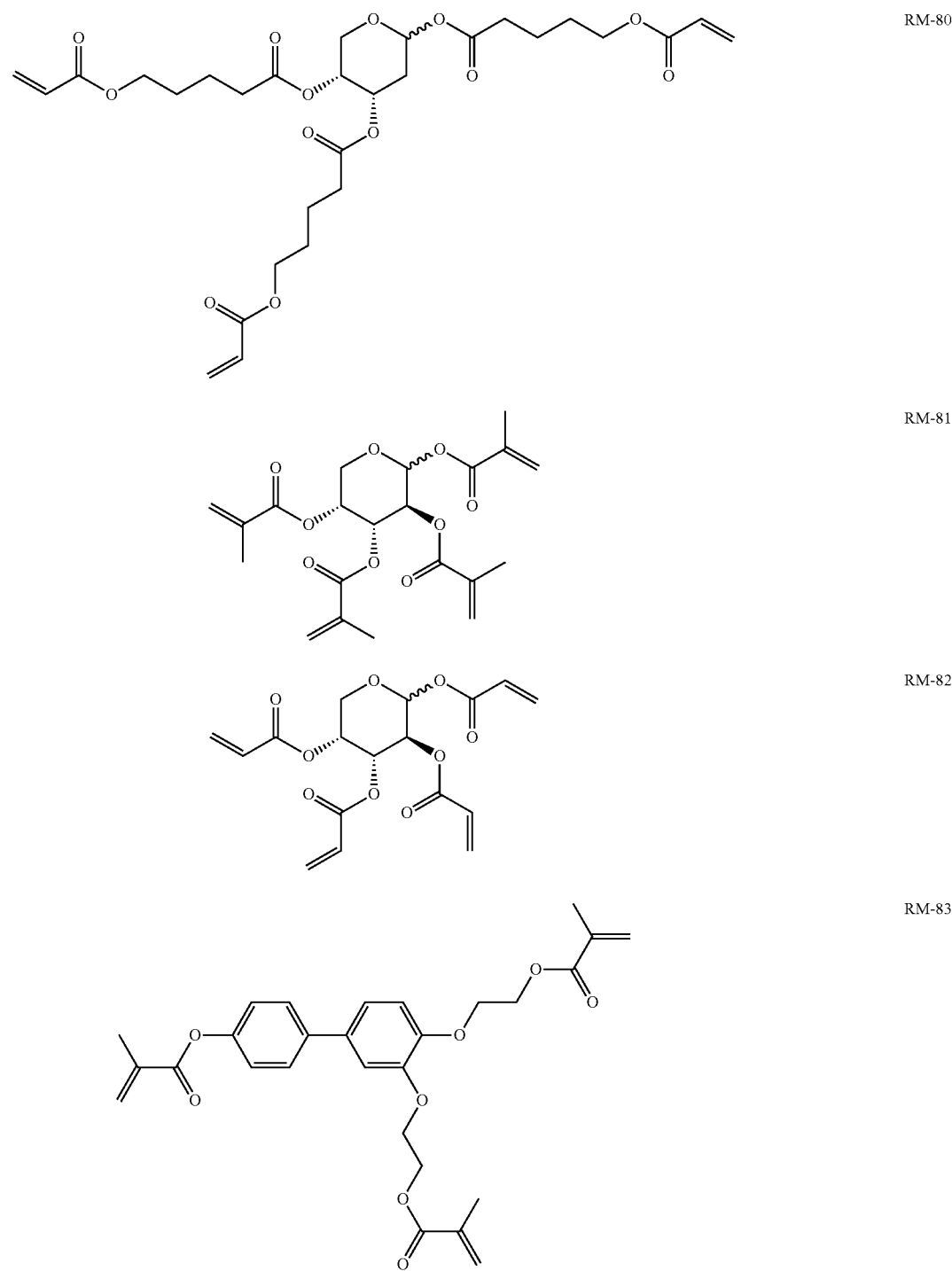

RM-80

RM-81

RM-82

RM-83

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

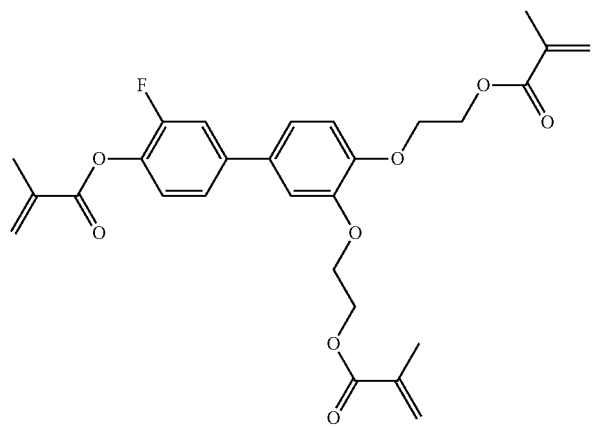 [SMILES: C=C(C)C(=O)OCCOc1ccc(-c2ccc(OC(=O)C(=C)C)c(F)c2)cc1OCCOC(=O)C(=C)C]

RM-84

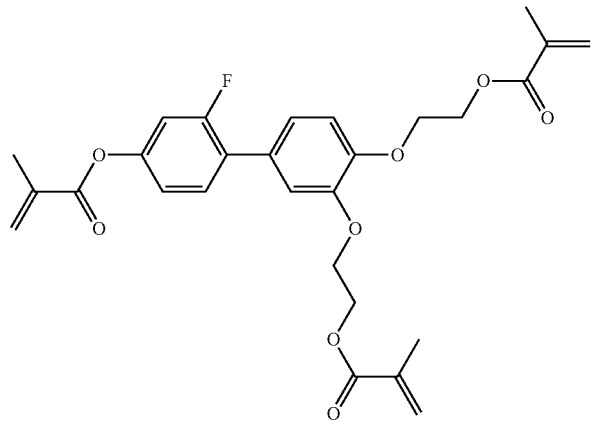 [SMILES: C=C(C)C(=O)OCCOc1ccc(-c2ccc(OC(=O)C(=C)C)cc2F)cc1OCCOC(=O)C(=C)C]

RM-85

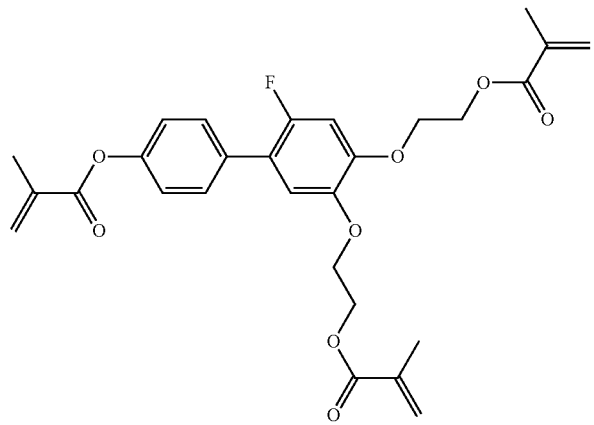

RM-86

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

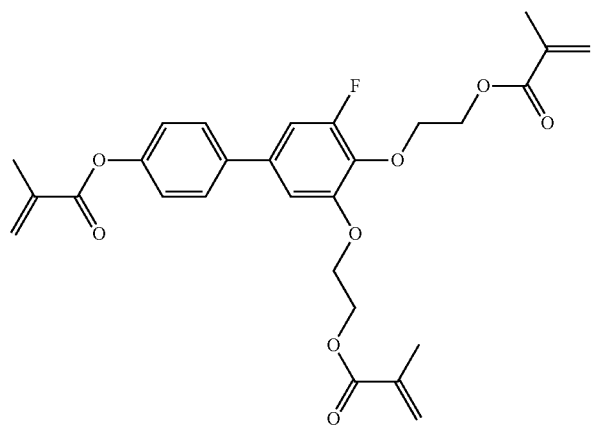 [SMILES: C=C(C)C(=O)OCCOc1cc(-c2ccc(OC(=O)C(=C)C)cc2)cc(F)c1OCCOC(=O)C(=C)C]

RM-87

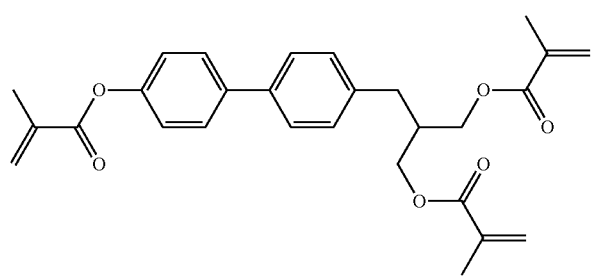 [SMILES: C=C(C)C(=O)OCC(COC(=O)C(=C)C)Cc1ccc(-c2ccc(OC(=O)C(=C)C)cc2)cc1]

RM-88

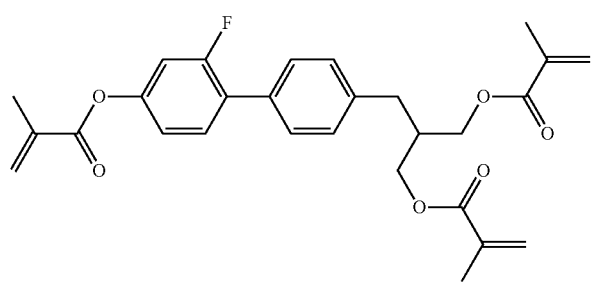 [SMILES: C=C(C)C(=O)OCC(COC(=O)C(=C)C)Cc1ccc(-c2ccc(OC(=O)C(=C)C)cc2F)cc1]

RM-89

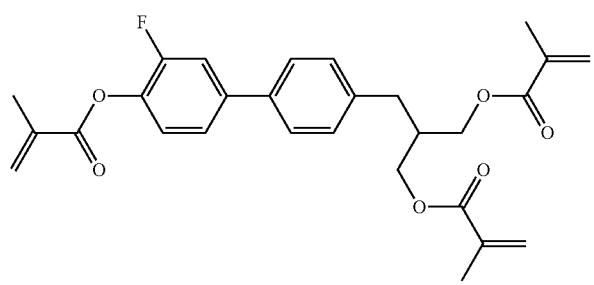 [SMILES: C=C(C)C(=O)OCC(COC(=O)C(=C)C)Cc1ccc(-c2ccc(OC(=O)C(=C)C)c(F)c2)cc1]

RM-90

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

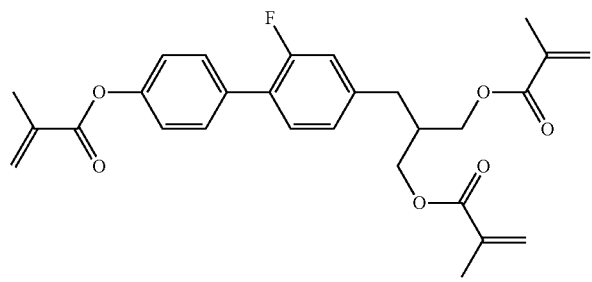 [SMILES: C=C(C)C(=O)OCC(COC(=O)C(=C)C)Cc1ccc(-c2ccc(OC(=O)C(=C)C)cc2)c(F)c1]

RM-91

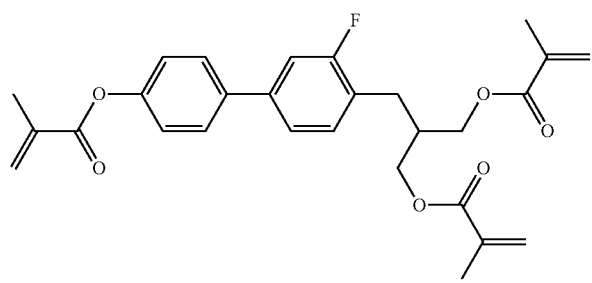 [SMILES: C=C(C)C(=O)OCC(COC(=O)C(=C)C)Cc1ccc(-c2ccc(OC(=O)C(=C)C)cc2)cc1F]

RM-92

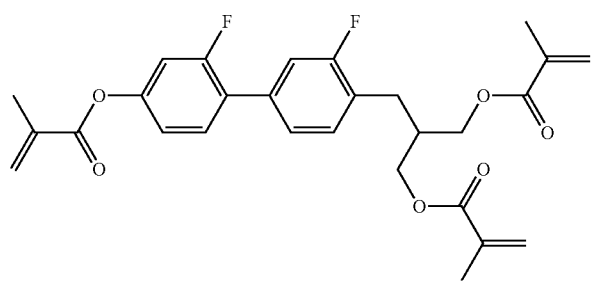 [SMILES: C=C(C)C(=O)OCC(COC(=O)C(=C)C)Cc1ccc(-c2ccc(OC(=O)C(=C)C)cc2F)cc1F]

RM-93

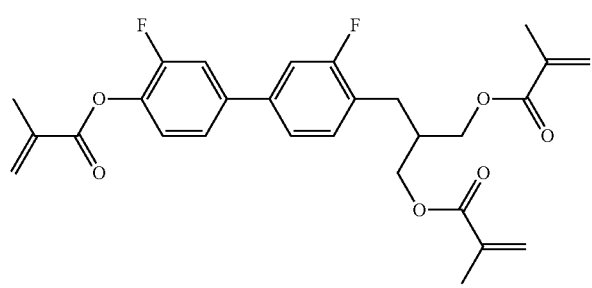 [SMILES: C=C(C)C(=O)OCC(COC(=O)C(=C)C)Cc1ccc(-c2ccc(OC(=O)C(=C)C)c(F)c2)cc1F]

RM-94

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

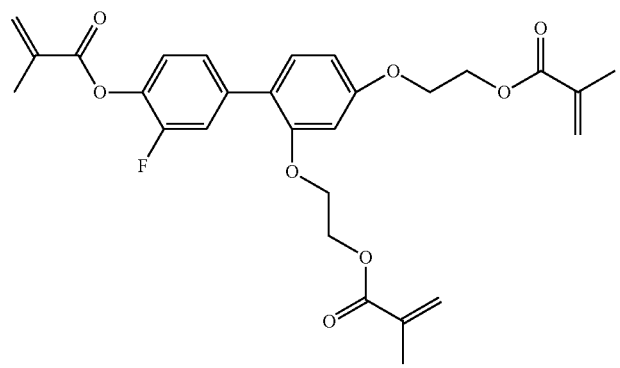 [SMILES: C=C(C)C(=O)OCCOc1ccc(-c2ccc(OC(=O)C(=C)C)c(F)c2)c(OCCOC(=O)C(=C)C)c1]
RM-95

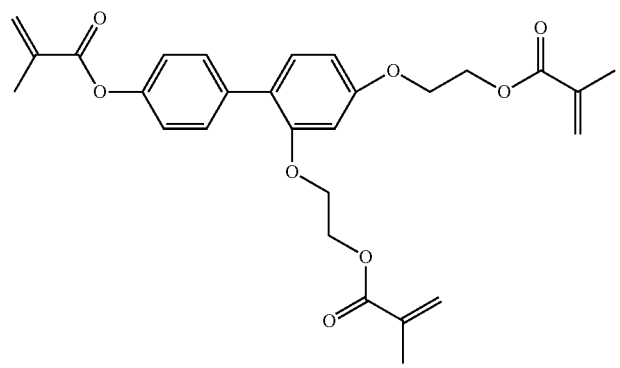 [SMILES: C=C(C)C(=O)OCCOc1ccc(-c2ccc(OC(=O)C(=C)C)cc2)c(OCCOC(=O)C(=C)C)c1]
RM-96

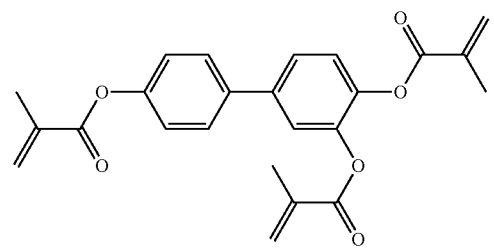 [SMILES: C=C(C)C(=O)Oc1ccc(-c2ccc(OC(=O)C(=C)C)c(OC(=O)C(=C)C)c2)cc1]
RM-97

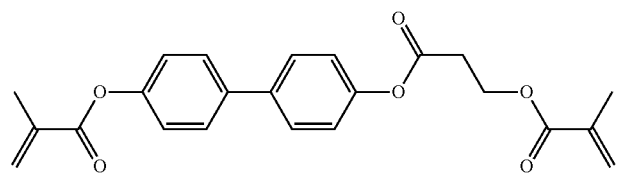 [SMILES: C=C(C)C(=O)OCCC(=O)Oc1ccc(-c2ccc(OC(=O)C(=C)C)cc2)cc1]
RM-98

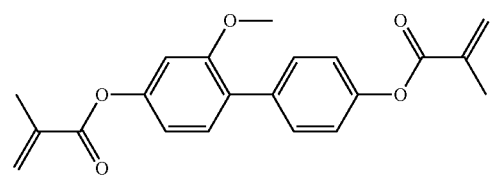
RM-99

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

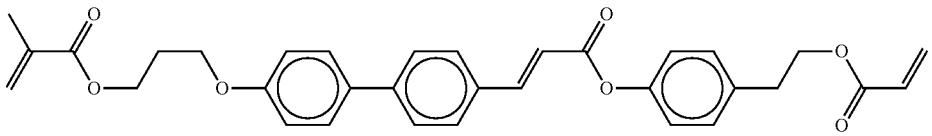
RM-100

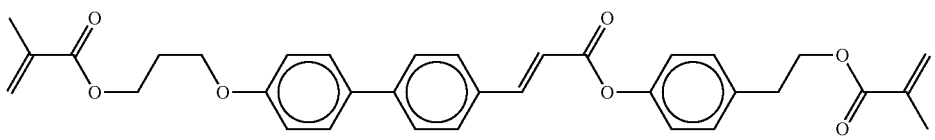
RM-101

In a preferred embodiment, the mixtures according to the invention comprise one or more polymerizable compounds, preferably selected from the polymerizable compounds of the formulae RM-1 to RM-94. Media of this type are particularly suitable for PS-FFS and PS-IPS applications. Of the reactive mesogens mentioned in Table E, compounds RM-1, RM-2, RM-3, RM-4, RM-5, RM-11, RM-17, RM-35, RM-41, RM-44, RM-62, RM-81 and RM-99 are particularly preferred.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 10 2015 009 955.8, filed Aug. 5, 2015, are incorporated by reference herein.

EXAMPLES m.p. denotes melting point, cl.p.=clearing point. Furthermore, C=crystalline state, N=nematic phase, S=smectic phase and I=isotropic phase. The data between these symbols represent the transition temperatures. Furthermore, $V_o$ denotes threshold voltage, capacitive [V] at 20° C.

$\Delta n$ denotes the optical anisotropy measured at 20° C. and 589 nm $\Delta\varepsilon$ denotes the dielectric anisotropy at 20° C. and 1 kHz cp. denotes clearing point [° C.]

$K_1$ denotes elastic constant, "splay" deformation at 20° C., [pN]

$K_3$ denotes elastic constant, "bend" deformation at 20° C., [pN]

$\gamma_1$ denotes rotational viscosity measured at 20° C. [mPa·s], determined by the transient current method in a electric field LTS denotes low-temperature stability (nematic phase), determined in glass vials.

Mixture Examples

The electro-optical data are measured in a TN cell at the 1st minimum (i.e. at a d·Δn value of 0.5 μm) at 20° C., unless expressly indicated otherwise. The optical data are measured at 20° C., unless expressly indicated otherwise. All physical properties are determined in accordance with "Merck Liquid Crystals, Physical Properties of Liquid Crystals" Status November 1997, Merck KGaA, Germany, and apply for a temperature of 20° C., unless explicitly indicated otherwise.

Example M1

| | | | |
|---|---|---|---|
| CC-3-V | 51.50% | Clearing point [° C.]: | 74 |
| CC-3-V1 | 5.00% | Δn [589 nm, 20° C.]: | 0.1175 |
| CCP-V-1 | 5.50% | Δε [1 kHz, 20° C.]: | 2.2 |
| CLP-3-T | 4.50% | $\varepsilon_{\parallel}$ [1 kHz, 20° C.]: | 4.9 |
| PGP-1-2V | 3.00% | $\varepsilon_{\perp}$ [1 kHz, 20° C.]: | 2.7 |
| PGP-2-2V | 14.50% | $\gamma_1$ [mPa · s, 20° C.]: | 45 |
| PGP-3-2V | 2.00% | $K_1$ [pN, 20° C.]: | 14.1 |
| PGU-2-F | 4.00% | $K_3$ [pN, 20° C.]: | 13.7 |
| PGUQU-3-F | 3.00% | LTS [bulk, −20° C.]: | >1000 h |
| PP-1-2V1 | 6.00% | | |
| PPGU-3-F | 1.00% | | |

Example M2

| | | | |
|---|---|---|---|
| CC-3-V | 51.50% | Clearing point [° C.]: | 73.5 |
| CC-3-V1 | 5.00% | Δn [589 nm, 20° C.]: | 0.1174 |
| CCP-V-1 | 6.00% | Δε [1 kHz, 20° C.]: | 2.2 |
| CLP-3-T | 3.50% | $\varepsilon_{\parallel}$ [1 kHz, 20° C.]: | 4.9 |
| PGP-1-2V | 3.00% | $\varepsilon_{\perp}$ [1 kHz, 20° C.]: | 2.7 |
| PGP-2-2V | 14.50% | $\gamma_1$ [mPa · s, 20° C.]: | 44 |
| PGP-3-2V | 2.00% | $K_1$ [pN, 20° C.]: | 13.9 |
| PGU-2-F | 4.50% | $K_3$ [pN, 20° C.]: | 13.6 |
| PGUQU-3-F | 3.00% | LTS [bulk, −20° C.]: | >1000 h |
| PP-1-2V1 | 6.00% | | |
| PPGU-3-F | 1.00% | | |

Example M3

| | | | |
|---|---|---|---|
| CC-3-V | 53.00% | Clearing point [° C.]: | 73.5 |
| CC-3-V1 | 3.00% | $\Delta n$ [589 nm, 20° C.]: | 0.1170 |
| CCP-V-1 | 7.00% | $\Delta\varepsilon$ [1 kHz, 20° C.]: | 2.2 |
| CLP-3-T | 3.00% | $\varepsilon_\parallel$ [1 kHz, 20° C.]: | 4.9 |
| PGP-1-2V | 3.00% | $\varepsilon_\perp$ [1 kHz, 20° C.]: | 2.7 |
| PGP-2-2V | 14.50% | $\gamma_1$ [mPa · s, 20° C.]: | 43 |
| PGP-3-2V | 2.00% | $K_1$ [pN, 20° C.]: | 13.7 |
| PGU-2-F | 5.00% | $K_3$ [pN, 20° C.]: | 13.5 |
| PGUQU-3-F | 3.00% | | |
| PP-1-2V1 | 5.50% | | |
| PPGU-3-F | 1.00% | | |

Example M4

| | | | |
|---|---|---|---|
| CC-3-V | 51.50% | Clearing point [° C.]: | 74 |
| CC-3-V1 | 5.00% | $\Delta n$ [589 nm, 20° C.]: | 0.1182 |
| CCP-V-1 | 5.00% | $\Delta\varepsilon$ [1 kHz, 20° C.]: | 2.2 |
| CLP-3-T | 4.50% | $\varepsilon_\parallel$ [1 kHz, 20° C.]: | 4.9 |
| PGP-1-2V | 3.00% | $\varepsilon_\perp$ [1 kHz, 20° C.]: | 2.7 |
| PGP-2-2V | 15.00% | $\gamma_1$ [mPa · s, 20° C.]: | 45 |
| PGP-3-2V | 2.00% | $K_1$ [pN, 20° C.]: | 14.2 |
| PGU-2-F | 4.00% | $K_3$ [pN, 20° C.]: | 13.7 |
| PGUQU-3-F | 3.00% | | |
| PP-1-2V1 | 6.00% | | |
| PPGU-3-F | 1.00% | | |

Example M5

| | | | |
|---|---|---|---|
| CC-3-V | 26.00% | Clearing point [° C.]: | 105 |
| CC-3-V1 | 10.00% | $\Delta n$ [589 nm, 20° C.]: | 0.1192 |
| CC-3-2V1 | 9.00% | $\Delta\varepsilon$ [1 kHz, 20° C.]: | 5.2 |
| CCP-V-1 | 11.00% | $\varepsilon_\parallel$ [1 kHz, 20° C.]: | 8.0 |
| CCP-V2-1 | 8.00% | $\varepsilon_\perp$ [1 kHz, 20° C.]: | 2.8 |
| CLP-3-T | 5.50% | $\gamma_1$ [mPa · s, 20° C.]: | 86 |
| PGP-2-3 | 2.50% | $K_1$ [pN, 20° C.]: | 19.6 |
| PGP-2-2V | 10.00% | $K_3$ [pN, 20° C.]: | 19.2 |
| APUQU-3-F | 6.50% | | |
| PGUQU-3-F | 2.50% | | |
| PGUQU-4-F | 6.00% | | |
| CPGU-3-OT | 3.00% | | |

Example M6

| | | | |
|---|---|---|---|
| CC-3-V | 28.00% | Clearing point [° C.]: | 102 |
| CC-3-V1 | 9.00% | $\Delta n$ [589 nm, 20° C.]: | 0.1184 |
| CC-3-2V1 | 9.00% | $\Delta\varepsilon$ [1 kHz, 20° C.]: | 5.2 |
| CCP-V-1 | 12.00% | $\varepsilon_\parallel$ [1 kHz, 20° C.]: | 8.0 |
| CCP-V2-1 | 6.00% | $\varepsilon_\perp$ [1 kHz, 20° C.]: | 2.8 |
| CLP-3-T | 6.00% | $\gamma_1$ [mPa · s, 20° C.]: | 83 |
| PGP-2-3 | 2.50% | $K_1$ [pN, 20° C.]: | 19.0 |
| PGP-2-2V | 10.00% | $K_3$ [pN, 20° C.]: | 18.7 |
| APUQU-3-F | 6.00% | LTS [bulk, −20° C.]: | >1000 h |
| PGUQU-3-F | 3.50% | | |
| PGUQU-4-F | 6.00% | | |
| CPGU-3-OT | 2.00% | | |

Example M7

| | | | |
|---|---|---|---|
| CC-3-V | 28.00% | Clearing point [° C.]: | 101 |
| CC-3-V1 | 9.50% | $\Delta n$ [589 nm, 20° C.]: | 0.1176 |
| CC-3-2V1 | 9.00% | $\Delta\varepsilon$ [1 kHz, 20° C.]: | 5.2 |
| CCP-V-1 | 12.00% | $\varepsilon_\parallel$ [1 kHz, 20° C.]: | 8.0 |
| CCP-V2-1 | 5.50% | $\varepsilon_\perp$ [1 kHz, 20° C.]: | 2.8 |
| CLP-3-T | 6.50% | $\gamma_1$ [mPa · s, 20° C.]: | 81 |
| PGP-2V | 12.50% | $K_1$ [pN, 20° C.]: | 18.7 |
| APUQU-3-F | 5.50% | $K_3$ [pN, 20° C.]: | 18.5 |
| PGUQU-3-F | 4.00% | | |
| PGUQU-4-F | 6.50% | | |
| CPGU-3-OT | 1.00% | | |

Example M8

| | | | |
|---|---|---|---|
| CC-3-V | 28.00% | Clearing point [° C.]: | 100 |
| CC-3-V1 | 10.00% | $\Delta n$ [589 nm, 20° C.]: | 0.1181 |
| CC-3-2V1 | 8.50% | $\Delta\varepsilon$ [1 kHz, 20° C.]: | 5.2 |
| CCP-V-1 | 12.00% | $\varepsilon_\parallel$ [1 kHz, 20° C.]: | 8.0 |
| CCP-V2-1 | 5.50% | $\varepsilon_\perp$ [1 kHz, 20° C.]: | 2.8 |
| CLP-3-T | 6.50% | $\gamma_1$ [mPa · s, 20° C.]: | 80 |
| PGP-2-2V | 13.00% | $K_1$ [pN, 20° C.]: | 18.6 |
| APUQU-3-F | 5.50% | $K_3$ [pN, 20° C.]: | 18.6 |
| PGUQU-3-F | 5.00% | | |
| PGUQU-4-F | 6.00% | | |

Example M9

| | | | |
|---|---|---|---|
| CC-3-V | 28.00% | Clearing point [° C.]: | 100.5 |
| CC-3-V1 | 10.00% | $\Delta n$ [589 nm, 20° C.]: | 0.1184 |
| CC-3-2V1 | 9.00% | $\Delta\varepsilon$ [1 kHz, 20° C.]: | 5.2 |
| CCP-V-1 | 11.50% | $\varepsilon_\parallel$ [1 kHz, 20° C.]: | 8.0 |
| CCP-V2-1 | 4.50% | $\varepsilon_\perp$ [1 kHz, 20° C.]: | 2.8 |
| CLP-3-T | 7.50% | $\gamma_1$ [mPa · s, 20° C.]: | 81 |
| PGP-2-2V | 13.00% | $K_1$ [pN, 20° C.]: | 19.1 |
| APUQU-3-F | 5.50% | $K_3$ [pN, 20° C.]: | 18.7 |
| PGUQU-3-F | 4.00% | | |
| PGUQU-4-F | 6.00% | | |
| CPGU-3-OT | 1.00% | | |

Example M10

| | | | |
|---|---|---|---|
| APUQU-2-F | 6.00% | Clearing point [° C.]: | 80 |
| APUQU-3-F | 4.00% | $\Delta n$ [589 nm, 20° C.]: | 0.1009 |
| CC-3-V | 41.00% | $\Delta\varepsilon$ [1 kHz, 20° C.]: | 9.5 |
| CC-3-V1 | 10.50% | $\varepsilon_\parallel$ [1 kHz, 20° C.]: | 12.7 |
| CLP-3-T | 7.00% | $\varepsilon_\perp$ [1 kHz, 20° C.]: | 3.2 |
| CCP-3OCF$_3$ | 4.50% | $\gamma_1$ [mPa · s, 20° C.]: | 69 |
| CCP-V-1 | 6.00% | $K_1$ [pN, 20° C.]: | 13.5 |
| PGUQU-3-F | 6.00% | $K_3$ [pN, 20° C.]: | 15.8 |
| PGUQU-4-F | 6.00% | | |
| PGUQU-5-F | 6.00% | | |
| PUQU-3-F | 3.00% | | |

Example M11

| | | | |
|---|---|---|---|
| APUQU-2-F | 6.00% | Clearing point [° C.]: | 79.5 |
| APUQU-3-F | 4.00% | $\Delta n$ [589 nm, 20° C.]: | 0.1006 |
| CC-3-V | 44.00% | $\Delta\varepsilon$ [1 kHz, 20° C.]: | 9.4 |

| | | | |
|---|---|---|---|
| CC-3-V1 | 6.50% | ε∥ [1 kHz, 20° C.]: | 12.6 |
| CLP-3-T | 7.00% | ε⊥ [1 kHz, 20° C.]: | 3.2 |
| CCP-3OCF₃ | 4.50% | γ₁ [mPa · s, 20° C.]: | 68 |
| CCP-V-1 | 7.00% | K₁ [pN, 20° C.]: | 13.2 |
| PGUQU-3-F | 6.00% | K₃ [pN, 20° C.]: | 15.4 |
| PGUQU-4-F | 6.00% | | |
| PGUQU-5-F | 6.00% | | |
| PUQU-3-F | 3.00% | | |

Example M12

| | | | |
|---|---|---|---|
| APUQU-2-F | 7.00% | Clearing point [° C.]: | 83.5 |
| APUQU-3-F | 5.00% | Δn [589 nm, 20° C.]: | 0.1014 |
| CC-3-V | 42.00% | Δε [1 kHz, 20° C.]: | 9.5 |
| CC-3-V1 | 9.00% | ε∥ [1 kHz, 20° C.]: | 12.7 |
| CLP-3-T | 6.00% | ε⊥ [1 kHz, 20° C.]: | 3.2 |
| CCP-3OCF₃ | 5.00% | γ₁ [mPa · s, 20° C.]: | 72 |
| CCP-V-1 | 7.00% | K₁ [pN, 20° C.]: | 13.8 |
| PGUQU-3-F | 7.00% | K₃ [pN, 20° C.]: | 16.0 |
| PGUQU-4-F | 6.00% | | |
| PGUQU-5-F | 6.00% | | |

Example M13

| | | | |
|---|---|---|---|
| APUQU-2-F | 6.00% | Clearing point [° C.]: | 83.5 |
| APUQU-3-F | 5.00% | Δn [589 nm, 20° C.]: | 0.1014 |
| CC-3-V | 40.50% | Δε [1 kHz, 20° C.]: | 9.5 |
| CC-3-V1 | 8.00% | ε∥ [1 kHz, 20° C.]: | 12.6 |
| CLP-3-T | 7.00% | ε⊥ [1 kHz, 20° C.]: | 3.2 |
| CCP-3OCF₃ | 5.00% | γ₁ [mPa · s, 20° C.]: | 73 |
| CCP-V-1 | 9.00% | K₁ [pN, 20° C.]: | 13.8 |
| PGUQU-3-F | 6.00% | K₃ [pN, 20° C.]: | 16.0 |
| PGUQU-4-F | 6.00% | | |
| PGUQU-5-F | 5.00% | | |
| PUQU-3-F | 2.50% | | |

Example M14

| | | | |
|---|---|---|---|
| APUQU-2-F | 7.00% | Clearing point [° C.]: | 83.5 |
| APUQU-3-F | 5.00% | Δn [589 nm, 20° C.]: | 0.1019 |
| CC-3-V | 42.00% | Δε [1 kHz, 20° C.]: | 9.5 |
| CC-3-V1 | 9.00% | ε∥ [1 kHz, 20° C.]: | 12.7 |
| CLP-3-T | 7.00% | ε⊥ [1 kHz, 20° C.]: | 3.2 |
| CCP-3OCF3 | 5.00% | γ₁ [mPa · s, 20° C.]: | 72 |
| CCP-V-1 | 6.50% | K₁ [pN, 20° C.]: | 14.0 |
| PGUQU-3-F | 7.00% | K₃ [pN, 20° C.]: | 15.7 |
| PGUQU-4-F | 6.00% | | |
| PGUQU-5-F | 5.50% | | |

Example M15

| | | | |
|---|---|---|---|
| CC-3-V | 28.50% | Clearing point [° C.]: | 94 |
| CC-3-V1 | 10.00% | Δn [589 nm, 20° C.]: | 0.1057 |
| CC-3-2V1 | 6.00% | Δε [1 kHz, 20° C.]: | 17.6 |
| CCP-V-1 | 6.00% | ε∥ [1 kHz, 20° C.]: | 21.5 |
| CLP-3-T | 5.50% | ε⊥ [1 kHz, 20° C.]: | 3.9 |
| APUQU-2-F | 6.00% | γ₁ [mPa · s, 20° C.]: | 111 |
| APUQU-3-F | 9.00% | K₁ [pN, 20° C.]: | 16.0 |
| PGUQU-3-F | 3.50% | K₃ [pN, 20° C.]: | 16.7 |
| CDUQU-3-F | 7.50% | | |
| DPGU-4-F | 6.00% | | |
| DGUQU-4-F | 8.00% | | |
| DGUQU-2-F | 3.00% | | |
| PGU-4-T | 1.00% | | |

Example M16

| | | | |
|---|---|---|---|
| CC-3-V | 29.00% | Clearing point [° C.]: | 94.5 |
| CC-3-V1 | 10.00% | Δn [589 nm, 20° C.]: | 0.1040 |
| CC-3-2V1 | 6.00% | Δε [1 kHz, 20° C.]: | 17.2 |
| CCP-V-1 | 6.00% | ε∥ [1 kHz, 20° C.]: | 21.1 |
| CLP-3-T | 5.50% | ε⊥ [1 kHz, 20° C.]: | 3.9 |
| APUQU-2-F | 6.00% | γ₁ [mPa · s, 20° C.]: | 108 |
| APUQU-3-F | 9.00% | K₁ [pN, 20° C.]: | 15.9 |
| PGUQU-3-F | 3.50% | K₃ [pN, 20° C.]: | 16.9 |
| CDUQU-3-F | 8.00% | | |
| DPGU-4-F | 6.00% | | |
| DGUQU-4-F | 8.00% | | |
| DGUQU-2-F | 3.00% | | |

Example M17

| | | | |
|---|---|---|---|
| CC-3-V | 29.00% | Clearing point [° C.]: | 93.5 |
| CC-3-V1 | 10.00% | Δn [589 nm, 20° C.]: | 0.1040 |
| CC-3-2V1 | 6.00% | Δε [1 kHz, 20° C.]: | 17.1 |
| CCP-V-1 | 5.00% | ε∥ [1 kHz, 20° C.]: | 20.9 |
| CLP-3-T | 7.00% | ε⊥ [1 kHz, 20° C.]: | 3.8 |
| APUQU-2-F | 6.00% | γ₁ [mPa · s, 20° C.]: | 110 |
| APUQU-3-F | 9.00% | K₁ [pN, 20° C.]: | 16.2 |
| PGUQU-3-F | 4.00% | K₃ [pN, 20° C.]: | 16.6 |
| CDUQU-3-F | 8.00% | | |
| DPGU-4-F | 5.00% | | |
| DGUQU-4-F | 8.00% | | |
| DGUQU-2-F | 3.00% | | |

Example M18

| | | | |
|---|---|---|---|
| CC-3-V | 50.00% | Clearing point [° C.]: | 77.5 |
| CC-3-V1 | 2.00% | Δn [589 nm, 20° C.]: | 0.1172 |
| CLP-3-OT | 7.50% | Δε [1 kHz, 20° C.]: | 2.3 |
| CLP-3-T | 11.00% | ε∥ [1 kHz, 20° C.]: | 4.8 |
| PGP-1-2V | 2.00% | ε⊥ [1 kHz, 20° C.]: | 2.6 |
| PGP-2-2V | 16.00% | γ₁ [mPa · s, 20° C.]: | 48 |
| PGP-3-2V | 1.00% | K₁ [pN, 20° C.]: | 17.3 |
| PGU-2-F | 2.50% | K₃ [pN, 20° C.]: | 14.4 |
| PP-1-2V1 | 8.00% | | |

Example M19

| | | | |
|---|---|---|---|
| CC-3-V | 51.50% | Clearing point [° C.]: | 75 |
| CC-3-V1 | 4.00% | Δn [589 nm, 20° C.]: | 0.1175 |
| CLP-3-OT | 6.00% | Δε [1 kHz, 20° C.]: | 2.3 |
| CLP-3-T | 7.00% | ε∥ [1 kHz, 20° C.]: | 4.9 |
| PGP-1-2V | 2.00% | ε⊥ [1 kHz, 20° C.]: | 2.7 |
| PGP-2-2V | 17.00% | γ₁ [mPa · s, 20° C.]: | 46 |
| PGP-3-2V | 2.00% | K₁ [pN, 20° C.]: | 15.6 |
| PGU-2-F | 5.50% | K₃ [pN, 20° C.]: | 13.6 |
| PP-1-2V1 | 5.00% | | |

Example M20

| | | | |
|---|---|---|---|
| CC-3-V | 53.50% | Clearing point [° C.]: | 75 |
| CC-3-V1 | 3.50% | Δn [589 nm, 20° C.]: | 0.1188 |
| CLP-3-OT | 7.00% | Δε [1 kHz, 20° C.]: | 2.3 |
| CLP-3-T | 3.00% | $\varepsilon_{\parallel}$ [1 kHz, 20° C.]: | 4.9 |
| PGP-1-2V | 2.50% | $\varepsilon_{\perp}$ [1 kHz, 20° C.]: | 2.7 |
| PGP-2-2V | 14.00% | $\gamma_1$ [mPa · s, 20° C.]: | 44 |
| PGP-3-2V | 2.00% | $K_1$ [pN, 20° C.]: | 14.5 |
| PGU-2-F | 5.00% | $K_3$ [pN, 20° C.]: | 13.8 |
| PGUQU-3-F | 3.00% | | |
| PP-1-2V1 | 5.50% | | |
| PPGU-3-F | 1.00% | | |

Example M21

| | | | |
|---|---|---|---|
| CC-3-V | 28.50% | Clearing point [° C.]: | 98.5 |
| CC-3-V1 | 10.00% | Δn [589 nm, 20° C.]: | 0.1183 |
| CC-3-2V1 | 10.00% | Δε [1 kHz, 20° C.]: | 5.2 |
| CLP-V-1 | 11.50% | $\varepsilon_{\parallel}$ [1 kHz, 20° C.]: | 7.9 |
| CCP-V-1 | 7.50% | $\varepsilon_{\perp}$ [1 kHz, 20° C.]: | 2.7 |
| CLP-3-T | 7.00% | $\gamma_1$ [mPa · s, 20° C.]: | 77 |
| PGP-2-2V | 8.00% | $K_1$ [pN, 20° C.]: | 19.6 |
| PGU-2-F | 4.00% | $K_3$ [pN, 20° C.]: | 18.2 |
| PGUQU-3-F | 6.00% | | |
| PGUQU-4-F | 6.00% | | |
| CPGU-3-OT | 1.50% | | |

Example M22

| | | | |
|---|---|---|---|
| CC-3-V | 28.50% | Clearing point [° C.]: | 98 |
| CC-3-V1 | 11.00% | Δn [589 nm, 20° C.]: | 0.1179 |
| CC-3-2V1 | 9.00% | Δε [1 kHz, 20° C.]: | 5.1 |
| CLP-V-1 | 11.50% | $\varepsilon_{\parallel}$ [1 kHz, 20° C.]: | 7.9 |
| CCP-V-1 | 8.00% | $\varepsilon_{\perp}$ [1 kHz, 20° C.]: | 2.8 |
| CLP-3-T | 7.00% | $\gamma_1$ [mPa · s, 20° C.]: | 76 |
| PGP-2-2V | 7.50% | $K_1$ [pN, 20° C.]: | 19.3 |
| PGU-2-F | 4.50% | $K_3$ [pN, 20° C.]: | 18.4 |
| PGUQU-3-F | 6.00% | | |
| PGUQU-4-F | 6.00% | | |
| CPGU-3-OT | 1.00% | | |

Example M23

| | | | |
|---|---|---|---|
| CC-3-V | 33.00% | Clearing point [° C.]: | 92 |
| CC-3-V1 | 7.00% | Δn [589 nm, 20° C.]: | 0.1042 |
| CC-3-2V1 | 4.00% | Δε [1 kHz, 20° C.]: | 16.7 |
| CLP-V-1 | 8.00% | $\varepsilon_{\parallel}$ [1 kHz, 20° C.]: | 20.5 |
| CLP-3-T | 5.50% | $\varepsilon_{\perp}$ [1 kHz, 20° C.]: | 3.8 |
| APUQU-2-F | 9.00% | $\gamma_1$ [mPa · s, 20° C.]: | 105 |
| APUQU-3-F | 9.00% | $K_1$ [pN, 20° C.]: | 15.8 |
| PGUQU-3-F | 3.50% | $K_3$ [pN, 20° C.]: | 16.4 |
| CDUQU-3-F | 8.00% | | |
| DPGU-4-F | 2.00% | | |
| DGUQU-4-F | 8.00% | | |
| DGUQU-2-F | 3.00% | | |

Example M24

| | | | |
|---|---|---|---|
| APUQU-2-F | 9.50% | Clearing point [° C.]: | 85 |
| APUQU-3-F | 7.50% | Δn [589 nm, 20° C.]: | 0.1035 |
| CC-3-V | 46.00% | Δε [1 kHz, 20° C.]: | 9.6 |
| CC-3-V1 | 6.00% | $\varepsilon_{\parallel}$ [1 kHz, 20° C.]: | 12.8 |
| CLP-3-T | 3.00% | $\varepsilon_{\perp}$ [1 kHz, 20° C.]: | 3.2 |
| CLP-V-1 | 10.00% | $\gamma_1$ [mPa · s, 20° C.]: | 70 |
| CCP-V-1 | 3.00% | $K_1$ [pN, 20° C.]: | 14.0 |
| PGUQU-3-F | 8.00% | $K_3$ [pN, 20° C.]: | 15.6 |
| PGUQU-4-F | 7.00% | | |

Example M25

| | | | |
|---|---|---|---|
| APUQU-2-F | 9.00% | Clearing point [° C.]: | 84 |
| APUQU-3-F | 7.50% | Δn [589 nm, 20° C.]: | 0.1013 |
| CC-3-V | 42.50% | Δε [1 kHz, 20° C.]: | 9.4 |
| CC-3-V1 | 11.00% | $\varepsilon_{\parallel}$ [1 kHz, 20° C.]: | 12.6 |
| CCP-V-1 | 6.50% | $\varepsilon_{\perp}$ [1 kHz, 20° C.]: | 3.2 |
| CLP-3-T | 4.00% | $\gamma_1$ [mPa · s, 20° C.]: | 70 |
| CLP-V-1 | 4.50% | $K_1$ [pN, 20° C.]: | 13.9 |
| PGUQU-3-F | 8.00% | $K_3$ [pN, 20° C.]: | 16.0 |
| PGUQU-4-F | 5.00% | | |
| PGUQU-5-F | 2.00% | | |

Example M26

| | | | |
|---|---|---|---|
| CC-3-V | 51.50% | Clearing point [° C.]: | 74 |
| CC-3-V1 | 5.00% | Δn [589 nm, 20° C.]: | 0.1174 |
| CCP-V-1 | 5.00% | Δε [1 kHz, 20° C.]: | 2.2 |
| CLP-3-OT | 4.50% | $\varepsilon_{\parallel}$ [1 kHz, 20° C.]: | 4.9 |
| PGP-1-2V | 3.00% | $\varepsilon_{\perp}$ [1 kHz, 20° C.]: | 2.7 |
| PGP-2-2V | 14.50% | $\gamma_1$ [mPa · s, 20° C.]: | 44 |
| PGP-3-2V | 2.00% | $K_1$ [pN, 20° C.]: | 13.7 |
| PGU-2-F | 4.00% | $K_3$ [pN 20° C.]: | 13.6 |
| PGUQU-3-F | 3.50% | LTS [bulk, −20° C.]: | >1000 h |
| PP-1-2V1 | 6.00% | | |
| PPGU-3-F | 1.00% | | |

Example M26a

Liquid-crystalline mixture M26 is additionally stabilized with 300 ppm of the compound of the formula ST-2
300 ppm of

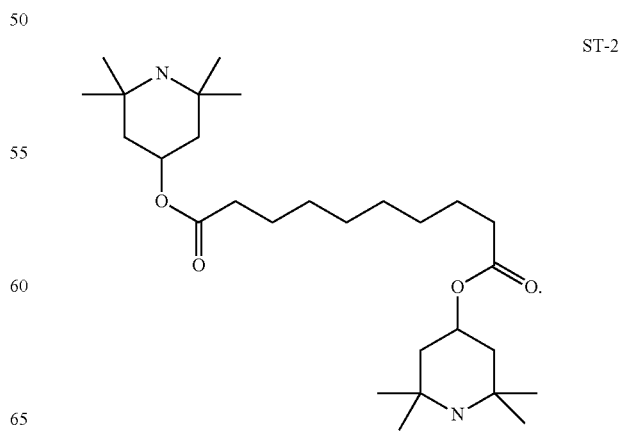

ST-2

Example M27

| | | | |
|---|---|---|---|
| CC-3-V | 51.50% | Clearing point [° C.]: | 73.5 |
| CC-3-V1 | 5.00% | Δn [589 nm, 20° C.]: | 0.1174 |
| CCP-V-1 | 6.00% | Δε [1 kHz, 20° C.]: | 2.2 |
| CLP-3-T | 3.50% | $\varepsilon_{\parallel}$ [1 kHz, 20° C.]: | 4.9 |
| PGP-1-2V | 3.00% | $\varepsilon_{\perp}$ [1 kHz, 20° C.]: | 2.7 |
| PGP-2-2V | 14.50% | $\gamma_1$ [mPa · s, 20° C.]: | 44 |
| PGP-3-2V | 2.00% | $K_1$ [pN, 20° C.]: | 13.9 |
| PGU-2-F | 4.50% | $K_3$ [pN, 20° C.]: | 13.6 |
| PGUQU-3-F | 3.00% | LTS [bulk, −20° C.]: | >1000 h |
| PP-1-2V1 | 6.00% | | |
| PPGU-3-F | 1.00% | | |

Example M27a

Liquid-crystalline mixture M27 is additionally stabilized with 300 ppm of the compound of the formula ST-2

300 ppm of

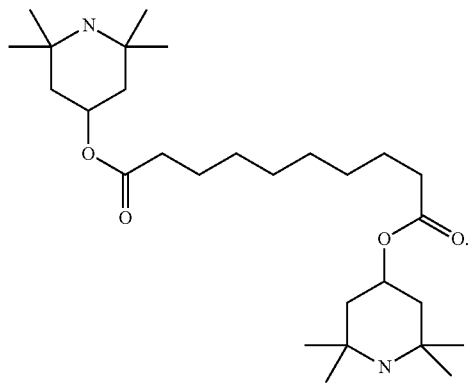

ST-2

Example M28

| | | | |
|---|---|---|---|
| CC-3-V | 48.00% | Clearing point [° C.]: | 88 |
| CCP-V-1 | 12.00% | Δn [589 nm, 20° C.]: | 0.1154 |
| CCP-V2-1 | 5.00% | Δε [1 kHz, 20° C.]: | 3.5 |
| PP-1-2V1 | 1.00% | $\varepsilon_{\parallel}$ [1 kHz, 20° C.]: | 6.3 |
| PGP-1-2V | 5.00% | $\varepsilon_{\perp}$ [1 kHz, 20° C.]: | 2.8 |
| PGP-2-2V | 7.50% | $\gamma_1$ [mPa · s, 20° C.]: | 59 |
| PGP-3-2V | 4.00% | $K_1$ [pN, 20° C.]: | 15.0 |
| CLP-3-T | 5.00% | $K_3$ [pN, 20° C.]: | 15.7 |
| PGUQU-4-F | 5.50% | LTS [bulk, −20° C.]: | >1000 h |
| APUQU-3-F | 4.00% | | |
| PGU-2-F | 3.00% | | |

Example M28a

Liquid-crystalline mixture M28 is additionally stabilized with 400 ppm of the compound of the formula ST-1 and 1000 ppm of the compound of the formula ST-2

400 ppm of

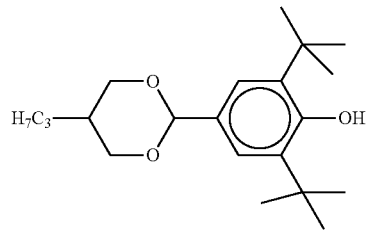

ST-1

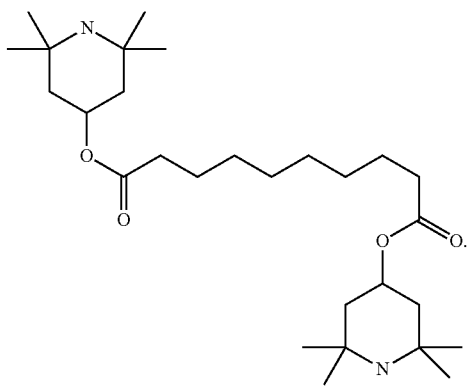

ST-2 and
1000 ppm of

Example M29

| | | | |
|---|---|---|---|
| CC-3-V | 49.50% | Clearing point [° C.]: | 89.5 |
| CCP-V-1 | 5.00% | Δn [589 nm, 20° C.]: | 0.1172 |
| CLP-V-1 | 8.50% | Δε [1 kHz, 20° C.]: | 3.5 |
| PP-1-2V1 | 1.00% | $\varepsilon_{\parallel}$ [1 kHz, 20° C.]: | 6.3 |
| PGP-1-2V | 5.00% | $\varepsilon_{\perp}$ [1 kHz, 20° C.]: | 2.8 |
| PGP-2-2V | 8.00% | $\gamma_1$ [mPa · s, 20° C.]: | 57 |
| PGP-3-2V | 4.50% | $K_1$ [pN, 20° C.]: | 15.2 |
| CCP-3OCF$_3$ | 6.50% | $K_3$ [pN, 20° C.]: | 15.8 |
| PGUQU-4-F | 5.00% | | |
| PGUQU-5-F | 2.50% | | |
| APUQU-3-F | 4.50% | | |

Example M29a

Liquid-crystalline mixture M29 is additionally stabilized with 400 ppm of the compound of the formula ST-1 and 1000 ppm of the compound of the formula ST-2

400 ppm of

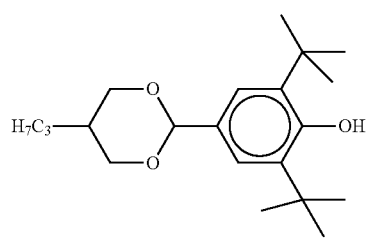

ST-1

-continued

ST-2

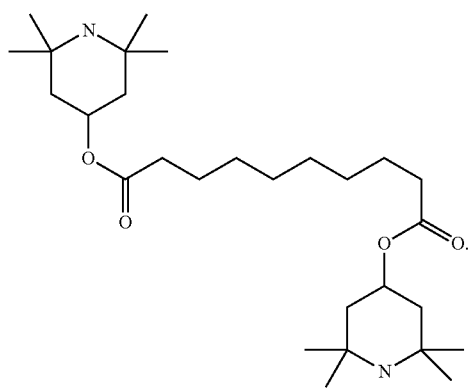

and
1000 ppm of

-continued

ST-2

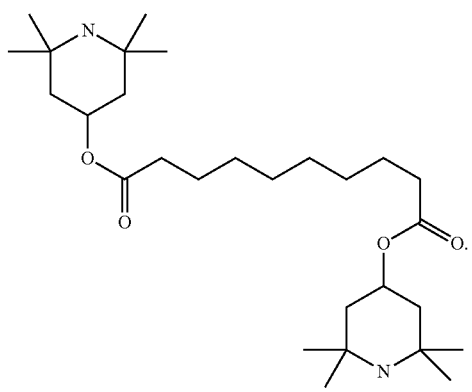

and
1000 ppm of

Example M30

| CC-3-V | 52.00% | Clearing point [° C.]: | 85.5 |
|---|---|---|---|
| CLP-V-1 | 11.50% | Δn [589 nm, 20° C.]: | 0.1187 |
| PP-1-2V1 | 3.00% | Δε [1 kHz, 20° C.]: | 3.5 |
| PGP-1-2V | 5.00% | $\varepsilon_\parallel$ [1 kHz, 20° C.]: | 6.2 |
| PGP-2-2V | 8.00% | $\varepsilon_\perp$ [1 kHz, 20° C.]: | 2.7 |
| PGP-3-2V | 3.00% | $\gamma_1$ [mPa · s, 20° C.]: | 56 |
| CLP-3-T | 7.00% | $K_1$ [pN, 20° C.]: | 16.2 |
| PGUQU-4-F | 5.00% | $K_3$ [pN, 20° C.]: | 15.4 |
| PGUQU-5-F | 2.50% | LTS [bulk, −20° C.]: | >1000 h |
| APUQU-3-F | 3.00% | | |

Example M31

| CC-3-V | 51.50% | Clearing point [° C.]: | 85.5 |
|---|---|---|---|
| CLP-V-1 | 11.50% | Δn [589 nm, 20° C.]: | 0.1175 |
| PP-1-2V1 | 3.00% | Δε [1 kHz, 20° C.]: | 4.1 |
| PGP-1-2V | 5.00% | $\varepsilon_\parallel$ [1 kHz, 20° C.]: | 6.8 |
| PGP-2-2V | 6.00% | $\varepsilon_\perp$ [1 kHz, 20° C.]: | 2.8 |
| PGP-3-2V | 3.00% | $\gamma_1$ [mPa · s, 20° C.]: | 58 |
| CLP-3-T | 7.00% | $K_1$ [pN, 20° C.]: | 16.0 |
| PGUQU-4-F | 5.00% | $K_3$ [pN, 20° C.]: | 15.5 |
| PGUQU-5-F | 5.00% | LTS [bulk, −20° C.]: | >1000 h |
| APUQU-3-F | 3.00% | | |

Example M30a

Liquid-crystalline mixture M30 is additionally stabilized with 400 ppm of the compound of the formula ST-1 and 1000 ppm of the compound of the formula ST-2

400 ppm of

ST-1

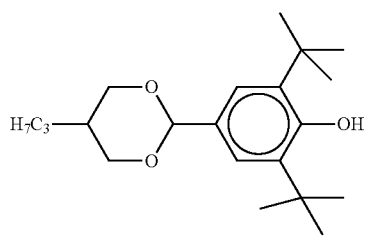

Example M31a

Liquid-crystalline mixture M31 is additionally stabilized with 400 ppm of the compound of the formula ST-1 and 1000 ppm of the compound of the formula ST-2

400 ppm of

ST-1

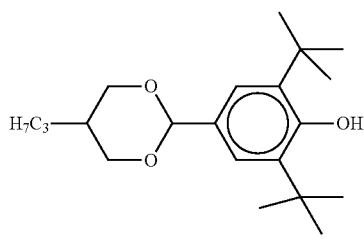

-continued

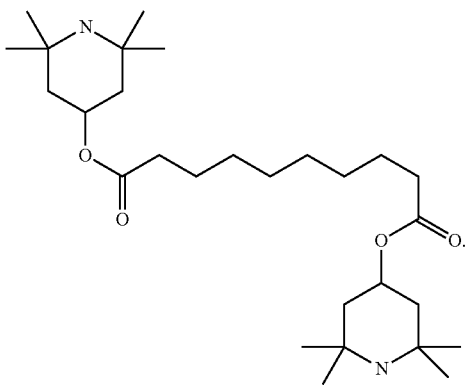

and
1000 ppm of

Example M32

| | | | |
|---|---|---|---|
| CC-3-V | 41.00% | Clearing point [° C.]: | 81 |
| B-5O-OT | 4.50% | Δn [589 nm, 20° C.]: | 0.1060 |
| B-2O-O5 | 6.00% | Δε [1 kHz, 20° C.]: | 4.6 |
| CCP-V-1 | 15.50% | ε∥ [1 kHz, 20° C.]: | 9.0 |
| CLP-V-1 | 6.00% | ε⊥ [1 kHz, 20° C.]: | 4.4 |
| PGP-2-2V | 2.00% | $\gamma_1$ [mPa · s, 20° C.]: | 64 |
| CCP-3OCF$_3$ | 7.50% | $K_1$ [pN, 20° C.]: | 14.5 |
| PUQU-3-F | 3.00% | $K_3$ [pN, 20° C.]: | 13.9 |
| PGU-3-F | 5.00% | $V_0$ [V, 20° C.]: | 1.88 |
| DGUQU-4-F | 5.00% | | |
| DPGU-4-F | 4.50% | | |

Example M33

| | | | |
|---|---|---|---|
| CC-3-V | 42.00% | Clearing point [° C.]: | 80.5 |
| B-5O-OT | 4.50% | Δn [589 nm, 20° C.]: | 0.1047 |
| B-2O-O5 | 6.00% | Δε [1 kHz, 20° C.]: | 4.5 |
| CCP-V-1 | 15.50% | ε∥ [1 kHz, 20° C.]: | 8.9 |
| CCP-V2-1 | 8.00% | ε⊥ [1 kHz, 20° C.]: | 4.4 |
| PGP-2-2V | 2.00% | $\gamma_1$ [mPa · s, 20° C.]: | 66 |
| CLP-3-T | 4.50% | $K_1$ [pN, 20° C.]: | 14.4 |
| PUQU-3-F | 3.00% | $K_3$ [pN, 20° C.]: | 14.0 |
| PGU-3-F | 5.00% | $V_0$ [V, 20° C.]: | 1.89 |
| DGUQU-4-F | 5.00% | | |
| DPGU-4-F | 4.50% | | |

Example M34

| | |
|---|---|
| CC-3-V | 33.00% |
| CC-3-V1 | 5.00% |
| B-2O-O5 | 4.00% |
| B(S)-2O-O4 | 3.00% |
| B(S)-2O-O5 | 4.00% |
| CLP-3-T | 3.00% |
| CCP-3OCF$_3$ | 3.00% |
| CCP-V-1 | 13.00% |
| CCP-V2-1 | 6.00% |
| CCVC-3-V | 5.00% |
| PUQU-3-F | 6.00% |
| CPGP-5-2 | 4.00% |
| APUQU-2-F | 2.50% |
| APUQU-3-F | 2.00% |

ST-2

| | |
|---|---|
| CDUQU-3-F | 2.50% |
| DGUQU-4-F | 2.00% |
| DPGU-4-F | 1.50% |
| PPGU-3-F | 0.50% |

Example M35

| | |
|---|---|
| CC-3-V | 30.00% |
| CC-3-V1 | 5.00% |
| B-2O-O5 | 4.00% |
| B(S)-2O-O4 | 6.00% |
| B(S)-2O-O5 | 6.00% |
| CLP-3-T | 3.00% |
| CCP-3OCF$_3$ | 5.00% |
| CCP-V-1 | 13.00% |
| CCP-V2-1 | 1.50% |
| CCVC-3-V | 5.00% |
| PUQU-3-F | 6.00% |
| CPGP-5-2 | 4.00% |
| APUQU-2-F | 2.50% |
| APUQU-3-F | 2.50% |
| CDUQU-3-F | 2.50% |
| DGUQU-4-F | 2.00% |
| DPGU-4-F | 1.50% |
| PPGU-3-F | 0.50% |

Example M36

| | |
|---|---|
| CC-3-V | 34.00% |
| CC-3-V1 | 7.50% |
| B-2O-O5 | 4.00% |
| B(S)-2O-O4 | 3.00% |
| B(S)-2O-O5 | 4.00% |
| CCP-3OCF$_3$ | 5.00% |
| CLP-3-T | 5.00% |
| CCP-V-1 | 13.00% |
| PUQU-3-F | 4.00% |
| APUQU-2-F | 5.00% |
| APUQU-3-F | 4.00% |
| CDUQU-3-F | 3.50% |
| DGUQU-4-F | 3.00% |
| DPGU-4-F | 2.00% |
| PPGU-3-F | 0.50% |
| CPGP-5-2 | 2.50% |

Example M37

| | |
|---|---|
| CC-3-V | 31.50% |
| CC-3-V1 | 7.50% |
| B-2O-O5 | 4.00% |
| B(S)-2O-O4 | 6.00% |
| B(S)-2O-O5 | 6.00% |
| CCP-3OCF$_3$ | 5.00% |
| CLP-3-T | 5.00% |
| CCP-V-1 | 9.50% |
| PUQU-3-F | 4.00% |
| APUQU-2-F | 4.00% |
| APUQU-3-F | 4.50% |
| CDUQU-3-F | 5.00% |
| DGUQU-4-F | 3.00% |
| DPGU-4-F | 2.00% |
| PPGU-3-F | 0.50% |
| CPGP-5-2 | 2.50% |

Example M38

| | |
|---|---|
| Y-4O-O4 | 10.50% |
| CC-3-V | 25.00% |
| CCP-3OCF$_3$ | 5.00% |
| CLP-3-T | 5.00% |
| CCP-V-1 | 14.00% |
| CCP-V2-1 | 4.50% |
| PGP-2-2V | 6.50% |
| DGUQU-4-F | 5.00% |
| DPGU-4-F | 5.00% |
| APUQU-2-F | 7.00% |
| APUQU-3-F | 8.00% |
| PGUQU-4-F | 4.00% |
| PPGU-3-F | 0.50% |

Example M39

| | |
|---|---|
| Y-4O-O4 | 10.50% |
| CC-3-V | 22.00% |
| B(S)-2O-O4 | 3.00% |
| B(S)-2O-O5 | 4.00% |
| CCP-3OCF$_3$ | 5.00% |
| CLP-3-T | 5.00% |
| CCP-V-1 | 13.00% |
| CCP-V2-1 | 6.00% |
| DGUQU-4-F | 5.00% |
| DPGU-4-F | 5.00% |
| APUQU-2-F | 7.00% |
| APUQU-3-F | 7.00% |
| CDUQU-3-F | 3.00% |
| PGUQU-4-F | 4.00% |
| PPGU-3-F | 0.50% |

Example M40

| | | | |
|---|---|---|---|
| CC-3-V | 49.00% | Clearing point [° C.]: | 80.5 |
| CC-3-V1 | 12.00% | Δn [589 nm, 20° C.]: | 0.0930 |
| CCP-V-1 | 10.00% | Δε [1 kHz, 20° C.]: | 2.7 |
| CLP-V-1 | 7.00% | ε$_\parallel$ [1 kHz, 20° C.]: | 5.3 |
| PGP-2-2V | 5.50% | ε$_\perp$ [1 kHz, 20° C.]: | 2.6 |
| CLP-3-T | 4.00% | γ$_1$ [mPa · s, 20° C.]: | 48 |
| PGUQU-3-F | 3.00% | K$_1$ [pN, 20° C.]: | 14.9 |
| APUQU-2-F | 6.00% | K$_3$ [pN, 20° C.]: | 16.0 |
| PP-1-2V1 | 3.00% | | |
| PPGU-3-F | 0.50% | | |

Liquid-crystalline mixture M40 is additionally stabilized with 400 ppm of the compound of the formula ST-1 and various concentrations of the compound of the formula ST-2 or ST-3:

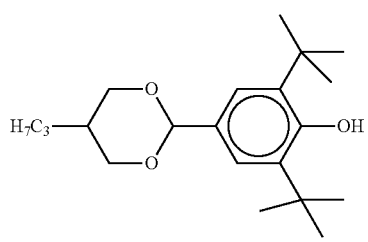

ST-1

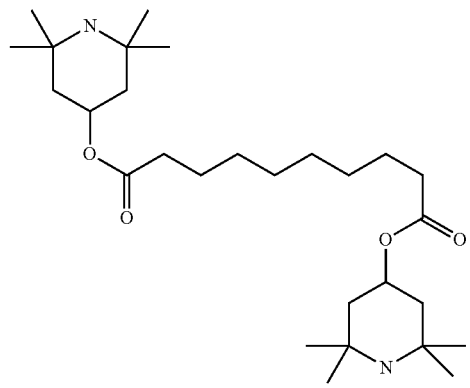

ST-2

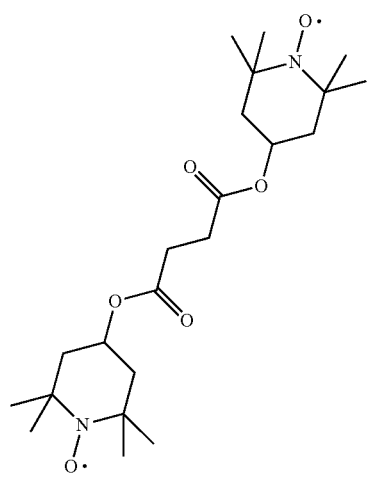

ST-3

| Mixture | ST-1 | ST-2 | ST-3 |
|---|---|---|---|
| Example M40a | 400 ppm | — | — |
| Example M40b | 400 ppm | 100 ppm | — |
| Example M40c | 400 ppm | 500 ppm | — |
| Example M40d | 400 ppm | 1000 ppm | — |
| Example M40e | 400 ppm | — | 100 ppm |
| Example M40f | 400 ppm | — | 500 ppm |
| Example M40g | 400 ppm | — | 1000 ppm |

Example M41

| | |
|---|---|
| CC-3-V | 42.50% |
| B-2O-O5 | 3.50% |
| B(S)-2O-O4 | 4.00% |
| B(S)-2O-O5 | 4.00% |
| CCP-3OCF$_3$ | 5.00% |
| CLP-3-T | 5.00% |
| CCP-V-1 | 1.50% |
| DGUQU-4-F | 5.00% |
| DPGU-4-F | 4.00% |
| APUQU-2-F | 7.00% |
| APUQU-3-F | 7.00% |
| CDUQU-3-F | 2.00% |
| PGUQU-3-F | 4.00% |
| PGUQU-4-F | 5.00% |
| PPGU-3-F | 0.50% |

Example M42

| | | | |
|---|---|---|---|
| CC-3-V | 43.00% | Clearing point [° C.]: | 80 |
| B-5O-OT | 5.00% | $\Delta n$ [589 nm, 20° C.]: | 0.1048 |
| B-2O-O5 | 5.50% | $\Delta\varepsilon$ [1 kHz, 20° C.]: | 4.6 |
| CCP-V-1 | 15.00% | $\varepsilon_\parallel$ [1 kHz, 20° C.]: | 9.0 |
| CCP-V2-1 | 6.00% | $\varepsilon_\perp$ [1 kHz, 20° C.]: | 4.4 |
| PGP-2-2V | 2.50% | $K_1$ [pN, 20° C.]: | 14.3 |
| CLP-3-T | 6.00% | $K_3$ [pN, 20° C.]: | 13.9 |
| PGU-3-F | 7.00% | $V_0$ [V, 20° C.]: | 1.88 |
| DGUQU-4-F | 5.50% | | |
| DPGU-4-F | 4.50% | | |

Example M43

| | |
|---|---|
| APUQU-2-F | 4.00% |
| APUQU-3-F | 5.50% |
| B-2O-O5 | 4.00% |
| CC-3-V | 22.00% |
| CC-3-V1 | 4.00% |
| CCP-3-1 | 4.00% |
| CCP-3OCF$_3$ | 8.00% |
| CCP-V-1 | 6.50% |
| CDUQU-3-F | 4.50% |
| DGUQU-4-F | 5.00% |
| DPGU-4-F | 3.00% |
| PGUQU-3-F | 3.00% |
| PPGU-3-F | 0.50% |
| PY-3-O2 | 9.50% |
| Y-4O-O4 | 5.00% |
| CCY-3-O2 | 4.50% |
| CLP-3-T | 5.00% |
| PGP-2-2V | 2.00% |

Example M44

| | |
|---|---|
| APUQU-2-F | 4.00% |
| APUQU-3-F | 5.00% |
| B-2O-O5 | 3.50% |
| CC-3-V | 33.00% |
| PP-2-2V1 | 2.00% |
| B(S)-2O-O4 | 4.00% |
| CC-3-V1 | 4.00% |
| CLP-3-T | 5.00% |
| B(S)-2O-O5 | 4.00% |
| CCP-3OCF$_3$ | 8.00% |
| CCP-V-1 | 5.00% |
| CDUQU-3-F | 4.00% |
| DGUQU-4-F | 5.00% |
| DPGU-4-F | 3.00% |
| PGUQU-3-F | 3.00% |
| PGUQU-4-F | 3.00% |
| PPGU-3-F | 1.50% |
| Y-4O-O4 | 3.00% |

Example M45

| | |
|---|---|
| APUQU-2-F | 4.00% |
| APUQU-3-F | 5.00% |
| B-2O-O5 | 3.50% |
| CC-3-V | 33.00% |
| PP-1-2V1 | 2.00% |
| B(S)-2O-O4 | 4.00% |
| CC-3-V1 | 4.00% |
| CLP-3-T | 5.00% |
| B(S)-2O-O5 | 4.00% |
| CCP-3OCF$_3$ | 8.00% |
| CCP-V-1 | 5.00% |
| CDUQU-3-F | 4.00% |
| DGUQU-4-F | 5.00% |
| DPGU-4-F | 3.00% |
| PGUQU-3-F | 3.00% |
| PGUQU-4-F | 3.00% |
| PPGU-3-F | 1.50% |
| Y-4O-O4 | 3.00% |

Example M46

| | | | |
|---|---|---|---|
| Y-4O-O4 | 10.50% | Clearing point [° C.]: | 81 |
| CC-3-V | 25.00% | $\Delta n$ [589 nm, 20° C.]: | 0.1141 |
| CCP-3OCF$_3$ | 6.00% | $\Delta\varepsilon$ [1 kHz, 20° C.]: | 10.6 |
| CLP-3-T | 3.50% | $\varepsilon_\parallel$ [1 kHz, 20° C.]: | 15.7 |
| CCP-V-1 | 14.00% | $\varepsilon_\perp$ [1 kHz, 20° C.]: | 5.1 |
| CCP-V2-1 | 4.50% | $\gamma_1$ [mPa·s, 20° C.]: | 87 |
| PGP-2-2V | 6.00% | $K_1$ [pN, 20° C.]: | 13.3 |
| DGUQU-4-F | 6.00% | $K_3$ [pN, 20° C.]: | 12.8 |
| DPGU-4-F | 5.00% | $V_0$ [V, 20° C.]: | 1.17 |
| APUQU-2-F | 7.00% | | |
| APUQU-3-F | 8.00% | | |
| PGUQU-4-F | 4.00% | | |
| PPGU-3-F | 0.50% | | |

Example M47

| | | | |
|---|---|---|---|
| Y-4O-O4 | 5.00% | Clearing point [° C.]: | 81 |
| CC-3-V | 21.50% | $\Delta n$ [589 nm, 20° C.]: | 0.1120 |
| CC-3-V1 | 4.00% | $\Delta\varepsilon$ [1 kHz, 20° C.]: | 7.9 |
| B-2O-O5 | 4.00% | $\varepsilon_\parallel$ [1 kHz, 20° C.]: | 14.0 |
| PY-3-O2 | 9.50% | $\varepsilon_\perp$ [1 kHz, 20° C.]: | 6.2 |
| CCP-3OCF$_3$ | 6.00% | $\gamma_1$ [mPa·s, 20° C.]: | 99 |
| CCP-V-1 | 14.00% | $K_1$ [pN, 20° C.]: | 14.3 |
| CCP-V2-1 | 1.50% | $K_3$ [pN, 20° C.]: | 13.9 |
| CLP-3-T | 4.00% | $V_0$ [V, 20° C.]: | 1.42 |
| CCY-3-O2 | 4.50% | | |
| APUQU-2-F | 4.00% | | |
| APUQU-3-F | 5.00% | | |
| CDUQU-3-F | 4.00% | | |
| DGUQU-4-F | 5.00% | | |
| DPGU-4-F | 3.50% | | |
| PGUQU-3-F | 4.00% | | |
| PPGU-3-F | 0.50% | | |

Example M48

| | |
|---|---|
| Y-4O-O4 | 7.00% |
| CC-3-V | 28.00% |
| B-2O-O5 | 4.00% |
| B(S)-2O-O4 | 3.50% |
| B(S)-2O-O5 | 4.00% |
| CCP-3OCF$_3$ | 6.50% |
| CCP-V-1 | 15.00% |
| PGP-2-2V | 4.00% |
| CLP-3-T | 4.00% |
| APUQU-2-F | 5.00% |
| APUQU-3-F | 6.50% |
| CDUQU-3-F | 4.50% |
| DGUQU-4-F | 5.00% |
| DPGU-4-F | 3.50% |
| PPGU-3-F | 0.50% |

Example M49

| | |
|---|---|
| Y-4O-O4 | 10.50% |
| CC-3-V | 24.00% |
| CCP-30CF$_3$ | 6.00% |
| CLP-3-T | 4.00% |
| CCP-V-1 | 13.00% |
| CCP-V2-1 | 5.00% |
| PGP-2-2V | 7.00% |
| DGUQU-4-F | 5.00% |
| DPGU-4-F | 3.50% |
| APUQU-2-F | 6.50% |
| APUQU-3-F | 7.50% |
| CDUQU-3-F | 3.50% |
| PGUQU-4-F | 4.00% |
| PPGU-3-F | 0.50% |

Example M50

| | | | |
|---|---|---|---|
| CC-3-V | 48.00% | Clearing point [° C.]: | 79.5 |
| CC-3-V1 | 10.50% | Δn [589 nm, 20° C.]: | 0.0930 |
| CCP-V-1 | 11.00% | Δε [1 kHz, 20° C.]: | 2.7 |
| CCP-V2-1 | 6.00% | $\varepsilon_{\|\|}$ [1 kHz, 20° C.]: | 5.3 |
| CLP-3-T | 5.50% | $\varepsilon_\perp$ [1 kHz, 20° C.]: | 2.6 |
| PGP-2-2V | 5.00% | $\gamma_1$ [mPa · s, 20° C.]: | 49 |
| PGUQU-3-F | 4.00% | K$_1$ [pN, 20° C.]: | 14.7 |
| APUQU-2-F | 4.50% | K$_3$ [pN, 20° C.]: | 16.3 |
| PP-1-2V1 | 5.00% | | |
| PPGU-3-F | 0.50% | | |

Liquid-crystalline mixture M50 is additionally stabilized with 400 ppm of the compound of the formula ST-1 and various concentrations of the compounds of the formula ST-2 or ST-3:

| Mixture | ST-1 | ST-2 | ST-3 |
|---|---|---|---|
| Example M50a | 400 ppm | — | — |
| Example M50b | 400 ppm | 100 ppm | — |
| Example M50c | 400 ppm | 500 ppm | — |
| Example M50d | 400 ppm | 1000 ppm | — |
| Example M50e | 400 ppm | — | 100 ppm |
| Example M50f | 400 ppm | — | 500 ppm |
| Example M50g | 400 ppm | — | 1000 ppm |

Example M51

| | | | |
|---|---|---|---|
| CC-3-V | 48.00% | Clearing point [° C.]: | 80.5 |
| CC-3-V1 | 12.00% | Δn [589 nm, 20° C.]: | 0.0937 |
| CCP-V-1 | 11.50% | Δε [1 kHz, 20° C.]: | 2.7 |
| CLP-V-1 | 9.00% | $\varepsilon_{\|\|}$ [1 kHz, 20° C.]: | 5.3 |
| PGP-2-2V | 4.50% | $\varepsilon_\perp$ [1 kHz, 20° C.]: | 2.6 |
| PGUQU-3-F | 3.00% | $\gamma_1$ [mPa · s, 20° C.]: | 49 |
| APUQU-2-F | 7.50% | K$_1$ [pN, 20° C.]: | 14.4 |
| PP-1-2V1 | 4.00% | K$_3$ [pN, 20° C.]: | 16.0 |
| PPGU-3-F | 0.50% | | |

Liquid-crystalline mixture M51 is additionally stabilized with 400 ppm of the compound of the formula ST-1 and various concentrations of the compounds of the formula ST-2 or ST-3:

| Mixture | ST-1 | ST-2 | ST-3 |
|---|---|---|---|
| Example M51a | 400 ppm | — | — |
| Example M51b | 400 ppm | 100 ppm | — |
| Example M51c | 400 ppm | 500 ppm | — |
| Example M51d | 400 ppm | 1000 ppm | — |
| Example M51e | 400 ppm | — | 100 ppm |
| Example M51f | 400 ppm | — | 500 ppm |
| Example M51g | 400 ppm | — | 1000 ppm |

Example M52

| | | | |
|---|---|---|---|
| CC-3-V | 48.50% | Clearing point [° C.]: | 79.0 |
| CC-3-V1 | 12.00% | Δn [589 nm, 20° C.]: | 0.0939 |
| CCP-V-1 | 10.50% | Δε [1 kHz, 20° C.]: | 2.9 |
| PGP-2-2V | 3.50% | $\varepsilon_{\|\|}$ [1 kHz, 20° C.]: | 5.4 |
| PGUQU-3-F | 5.00% | $\varepsilon_\perp$ [1 kHz, 20° C.]: | 2.6 |
| APUQU-2-F | 6.00% | $\gamma_1$ [mPa · s, 20° C.]: | 48 |
| PP-1-2V1 | 5.00% | K$_1$ [pN, 20° C.]: | 14.1 |
| PPGU-3-F | 0.50% | K$_3$ [pN, 20° C.]: | 15.8 |
| CLP-V-1 | 9.00% | | |

Example M53

| | | | |
|---|---|---|---|
| CC-3-V | 48.00% | Clearing point [° C.]: | 80.6 |
| CC-3-V1 | 12.00% | Δn [589 nm, 20° C.]: | 0.0930 |
| CCP-V-1 | 11.50% | Δε [1 kHz, 20° C.]: | 2.7 |
| PGP-2-2V | 4.50% | $\varepsilon_{\|\|}$ [1 kHz, 20° C.]: | 6.3 |
| PGUQU-3-F | 3.00% | $\varepsilon_\perp$ [1 kHz, 20° C.]: | 2.6 |
| APUQU-2-F | 6.00% | $\gamma_1$ [mPa · s, 20° C.]: | 49 |
| PP-1-2V1 | 4.00% | K$_1$ [pN, 20° C.]: | 15.0 |
| PPGU-3-F | 0.50% | K$_3$ [pN, 20° C.]: | 17.1 |
| CLP-3-T | 4.00% | | |
| CLP-V-1 | 6.50 | | |

Example M54

| | | | |
|---|---|---|---|
| CC-3-V | 48.00% | Clearing point [° C.]: | 80.0 |
| CC-3-V1 | 10.50% | Δn [589 nm, 20° C.]: | 0.0956 |
| CCP-V-1 | 11.00% | Δε [1 kHz, 20° C.]: | 2.7 |
| PGP-2-2V | 5.00% | $\varepsilon_{\|\|}$ [1 kHz, 20° C.]: | 5.3 |
| PGUQU-3-F | 4.00% | $\varepsilon_\perp$ [1 kHz, 20° C.]: | 2.6 |
| APUQU-2-F | 4.50% | $\gamma_1$ [mPa · s, 20° C.]: | 49 |
| PP-1-2V1 | 5.00% | K$_1$ [pN, 20° C.]: | 15.0 |
| PPGU-3-F | 0.50% | K$_3$ [pN, 20° C.]: | 16.3 |
| CLP-3-T | 5.50% | | |
| CLP-V-1 | 6.00 | | |

Example M55

| | | | |
|---|---|---|---|
| PGUQU-3-F | 3.00% | Clearing point [° C.]: | 70.2 |
| PPGU-3-F | 0.50% | Δn [589 nm, 20° C.]: | 0.1345 |
| PGP-1-2V | 7.00% | Δε [1 kHz, 20° C.]: | 5.3 |
| PGP-2-2V | 11.00% | $\varepsilon_{\|\|}$ [1 kHz, 20° C.]: | 8.3 |
| PGU-3-F | 6.50% | $\varepsilon_\perp$ [1 kHz, 20° C.]: | 3.0 |
| PUQU-3-F | 10.00% | $\gamma_1$ [mPa · s, 20° C.]: | 55 |

-continued

| | | | |
|---|---|---|---|
| CC-3-V | 34.00% | $K_1$ [pN, 20° C.]: | 15.7 |
| PP-1-2V1 | 10.00% | $K_3$ [pN, 20° C.]: | 13.3 |
| CLP-3-T | 6.00% | $V_0$ [V, 20° C.]: | 1.81 |
| CCP-V-1 | 2.00% | | |
| CC-3-V1 | 6.00% | | |
| CC-3-2V1 | 4.00% | | |

Liquid-crystalline mixture M55 is additionally stabilized with 0.05% of the compound of the formula ST-1

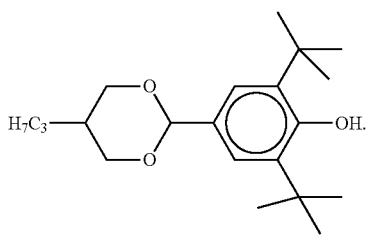

ST-1

Example M56

| | | | |
|---|---|---|---|
| PGUQU-3-F | 1.50% | Clearing point [° C.]: | 63.1 |
| PPGU-3-F | 0.50% | Δn [589 nm, 20° C.]: | 0.1337 |
| PGP-1-2V | 6.50% | Δε [1 kHz, 20° C.]: | 5.1 |
| PGP-2-2V | 10.50% | $\varepsilon_\parallel$ [1 kHz, 20° C.]: | 8.1 |
| PGU-3-F | 7.50% | $\varepsilon_\perp$ [1 kHz, 20° C.]: | 3.0 |
| PUQU-3-F | 10.00% | $\gamma_1$ [mPa·s, 20° C.]: | 49 |
| CC-3-V | 42.00% | $K_1$ [pN, 20° C.]: | 14.6 |
| PP-1-2V1 | 14.00% | $K_3$ [pN, 20° C.]: | 11.8 |
| CLP-3-T | 7.50% | $V_0$ [V, 20° C.]: | 1.78 |

Liquid-crystalline mixture M56 is additionally stabilized with 0.05% of the compound of the formula ST-1

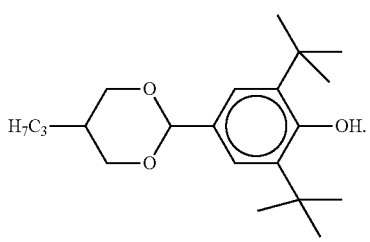

ST-1

Example M57

| | | | |
|---|---|---|---|
| APUQU-2-F | 2.00% | Clearing point [° C.]: | 104 |
| DGUQU-4-F | 4.00% | Δn [589 nm, 20° C.]: | 0.0949 |
| DPGU-4-F | 2.00% | Δε [1 kHz, 20° C.]: | 4.5 |
| CCG-V-F | 17.00% | $\varepsilon_\parallel$ [1 kHz, 20° C.]: | 7.4 |
| CCP-30CF3 | 4.00% | $\varepsilon_\perp$ [1 kHz, 20° C.]: | 2.9 |
| CCP-50CF3 | 3.00% | $\gamma_1$ [mPa·s, 20° C.]: | 84 |
| CCP-V-1 | 10.00% | $K_1$ [pN, 20° C.]: | 16.0 |
| CCP-V2-1 | 4.00% | $K_3$ [pN, 20° C.]: | 20.2 |
| CCQU-3-F | 5.50% | $V_0$ [V, 20° C.]: | 1.98 |
| CCVC-3-V | 5.00% | | |
| CLP-3-T | 3.00% | | |
| PGP-2-2V | 3.00% | | |

-continued

| | | | |
|---|---|---|---|
| CC-3-2V1 | 4.00% | | |
| CC-3-V | 23.50% | | |
| CC-3-V1 | 5.50% | | |
| PP-1-2V1 | 4.50% | | |

Example M58

| | | | |
|---|---|---|---|
| DGUQU-4-F | 1.50% | Clearing point [° C.]: | 79.5 |
| CCG-V-F | 6.00% | Δn [589 nm, 20° C.]: | 0.1051 |
| CCQU-2-F | 3.50% | Δε [1 kHz, 20° C.]: | 4.5 |
| CCVC-3-V | 6.50% | $\varepsilon_\parallel$ [1 kHz, 20° C.]: | 7.9 |
| CDU-2-F | 13.00% | $\varepsilon_\perp$ [1 kHz, 20° C.]: | 3.4 |
| CLP-3-T | 4.00% | $\gamma_1$ [mPa·s, 20° C.]: | 61 |
| PGP-1-2V | 12.00% | $K_1$ [pN, 20° C.]: | 13.4 |
| PGP-2-2V | 4.00% | $K_3$ [pN, 20° C.]: | 13.3 |
| PGU-2-F | 4.00% | $V_0$ [V, 20° C.]: | 1.80 |
| CC-3-V | 31.50% | | |
| CCH-34 | 4.00% | | |
| PCH-302 | 10.00% | | |

Example M59

| | | | |
|---|---|---|---|
| CC-3-2V1 | 3.50% | Clearing point [° C.]: | 74.8 |
| CC-3-V | 49.00% | Δn [589 nm, 20° C.]: | 0.1189 |
| CC-3-V1 | 4.00% | Δε [1 kHz, 20° C.]: | 3.1 |
| CLP-3-T | 6.50% | $\varepsilon_\parallel$ [1 kHz, 20° C.]: | 5.9 |
| PGP-1-2V | 6.00% | $\varepsilon_\perp$ [1 kHz, 20° C.]: | 2.8 |
| PGP-2-2V | 12.00% | $\gamma_1$ [mPa·s, 20° C.]: | 45 |
| PGP-3-2V | 4.00% | $K_1$ [pN, 20° C.]: | 13.6 |
| PGU-2-F | 5.00% | $K_3$ [pN, 20° C.]: | 13.1 |
| PGUQU-3-F | 3.00% | $V_0$ [V, 20° C.]: | 2.20 |
| PP-1-2V1 | 3.00% | | |
| PPGU-3-F | 1.00% | | |
| PUQU-3-F | 3.00% | | |

Liquid-crystalline mixture M59 is additionally stabilized with 0.04% of the compound of the formula ST-1

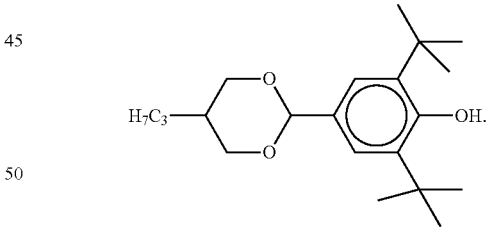

ST-1

Example M60

| | | | |
|---|---|---|---|
| APUQU-2-F | 6.00% | Clearing point [° C.]: | 90.6 |
| APUQU-3-F | 7.00% | Δn [589 nm, 20° C.]: | 0.1155 |
| CC-3-V | 27.50% | Δε [1 kHz, 20° C.]: | 10.4 |
| CC-3-V1 | 8.00% | $\varepsilon_\parallel$ [1 kHz, 20° C.]: | 13.9 |
| CCP-V-1 | 9.00% | $\varepsilon_\perp$ [1 kHz, 20° C.]: | 3.5 |
| CCP-V2-1 | 6.50% | $\gamma_1$ [mPa·s, 20° C.]: | 73 |
| CDUQU-3-F | 8.50% | $K_1$ [pN, 20° C.]: | 13.9 |
| CLP-3-T | 3.00% | $K_3$ [pN, 20° C.]: | 15.5 |
| PGP-1-2V | 5.00% | $V_0$ [V, 20° C.]: | 1.22 |
| PGP-2-2V | 5.00% | | |

-continued

| | |
|---|---|
| PGUQU-3-F | 1.00% |
| PPGU-3-F | 1.00% |
| PUQU-3-F | 12.50% |

Liquid-crystalline mixture M60 is additionally stabilized with 0.04% of the compound of the formula ST-1

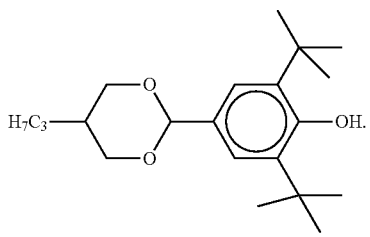

ST-1

Example M61

| | | | |
|---|---|---|---|
| APUQU-2-F | 6.00% | Clearing point [° C.]: | 90.4 |
| APUQU-3-F | 7.00% | Δn [589 nm, 20° C.]: | 0.1179 |
| CC-3-V | 28.00% | Δε [1 kHz, 20° C.]: | 10.9 |
| CC-3-V1 | 8.00% | ε$_{\parallel}$ [1 kHz, 20° C.]: | |
| CCP-V-1 | 9.00% | ε$_{\perp}$ [1 kHz, 20° C.]: | |
| CCP-V2-1 | 5.50% | γ$_1$ [mPa · s, 20° C.]: | 91 |
| CDUQU-3-F | 8.00% | K$_1$ [pN, 20° C.]: | 14.7 |
| CLP-3-T | 4.00% | K$_3$ [pN, 20° C.]: | 16.4 |
| PGP-1-2V | 5.00% | V$_0$ [V, 20° C.]: | 1.23 |
| PGP-2-2V | 5.00% | | |
| PQUQU-3-F | 1.50% | | |
| PPGU-3-F | 1.00% | | |
| PUQU-3-F | 12.00% | | |

Liquid-crystalline mixture M61 is additionally stabilized with 0.04% of the compound of the formula ST-1

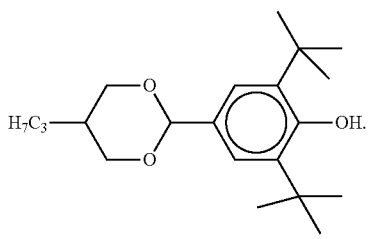

ST-1

Example M62

| | | | |
|---|---|---|---|
| CC-3-V | 47.50% | Clearing point [° C.]: | 74.8 |
| CC-3-V1 | 7.50% | Δn [589 nm, 20° C.]: | 0.1192 |
| CLP-3-T | 7.00% | Δε [1 kHz, 20° C.]: | 4.7 |
| CPGU-3-OT | 2.00% | ε$_{\parallel}$ [1 kHz, 20° C.]: | 7.6 |
| PGP-2-2V | 16.00% | ε$_{\perp}$ [1 kHz, 20° C.]: | 2.9 |
| PGU-2-F | 11.00% | γ$_1$ [mPa · s, 20° C.]: | 45 |
| PGUQU-3-F | 6.00% | K$_1$ [pN, 20° C.]: | 13.3 |
| PP-1-2V1 | 2.00% | K$_3$ [pN, 20° C.]: | 12.6 |
| PPGU-3-F | 1.00% | V$_0$ [V, 20° C.]: | 1.78 |

Liquid-crystalline mixture M62 is additionally stabilized with 0.04% of the compound of the formula ST-1

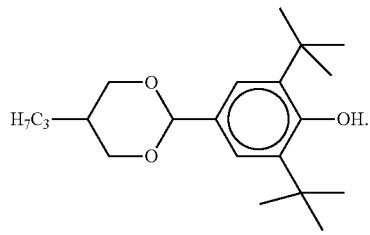

ST-1

Example M63

| | | | |
|---|---|---|---|
| CC-3-2V1 | 7.00% | Clearing point [° C.]: | 70.0 |
| CC-3-V | 46.00% | Δn [589 nm, 20° C.]: | 0.1185 |
| CC-3-V1 | 3.00% | Δε [1 kHz, 20° C.]: | 3.0 |
| CLP-3-T | 5.00% | ε$_{\parallel}$ [1 kHz, 20° C.]: | 5.7 |
| PGP-1-2V | 7.00% | ε$_{\perp}$ [1 kHz, 20° C.]: | 2.8 |
| PGP-2-2V | 11.00% | γ$_1$ [mPa · s, 20° C.]: | 45 |
| PGP-3-2V | 2.50% | K$_1$ [pN, 20° C.]: | 13.2 |
| PGU-2-F | 5.50% | K$_3$ [pN, 20° C.]: | 12.8 |
| PP-1-2V1 | 6.00% | V$_0$ [V, 20° C.]: | 2.21 |
| PPGU-3-F | 1.00% | | |
| PUQU-3-F | 6.00% | | |

Liquid-crystalline mixture M63 is additionally stabilized with 0.04% of the compound of the formula ST-1

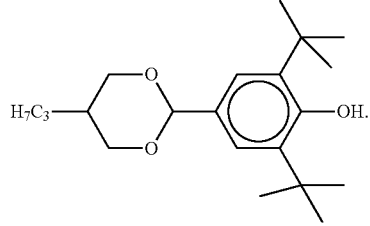

ST-1

Example M64

| | | | |
|---|---|---|---|
| APUQU-2-F | 6.00% | Clearing point [° C.]: | 80.0 |
| APUQU-3-F | 5.00% | Δn [589 nm, 20° C.]: | 0.1129 |
| PGUQU-3-F | 2.00% | Δε [1 kHz, 20° C.]: | 3.9 |
| PPGU-3-F | 0.50% | ε$_{\parallel}$ [1 kHz, 20° C.]: | 6.7 |
| CCP-V-1 | 2.50% | ε$_{\perp}$ [1 kHz, 20° C.]: | 2.8 |
| PGP-1-2V | 4.00% | γ$_1$ [mPa · s, 20° C.]: | 52 |
| PGP-2-2V | 16.50% | K$_1$ [pN, 20° C.]: | 14.1 |
| CC-3-V | 52.00% | K$_3$ [pN, 20° C.]: | 14.1 |
| CC-3-V1 | 6.50% | V$_0$ [V, 20° C.]: | 2.03 |
| CLP-3-T | 5.00% | | |

Example M65

| | | | |
|---|---|---|---|
| APUQU-2-F | 5.00% | Clearing point [° C.]: | 80.0 |
| PGUQU-3-F | 6.00% | Δn [589 nm, 20° C.]: | 0.1131 |
| PPGU-3-F | 0.50% | Δε [1 kHz, 20° C.]: | 3.5 |

| | | | | |
|---|---|---|---|---|
| CCP-V-1 | 8.50% | ε∥ [1 kHz, 20° C.]: | 6.2 | |
| PGP-2-2V | 16.50% | ε⊥ [1 kHz, 20° C.]: | 2.7 | |
| PP-1-2V1 | 4.00% | $\gamma_1$ [mPa · s, 20° C.]: | 51 | |
| CC-3-V | 48.00% | $K_1$ [pN, 20° C.]: | 14.6 | |
| CC-3-V1 | 6.50% | $K_3$ [pN, 20° C.]: | 14.7 | |
| CLP-3-T | 5.00% | $V_0$ [V, 20° C.]: | 2.17 | |

Example M66

| | | | |
|---|---|---|---|
| APUQU-2-F | 4.00% | Clearing point [° C.]: | 76.0 |
| PGUQU-3-F | 3.00% | Δn [589 nm, 20° C.]: | 0.1176 |
| PPGU-3-F | 0.50% | Δε [1 kHz, 20° C.]: | 2.4 |
| CCP-V-1 | 4.00% | ε∥ [1 kHz, 20° C.]: | 5.1 |
| PGP-1-2V | 6.00% | ε⊥ [1 kHz, 20° C.]: | 2.7 |
| PGP-2-2V | 15.50% | $\gamma_1$ [mPa · s, 20° C.]: | 48 |
| PP-1-2V1 | 6.00% | $K_1$ [pN, 20° C.]: | 14.3 |
| CC-3-V | 52.00% | $K_3$ [pN, 20° C.]: | 14.6 |
| CC-3-V1 | 4.50% | | |
| CLP-3-T | 4.50% | | |

Example M67

| | | | |
|---|---|---|---|
| APUQU-2-F | 7.00% | Clearing point [° C.]: | 76.0 |
| PGUQU-3-F | 6.00% | Δn [589 nm, 20° C.]: | 0.1173 |
| PPGU-3-F | 0.50% | Δε [1 kHz, 20° C.]: | 4.0 |
| CCP-V-1 | 1.00% | ε∥ [1 kHz, 20° C.]: | 6.8 |
| PGP-1-2V | 4.00% | ε⊥ [1 kHz, 20° C.]: | 2.8 |
| PGP-2-2V | 15.00% | $\gamma_1$ [mPa · s, 20° C.]: | 51 |
| PP-1-2V1 | 4.50% | $K_1$ [pN, 20° C.]: | 14.5 |
| CC-3-V | 50.00% | $K_3$ [pN, 20° C.]: | 14.6 |
| CC-3-V1 | 5.00% | | |
| CC-3-2V1 | 2.00% | | |
| CLP-3-T | 5.00% | | |

Example M68

| | | | |
|---|---|---|---|
| APUQU-2-F | 3.00% | Clearing point [° C.]: | 76.5 |
| PGUQU-3-F | 2.00% | Δn [589 nm, 20° C.]: | 0.1177 |
| PPGU-3-F | 0.50% | Δε [1 kHz, 20° C.]: | 2.5 |
| CLP-V-1 | 7.00% | ε∥ [1 kHz, 20° C.]: | 5.1 |
| PGP-1-2V | 2.50% | ε⊥ [1 kHz, 20° C.]: | 2.6 |
| PGP-2-2V | 14.00% | $\gamma_1$ [mPa · s, 20° C.]: | 51 |
| PP-1-2V1 | 7.00% | $K_1$ [pN, 20° C.]: | 15.4 |
| CC-3-V | 49.00% | $K_3$ [pN, 20° C.]: | 14.4 |
| CC-3-V1 | 6.00% | | |
| CLP-3-T | 4.50% | | |
| PUQU-3-F | 2.00% | | |
| PGP-3-2V | 2.50% | | |

Example M69

| | | | |
|---|---|---|---|
| CC-3-2V1 | 1.00% | Clearing point [° C.]: | 77.5 |
| CC-3-V | 50.00% | Δn [589 nm, 20° C.]: | 0.1169 |
| CC-3-V1 | 2.00% | Δε [1 kHz, 20° C.]: | 4.2 |
| CCP-V-1 | 2.00% | ε∥ [1 kHz, 20° C.]: | 7.0 |
| CLP-3-T | 6.00% | ε⊥ [1 kHz, 20° C.]: | 2.8 |
| CLP-V-1 | 6.50% | $\gamma_1$ [mPa · s, 20° C.]: | 51 |
| PGP-2-2V | 12.50% | $K_1$ [pN, 20° C.]: | 15.0 |
| PP-1-2V1 | 6.00% | $K_3$ [pN, 20° C.]: | 13.9 |
| PGU-4-T | 3.50% | | |

| | |
|---|---|
| PGUQU-3-F | 5.00% |
| PGUQU-4-F | 5.00% |
| PPGU-3-F | 0.50% |

Example M70

| | | | |
|---|---|---|---|
| APUQU-2-F | 3.00% | Clearing point [° C.]: | 75.0 |
| CC-3-V | 49.50% | Δn [589 nm, 20° C.]: | 0.1186 |
| CC-3-V1 | 6.00% | Δε [1 kHz, 20° C.]: | 2.3 |
| CLP-1V2-1 | 5.50% | ε∥ [1 kHz, 20° C.]: | 5.0 |
| CLP-3-T | 4.00% | ε⊥ [1 kHz, 20° C.]: | 2.6 |
| PGP-1-2V | 3.00% | $\gamma_1$ [mPa · s, 20° C.]: | 50 |
| PGP-2-2V | 13.00% | $K_1$ [pN, 20° C.]: | 15.2 |
| PGP-3-2V | 2.50% | $K_3$ [pN, 20° C.]: | 15.1 |
| PGUQU-3-F | 2.00% | | |
| PP-1-2V1 | 9.00% | | |
| PPGU-3-F | 0.50% | | |
| PUQU-3-F | 2.00% | | |

Example M71

| | | | |
|---|---|---|---|
| APUQU-2-F | 3.00% | Clearing point [° C.]: | 76.5 |
| CC-3-V | 49.50% | Δn [589 nm, 20° C.]: | 0.1178 |
| CC-3-V1 | 6.00% | Δε [1 kHz, 20° C.]: | 2.4 |
| CLP-1V-1 | 6.00% | ε∥ [1 kHz, 20° C.]: | 5.0 |
| CLP-3-T | 4.50% | ε⊥ [1 kHz, 20° C.]: | 2.7 |
| PGP-1-2V | 3.00% | $\gamma_1$ [mPa · s, 20° C.]: | 50 |
| PGP-2-2V | 13.00% | $K_1$ [pN, 20° C.]: | 15.2 |
| PGP-3-2V | 2.50% | $K_3$ [pN, 20° C.]: | 15.1 |
| PGUQU-3-F | 2.00% | | |
| PP-1-2V1 | 8.00% | | |
| PPGU-3-F | 0.50% | | |
| PUQU-3-F | 2.00% | | |

Example M72

| | |
|---|---|
| APUQU-2-F | 3.00% |
| CC-3-V | 49.50% |
| CC-3-V1 | 6.00% |
| CLP-1V2-1 | 6.00% |
| CLP-3-T | 4.50% |
| PGP-1-2V | 3.00% |
| PGP-2-2V | 13.00% |
| PGP-3-2V | 2.50% |
| PGUQU-3-F | 2.00% |
| PP-1-2V1 | 8.00% |
| PPGU-3-F | 0.50% |
| PUQU-3-F | 2.00% |

Example M73

| | | | |
|---|---|---|---|
| CC-3-V | 46.00% | Clearing point [° C.]: | 76.0 |
| CC-3-V1 | 6.00% | Δn [589 nm, 20° C.]: | 0.1180 |
| CCP-V-1 | 1.50% | Δε [1 kHz, 20° C.]: | 2.9 |
| PGP-2-2V | 12.00% | ε∥ [1 kHz, 20° C.]: | 6.8 |
| PGP-3-2V | 2.50% | ε⊥ [1 kHz, 20° C.]: | 3.9 |
| PGU-2-F | 6.50% | $\gamma_1$ [mPa · s, 20° C.]: | 54 |
| PGUQU-3-F | 5.00% | $K_1$ [pN, 20° C.]: | 15.0 |
| CLP-3-T | 5.00% | $K_3$ [pN, 20° C.]: | 13.4 |
| B(S)-2O-O4 | 3.50% | | |

| | |
|---|---|
| B(S)-2O-O5 | 3.50% |
| CC-3-2V1 | 1.00% |
| DGUQU-4-F | 1.50% |
| CY-3-O2 | 2.50% |
| CLP-V-1 | 3.50% |

Example M74

| | | | |
|---|---|---|---|
| CC-3-V | 44.00% | Clearing point [° C.]: | 85.00 |
| CC-3-V1 | 6.00% | Δn [589 nm, 20° C.]: | 0.1178 |
| CC-3-2V1 | 4.00% | Δε [1 kHz, 20° C.]: | 3.2 |
| CCP-V-1 | 1.50% | ε∥ [1 kHz, 20° C.]: | 6.9 |
| PGP-2-2V | 10.50% | ε⊥ [1 kHz, 20° C.]: | 3.7 |
| PGP-3-2V | 5.00% | γ₁ [mPa·s, 20° C.]: | 62 |
| DGUQU-4-F | 4.50% | K₁ [pN, 20° C.]: | 16.7 |
| PGUQU-3-F | 6.50% | K₃ [pN, 20° C.]: | 15.5 |
| CLP-3-T | 5.00% | | |
| B(S)-2O-O4 | 4.00% | | |
| B(S)-2O-O5 | 3.50% | | |
| CLP-V-1 | 5.50% | | |

Example M75

| | | | |
|---|---|---|---|
| CC-3-V | 44.00% | Clearing point [° C.]: | 80.0 |
| CC-3-V1 | 6.00% | Δn [589 nm, 20° C.]: | 0.1186 |
| CC-3-2V1 | 5.00% | Δε [1 kHz, 20° C.]: | 3.0 |
| PGP-2-2V | 10.50% | ε∥ [1 kHz, 20° C.]: | 6.9 |
| PGP-3-2V | 4.00% | ε⊥ [1 kHz, 20° C.]: | 3.8 |
| DGUQU-4-F | 2.50% | γ₁ [mPa·s, 20° C.]: | 60 |
| PGUQU-3-F | 6.50% | K₁ [pN, 20° C.]: | 16.2 |
| CLP-3-T | 5.00% | K₃ [pN, 20° C.]: | 14.9 |
| B(S)-2O-O4 | 4.00% | | |
| B(S)-2O-O5 | 3.50% | | |
| CLP-V-1 | 4.50% | | |
| PGU-2-F | 3.00% | | |
| PY-3-O2 | 1.50% | | |

Example M76

| | |
|---|---|
| Y-4O-O4 | 7.00% |
| CC-3-V | 28.00% |
| B-2O-O5 | 4.00% |
| B(S)-2O-O4 | 3.50% |
| B(S)-2O-O5 | 4.00% |
| CCP-30CF₃ | 6.50% |
| CCP-V-1 | 15.00% |
| PGP-2-2V | 4.00% |
| CLP-1V2-T | 4.00% |
| APUQU-2-F | 5.00% |
| APUQU-3-F | 6.50% |
| CDUQU-3-F | 4.50% |
| DGUQU-4-F | 5.00% |
| DPGU-4-F | 3.50% |
| PPGU-3-F | 0.50% |

Example M77

| | |
|---|---|
| Y-4O-O4 | 10.50% |
| CC-3-V | 24.00% |
| CCP-30CF₃ | 6.00% |
| CLP-V2-T | 4.00% |
| CCP-V-1 | 13.00% |
| CCP-V2-1 | 5.00% |
| PGP-2-2V | 7.00% |
| DGUQU-4-F | 5.00% |
| DPGU-4-F | 3.50% |
| APUQU-2-F | 6.50% |
| APUQU-3-F | 7.50% |
| CDUQU-3-F | 3.50% |
| PGUQU-4-F | 4.00% |
| PPGU-3-F | 0.50% |

Example M78

| | |
|---|---|
| CC-3-V | 49.50% |
| CCP-V-1 | 5.00% |
| CLP-1V2-1 | 8.50% |
| PP-1-2V1 | 1.00% |
| PGP-1-2V | 5.00% |
| PGP-2-2V | 8.00% |
| PGP-3-2V | 4.50% |
| CCP-30CF₃ | 6.50% |
| PGUQU-C4-F | 5.00% |
| PGUQU-C5-F | 2.50% |
| APUQU-C3-F | 4.50% |

Example M79

| | |
|---|---|
| Y-4O-O4 | 10.50% |
| CC-3-V | 24.00% |
| CCP-30CF₃ | 6.00% |
| CLP-V2-1 | 4.00% |
| CCP-V-1 | 13.00% |
| CCP-V2-1 | 5.00% |
| PGP-2-2V | 7.00% |
| DGUQU-4-F | 5.00% |
| DPGU-4-F | 3.50% |
| APUQU-2-F | 6.50% |
| APUQU-3-F | 7.50% |
| CDUQU-3-F | 3.50% |
| PGUQU-4-F | 4.00% |
| PPGU-3-F | 0.50% |

Example M80

| | | | |
|---|---|---|---|
| CC-3-V | 48.00% | Clearing point [° C.]: | 79.0 |
| CC-3-V1 | 10.50% | Δn [589 nm, 20° C.]: | 0.0932 |
| CCP-V-1 | 11.00% | Δε [1 kHz, 20° C.]: | 2.6 |
| CCP-V2-1 | 6.00% | ε∥ [1 kHz, 20° C.]: | 5.2 |
| PGP-2-2V | 5.00% | ε⊥ [1 kHz, 20° C.]: | 2.6 |
| PGUQU-3-F | 4.00% | γ₁ [mPa·s, 20° C.]: | 49 |
| APUQU-2-F | 4.50% | K₁ [pN, 20° C.]: | 14.3 |
| PP-1-2V1 | 5.00% | K₃ [pN, 20° C.]: | 15.9 |
| PPGU-3-F | 0.50% | | |
| CLP-V-T | 5.50% | | |

Example M81

| | | | |
|---|---|---|---|
| CC-3-V | 48.00% | Clearing point [° C.]: | 79.0 |
| CC-3-V1 | 10.50% | Δn [589 nm, 20° C.]: | 0.0930 |

-continued

| | | | |
|---|---|---|---|
| CCP-V-1 | 11.00% | Δε [1 kHz, 20° C.]: | 2.5 |
| CCP-V2-1 | 6.00% | ε∥ [1 kHz, 20° C.]: | 5.0 |
| PGP-2-2V | 5.00% | ε⊥ [1 kHz, 20° C.]: | 2.5 |
| PGUQU-3-F | 4.00% | $\gamma_1$ [mPa · s, 20° C.]: | 48 |
| APUQU-2-F | 4.50% | $K_1$ [pN, 20° C.]: | 13.9 |
| PP-1-2V1 | 5.00% | $K_3$ [pN, 20° C.]: | 15.9 |
| PPGU-3-F | 0.50% | | |
| CLP-V-OT | 5.50% | | |

Example M82

| | | | |
|---|---|---|---|
| APUQU-2-F | 6.00% | Clearing point [° C.]: | 80.0 |
| DGUQU-4-F | 5.50% | Δn [589 nm, 20° C.]: | 0.0983 |
| DPGU-4-F | 4.00% | Δε [1 kHz, 20° C.]: | 5.9 |
| PGUQU-3-F | 3.50% | ε∥ [1 kHz, 20° C.]: | 8.9 |
| PPGU-3-F | 0.50% | ε⊥ [1 kHz, 20° C.]: | 3.0 |
| CC-3-2V1 | 9.00% | $\gamma_1$ [mPa · s, 20° C.]: | 58 |
| CC-3-V | 48.50% | $K_1$ [pN, 20° C.]: | 14.7 |
| CC-3-V1 | 7.00% | $K_3$ [pN, 20° C.]: | 15.2 |
| CLP-3-T | 4.00% | | |
| CLP-1V2-OT | 3.00% | | |
| PGP-2-2V | 9.00% | | |

Example M83

| | | | |
|---|---|---|---|
| APUQU-2-F | 6.00% | Clearing point [° C.]: | 79.0 |
| DGUQU-4-F | 5.50% | Δn [589 nm, 20° C.]: | 0.0987 |
| DPGU-4-F | 4.00% | Δε [1 kHz, 20° C.]: | 5.9 |
| PGUQU-3-F | 4.00% | ε∥ [1 kHz, 20° C.]: | 8.8 |
| PPGU-3-F | 0.50% | ε⊥ [1 kHz, 20° C.]: | 2.9 |
| CC-3-2V1 | 6.00% | $\gamma_1$ [mPa · s, 20° C.]: | 58 |
| CC-3-V | 49.00% | $K_1$ [pN, 20° C.]: | 14.1 |
| CC-3-V1 | 9.00% | $K_3$ [pN, 20° C.]: | 15.3 |
| CLP-1V2-OT | 7.00% | LTS bulk [−20° C.]: | >1000 h |
| PGP-2-2V | 8.00% | | |
| PP-1-2V1 | 1.00% | | |

Example M84

| | | | |
|---|---|---|---|
| APUQU-3-F | 1.00% | Clearing point [° C.]: | 75.5 |
| PPGU-3-F | 0.50% | Δn [589 nm, 20° C.]: | 0.0987 |
| CCP-V-1 | 12.00% | Δε [1 kHz, 20° C.]: | 2.3 |
| PGP-2-3 | 6.00% | ε∥ [1 kHz, 20° C.]: | 4.9 |
| PGP-2-4 | 7.00% | ε⊥ [1 kHz, 20° C.]: | 2.6 |
| PGP-2-5 | 2.00% | $\gamma_1$ [mPa · s, 20° C.]: | 52 |
| PUQU-3-F | 7.00% | $K_1$ [pN, 20° C.]: | 14.2 |
| CC-3-2V1 | 3.00% | $K_3$ [pN, 20° C.]: | 14.8 |
| CC-3-V | 46.50% | | |
| CC-3-V1 | 10.00% | | |
| CLP-1V2-T | 5.00% | | |

Example M85

| | | | |
|---|---|---|---|
| CC-3-V | 48.00% | Clearing point [° C.]: | 80.5 |
| CC-3-V1 | 10.50% | Δn [589 nm, 20° C.]: | 0.0938 |
| CCP-V-1 | 11.00% | Δε [1 kHz, 20° C.]: | 2.7 |
| CCP-V2-1 | 6.00% | ε∥ [1 kHz, 20° C.]: | 5.2 |
| CLP-1V2-T | 5.50% | ε⊥ [1 kHz, 20° C.]: | 2.6 |
| PGP-2-2V | 5.00% | $\gamma_1$ [mPa · s, 20° C.]: | 54 |
| PGUQU-3-F | 4.00% | $K_1$ [pN, 20° C.]: | 15.0 |
| APUQU-2-F | 4.50% | $K_3$ [pN, 20° C.]: | 17.0 |
| PP-1-2V1 | 5.00% | LTS bulk [−20° C.]: | >1000 h |
| PPGU-3-F | 0.50% | | |

Example M86

| | |
|---|---|
| CC-3-V | 48.00% |
| CC-3-V1 | 10.50% |
| CCP-V-1 | 11.00% |
| CLP-V-1 | 6.00% |
| CLP-1V2-T | 5.50% |
| PGP-2-2V | 5.00% |
| PGUQU-3-F | 4.00% |
| APUQU-2-F | 4.50% |
| PP-1-2V1 | 5.00% |
| PPGU-3-F | 0.50% |

Example M87

| | | | |
|---|---|---|---|
| CC-3-V | 48.00% | Clearing point [° C.]: | 80.5 |
| CC-3-V1 | 10.50% | Δn [589 nm, 20° C.]: | 0.0941 |
| CCP-V-1 | 11.00% | Δε [1 kHz, 20° C.]: | 2.7 |
| CCP-V2-1 | 6.00% | ε∥ [1 kHz, 20° C.]: | 5.3 |
| CLP-1V-T | 5.50% | ε⊥ [1 kHz, 20° C.]: | 2.6 |
| PGP-2-2V | 5.00% | $\gamma_1$ [mPa · s, 20° C.]: | 50 |
| PGUQU-3-F | 4.00% | $K_1$ [pN, 20° C.]: | 14.7 |
| APUQU-2-F | 4.50% | $K_3$ [pN, 20° C.]: | 16.8 |
| PP-1-2V1 | 5.00% | | |
| PPGU-3-F | 0.50% | | |

Example M88

| | | | |
|---|---|---|---|
| APUQU-2-F | 4.00% | Clearing point [° C.]: | 76.0 |
| PGUQU-3-F | 3.00% | Δn [589 nm, 20° C.]: | 0.1180 |
| PPGU-3-F | 0.50% | Δε [1 kHz, 20° C.]: | 2.4 |
| CCP-V-1 | 4.00% | ε∥ [1 kHz, 20° C.]: | 5.1 |
| PGP-1-2V | 6.00% | ε⊥ [1 kHz, 20° C.]: | 2.7 |
| PGP-2-2V | 15.50% | $\gamma_1$ [mPa · s, 20° C.]: | 48 |
| PP-1-2V1 | 6.00% | $K_1$ [pN, 20° C.]: | 14.4 |
| CC-3-V | 52.00% | $K_3$ [pN, 20° C.]: | 14.4 |
| CC-3-V1 | 4.50% | | |
| CLP-1V-T | 4.50% | | |

Example M89

| | | | |
|---|---|---|---|
| APUQU-2-F | 7.00% | Clearing point [° C.]: | 76.5 |
| PGUQU-3-F | 6.00% | Δn [589 nm, 20° C.]: | 0.1184 |
| PPGU-3-F | 0.50% | Δε [1 kHz, 20° C.]: | 4.0 |
| CCP-V-1 | 1.00% | ε∥ [1 kHz, 20° C.]: | 6.8 |
| PGP-1-2V | 4.00% | ε⊥ [1 kHz, 20° C.]: | 2.8 |
| PGP-2-2V | 15.00% | $\gamma_1$ [mPa · s, 20° C.]: | 52 |
| PP-1-2V1 | 4.50% | $K_1$ [pN, 20° C.]: | 14.5 |
| CC-3-V | 50.00% | $K_3$ [pN, 20° C.]: | 14.3 |
| CC-3-V1 | 5.00% | | |
| CC-3-2V1 | 2.00% | | |
| CLP-1V-T | 5.00% | | |

Example M90

| | | | |
|---|---|---|---|
| CC-3-V | 49.00% | Clearing point [° C.]: | 79.5 |
| CC-3-V1 | 12.00% | Δn [589 nm, 20° C.]: | 0.0938 |
| CCP-V-1 | 11.00% | Δε [1 kHz, 20° C.]: | 2.7 |
| CLP-1V-1 | 8.00% | $\varepsilon_\parallel$ [1 kHz, 20° C.]: | 5.3 |
| PGP-2-2V | 3.00% | $\varepsilon_\perp$ [1 kHz, 20° C.]: | 2.6 |
| PGUQU-3-F | 3.50% | $\gamma_1$ [mPa · s, 20° C.]: | 49 |
| APUQU-2-F | 7.00% | $K_1$ [pN, 20° C.]: | 14.6 |
| PP-1-2V1 | 6.00% | $K_3$ [pN, 20° C.]: | 16.9 |
| PPGU-3-F | 0.50% | | |

Example M91

| | | | |
|---|---|---|---|
| CC-3-V | 49.00% | Clearing point [° C.]: | 81.0 |
| CC-3-V1 | 10.00% | Δε [1 kHz, 20° C.]: | 2.7 |
| CCP-V-1 | 8.00% | $\varepsilon_\parallel$ [1 kHz, 20° C.]: | 5.3 |
| CLP-V-1 | 7.50% | $\varepsilon_\perp$ [1 kHz, 20° C.]: | 2.5 |
| CLP-1V-1 | 3.50% | $\gamma_1$ [mPa · s, 20° C.]: | 50 |
| CLP-3-T | 5.50% | $K_1$ [pN, 20° C.]: | 15.6 |
| PGP-2-2V | 2.00% | $K_3$ [pN, 20° C.]: | 17.1 |
| PGUQU-3-F | 4.00% | | |
| APUQU-2-F | 4.50% | | |
| PP-1-2V1 | 5.50% | | |
| PPGU-3-F | 0.50% | | |

Example M92

| | | | |
|---|---|---|---|
| CC-3-V | 49.00% | Clearing point [° C.]: | 81.0 |
| CC-3-V1 | 10.50% | Δε [1 kHz, 20° C.]: | 2.7 |
| CCP-V-1 | 10.00% | $\varepsilon_\parallel$ [1 kHz, 20° C.]: | 5.3 |
| CLP-V2-1 | 5.00% | $\varepsilon_\perp$ [1 kHz, 20° C.]: | 2.6 |
| CLP-1V-1 | 3.50% | $\gamma_1$ [mPa · s, 20° C.]: | 50 |
| CLP-3-T | 5.50% | $K_1$ [pN, 20° C.]: | 15.5 |
| PGP-2-2V | 2.00% | $K_3$ [pN, 20° C.]: | 17.2 |
| PGUQU-3-F | 4.00% | | |
| APUQU-2-F | 4.50% | | |
| PP-1-2V1 | 5.50% | | |
| PPGU-3-F | 0.50% | | |

Example M93

| | | | |
|---|---|---|---|
| APUQU-3-F | 1.00% | Clearing point [° C.]: | 76.5 |
| PPGU-3-F | 0.50% | Δn [589 nm, 20° C.]: | 0.0995 |
| CCP-V-1 | 5.00% | Δε [1 kHz, 20° C.]: | 2.3 |
| CLP-1V-1 | 9.00% | $\varepsilon_\parallel$ [1 kHz, 20° C.]: | 4.9 |
| PGP-2-3 | 6.00% | $\varepsilon_\perp$ [1 kHz, 20° C.]: | 2.6 |
| PGP-2-4 | 7.00% | $\gamma_1$ [mPa · s, 20° C.]: | 53 |
| PUQU-3-F | 9.00% | $K_1$ [pN, 20° C.]: | 14.6 |
| CC-3-2V1 | 6.50% | $K_3$ [pN, 20° C.]: | 15.4 |
| CC-3-V | 46.00% | | |
| CC-3-V1 | 10.00% | | |

Example M94

| | |
|---|---|
| APUQU-3-F | 1.50% |
| PPGU-3-F | 0.50% |
| CLP-V-1 | 10.00% |
| CLP-1V-1 | 5.00% |
| PGP-2-3 | 5.00% |

-continued

| | |
|---|---|
| PGP-2-4 | 7.00% |
| PUQU-3-F | 8.50% |
| CC-3-2V1 | 6.50% |
| CC-3-V | 47.00% |
| CC-3-V1 | 9.00% |

Example M95

| | |
|---|---|
| CC-3-V | 49.50% |
| CC-3-V1 | 10.00% |
| CCP-V-1 | 10.00% |
| CLP-1V-1 | 6.00% |
| CLP-1V2-T | 5.50% |
| PGP-2-2V | 4.00% |
| PGUQU-3-F | 4.00% |
| APUQU-2-F | 4.50% |
| PP-1-2V1 | 6.00% |
| PPGU-3-F | 0.50% |

Example M96

| | | | |
|---|---|---|---|
| APUQU-2-F | 3.00% | Clearing point [° C.]: | 75.5 |
| CC-3-V | 49.50% | Δn [589 nm, 20° C.]: | 0.1132 |
| CC-3-V1 | 8.50% | Δε [1 kHz, 20° C.]: | 2.5 |
| CLP-1V-1 | 6.00% | $\varepsilon_\parallel$ [1 kHz, 20° C.]: | 5.1 |
| CLP-3-T | 4.50% | $\varepsilon_\perp$ [1 kHz, 20° C.]: | 2.6 |
| PGP-2-2V | 14.00% | $\gamma_1$ [mPa · s, 20° C.]: | 50 |
| PGP-3-2V | 2.50% | $K_1$ [pN, 20° C.]: | 15.1 |
| PGUQU-3-F | 2.50% | $K_3$ [pN, 20° C.]: | 15.0 |
| PP-1-2V1 | 7.00% | | |
| PPGU-3-F | 0.50% | | |
| PUQU-3-F | 2.00 | | |

Example M97

| | | | |
|---|---|---|---|
| APUQU-2-F | 7.50% | Clearing point [° C.]: | 76.0 |
| CC-3-V | 50.00% | Δn [589 nm, 20° C.]: | 0.1091 |
| CC-3-V1 | 9.50% | Δε [1 kHz, 20° C.]: | 2.5 |
| CLP-1V-1 | 6.00% | $\varepsilon_\parallel$ [1 kHz, 20° C.]: | 5.1 |
| CLP-3-T | 4.50% | $\varepsilon_\perp$ [1 kHz, 20° C.]: | 2.6 |
| PGP-2-2V | 15.00% | $\gamma_1$ [mPa · s, 20° C.]: | 50 |
| PP-1-2V1 | 7.00% | $K_1$ [pN, 20° C.]: | 15.2 |
| PPGU-3-F | 0.50% | $K_3$ [pN, 20° C.]: | 15.0 |

Example M98

| | | | |
|---|---|---|---|
| APUQU-2-F | 7.50% | Clearing point [° C.]: | 76.5 |
| CC-3-V | 52.00% | Δn [589 nm, 20° C.]: | 0.1062 |
| CC-3-V1 | 7.50% | Δε [1 kHz, 20° C.]: | 2.5 |
| CCP-V-1 | 2.00% | $\varepsilon_\parallel$ [1 kHz, 20° C.]: | 5.1 |
| CLP-1V-1 | 6.00% | $\varepsilon_\perp$ [1 kHz, 20° C.]: | 2.6 |
| CLP-3-T | 4.50% | $\gamma_1$ [mPa · s, 20° C.]: | 50 |
| PGP-2-2V | 14.00% | | |
| PP-1-2V1 | 6.00% | | |
| PPGU-3-F | 0.50% | | |

Example M99

| | |
|---|---|
| CC-3-V | 46.00% |
| CC-3-V1 | 7.00% |
| CLP-1V-1 | 8.00% |
| CLP-3-T | 7.00% |
| PGP-1-2V | 2.00% |
| PGP-2-2V | 14.50% |
| PP-1-2V1 | 9.00% |
| PPGU-3-F | 0.50% |
| PUQU-3-F | 4.50% |
| PGUQU-3-F | 1.50% |

Example M100

| | | | |
|---|---|---|---|
| APUQU-2-F | 7.50% | Clearing point [° C.]: | 81.5 |
| DGUQU-4-F | 5.00% | Δn [589 nm, 20° C.]: | 0.0989 |
| DPGU-4-F | 4.50% | Δε [1 kHz, 20° C.]: | 6.1 |
| PGUQU-3-F | 3.00% | $\varepsilon_\parallel$ [1 kHz, 20° C.]: | 9.1 |
| PPGU-3-F | 0.50% | $\varepsilon_\perp$ [1 kHz, 20° C.]: | 3.0 |
| CLP-1V-1 | 3.50% | $\gamma_1$ [mPa · s, 20° C.]: | 58 |
| CC-3-2V1 | 5.00% | $K_1$ [pN, 20° C.]: | 14.8 |
| CC-3-V | 50.00% | $K_3$ [pN, 20° C.]: | 15.2 |
| CC-3-V1 | 8.00% | | |
| CLP-3-T | 5.00% | | |
| PGP-2-2V | 8.00% | | |

Example M101

| | |
|---|---|
| CC-3-V | 48.00% |
| CC-3-V1 | 10.50% |
| CCP-V-1 | 11.00% |
| CLP-V-1 | 6.00% |
| CLP-1V2-T | 2.50% |
| CLP-3-T | 3.00% |
| PGP-2-2V | 5.00% |
| PGUQU-3-F | 4.00% |
| APUQU-2-F | 4.50% |
| PP-1-2V1 | 5.00% |
| PPGU-3-F | 0.50% |

Example M102

| | |
|---|---|
| CC-3-V | 49.50% |
| CC-3-V1 | 10.00% |
| CCP-V-1 | 10.00% |
| CLP-1V-1 | 6.00% |
| CLP-1V2-T | 5.50% |
| PGP-2-2V | 4.00% |
| PGUQU-3-F | 4.00% |
| APUQU-2-F | 4.50% |
| PP-1-2V1 | 6.00% |
| PPGU-3-F | 0.50% |

Example M103

| | | | |
|---|---|---|---|
| APUQU-2-F | 4.00% | Clearing point [° C.]: | 76.5 |
| PGUQU-3-F | 3.00% | Δn [589 nm, 20° C.]: | 0.1182 |
| PPGU-3-F | 0.50% | Δε [1 kHz, 20° C.]: | 2.4 |
| CCP-V-1 | 4.00% | $\varepsilon_\parallel$ [1 kHz, 20° C.]: | 5.1 |
| PGP-1-2V | 6.00% | $\varepsilon_\perp$ [1 kHz, 20° C.]: | 2.7 |
| PGP-2-2V | 15.50% | $\gamma_1$ [mPa · s, 20° C.]: | 50 |
| PP-1-2V1 | 6.00% | $K_1$ [pN, 20° C.]: | 14.4 |
| CC-3-V | 52.00% | $K_3$ [pN, 20° C.]: | 14.6 |
| CC-3-V1 | 4.50% | | |
| CLP-1V2-T | 4.50% | | |

Example M104

| | | | |
|---|---|---|---|
| APUQU-2-F | 7.00% | Clearing point [° C.]: | 77 |
| PGUQU-3-F | 6.00% | Δn [589 nm, 20° C.]: | 0.1179 |
| PPGU-3-F | 0.50% | Δε [1 kHz, 20° C.]: | 4.0 |
| CCP-V-1 | 1.00% | $\varepsilon_\parallel$ [1 kHz, 20° C.]: | 6.8 |
| PGP-1-2V | 4.00% | $\varepsilon_\perp$ [1 kHz, 20° C.]: | 2.8 |
| PGP-2-2V | 15.00% | $\gamma_1$ [mPa · s, 20° C.]: | 53 |
| PP-1-2V1 | 4.50% | $K_1$ [pN, 20° C.]: | 14.4 |
| CC-3-V | 50.00% | $K_3$ [pN, 20° C.]: | 14.8 |
| CC-3-V1 | 5.00% | | |
| CC-3-2V1 | 2.00% | | |
| CLP-1V2-T | 5.00% | | |

Example M105

| | | | |
|---|---|---|---|
| APUQU-2-F | 5.50% | Clearing point [° C.]: | 81 |
| DGUQU-4-F | 5.50% | Δn [589 nm, 20° C.]: | 0.0982 |
| DPGU-4-F | 5.00% | Δε [1 kHz, 20° C.]: | 6.1 |
| PGUQU-3-F | 3.00% | $\varepsilon_\parallel$ [1 kHz, 20° C.]: | 9.0 |
| PPGU-3-F | 0.50% | $\varepsilon_\perp$ [1 kHz, 20° C.]: | 3.0 |
| CCP-V-1 | 1.00% | $\gamma_1$ [mPa · s, 20° C.]: | 60 |
| CC-3-2V1 | 9.00% | $K_1$ [pN, 20° C.]: | 15.3 |
| CC-3-V | 48.00% | $K_3$ [pN, 20° C.]: | 15.5 |
| CC-3-V1 | 7.00% | | |
| CLP-3-T | 4.00% | | |
| CLP-1V-T | 3.00% | | |
| PGP-2-2V | 8.50% | | |

Example M106

| | | | |
|---|---|---|---|
| CC-3-V | 50.00% | Clearing point [° C.]: | 83 |
| CC-3-V1 | 11.50% | Δn [589 nm, 20° C.]: | 0.0943 |
| CLP-V-1 | 11.00% | Δε [1 kHz, 20° C.]: | 2.7 |
| CLP-1-V1 | 6.00% | $\varepsilon_\parallel$ [1 kHz, 20° C.]: | 5.2 |
| CLP-3-T | 6.00% | $\varepsilon_\perp$ [1 kHz, 20° C.]: | 2.5 |
| PGP-2-2V | 3.00% | $\gamma_1$ [mPa · s, 20° C.]: | 53 |
| PGUQU-3-F | 3.00% | $K_1$ [pN, 20° C.]: | 16.6 |
| APUQU-3-F | 5.00% | $K_3$ [pN, 20° C.]: | 17.3 |
| PP-1-2V1 | 4.00% | | |
| PPGU-3-F | 0.50% | | |

Example M107

| | | | |
|---|---|---|---|
| CC-3-V | 51.50% | Clearing point [° C.]: | 82 |
| CC-3-V1 | 11.50% | Δn [589 nm, 20° C.]: | 0.0923 |
| CLP-1V-1 | 9.00% | Δε [1 kHz, 20° C.]: | 2.7 |
| CLP-V2-1 | 6.50% | $\varepsilon_\parallel$ [1 kHz, 20° C.]: | 5.2 |
| CLP-3-T | 6.00% | $\varepsilon_\perp$ [1 kHz, 20° C.]: | 2.5 |

-continued

| | | | | |
|---|---|---|---|---|
| PGP-2-2V | 2.00% | $\gamma_1$ [mPa · s, 20° C.]: | | 54 |
| PGUQU-3-F | 3.00% | $K_1$ [pN, 20° C.]: | | 16.5 |
| APUQU-2-F | 5.00% | $K_3$ [pN, 20° C.]: | | 18.0 |
| PP-1-2V1 | 5.00% | | | |
| PPGU-3-F | 0.50% | | | |

Example M108

| | | | | |
|---|---|---|---|---|
| CC-3-V | 50.00% | Clearing point [° C.]: | | 81 |
| CC-3-V1 | 11.50% | $\Delta n$ [589 nm, 20° C.]: | | 0.0956 |
| CLP-1V-1 | 11.00% | $\Delta\varepsilon$ [1 kHz, 20° C.]: | | 2.7 |
| CLP-V2-1 | 6.00% | $\varepsilon_\parallel$ [1 kHz, 20° C.]: | | 5.2 |
| CLP-3-T | 6.00% | $\varepsilon_\perp$ [1 kHz, 20° C.]: | | 2.5 |
| PGP-2-2V | 1.00% | $\gamma_1$ [mPa · s, 20° C.]: | | 51 |
| PGUQU-3-F | 3.00% | $K_1$ [pN, 20° C.]: | | 16.4 |
| APUQU-2-F | 5.00% | $K_3$ [pN, 20° C.]: | | 17.3 |
| PP-1-2V1 | 6.00% | | | |
| PPGU-3-F | 0.50% | | | |

Example M109

| | |
|---|---|
| CC-3-V | 51.50% |
| CC-3-V1 | 11.50% |
| CLP-1V-1 | 8.00% |
| CLP-V2-1 | 6.00% |
| CLP-3-T | 6.50% |
| PGP-2-2V | 2.00% |
| PGUQU-3-F | 3.00% |
| APUQU-2-F | 5.00% |
| PP-1-2V1 | 6.00% |
| PPGU-3-F | 0.50% |

Example M110

| | | | | |
|---|---|---|---|---|
| CC-3-2V1 | 1.00% | Clearing point [° C.]: | | 77.5 |
| CC-3-V | 50.00% | $\Delta n$ [589 nm, 20° C.]: | | 0.1175 |
| CC-3-V1 | 2.00% | $\Delta\varepsilon$ [1 kHz, 20° C.]: | | 4.2 |
| CCP-V-1 | 2.00% | $\varepsilon_\parallel$ [1 kHz, 20° C.]: | | 7.0 |
| CLP-3-T | 6.00% | $\varepsilon_\perp$ [1 kHz, 20° C.]: | | 2.7 |
| CLP-1V-1 | 6.50% | $\gamma_1$ [mPa · s, 20° C.]: | | 54 |
| PGP-2-2V | 11.50% | $K_1$ [pN, 20° C.]: | | 16.6 |
| PP-1-2V1 | 7.00% | $K_3$ [pN, 20° C.]: | | 14.9 |
| PGU-4-T | 3.50% | | | |
| PGUQU-3-F | 5.00% | | | |
| PGUQU-4-F | 5.00% | | | |
| PPGU-3-F | 0.50% | | | |

Example M111

| | | | | |
|---|---|---|---|---|
| APUQU-2-F | 3.00% | Clearing point [° C.]: | | 76.5 |
| CC-3-V | 49.50% | $\Delta n$ [589 nm, 20° C.]: | | 0.1178 |
| CC-3-V1 | 6.00% | $\Delta\varepsilon$ [1 kHz, 20° C.]: | | 2.4 |
| CLP-1V-1 | 6.00% | $\varepsilon_\parallel$ [1 kHz, 20° C.]: | | 5.0 |
| CLP-3-T | 4.50% | $\varepsilon_\perp$ [1 kHz, 20° C.]: | | 2.7 |
| PGP-1-2V | 3.00% | $\gamma_1$ [mPa · s, 20° C.]: | | 50 |
| PGP-2-2V | 13.00% | $K_1$ [pN, 20° C.]: | | 15.2 |
| PGP-3-2V | 2.50% | $K_3$ [pN, 20° C.]: | | 15.1 |
| PGUQU-3-F | 2.00% | | | |
| PP-1-2V1 | 8.00% | | | |
| PPGU-3-F | 0.50% | | | |
| PUQU-3-F | 2.00% | | | |

Example M112

| | | | | |
|---|---|---|---|---|
| APUQU-2-F | 2.00% | Clearing point [° C.]: | | 75 |
| PGUQU-3-F | 5.00% | $\Delta n$ [589 nm, 20° C.]: | | 0.1171 |
| PPGU-3-F | 0.50% | $\Delta\varepsilon$ [1 kHz, 20° C.]: | | 2.4 |
| CCP-V-1 | 2.50% | $\varepsilon_\parallel$ [1 kHz, 20° C.]: | | 5.0 |
| LPP-3-2 | 3.50% | $\varepsilon_\perp$ [1 kHz, 20° C.]: | | 2.7 |
| PGP-2-2V | 15.00% | $\gamma_1$ [mPa · s, 20° C.]: | | 46 |
| PP-1-2V1 | 9.00% | $K_1$ [pN, 20° C.]: | | 15.3 |
| CC-3-V | 51.00% | $K_3$ [pN, 20° C.]: | | 14.3 |
| CC-3-V1 | 5.00% | | | |
| CLP-3-T | 4.50% | | | |
| CLP-1V-1 | 2.00% | | | |

Example M113

| | | | | |
|---|---|---|---|---|
| CC-3-V | 46.00% | Clearing point [° C.]: | | 77.5 |
| CC-3-V1 | 6.00% | $\Delta n$ [589 nm, 20° C.]: | | 0.1196 |
| CLP-1V-1 | 1.50% | $\Delta\varepsilon$ [1 kHz, 20° C.]: | | 2.9 |
| PGP-2-2V | 11.00% | $\varepsilon_\parallel$ [1 kHz, 20° C.]: | | 6.8 |
| PGP-3-2V | 2.00% | $\varepsilon_\perp$ [1 kHz, 20° C.]: | | 3.9 |
| PGU-2-F | 6.50% | $\gamma_1$ [mPa · s, 20° C.]: | | 57 |
| PGUQU-3-F | 5.00% | $K_1$ [pN, 20° C.]: | | 15.6 |
| CLP-3-T | 5.00% | $K_3$ [pN, 20° C.]: | | 14.2 |
| B(S)-2O-O4 | 3.50% | | | |
| B(S)-2O-O5 | 3.50% | | | |
| CC-3-2V1 | 1.00% | | | |
| DGUQU-4-F | 1.50% | | | |
| PY-3-O2 | 2.50% | | | |
| CLP-1-V1 | 5.00% | | | |

Example M114

| | |
|---|---|
| APUQU-2-F | 4.50% |
| PGUQU-3-F | 4.00% |
| PPGU-3-F | 0.50% |
| CLP-1V-1 | 6.00% |
| PGP-1-2V | 2.50% |
| PGP-2-2V | 16.50% |
| PP-1-2V1 | 7.50% |
| CC-3-V | 52.50% |
| CC-3-V1 | 6.00% |

Example M115

| | | | | |
|---|---|---|---|---|
| CC-3-V | 47.50% | Clearing point [° C.]: | | 79.5 |
| CC-3-V1 | 5.50% | $\Delta n$ [589 nm, 20° C.]: | | 0.1178 |
| PGP-2-2V | 12.00% | $\Delta\varepsilon$ [1 kHz, 20° C.]: | | 2.9 |
| PGP-3-2V | 2.50% | $\varepsilon_\parallel$ [1 kHz, 20° C.]: | | 6.6 |
| PGU-2-F | 5.50% | $\varepsilon_\perp$ [1 kHz, 20° C.]: | | 3.8 |
| PGUQU-3-F | 2.00% | $\gamma_1$ [mPa · s, 20° C.]: | | 58 |
| CLP-3-T | 5.00% | $K_1$ [pN, 20° C.]: | | 15.8 |
| B(S)-2O-O4 | 3.50% | $K_3$ [pN, 20° C.]: | | 14.7 |
| B(S)-2O-O5 | 3.50% | | | |
| CC-3-2V1 | 2.50% | | | |

Example M116

| | | | |
|---|---|---|---|
| CC-3-V | 47.50% | Clearing point [° C.]: | 81.5 |
| CC-3-V1 | 2.00% | Δn [589 nm, 20° C.]: | 0.1195 |
| PGP-2-2V | 12.00% | Δε [1 kHz, 20° C.]: | 2.9 |
| PGP-3-2V | 1.00% | $\varepsilon_{\parallel}$ [1 kHz, 20° C.]: | 6.7 |
| PGU-2-F | 7.50% | $\varepsilon_{\perp}$ [1 kHz, 20° C.]: | 3.8 |
| PGUQU-3-F | 1.00% | | |
| CLP-3-T | 5.00% | | |
| B(S)-2O-O4 | 3.50% | | |
| B(S)-2O-O5 | 3.50% | | |
| CC-3-2V1 | 3.00% | | |
| DGUQU-4-F | 3.00% | | |
| CLP-1V-1 | 4.00% | | |
| PGIY-2-O4 | 1.00% | | |
| APUQU-2-F | 1.00% | | |
| CLP-V-1 | 5.00% | | |

-continued

| | | | |
|---|---|---|---|
| DGUQU-4-F | 3.00% | | |
| CLP-1V-1 | 4.50% | | |
| PGIY-2-O4 | 1.50% | | |
| APUQU-2-F | 1.50% | | |

Example M117

| | | | |
|---|---|---|---|
| APUQU-2-F | 6.00% | Clearing point [° C.]: | 80 |
| APUQU-3-F | 5.00% | Δn [589 nm, 20° C.]: | 0.1129 |
| PGUQU-3-F | 2.00% | Δε [1 kHz, 20° C.]: | 3.9 |
| PPGU-3-F | 0.50% | $\varepsilon_{\parallel}$ [1 kHz, 20° C.]: | 6.7 |
| CCP-V-1 | 2.50% | $\varepsilon_{\perp}$ [1 kHz, 20° C.]: | 2.8 |
| PGP-1-2V | 4.00% | $\gamma_1$ [mPa · s, 20° C.]: | 52 |
| PGP-2-2V | 16.50% | $K_1$ [pN, 20° C.]: | 14.1 |
| CC-3-V | 52.00% | $K_3$ [pN, 20° C.]: | 14.1 |
| CC-3-V1 | 6.50% | $V_0$ [V, 20° C.]: | 2.03 |
| CLP-3-T | 5.00% | | |

Liquid-crystalline mixture M117 is additionally stabilized with 0.05% of the compound of the formula ST-1

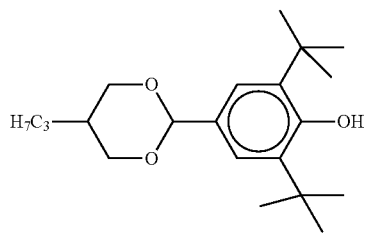

ST-1

Example M118

| | | | |
|---|---|---|---|
| APUQU-2-F | 5.00% | Clearing point [° C.]: | 80 |
| PGUQU-3-F | 6.00% | Δn [589 nm, 20° C.]: | 0.1131 |
| PPGU-3-F | 0.50% | Δε [1 kHz, 20° C.]: | 3.5 |
| CCP-V-1 | 8.50% | $\varepsilon_{\parallel}$ [1 kHz, 20° C.]: | 6.2 |
| PGP-2-2V | 16.50% | $\varepsilon_{\perp}$ [1 kHz, 20° C.]: | 2.7 |
| PP-1-2V1 | 4.00% | $\gamma_1$ [mPa · s, 20° C.]: | 51 |
| CC-3-V | 48.00% | $K_1$ [pN, 20° C.]: | 14.6 |
| CC-3-V1 | 6.50% | $K_3$ [pN, 20° C.]: | 14.7 |
| CLP-3-T | 5.00% | $V_0$ [V, 20° C.]: | 2.17 |

Liquid-crystalline mixture M118 is additionally stabilized with 0.05% of the compound of the formula ST-1

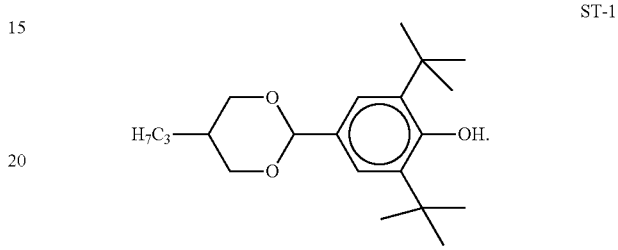

ST-1

Example M119

| | | | |
|---|---|---|---|
| APUQU-2-F | 2.50% | Clearing point [° C.]: | 85 |
| CC-3-2V1 | 5.00% | Δn [589 nm, 20° C.]: | 0.1093 |
| CC-3-V | 24.50% | Δε [1 kHz, 20° C.]: | 8.6 |
| CC-3-V1 | 5.00% | $\varepsilon_{\parallel}$ [1 kHz, 20° C.]: | 10.6 |
| CCP-3OCF$_3$ | 3.00% | $\varepsilon_{\perp}$ [1 kHz, 20° C.]: | 2.0 |
| CCP-V-1 | 9.00% | $\gamma_1$ [mPa · s, 20° C.]: | 94 |
| CCP-V2-1 | 8.00% | $K_1$ [pN, 20° C.]: | 14.9 |
| CLP-3-T | 7.00% | $K_3$ [pN, 20° C.]: | 14.6 |
| CPGP-4-3 | 2.00% | $V_0$ [V, 20° C.]: | 1.39 |
| DGUQU-4-F | 5.00% | | |
| DPGU-4-F | 5.50% | | |
| PGP-2-2V | 2.00% | | |
| PGUQU-3-F | 6.00% | | |
| PGUQU-4-F | 6.00% | | |
| PPGU-3-F | 0.50% | | |
| Y-4O-O4 | 9.00% | | |

Liquid-crystalline mixture M119 is additionally stabilized with 0.04% of the compound of the formula ST-1 and with 0.02% of the compound of the formula ST-3

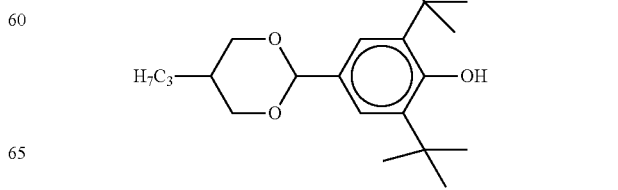

ST-1

-continued

ST-3

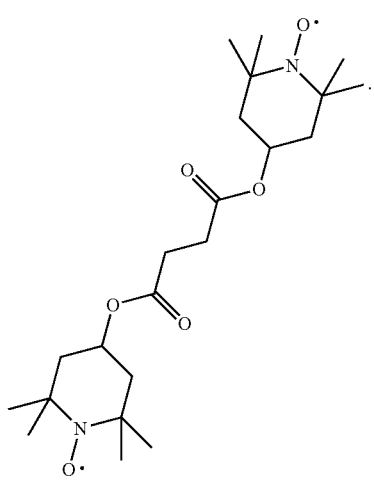

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. Shutter spectacles having 3D effects, LC lenses or positive VA displays containing in said shutter spectacles, LC lenses or positive VA displays, a nematic liquid-crystalline medium, comprising in said nematic liquid-crystalline medium:

one or more compounds of formula I,

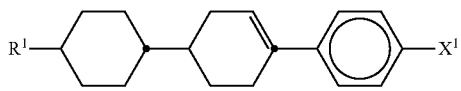
I in which
$R^1$ denotes a straight-chain alkyl radical having 3 to 5 C atoms, and
$X^1$ denotes $CF_3$;
and further comprising:
one or more compounds of formulae II and/or III,

II

III in which
A denotes 1,4-phenylene or trans-1,4-cyclohexylene,
a denotes 0 or 1, $R^3$ denotes alkenyl having 2 to 9 C atoms, and
$R^4$ denotes an alkyl radical having 1 to 15 C atoms, wherein at least one $CH_2$ group is replaced by —CH=CH—, and optionally one or more $CH_2$ groups in these radicals may each be replaced, independently of one another, by

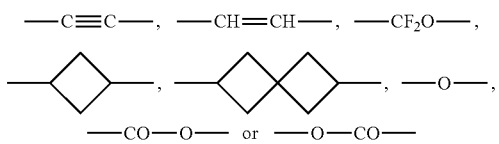

in such a way that O atoms are not linked directly to one another, and in which, in addition, one or more H atoms may be replaced by halogen, or $C_{1-15}$ alkyl in which one or more $CH_2$ group is replaced, independently of one another, by

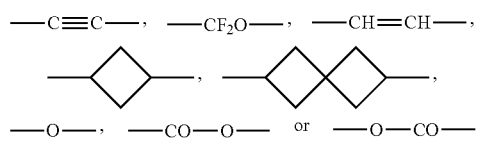

in such a way that O atoms are not linked directly to one another, and in which, in addition, one or more H atoms may be replaced by halogen;
or
one or more compounds of formulae X and/or XI,

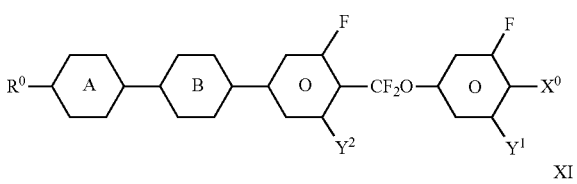
X

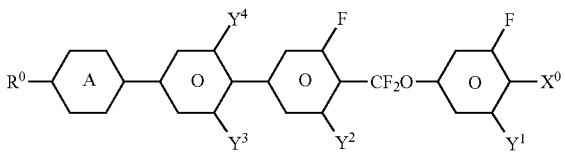
XI in which

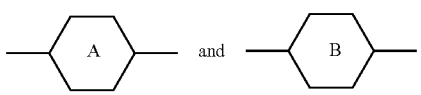

each, independently of one another, denote

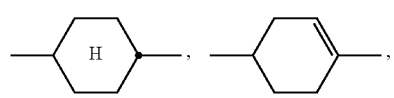

-continued

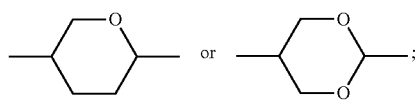

R⁰ denotes an alkyl or alkoxy radical having 1 to 15 C atoms, where, in addition, one or more CH₂ groups in these radicals may each be replaced, independently of one another, by

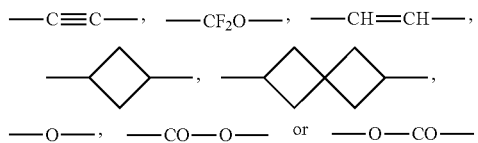

in such a way that O atoms are not linked directly to one another, and in which, in addition, one or more H atoms may be replaced by halogen, cycloalkyl with 3 to 6 C atoms, X⁰ denotes F, Cl, a mono- or polyfluorinated alkyl or alkoxy radical having 1 to 6 C atoms, a mono- or polyfluorinated alkenyl or alkenyloxy radical having 2 to 6 C atoms, and $Y^{1-4}$ each, independently of one another, denote H or F;

or one or more compounds of formulae D1, D2, D3, D4 or D5,

D1

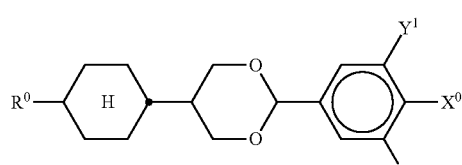

D2

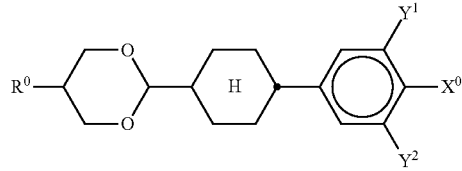

D3

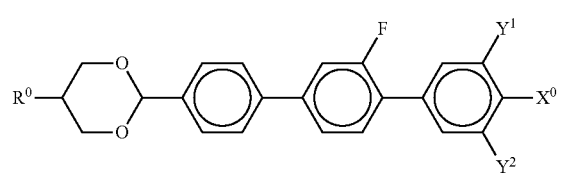

D4

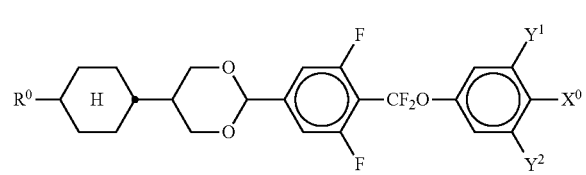

D5

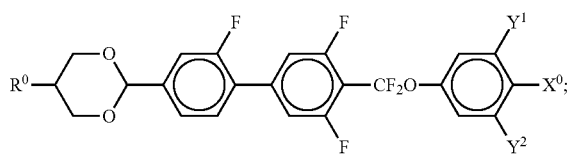

in which $R^0$, $X^0$ and $Y^1$-$Y^2$ independently have one of the meanings as defined above;

or one or more compounds of formulae Y-1, Y-2, Y-3 or Y-4,

Y-1

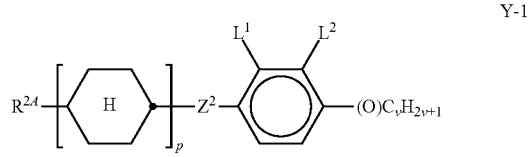

Y-2

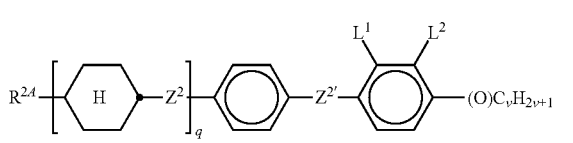

Y-3

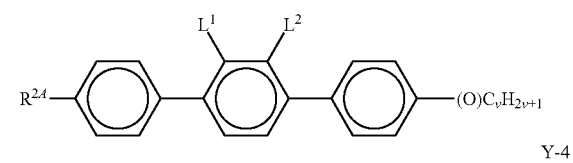

Y-4

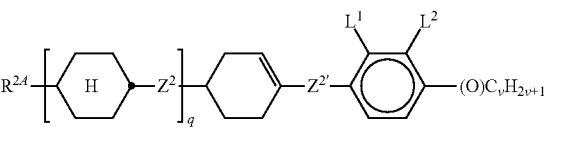

in which $R^{2A}$ denotes H, an alkyl or alkoxy radical having 1 to 15 C atoms, where, in addition, one or more CH₂ groups in these radicals may each be replaced, independently of one another, by

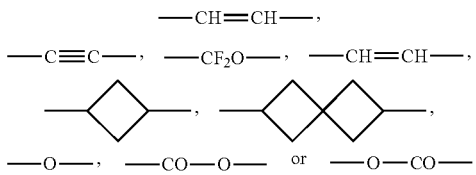

in such a way that O atoms are not linked directly to one another, and in which, in addition, one or more H atoms may be replaced by halogen, $L^1$ and $L^2$ each, independently of one another, denote F, Cl, CF₃ or CHF₂, $Z^2$ and $Z^{2'}$ each, independently of one another, denote a single bond, —CH₂CH₂—, —CH═CH—, —CF₂O—, —OCF₂—, —CH₂O—, —OCH₂—, —COO—, —OCO—, —C₂F₄—, —CF═CF— or —CH═CHCH₂O—, p denotes 0, 1 or 2,
q denotes 0 or 1,
(O)C$_v$H$_{2v+1}$ denotes OC$_v$H$_{2v+1}$ or C$_v$H$_{2v+1}$, and
v denotes 1 to 6;
or
one or more compounds of formulae CR, PH-1, PH-2, or BS,

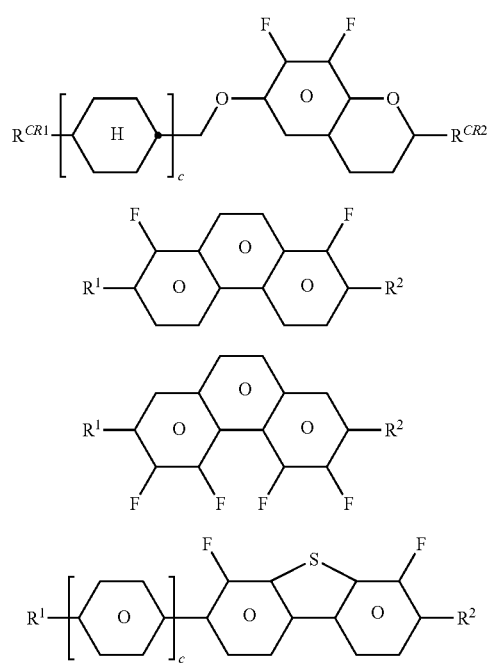

CR

PH-1

PH-2

BS in which
R$^{B1}$, R$^{B2}$, R$^{CR1}$, R$^{CR2}$, R$^1$ and R$^2$ each, independently of one another, denotes H, an alkyl or alkoxy radical having 1 to 15 C atoms, where, in addition, one or more CH$_2$ groups in these radicals may each be replaced, independently of one another, by

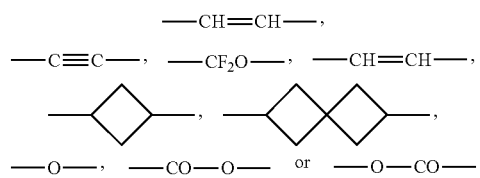

in such a way that O atoms are not linked directly to one another, and in which, in addition, one or more H atoms may be replaced by halogen, and
c denotes 0, 1 or 2.

2. The shutter spectacles having 3D effects, LC lenses or positive VA displays according to claim 1, wherein the liquid crystalline medium comprises one or more compounds of formulae II and/or III.

3. The shutter spectacles having 3D effects, LC lenses or positive VA displays according to claim 2, wherein the liquid crystalline medium comprises one or more compounds of the following formulae,

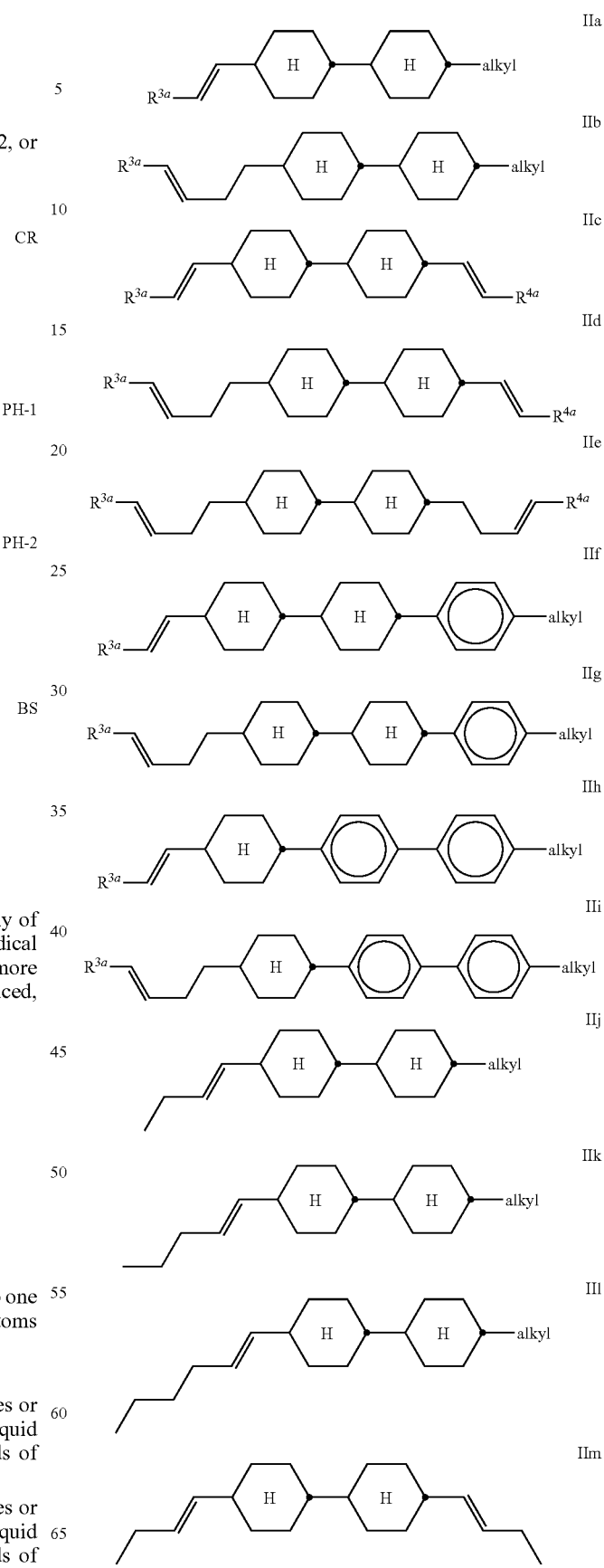

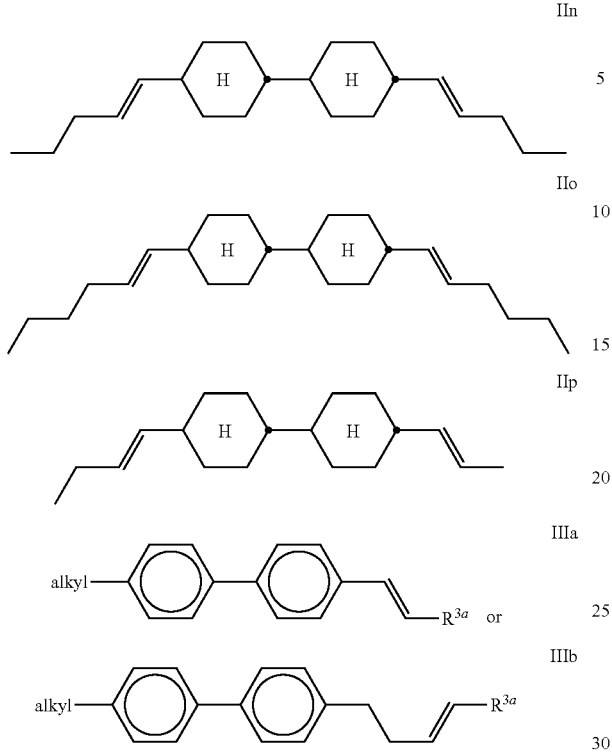

in which $R^{3a}$ and $R^{4a}$ each, independently of one another, denote H, $CH_3$, $C_2H_5$ or $C_3H_7$, and alkyl denotes a straight-chain alkyl group having 1 to 8 C atoms.

4. The shutter spectacles having 3D effects, LC lenses or positive VA displays according to claim 1, wherein the liquid crystalline medium additionally comprises one or more compounds of formulae IV to VIII,

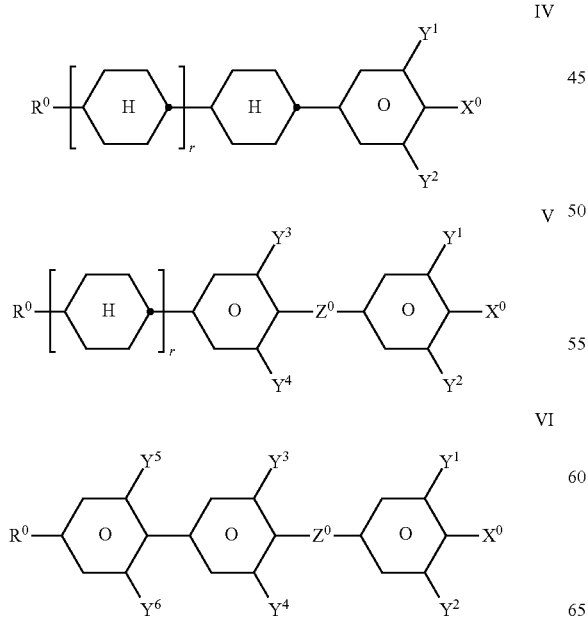

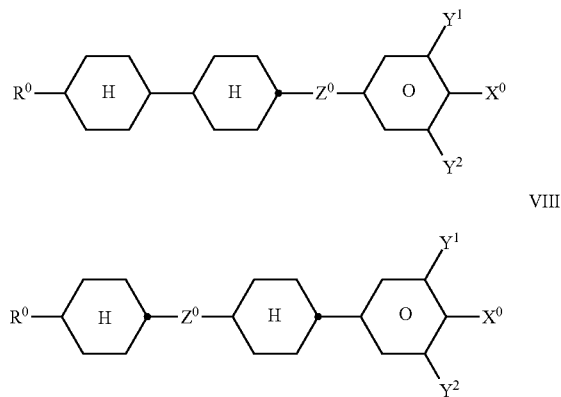

in which $R^0$ denotes an alkyl or alkoxy radical having 1 to 15 C atoms, where, in addition, one or more $CH_2$ groups in these radicals may each be replaced, independently of one another, by

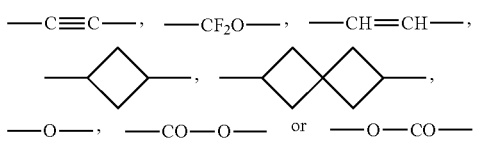

in such a way that O atoms are not linked directly to one another, and in which, in addition, one or more H atoms may be replaced by halogen, cycloalkyl with 3 to 6 C atoms, $X^0$ denotes F, Cl, a mono- or polyfluorinated alkyl or alkoxy radical having 1 to 6 C atoms, a mono- or polyfluorinated alkenyl or alkenyloxy radical having 2 to 6 C atoms, $Y^{1-6}$ each, independently of one another, denote H or F, $Z^0$ denotes $—C_2H_4—$, $—(CH_2)_4—$, $—CH=CH—$, $—CF=CF—$, $—C_2F_4—$, $—CH_2CF_2—$, $—CF_2CH_2—$, $—CH_2O—$, $—OCH_2—$, $—COO—$, $—CF_2O—$ or $—OCF_2—$, in the formulae V and VI also a single bond, and r denotes 0 or 1.

5. The shutter spectacles having 3D effects, LC lenses or positive VA displays according to claim 4, wherein the liquid crystalline medium comprises one or more compounds of formula V which is selected from compounds of the formulae Va to Vj,

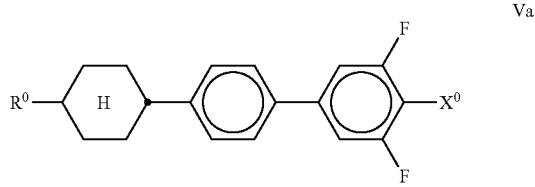

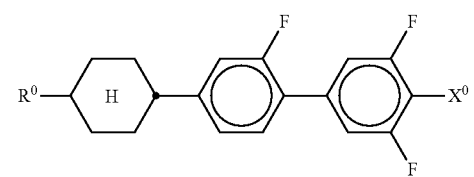
Vb

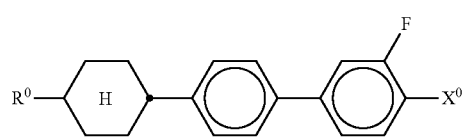
Vc

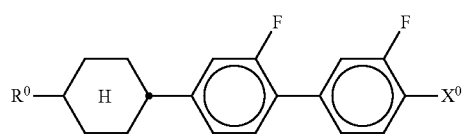
Vd

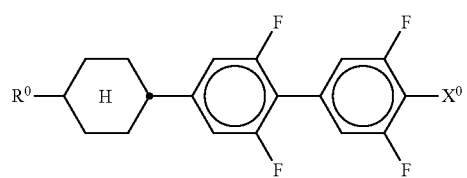
Ve

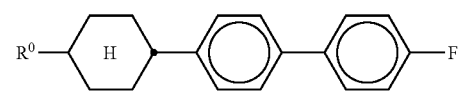
Vf

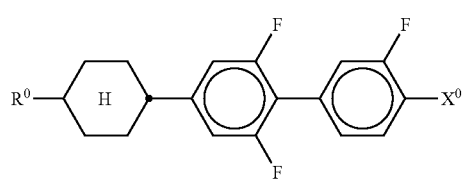
Vg

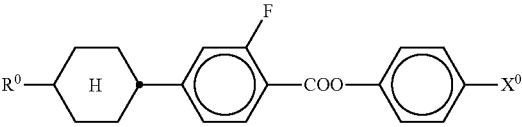
Vh

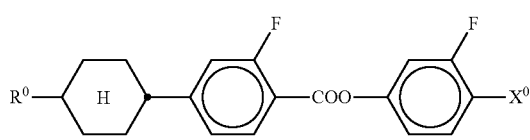
Vi

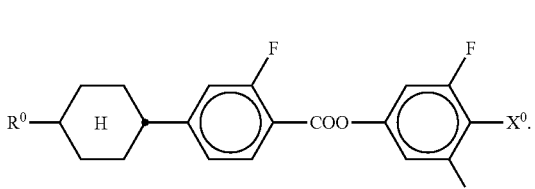
Vj

6. The shutter spectacles having 3D effects, LC lenses or positive VA displays according to claim 4, wherein the liquid crystalline medium comprises one or more compounds of formula VI which are selected from compounds of the formulae VI-1a to VI-1d,

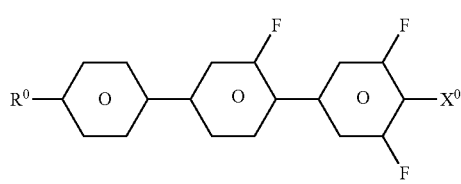
VI-1a

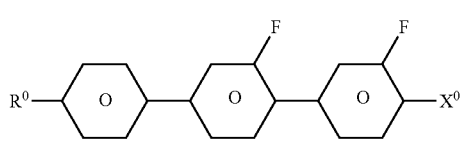
VI-1b

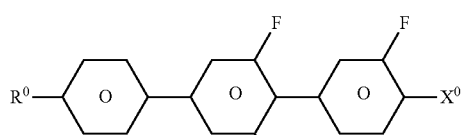
VI-1c

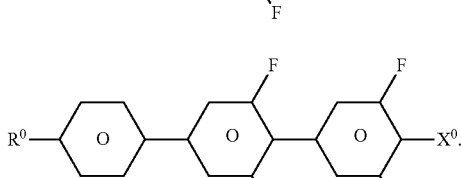
VI-1d

7. The shutter spectacles having 3D effects, LC lenses or positive VA displays according to claim 4, wherein the liquid crystalline medium comprises one or more compounds of formula VI which are selected from compounds of the formulae VI-2a to VI-2f,

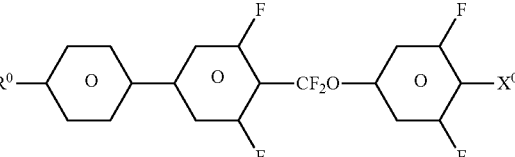
VI-2a

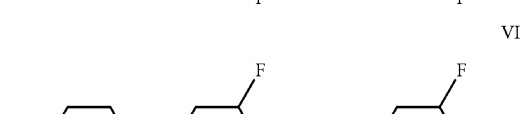
VI-2b

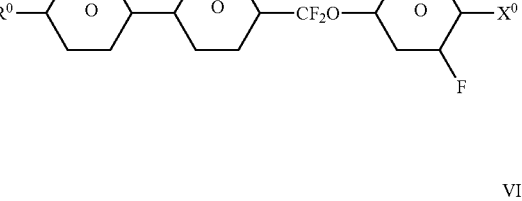
VI-2c

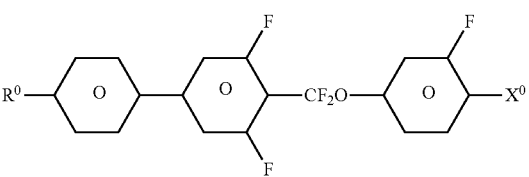

-continued

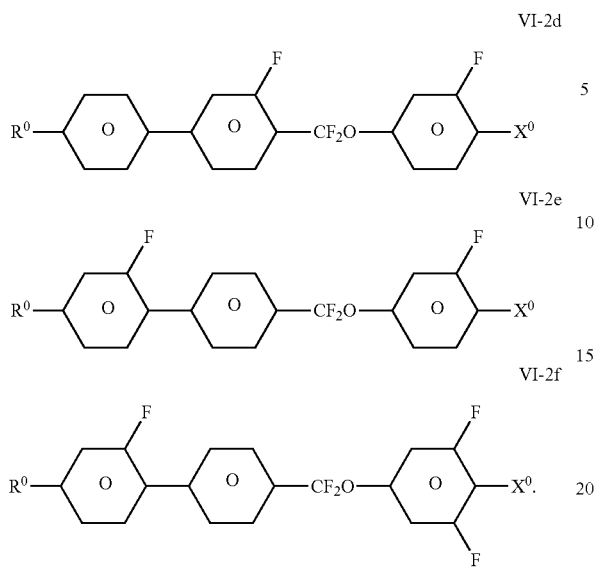

8. The shutter spectacles having 3D effects, LC lenses or positive VA displays according to claim 4, wherein the liquid crystalline medium comprises one or more compounds of formulae X and/or XI.

9. The shutter spectacles having 3D effects, LC lenses or positive VA displays according to claim 1, wherein the liquid crystalline medium additionally comprises one or more compounds of formula XII,

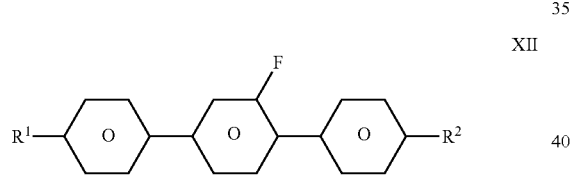

in which
$R^1$ and $R^2$ each, independently of one another, denote $C_{1-9}$-alkyl, $C_{2-9}$-alkenyl, $C_{1-9}$-alkoxy, $C_{1-9}$-oxaalkyl, $C_{1-9}$-fluoroalkyl or $C_{2-9}$-alkenyloxy.

10. The shutter spectacles having 3D effects, LC lenses or positive VA displays according to claim 4, wherein the liquid crystalline medium additionally comprises one or more compounds of formulae XIII to XVI,

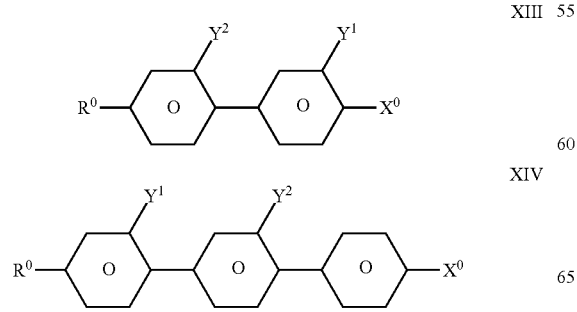

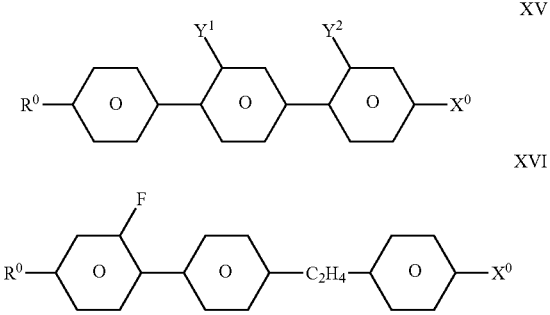

in which
$R^0$ denotes an alkyl or alkoxy radical having 1 to 15 C atoms, where, in addition, one or more $CH_2$ groups in these radicals may each be replaced, independently of one another, by

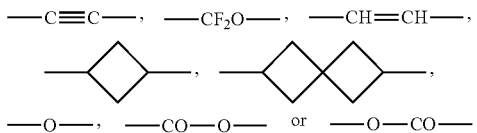

in such a way that O atoms are not linked directly to one another, and in which, in addition, one or more H atoms may be replaced by halogen, cycloalkyl with 3 to 6 C atoms, $X^0$ denotes F, Cl, a mono- or polyfluorinated alkyl or alkoxy radical having 1 to 6 C atoms, a mono- or polyfluorinated alkenyl or alkenyloxy radical having 2 to 6 C atoms, and $Y^{1-2}$ each, independently of one another, denote H or F.

11. The shutter spectacles having 3D effects, LC lenses or positive VA displays according to claim 1, wherein the liquid crystalline medium additionally comprises one or more compounds of formulae

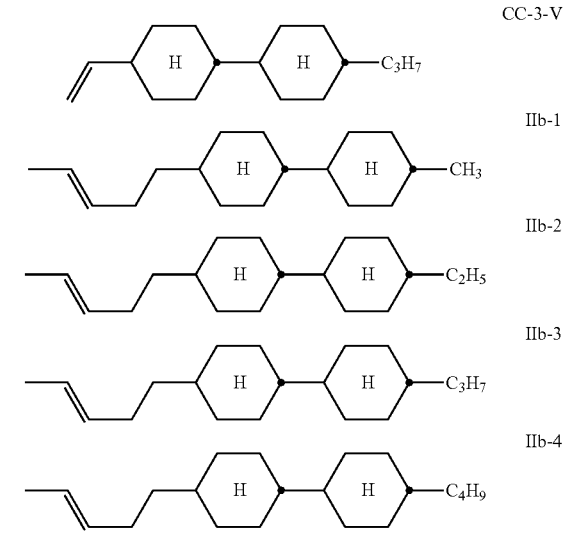

-continued

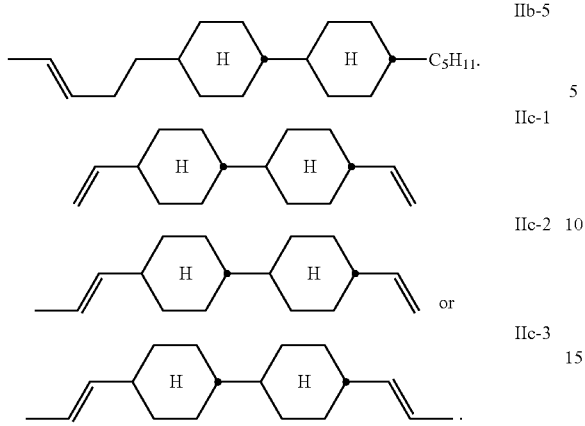

IIb-5

IIc-1

IIc-2 or

IIc-3

12. The shutter spectacles having 3D effects, LC lenses or positive VA displays according to claim 1, wherein the liquid crystalline medium comprises one or more compounds of formulae D1, D2, D3, D4 or D5.

13. The shutter spectacles having 3D effects, LC lenses or positive VA displays according to claim 1, wherein the liquid crystalline medium comprises one or more compounds of formulae Y-1, Y-2, Y-3 or Y-4.

14. The shutter spectacles having 3D effects, LC lenses or positive VA displays according to claim 1, wherein the liquid crystalline medium comprises one or more compounds of formulae BC, CR, PH-1, PH-2, BF or BS.

15. The shutter spectacles having 3D effects, LC lenses or positive VA displays according to claim 1, wherein the liquid crystalline medium comprises 1-30% by weight of compounds of the formula I.

16. The shutter spectacles having 3D effects, LC lenses or positive VA displays according to claim 1, wherein the liquid crystalline medium additionally comprises one or more UV stabilizers and/or antioxidants.

17. The shutter spectacles having 3D effects, LC lenses or positive VA displays according to claim 1, wherein the liquid crystalline medium additionally comprises one or more polymerizable compounds.

18. The shutter spectacles having 3D effects, LC lenses or positive VA displays according to claim 1, wherein in the liquid crystalline medium R1 is propyl.

19. The shutter spectacles having 3D effects, LC lenses or positive VA displays according to claim 1, wherein the medium has a rotational viscosity, $\gamma_1$, of <120 mPa·s.

20. The shutter spectacles having 3D effects, LC lenses or positive VA displays according to claim 1, wherein the liquid crystalline medium comprises one or more compounds of formulae X and/or XI.

21. The shutter spectacles having 3D effects, LC lenses or positive VA displays according to claim 1, wherein the liquid crystalline medium additionally comprises one or more compounds of formulae XIII to XVI,

XIII

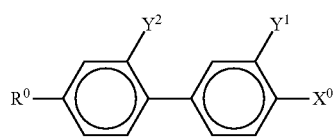

-continued

XIV

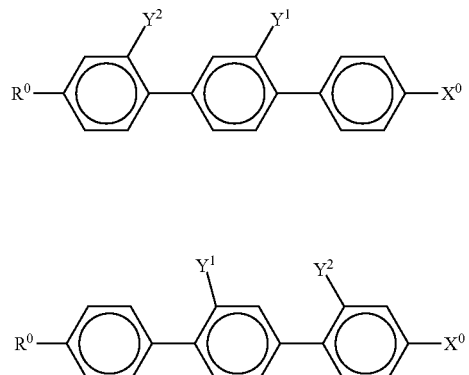

XV

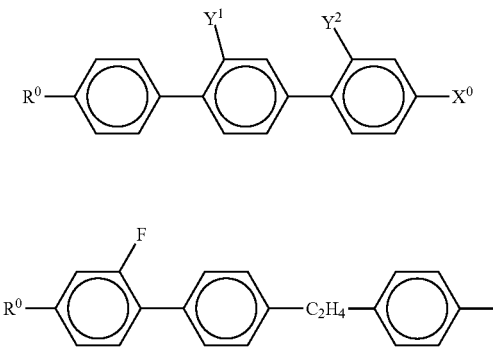

XVI

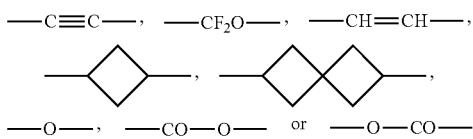

in which $R^0$ denotes an alkyl or alkoxy radical having 1 to 15 C atoms, where, in addition, one or more $CH_2$ groups in these radicals may each be replaced, independently of one another, by

—C≡C—, —CF$_2$O—, —CH=CH—,

, ,

—O—, —CO—O— or —O—CO— in such a way that O atoms are not linked directly to one another, and in which, in addition, one or more H atoms may be replaced by halogen, cycloalkyl with 3 to 6 C atoms, $X^0$ denotes F, Cl, a mono- or polyfluorinated alkyl or alkoxy radical having 1 to 6 C atoms, a mono- or polyfluorinated alkenyl or alkenyloxy radical having 2 to 6 C atoms, and $Y^{1-2}$ each, independently of one another, denote H or F.

22. Shutter spectacles having 3D effects, LC lenses or positive VA displays, comprising in said shutter spectacles, LC lenses or positive VA displays a nematic liquid-crystalline medium, comprising in said nematic liquid-crystalline medium:

one or more compounds of formula I,

I

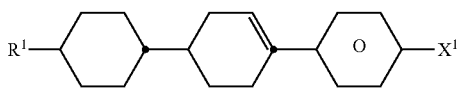

in which
R$^1$ denotes a straight-chain alkyl radical having 3 to 5 C atoms, and
X$^1$ denotes CF$_3$;
and further comprising:
one or more compounds of formulae II and/or III,

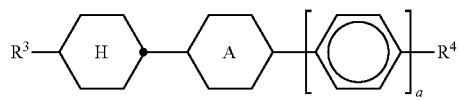

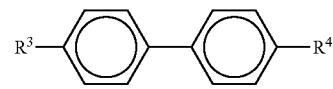

in which
A denotes 1,4-phenylene or trans-1,4-cyclohexylene,
a denotes 0 or 1,
R$^3$ denotes alkenyl having 2 to 9 C atoms, and
R$^4$ denotes an alkyl radical having 1 to 15 C atoms, wherein at least one CH$_2$ group is replaced by —CH=CH—, and optionally one or more CH$_2$ groups in these radicals may each be replaced, independently of one another, by

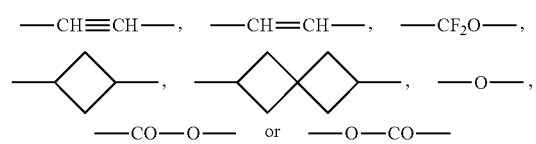

in such a way that O atoms are not linked directly to one another, and in which, in addition, one or more H atoms may be replaced by halogen, or C$_{1-15}$ alkyl in which one or more CH$_2$ group is replaced, independently of one another, by

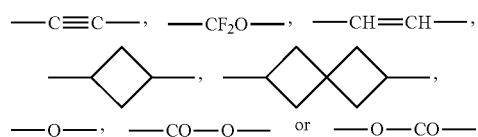

in such a way that O atoms are not linked directly to one another, and in which, in addition, one or more H atoms may be replaced by halogen;
or
one or more compounds of formulae X and/or XI,

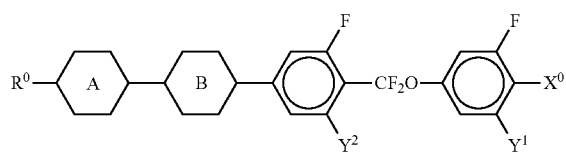

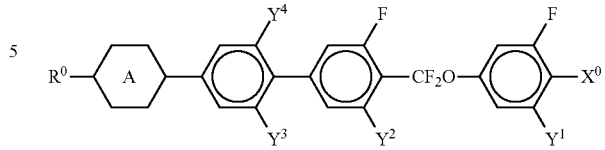

in which

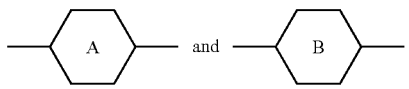

each, independently of one another, denote

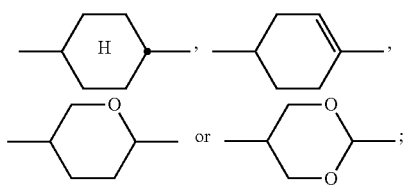

R$^0$ denotes an alkyl or alkoxy radical having 1 to 15 C atoms, where, in addition, one or more CH$_2$ groups in these radicals may each be replaced, independently of one another, by

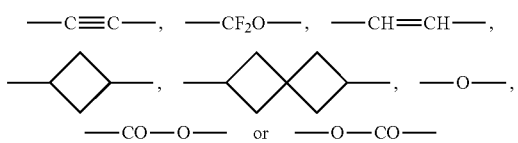

in such a way that O atoms are not linked directly to one another, and in which, in addition, one or more H atoms may be replaced by halogen, cycloalkyl with 3 to 6 C atoms,
X$^0$ denotes F, Cl, a mono- or polyfluorinated alkyl or alkoxy radical having 1 to 6 C atoms, a mono- or polyfluorinated alkenyl or alkenyloxy radical having 2 to 6 C atoms, and
Y$^{1-4}$ each, independently of one another, denote H or F;
or
one or more compounds of formulae D1, D2, D3, D4 or D5,

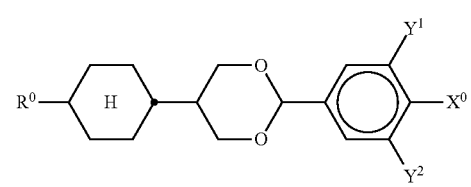

-continued

D2
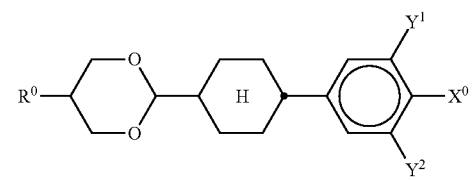

D3
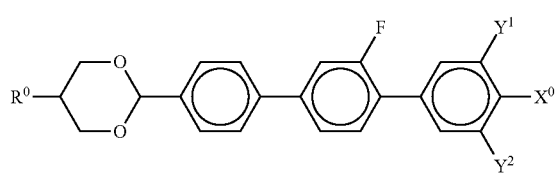

D4
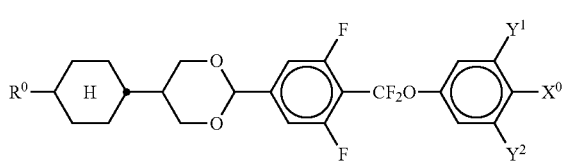

D5
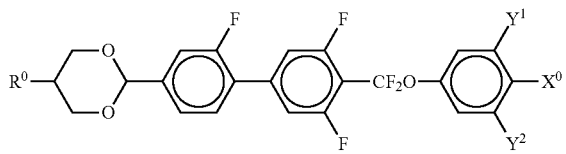

in which $R^0$, $X^0$ and $Y^1$-$Y^2$ independently have one of the meanings as defined above;

or one or more compounds of formulae Y-1, Y-2, Y-3 or Y-4,

Y-1
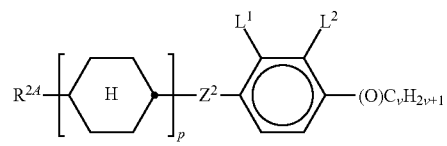

Y-2
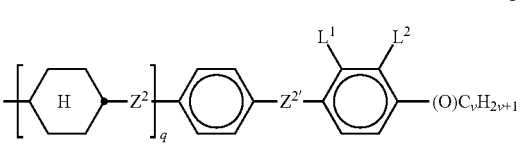

Y-3
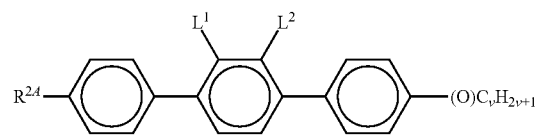

Y-4
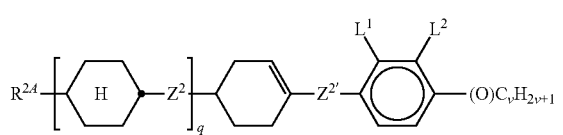

in which
$R^{2A}$ denotes H, an alkyl or alkoxy radical having 1 to 15 C atoms, where, in addition, one or more $CH_2$ groups in these radicals may each be replaced, independently of one another, by

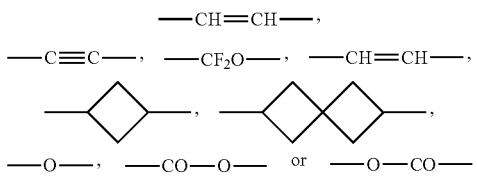

in such a way that O atoms are not linked directly to one another, and in which, in addition, one or more H atoms may be replaced by halogen, $L^1$ and $L^2$ each, independently of one another, denote F, Cl, $CF_3$ or $CHF_2$, $Z^2$ and $Z^{2'}$ each, independently of one another, denote a single bond, —$CH_2CH_2$—, —CH═CH—, —$CF_2O$—, —$OCF_2$—, —$CH_2O$—, —$OCH_2$—, —COO—, —OCO—, —$C_2F_4$—, —CF═CF— or —CH═CHCH$_2$O—, p denotes 0, 1 or 2, q denotes 0 or 1, $(O)C_vH_{2v+1}$ denotes $OC_vH_{2v+1}$ or $C_vH_{2v+1}$, and v denotes 1 to 6;

or one or more compounds of formula BS

BS
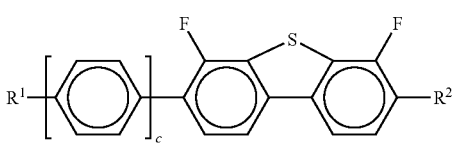

in which
$R^1$ and $R^2$ each, independently of one another, denotes H, an alkyl or alkoxy radical having 1 to 15 C atoms, where, in addition, one or more $CH_2$ groups in these radicals may each be replaced, independently of one another, by

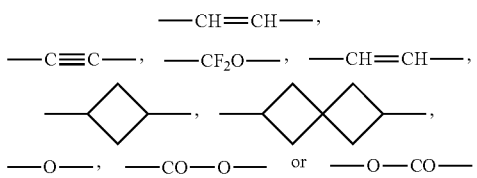

in such a way that O atoms are not linked directly to one another, and in which, in addition, one or more H atoms may be replaced by halogen, and c denotes 0, 1 or 2.

23. Shutter spectacles having 3D effects, LC lenses or positive VA displays, comprising in said shutter spectacles, LC lenses or positive VA displays, a nematic liquid-crystalline medium, comprising in said nematic liquid-crystalline medium:

one or more compounds of formula CLP-n-T,

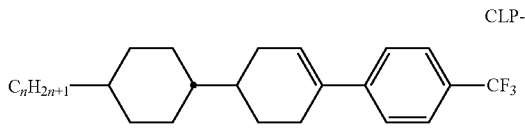

in which n is 3, and further comprising:

one or more compounds of formulae II and/or III,

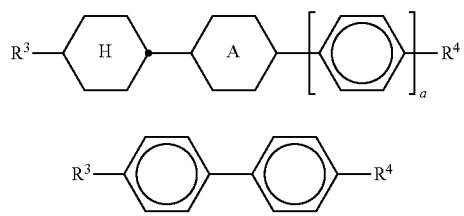

in which

A denotes 1,4-phenylene or trans-1,4-cyclohexylene, a denotes 0 or 1, $R^3$ denotes alkenyl having 2 to 9 C atoms, and $R^4$ denotes an alkyl radical having 1 to 15 C atoms, wherein at least one $CH_2$ group is replaced by —CH=CH—, and optionally one or more $CH_2$ groups in these radicals may each be replaced, independently of one another, by

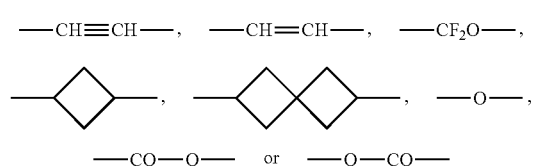

in such a way that O atoms are not linked directly to one another, and in which, in addition, one or more H atoms may be replaced by halogen, or $C_{1-15}$ alkyl in which one or more $CH_2$ group is replaced, independently of one another, by

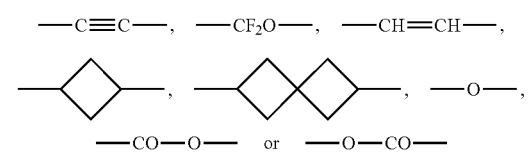

in such a way that O atoms are not linked directly to one another, and in which, in addition, one or more H atoms may be replaced by halogen;

or one or more compounds of formulae X and/or XI,

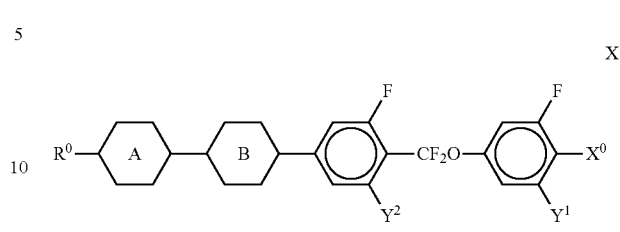

in which

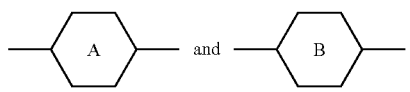

each, independently of one another, denote

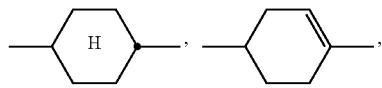

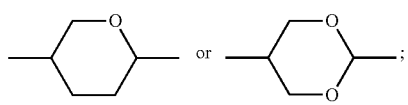

$R^0$ denotes an alkyl or alkoxy radical having 1 to 15 C atoms, where, in addition, one or more $CH_2$ groups in these radicals may each be replaced, independently of one another, by

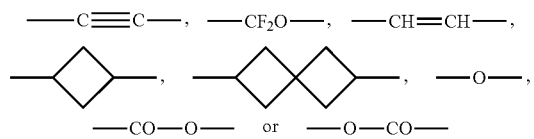

in such a way that O atoms are not linked directly to one another, and in which, in addition, one or more H atoms may be replaced by halogen, cycloalkyl with 3 to 6 C atoms, $X^0$ denotes F, Cl, a mono- or polyfluorinated alkyl or alkoxy radical having 1 to 6 C atoms, a mono- or polyfluorinated alkenyl or alkenyloxy radical having 2 to 6 C atoms, and $Y^{1-4}$ each, independently of one another, denote H or F;

or one or more compounds of formulae D1, D2, D3, D4 or D5,

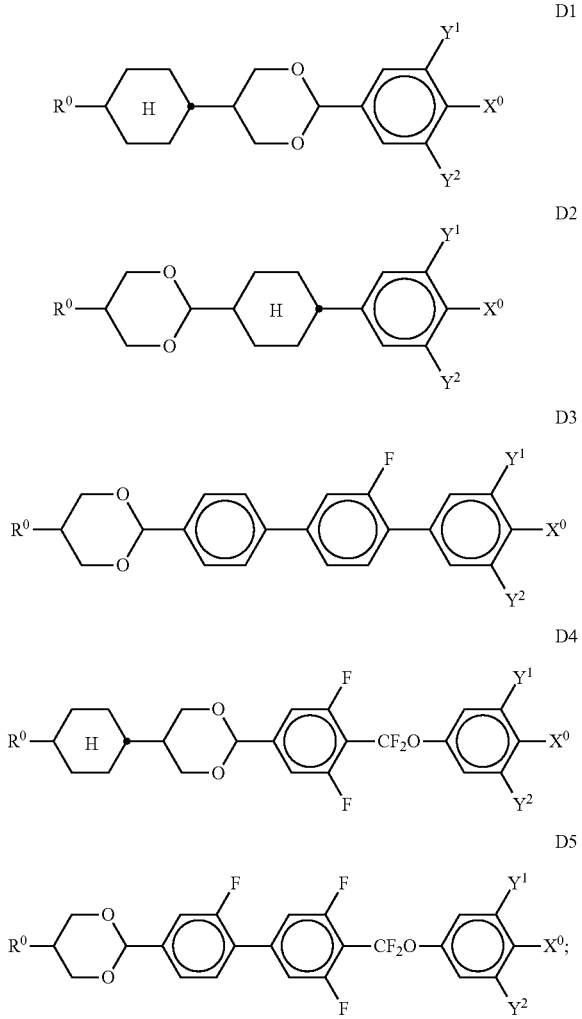

in which $R^0$, $X^0$ and $Y^1$-$Y^2$ independently have one of the meanings as defined above;

or one or more compounds of formulae Y-1, Y-2, Y-3 or Y-4,

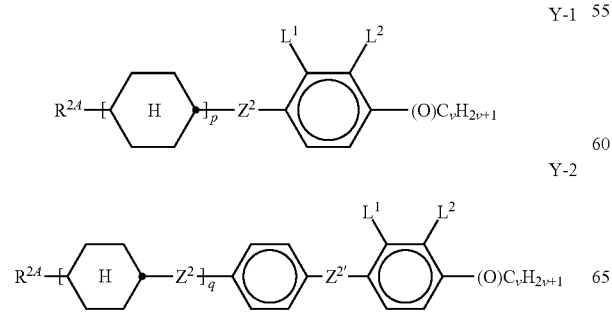

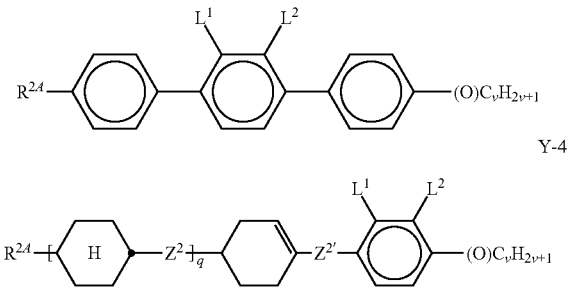

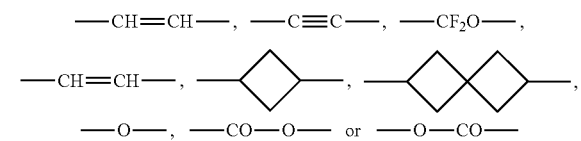

in which $R^{2A}$ denotes H, an alkyl or alkoxy radical having 1 to 15 C atoms, where, in addition, one or more $CH_2$ groups in these radicals may each be replaced, independently of one another, by

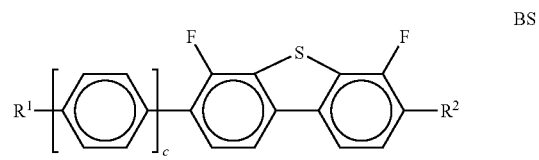

in such a way that O atoms are not linked directly to one another, and in which, in addition, one or more H atoms may be replaced by halogen, $L^1$ and $L^2$ each, independently of one another, denote F, Cl, $CF_3$, or $CHF_2$, $Z^2$ and $Z^{2'}$ each, independently of one another, denote a single bond, $—CH_2CH_2—$, $—CH=CH—$, $—CF_2O—$, $—OCF_2—$, $—CH_2O—$, $—OCH_2—$, $—COO—$, $—OCO—$, $—C_2F_4—$, $—CF=CF—$ or $—CH=CHCH_2O—$, p denotes 0, 1 or 2, q denotes 0 or 1, $(O)C_vH_{2v+1}$ denotes $OC_vH_{2v+1}$ or $C_vH_{2v+1}$, and v denotes 1 to 6;

or one or more compounds of formula BS

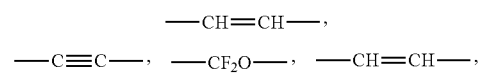

in which $R^1$ and $R^2$ each, independently of one another, denotes H, an alkyl or alkoxy radical having 1 to 15 C atoms, where, in addition, one or more $CH_2$ groups in these radicals may each be replaced, independently of one another, by $—CH=CH—$, $—C≡C—$, $—CF_2O—$, $—CH=CH—$, -continued
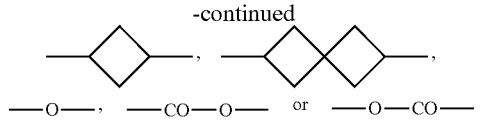
in such a way that O atoms are not linked directly to one another, and in which, in addition, one or more H atoms may be replaced by halogen, and
c denotes 0, 1 or 2.
* * * * *